US008293500B2

(12) United States Patent
Wiley et al.

(10) Patent No.: US 8,293,500 B2
(45) Date of Patent: Oct. 23, 2012

(54) METHODS FOR IDENTIFYING POLYPEPTIDE TARGETS AND USES THEREOF FOR TREATING IMMUNOLOGICAL DISEASES

(75) Inventors: Steven Wiley, Seattle, WA (US); Craig A Smith, Seattle, WA (US); Ajamete Kaykas, Seattle, WA (US)

(73) Assignee: Viral Logic Systems Technology Corp., Seattle, WA (US)

(*) Notice: Subject to any disclaimer, the term of this patent is extended or adjusted under 35 U.S.C. 154(b) by 0 days.

(21) Appl. No.: 11/728,329

(22) Filed: Mar. 22, 2007

(65) Prior Publication Data

US 2007/0264654 A1 Nov. 15, 2007

Related U.S. Application Data

(60) Provisional application No. 60/784,620, filed on Mar. 22, 2006.

(51) Int. Cl.
C12P 21/04 (2006.01)
(52) U.S. Cl. ...................... 435/70.1; 424/192.1; 530/413
(58) Field of Classification Search ........................ None
See application file for complete search history.

(56) References Cited

U.S. PATENT DOCUMENTS

| | | | |
|---|---|---|---|
| 5,011,912 A | 4/1991 | Hopp et al. | 530/387 |
| 5,100,788 A | 3/1992 | Löfdahl et al. | 435/69.7 |
| 5,168,049 A | 12/1992 | Meade et al. | 435/69.1 |
| 5,272,254 A | 12/1993 | Meade et al. | 530/350 |
| 5,359,039 A | 10/1994 | Smith et al. | 530/350 |
| 5,489,528 A | 2/1996 | Kopetzki et al. | 435/240.2 |
| 5,608,035 A | 3/1997 | Yanofsky et al. | 530/324 |
| 5,672,691 A | 9/1997 | Kopetzki et al. | 530/413 |
| 5,773,569 A | 6/1998 | Wrighton et al. | 530/300 |
| 5,786,331 A | 7/1998 | Barrett et al. | 514/15 |
| 5,869,451 A | 2/1999 | Dower et al. | 514/13 |
| 5,871,740 A | 2/1999 | Smith | 424/186.1 |
| 5,880,096 A | 3/1999 | Barrett et al. | 514/15 |
| 5,932,946 A | 8/1999 | Miyasaka et al. | 310/90.5 |
| 6,355,252 B1 | 3/2002 | Smith et al. | 424/232.1 |
| 6,512,095 B2 | 1/2003 | Baum | 530/350 |
| 6,660,843 B1 | 12/2003 | Feige et al. | 530/391.7 |
| 6,680,840 B2 | 1/2004 | Brooks | 361/160 |
| 6,843,991 B1 | 1/2005 | Efstathiou et al. | 424/186.1 |
| 6,852,486 B2 | 2/2005 | Smith et al. | 435/5 |
| 7,235,362 B2* | 6/2007 | Braman et al. | 435/6 |
| 2004/0115742 A1* | 6/2004 | Tan et al. | 435/7.2 |
| 2004/0265799 A1 | 12/2004 | Novik et al. | 435/5 |
| 2005/0106663 A1 | 5/2005 | Braman et al. | 435/69.1 |
| 2005/0118646 A1* | 6/2005 | Boniface et al. | 435/7.1 |
| 2005/0272919 A1* | 12/2005 | Duellman et al. | 530/413 |
| 2007/0134234 A1 | 6/2007 | Smith et al. | 424/133.1 |

FOREIGN PATENT DOCUMENTS

| | | |
|---|---|---|
| EP | 0 511 747 A1 | 11/1992 |
| EP | 2 005 185 | 10/2010 |
| FR | 2 830 020 | 3/2003 |
| WO | WO 89/03422 | 4/1989 |
| WO | WO 93/24631 | 12/1993 |
| WO | WO 98/37217 | 8/1998 |
| WO | WO 2005/002526 | 1/2005 |
| WO | WO 2007/041317 | 4/2007 |

OTHER PUBLICATIONS

Underhill-Day et al., Functional Characterization of W147A: A High-Affinity Interleukin-11 Antagonist, 2003, Endocrinology, vol. 144, No. 8, pp. 3406-3414.*
Trauger et al., The Identification of an Adenovirus Receptor by Using Affinity Capture and Mass Spectrometry, 2004, ChemBioChem, vol. 5, pp. 1095-1099.*
Wang et al., Myxoma Virus M11L Prevents Apoptosis through Constitutive Interaction with Bak, 2004, Journal of Virology, vol. 78, No. 13, pp. 7097-7111.*
Schmanski et al., Highly Efficient Tandem Affinity Purification of Trypanosome Protein Complexes Based on a Novel Epitope Combination, 2005, Eukaryotic Cell, vol. 4, No. 11, pp. 1942-1950.*
Seraphin et al., Tandem Affinity Purification to Enhance Interacting Protein Identification, Protein-Protein Interactions: A molecular cloning manual, Laboratory press, Chapter 17, pp. 313-328.*
Alcamíet al., "Poxviruses: Capturing Cytokines and Chemokines," *Seminars in Virology* 8:419-427, 1998.
Anthony and Burgess, "Conformational Flexibility in $\sigma^{70}$ Region 2 During Transcription Initiation," *The Journal of Biological Chemistry* 277(48): 46433-46441, Nov. 29, 2002.
Bugert and Darai, "Poxvirus Homologues of Cellular Genes," *Virus Genes* 21(1/2):111-133, 2000.
Dziembowski and Séraphin, "Recent Developments in the Analysis of Protein Complexes," *FEBS Letters* 556(1-3):1-6, Jan. 2, 2004.
Engelhardt et al., "Association of the Influenza A Virus RNA-dependent RNA Polymerase with Cellular RNA Polymerase II," *Journal of Virology* 79(9):5812-5818, May 2005.
GenBank Accession No. M74186, Jun. 21, 1993, URL=http://www.ncbi.nlm.nih.gov/entrez, download date Dec. 12, 2007.
GenBank Accession No. M74187, May 23, 1996, URL=http://www.ncbi.nlm.nih.gov/entrez, download date Dec. 12, 2007.
Goebel et al., "The Complete DNA Sequence of Vaccinia Virus," *Virology* 179:247-266, 1990.
Gould et al., "Tandem Affinity Purification and Identification of Protein Complex Components," *Methods* 33:239-244, 2004.
Hopp et al., "A Short Polypeptide Marker Sequence Useful for Recombinant Protein Identification and Purification," *Bio/Technology* 6: 1204-1210, Oct. 1988.
Jansson et al., "All Individual Domains of Staphylococcal Protein A Show Fab Binding," *FEMS Immunology and Medical Microbiology* 20:69-78, 1998.

(Continued)

Primary Examiner — Benjamin P Blumel
(74) Attorney, Agent, or Firm — Seed IP Law Group PLLC

(57) ABSTRACT

The present invention provides methods for identifying viral virulence factors and for identifying cellular polypeptides to which the viral polypeptides bind. The cellular polypeptide is useful as a therapeutic target or as a therapeutic agent for treating diseases and disorders, including immunological diseases or disorders.

38 Claims, 8 Drawing Sheets

OTHER PUBLICATIONS

Figure 1:
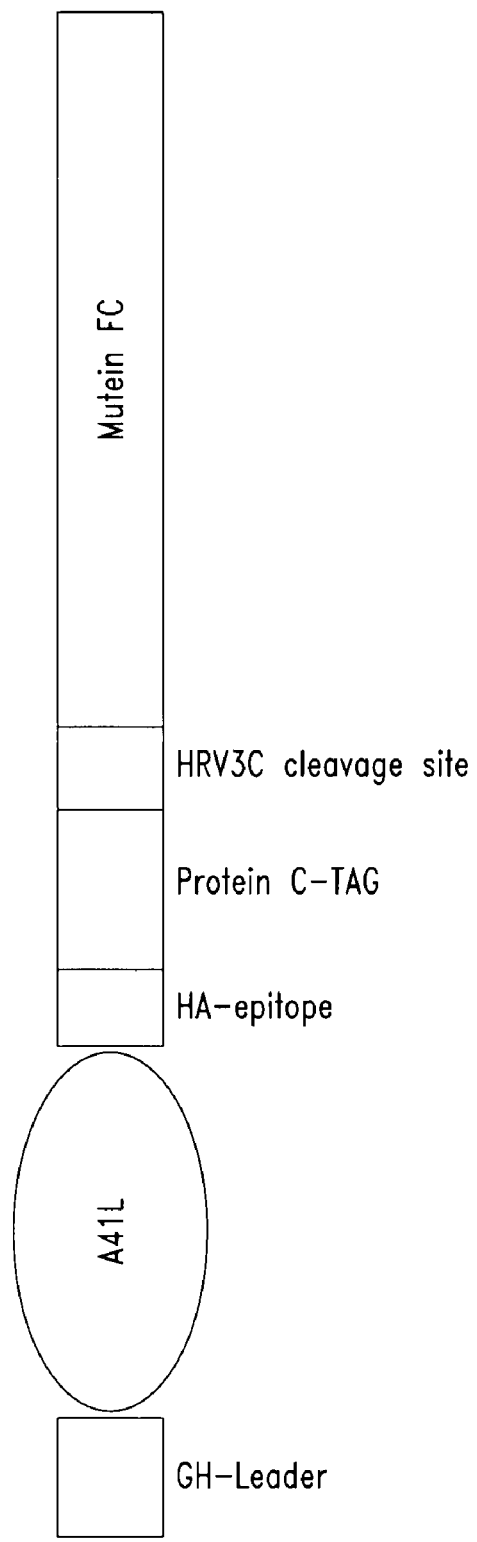

Knuesel et al., "Identification of Novel Protein-Protein Interactions Using a Versatile Mammalian Tandem Affinity Purification Expression System," *Molecular and Cellular Proteomics* 2(11):1225-1233, 2003.

Lamla and Erdmann, "The Nano-Tag, a Streptavidin-Binding Peptide for the Purification and Detection of Recombinant Proteins," *Protein Expression and Purification* 33:39-47, 2004.

Ljungberg et al., "The Interaction Between Different Domains of Staphylococcal Protein A and Human Polyclonal IgG, IgA, IgM and F(ab')$_2$: Separation of Affinity from Specificity," *Molecular Immunology* 30(14):1279-1285, 1993.

McFadden and Barry, "How Poxviruses Oppose Apoptosis," *Seminars in Virology* 8(5):429-442, Apr. 1998.

Ng et al., "The Vaccinia Virus A41L Protein is a Soluble 30 kDa Glycoprotein that Affects Virus Virulence," *Journal of General Virology* 82:2095-2105, 2001.

Nilsson et al., "A Synthetic IgG-Binding Domain Based on Staphylococcal Protein A," *Protein Engineering* 1(2):107-113, Feb./Mar. 1987.

Nizard et al., "Anchoring Antibodies to Membranes Using a Diphtheria Toxin T Domain-ZZ Fusion Protein as a pH Sensitive Membrane Anchor," *FEBs Letters* 433:83-88, 1998.

Nizard et al., "Prolonged Display or Rapid Internalization of the IgG-Binding Protein ZZ Anchored to the Surface of Cells Using the Diphtheria Toxin T Domain," *Protein Engineering* 14(6):439-446, 2001.

Puig et al., "The Tandem Affinity Purification (TAP) Method: A General Procedure of Protein Complex Purification," *Methods* 24:218-229, 2001.

Rigaut et al., "A Generic Protein Purification Method for Protein Complex Characterization and Proteome Exploration," *Nature Biotechnology* 17(10):1030-1032, Oct. 1999.

Smith et al., "A Receptor for Tumor Necrosis Factor Defines an Unusual Family of Cellular and Viral Proteins," *Science* 248(4958):1019-1023, May 25, 1990.

Su et al., "Myxoma Virus M11L Blocks Apoptosis through Inhibition of Conformational Activation of Bax at the Mitochondria," *Journal of Virology* 80(3):1140-1151, Feb. 2006.

Tasto et al., "Vectors and Gene Targeting Modules for Tandem Affinity Purification in *Schizosaccharomyces pombe*," *Yeast* 18:657-662, 2001.

Thompson et al., "Isolation and Characterization of a Polyol-Responsive Monoclonal Antibody Useful for Gentle Purification of *Escherichia coli* RNA Polymerase," *Biochemistry* 31(30):7003-7008, Aug. 4, 1992.

Zhang et al., "HBx Protein of Hepatitis B Virus (HBV) can form complex with Mitochondrial HSP60 and HSP70" *Archives of Virology* 150(8):1579-1590, Aug. 2005.

Johnston et al., "Poxvirus Immunomodulatory Strategies: Current Perspectives," *Journal of Virology* 77(11): 6093-6100, Jun. 2003.

Schimanski et al., "Highly Efficient Tandem Affinity Purification of Trypanosome Protein Complexes Based on a Novel Epitope Combination," *Eukaryotic Cell* 4(11): 1942-1950, Nov. 2005.

Takebe et al., "Purification of Components of the Translation Elongation Factor Complex of *Plasmodium falciparum* by Tandem Affinity Purification," *Eukaryotic Cell* 6(4): 584-591, Apr. 2007.

Vakili et al., "High Throughput Bioinformatic and Proteomic Platform to Identify Viral Virulence Genes and Their Cellular Targets," poster presentation at Pathogenesis and Control of Emerging Infections and Drug-Resistant Organisms, Bangkok, Thailand, Oct. 22-27, 2008, single page poster.

Vakili et al., "High Throughput Bioinformatic and Proteomic Platform to Identify Viral Virulence Genes and Their Cellular Targets," poster presentation at Pathogenesis and Control of Emerging Infections and Drug-Resistant Organisrns, Bangkok, Thailand, Oct. 22-27, 2008, pp. 1-10.

* cited by examiner

LAR

MAPEPAPGRTMVPLVPALVMLGLVAGAHGDSKPVFIKVPEDQTGLSGGVASFV
CQATGEPKPRITWMKKGKKVSSQRFEVIEFDDGAGSVLRIQPLRVQRDEAIYE
CTAT NSLGEINTSA KLSVLEEEQL PPGFPSIDMG PQLKVVEKAR
TATMLCAAGG NPDPEISWFKDFLPVDPATSNGRIKQLRSG ALQIESSEES
DQGKYECVAT NSAGTRYSAP ANLYVRVRRV APRFSIPPSS QEVMPGGSVN
LTCVAVGAPMPYVKWMMGAEELTKEDEMPV GRNVLELSNV VRSANYTCVA
ISSLGMIEAT AQVTVKALPKPPIDLVVTET TATSVTLTWD
SGNSEPVTYYGIQYRAAGTE GPFQEVDGVA TTRYSIGGLS PFSEYAFRVL
AVNSIGRGPP SEAVRARTGEQAPSSPPRRV QARMLSASTM
LVQWEPPEEPNGLVRGYRVY YTPDSRRPPN AWHKHNTDAG LLTTVGSLLP
GITYSLRVLAFTAVGDGPPSPTIQVKTQQG VPAQPADFQA
EVESDTRIQLSWLLPPQERI IMYELVYWAA EDEDQQHKVT
FDPTSSYTLEDLKPDTLYRFQLAARSDMGVGVFTPTIEARTAQSTPSAPP
QKVMCVSMGS TTVRVSWVPP PADSRNGVIT QYSVAYEAVD GEDRGRHVVD
GISREHSSWD LVGLEKWTEYRVWVRAHTDV GPGPESSPVL VRTDEDVPSG
PPRKVEVEPL NSTAVHVYWK LPVPSKQHGQIRGYQVTYVR LENGEPRGLP
IIQDVMLAEAQETTISGLTP ETTYSVTVAA YTTKGDGARS
KPKIVTTTGAVPGRPTMMISTTAMNTALLQ WHPPKELPGE LLGYRLQYCR
ADEARPNTID FGKDDQHFTV TGLHKGTTYI FRLAAKNRAG LGEEFEKEIR
TPEDLPSGFP QNLHVTGLTT STTELAWDPP VLAERNGRII SYTVVFRDIN
SQQELQNITT DTRFTLTGLK PDTTYDIKVRAWTSKGSGPL SPSIQSRTMP
VEQVFAKNFR VAAAMKTSVL LSWEVPDSYK SAVPFKILYN GQSVEVDGHS
MRKLIADLQP NTEYSFVLMN RGSSAGGLQH LVSIRTAPDL LPHKPLPASA
YIEDGRFDLS MPHVQDPSLV RWFYIVVVPI DRVGGSMLTP RWSTPEELEL
DELLEAIEQG GEEQRRRRRQ AERLKPYVAA QLDVLPETFT LGDKKNYRGF
YNRPLSPDLS YQCFVLASLK EPMDQKRYAS SPYSDEIVVQ VTPAQQQEEP
EMLWVTGPVL AVILIILIVI AILLFKRKRT HSPSSKDEQS IGLKDSLLAH
SSDPVEMRRL NYQTPGMRDH PPIPITDLAD NIERLKANDG LKFSQEYESI
DPGQQFTWEN SNLEVNKPKN RYANVIAYDH SRVILTSIDG VPGSDYINAN
YIDGYRKQNA YIATQGPLPE TMGDFWRMVW EQRTATVVMM TRLEEKSRVK
CDQYWPARGT ETCGLIQVTL LDTVELATYT VRTFALHKSG SSEKRELRQF
QFMAWPDHGV PEYPTPILAF LRRVKACNPL DAGPMVVHCSAGVGR
TGCFIVIDAM LERMKHEKTV
DIYGHVTCMRSQRNYMVQTEDQYVFIHEALLEAATCGHTEVPARNLYAHIQKL
GQVPPGESVTAMELEFKLLASSKAHTSRFISANLPCNFKNRLVNIMPYELTRV
CLQPIRGV EGSDYINASF LDGYRQQKAY IATQGPLAES TEDFWRMLWE
HNSTIIVMLT KLREMGREKC HQYWPAERSA RYQYFVVDPM
AEYNMPQYILREFKVTDARDGQSRTIRQFQFTDWPEQGVPKTGEGFIDFIGQV
HKTKEQFGQDGPITVHCSAGVGRTGVFITLSIVLERM RYEGVVDMFQ
TVKTLRTQRPAMVQTEDQYQCYRAALEYL GSFDHYAT

*FIG. 3A*

PTP-σ

MAPTWGPGMV SVVGPMGLLV VLLVGGCAAE EPPRFIKEPK DQIGVSGGVA
SFVCQATGDP KPRVTWNKKG KKVNSQRFET IEFDESAGAV LRIQPLRTPR
DENVYECVAQ NSVGEITVHA KLTVLREDQL PSGFPNIDMG PQLKVVERTR
TATMLCAASG NPDPEITWFK DFLPVDPSAS NGRIKQLRSD QAFSHLPTGA
LQIESSEETD QGKYECVATN SAGVRYSSPA NLYVRALLKL RRVAPRFSIL
PMSHEIMPGG NVNITCVAVG SPMPYVKWMQ GAEDLTPEDD MPVGRNVLEL
TDVKDSANYT CVAMSSLGVI EAVAQITVKS LPKAPGTPMV TENTATSITI
TWDSGNPDPV SYYVIEYKSK SQDGPYQIKE DITTTRYSIG GLSPNSEYEI
WVSAVNSIGQ GPPSESVVTR TGEQAPASAP RNVQARMLSA TTMIVQWEEP
VEPNGLIRGY RVYYTMEPEH PVGNWQKHNV DDSLLTTVGS LLEDETYTVR
VLAFTSVGDG PLSDPIQVKT QQGVPGQPMN LRAEARSETS ITLSWSPPRQ
ESIIKYELLF REGDHGREVG RTFDPTTSYV VEDLKPNTEY AFRLAARSPQ
GLGAFTPVVR QRTLQSKPSA PPQDVKCVSV RSTAILVSWR PPPPETHNGA
LVGYSVRYRP LGSEDPEPKE VNGIPPTTTQ ILLEALEKWT QYRITTVAHT
EVGPGPESSP VVVRTDEDVP SAPPRKVEAE ALNATAIRVL WRSPAPGRQH
GQIRGYQVHY VRMEGAEARG PPRIKDVMLA DAQWETDDTA EYEMVITNLQ
PETAYSITVA AYTMKGDGAR SKPKVVVTKG AVLGRPTLSV QQTPEGSLLA
RWEPPAGTAE DQVLGYRLQF GREDSTPLAT LEFPPSEDRY TASGVHKGAT
YVFRLAARSR GGLGEEAAEV LSIPEDTPRG HPQILEAAGN ASAGTVLLRW
LPPVPAERNG AIVKYTVAVR EAGALGPARE TELPAAAEPG AENALTLQGL
KPDTAYDLQV RAHTRRGPGP FSPPVRYRTF LRDQVSPKNF KVKMIMKTSV
LLSWEFPDNY NSPTPYKIQY NGLTLDVDGR TTKKLITHLK PHTFYNFVLT
NRGSSLGGLQ QTVTAWTAFN LLNGKPSVAP KPDADGFIMV YLPDGQSPVP
VQSYFIVMVP LRKSRGGQFL TPLGSPEDMD LEELIQDISR LQRRSLRHSR
QLEVPRPYIA ARFSVLPPTF HPGDQKQYGG FDNRGLEPGH RYVLFVLAVL
QKSEPTFAAS PFSDPFQLDN PDPQPIVDGE EGLIWVIGPV LAVVFIICIV
IAILLYKNKP DSKRKDSEPR TKCLLNNADL APHHPKDPVE MRRINFQTPD
SGLRSPLREP GFHFESMLSH PPIPIADMAE HTERLKANDS LKLSQEYESI
DPGQQFTWEH SNLEVNKPKN RYANVIAYDH SRVILQPIEG IMGSDYINAN
YVDGYRCQNA YIATQGPLPE TFGDFWRMVW EQRSATIVMM TRLEEKSRIK
CDQYWPNRGT ETYGFIQVTL LDTIELATFC VRTFSLHKNG SSEKREVRQF
QFTAWPDHGV PEYPTPFLAF LRRVKTCNPP DAGPIVVHCS AGVGRTGCFI
VIDAMLERIK PEKTVDVYGH VTLMRSQRNY MVQTEDQYSF IHEALLEAVG
CGNTEVPARS LYAYIQKLAQ VEPGEHVTGM ELEFKRLANS KAHTSRF**ISA
NLPCNKFKNR LVNIMPYEST RVCLQPIRGV EGSDYINASF IDGYRQQKAY**
IATQGPLAET TEDFWRMLWE NNSTIVVMLT KLREMGREKC HQYWPAERSA
RYQYFVVDPM AEYNMPQYIL REFKVTDARD GQSRTVRQFQ FTDWPEQGVP
KSGEGFIDFI GQVHKTKEQF GQDGPISVHC SAGVGRTGVF ITLSIVLERM
RYEGVVDIFQ TVKMLRTQRP AMVQTEDEYQ FCYQAALEYL GSFDHYAT

*FIG. 3B*

PTP-δ

MVHVARLLLLLLTFFLRTDAETPPRFTRTPVDQTGVSGGVASFICQATGDPRPKI
VVWNKKGKKVSNQRFEVIEFDDGSGS VLRIQPLRTP RDEAIYECVA
SNNVGEISVS TRLTVLREDQ IPRGFPTIDM GPQLKVVERT RTATMLCAAS
GNPDPEITWF KDFLPVDTSN NNGRIKQLRS GRVFKRLNRR ALQIEQSEES
DQGKYECVAT NSAGTRYSAP ANLYVRVETP QVRRVPPRFS IPPTNHEIMP
GGSVNITCVA VGSPMPYVKW MLGAEDLTPE DDMPIGRNVL ELNDVRQSAN
YTCVAMSTLG VIEAIAQITV KALPKPPGTP VVTESTATSI TLTWDSGNPE
PVSYYIIQHK PKNSEELYKE IDGVATTRYS VAGLSPYSDY EFRVVAVNNI
GRGPPSEPVL TQTSEQAPSS APRDVQARML SSTTILVQWK EPEEPNGQIQ
GYRVYYTMDP TQHVNNWMKH NVADSQITTI GNLVPQKTYS VKVLAFTSIG
DGPLSSDIQV ITQTGVPGQP LNFKAEPESE TSILLSWTPP RSDTIANYEL
VYKDGEHGEE QRITIEPGTS YRLQGLKPNS LYYFRLAARS PQGLGASTAE
ISARTMQSKP SAPPQDISCT SPSSTSILVS WQPPPVEKQN GIITEYSIKY
TAVDGEDDKP HEILGIPSDT TKYLLEQLEK WTEYRITVTA HTDVGPGPES
LSVLIRTNED VPSGPPRKVE VEAVNSTSVK VSWRSPVPNK QHGQIRGYQV
HYVRMENGEP KGQPMLKDVM LADAQWEFDD TTEHDMIISG LQPETSYSLT
VTAYTTKGDG ARSKPKLVST TGAVPGKPRL VINHTQMNTA LIQWHPPVDT
FGPLQGYRLK FGRKDMEPLT TLEFSEKEDH FTATDIHKGA SYVFRLSARN
KVGFGEEMVK EISIPEEVPT GFPQNLHSEG TTSTSVQLSW QPPVLAERNG
IITKYTLLYR DINIPLLPME QLIVPADTTM TLTGLKPDTT YDVKVRAHTS
KGPGPYSPSV QFRTLPVDQV FAKNFHVKAV MKTSVLLSWE IPENYNSAMP
FKILYDDGKM VEEVDGRATQ KLIVNLKPEK SYSFVLTNRG NSAGGLQHRV
TAKTAPDVLR TKPAFIGKTN LDGMITVQLP EVPANENIKG YYIIIVPLKK
SRGKFIKPWE SPDEMELDEL LKEISRKRRS IRYGREVELK PYIAAHFDVL
PTEFTLGDDK HYGGFTNKQL QSGQEYVFFV LAVMEHAESK MYATSPYSDP
VVSMDLDPQP ITDEEEGLIW VVGPVLAVVF IICIVIAILL YKRKRAESDS
RKSSIPNNKE IPSHHPTDPV ELRRLNFQTP GMASHPPIPI LELADHIERL
KANDNLKFSQ EYESIDPGQQ FTWEHSNLEV NKPKNRYANV IAYDHSRVLL
SAIEGIPGSD YVNANYIDGY RKQNAYIATQ GSLPETFGDF WRMIWEQRSA
TVVMMTKLEE RSRVKCDQYW PSRGTETHGL VQVTLLDTVE LATYCVRTFA
LYKNGSSEKR EVRQFQFTAW PDHGVPEHPT PFLAFLRRVK TCNPPDAGPM
VVHCSAGVGR TGCFIVIDAM LERIKHEKTV DIYGHVTLMR AQRNYMVQTE
DQYIFIHDAL LEAVTCGNTE VPARNLYAYI QKLTQIETGE NVTGMELEFK
RLASSKAHTS RFISANLPCN KFKNRLVNIM PYESTRVCLQ PIRG**VEGSDY
INASFIDGYR** QQKAYIATQG PLAETTEDFW RMLWEHNSTI VVMLTKLREM
GREKCHQYWP AERSARYQYF VVDPMAEYNM PQYILREFKV TDARDGQSRT
VRQFQFTDWP EQGVPKSGEG FIDFIGQVHK TKEQFGQDGP ISVHCSAGVG
RTGVFITLSI VLERMRYEGV VDIFQTVKML RTQRPAMVQT EDQYQFSYRA
ALEYLGSFDH YAT

*FIG. 3C*

METHODS FOR IDENTIFYING POLYPEPTIDE TARGETS AND USES THEREOF FOR TREATING IMMUNOLOGICAL DISEASES

CROSS-REFERENCE TO RELATED APPLICATION

This application claims the benefit U.S. Provisional Patent Application No. 60/784,620 filed Mar. 22, 2006, which is incorporated herein by reference in its entirety.

STATEMENT REGARDING SEQUENCE LISTING SUBMITTED ON CD-ROM

The Sequence Listing associated with this application is provided on CD-ROM in lieu of a paper copy, and is hereby incorporated by reference into the specification. Three CD-ROMs are provided, containing identical copies of the sequence listing: CD-ROM No. 1 is labeled COPY 1, contains the file 402.app.txt which is 108 KB and created on Mar. 22, 2007; CD-ROM No. 2 is labeled COPY 2, contains the file 402.app.txt which is 108 KB and created on Mar. 22, 2007; CD-ROM No. 3 is labeled CRF (Computer Readable Form), contains the file 402.app.txt which is 108 KB and created on Mar. 22, 2007.

BACKGROUND OF THE INVENTION

1. Field of the Invention

The present invention provides a method for identifying cellular polypeptides, which when a biological activity of the cellular polypeptide is altered, a disease or disorder, in particular, an immunological disease or disorder may be treated. The method comprises identifying a viral virulence factor and its cellular target(s). Also provided herein are agents and methods for identifying such agents that affect a biological activity of the cellular target and that may be used as therapeutic molecules for treating a disease or disorder. Such agents are useful for altering immunoresponsiveness of the immune system and for treating immunological disorders in a subject.

2. Description of the Related Art

Immunological diseases and disorders, including autoimmune diseases and inflammatory diseases, afflict more than twenty million people in the United States. Many immunological diseases are debilitating and chronic, and thus affect a patient's productivity, well-being, as well as general health.

A need exists to identify cellular polypeptides that are effectors or modulators of an immune response and also to identify agents that modulate the immune response by interacting with the cellular polypeptides. Such agents are useful for treating and/or preventing immunological diseases and disorders and other related diseases and disorders. Provided herein are methods for identifying cellular polypeptides that are useful as therapeutic targets.

BRIEF SUMMARY OF THE INVENTION

The present invention relates to the discovery of a method for rapidly identifying cellular targets that are important in modulating the human immune system, and then identifying the counterstructures that will bind and modulate those targets.

In one embodiment, a method is provided for identifying a cellular polypeptide to which a viral polypeptide binds comprising (a) contacting a cell, or a fraction or a supernatant of the cell, and a fusion protein comprising a viral polypeptide fused to an affinity tag, under conditions and for a time sufficient that permit a viral polypeptide moiety of the fusion protein to interact with a polypeptide associated with the cell, or the fraction or the supernatant of the cell, to provide a fusion protein:cellular polypeptide complex, wherein the viral polypeptide exhibits at least one virulence trait; (b) isolating the fusion protein:cellular polypeptide complex; and (c) determining the amino acid sequence of the cellular polypeptide or of at least one cellular polypeptide fragment comprising at least eight amino acids, and thereby identifying a cellular polypeptide to which a viral polypeptide binds. In a certain embodiment, further comprising prior to step (a), (i) identifying in the genome of a virus, a polynucleotide sequence that encodes a viral polypeptide, which viral polypeptide comprises at least 40 amino acids; and (ii) producing a fusion protein comprising the viral polypeptide fused to an affinity tag sequence. In a specific embodiment at least one virulence trait comprises the trait that expression of a mutant viral polypeptide in a cell infected by the virus correlates with a decrease in virulence of the virus. In another specific embodiment, at least one virulence trait comprises the trait that absence of expression of the viral polypeptide in a cell infected by the virus correlates with a decrease in virulence of the virus. In yet another specific embodiment, the viral polypeptide (a) is secreted by a cell infected with the virus, (b) is associated with a cellular membrane, or (c) is intracellular. In a particular embodiment, the viral polypeptide is secreted by the infected cell. In another specific embodiment, the at least one virulence trait comprises the trait that the viral polypeptide is secreted by a cell infected with the virus or the viral polypeptide is associated with a cellular membrane of a cell that is infected by the virus.

In another specific embodiment of the aforementioned method, the at least one virulence trait comprises the trait that the polynucleotide sequence in the virus genome is located in a genomic region that encodes at least one other viral polypeptide (i.e., a second viral polypeptide) that is a viral virulence factor, wherein the region is at the 5' terminal end or the 3' terminal end of the virus genome. In one certain embodiment, the virus is a poxvirus. In certain embodiments, the virus comprises a DNA genome, a double-stranded RNA genome, or a single-stranded RNA genome. In a particular embodiment, the virus comprises a DNA genome, and the virus is a poxvirus, adenovirus, herpesvirus, or a hepatitis B virus. In another specific embodiment, the virus comprises an RNA genome and the virus is selected from a picornavirus, a retrovirus, a hemorrhagic fever virus, or a hepatitis C virus.

In certain embodiments, prior to step (b) of the aforementioned method, the cell is subjected to at least one stimulus, and in certain embodiments, the cell is an immune cell and the at least one stimulus is selected from (a) an antibody that specifically binds to a cognate antigen expressed by the cell; (b) a phorbol ester; (c) concanavalin A; (d) a cytokine; (e) a chemokine; and (f) ionomycin. In other certain embodiments, the immune cell is subjected to at least two or to at least three of the aforementioned stimuli. In another embodiment, the fraction of the cell is selected from a cell lysate, a cell extract, or at least one isolated cell organelle. In a particular embodiment, the affinity tag comprises a detectable moiety, and in other particular embodiments, the affinity tag comprises a polypeptide tag and a detectable moiety. In a particular embodiment, the detectable moiety is selected from a fluorophore, a radionuclide, an enzyme, and biotin.

In yet another embodiment of the aforementioned methods, the affinity tag comprises a polypeptide tag. In a specific embodiment, the affinity tag further comprises a protease recognition sequence. In yet another specific embodiment, the protease recognition sequence is located between the viral polypeptide and the polypeptide tag. In particular embodiments, the polypeptide tag is selected from a hemagglutinin peptide; a calmodulin binding polypeptide, a streptavidin binding peptide, an immunoglobulin Fc polypeptide, an immunoglobulin mutein Fc polypeptide, a protein C-tag, an at least one immunoglobulin binding staphylococcal protein A domain, and Softag™. In a particular embodiment, the affinity tag comprises the hemagglutinin peptide, which comprises the amino acid sequence YPYDVDYA (SEQ ID NO:1). In another particular embodiment, the affinity tag comprises the calmodulin binding polypeptide, which comprises the amino acid sequence KRRWKKNFIAVSAANRFKKISSS-GAL (SEQ ID NO:3). In still another particular embodiment, the affinity tag comprises an immunoglobulin Fc polypeptide wherein the Fc polypeptide is a human IgG immunoglobulin Fc polypeptide, and in certain particular embodiments, the human IgG immunoglobulin Fc polypeptide is a human IgG1 immunoglobulin Fc polypeptide. In certain other particular embodiments, the polypeptide tag is an immunoglobulin mutein Fc polypeptide, wherein the immunoglobulin mutein Fc polypeptide is a human IgG1 immunoglobulin mutein Fc polypeptide. In still another particular embodiment, the affinity tag comprises the protein C-tag, which comprises the amino acid sequence EDQVDPRLIDGK (SEQ ID NO:4). In yet still another particular embodiment, the affinity tag comprises the streptavidin binding peptide comprises the amino acid sequence selected from MDEKTTGWRGGH-VVEGLAGELEQLRARLEHHPQGQREP (SEQ ID NO:6) or DVEAWLDERVPLVET; SEQ ID NO:7). In still another particular embodiment, the affinity tag comprises the at least one immunoglobulin binding staphylococcal protein A domain, which comprises an IgG-binding protein ZZ. In yet another specific embodiment, the Softag™ comprises the amino sequence SLAELLNAGLGGS (SEQ ID NO:11).

In another embodiment of the aforementioned methods, the affinity tag comprises a first polypeptide tag and a second polypeptide tag. In a specific embodiment, the affinity tag further comprises a protease recognition sequence, and in a particular embodiment, the protease recognition sequence is located between the first polypeptide tag and the second polypeptide tag. In certain embodiments, the first polypeptide tag and the second polypeptide tag are selected from a hemagglutinin peptide; a calmodulin binding polypeptide, a streptavidin binding peptide, an immunoglobulin Fc polypeptide, an immunoglobulin mutein Fc polypeptide, a protein C-tag, an at least one immunoglobulin binding staphylococcal protein A domain, and Softag™.

In still other embodiments, the affinity tag further comprises a third polypeptide tag, wherein the first polypeptide tag, the second polypeptide tag, and the third polypeptide tag are each selected from a hemagglutinin peptide; a calmodulin binding polypeptide, a streptavidin binding peptide, an immunoglobulin Fc polypeptide, an immunoglobulin mutein Fc polypeptide, a protein C-tag, an at least one immunoglobulin binding staphylococcal protein A domain, and Softag™. In a specific embodiment, the first polypeptide tag is a hemagglutinin peptide; the second polypeptide tag is a protein C-tag; and the third polypeptide tag is Softag™. In other certain embodiments, the affinity tag comprises at least one protease recognition sequence. In a specific embodiment, the first polypeptide tag is a hemagglutinin peptide; the second polypeptide tag is a protein C-tag; and the third polypeptide tag is an at least one immunoglobulin binding staphylococcal protein A domain; and the at least one protease recognition sequence is a tobacco etch virus protease recognition sequence or a Human Rhinovirus HRV3C protease recognition sequence. In still yet another specific embodiment, the first polypeptide tag is a hemagglutinin peptide; the second polypeptide tag is a protein C-tag; and the third polypeptide tag is an immunoglobulin mutein Fc polypeptide; and the at least one protease recognition sequence is a tobacco etch virus protease recognition sequence or a Human Rhinovirus HRV3C protease recognition sequence. In yet another specific embodiment, the affinity tag comprises a first polypeptide tag, a second polypeptide tag, a third polypeptide tag, and at least one protease recognition sequence, wherein the at least one protease recognition sequence is located between the first polypeptide tag and the second polypeptide tag, or wherein the protease recognition sequence is located between the second polypeptide tag and the third polypeptide tag. In another specific embodiment, the affinity tag further comprises a second protease recognition sequence.

In yet another embodiment of the aforementioned methods, the affinity tag further comprises a fourth polypeptide tag. In a particular embodiment, each of the first, second, third, and fourth polypeptide tags is selected from a hemagglutinin peptide, a calmodulin binding polypeptide, a streptavidin binding peptide, an immunoglobulin Fc polypeptide, an immunoglobulin mutein Fc polypeptide, a protein C-tag, an at least one immunoglobulin binding staphylococcal protein A domain, and Softag™. In yet another particular embodiment, the first polypeptide tag is a hemagglutinin tag; the second polypeptide tag is a calmodulin binding polypeptide; the third polypeptide tag is a streptavidin binding peptide; the fourth polypeptide tag is an immunoglobulin mutein Fc polypeptide; and the at least one protease recognition sequence is a tobacco etch virus protease recognition sequence. In still other embodiments, the fourth polypeptide tag is the same as the first, second, or third polypeptide tag. In a specific embodiment, the first polypeptide tag is a hemagglutinin polypeptide; the second polypeptide tag is a protein C-tag; the third polypeptide tag and is a streptavidin binding peptide; and the fourth polypeptide tag is a repeat of the third polypeptide tag. In a particular embodiment, the affinity tag further comprises a protease recognition sequence between the second polypeptide tag and the third polypeptide tag, wherein in a specific embodiment, the protease recognition sequence is a Human Rhinovirus HRV3C protease recognition sequence. In another specific embodiment, the affinity tag further comprises a second protease recognition sequence.

According to any of the aforementioned methods, the fusion protein further comprises a signal peptide sequence a signal peptide sequence. In certain embodiments, the signal peptide sequence comprises the amino acid sequence of a human growth hormone signal peptide sequence, which in certain embodiments comprises the amino acid sequence MATGSRTSLLLAFGLLCLPWLQEGSA (SEQ ID NO:12).

In another embodiment of the aforementioned methods, step (c) comprises (i) cleaving the isolated cellular polypeptide with a protease to generate at least one polypeptide fragment or a plurality of polypeptide fragments of the cellular polypeptide; (ii) determining the amino acid sequence of at least one polypeptide fragment, wherein the fragment comprises at least eight amino acids; and (iii) comparing the amino acid sequence of the at least one polypeptide fragment with the amino acid sequence of a known cellular polypeptide, thereby identifying the cellular polypeptide to which the viral polypeptide binds. In a particular embodiment, the amino acid sequence is determined by a method comprising liquid chromatography and mass spectrometry, wherein in certain embodiments, the method comprises liquid chromatography and tandem mass spectrometry.

In still another embodiment of the aforementioned methods, step (b) comprises (i) contacting the fusion protein: cellular polypeptide complex and a cognate ligand of the affinity tag under conditions and for a time sufficient to permit formation of a cognate ligand:fusion protein:cellular polypeptide complex; and (ii) isolating the fusion polypeptide:cellular polypeptide from the cognate ligand:fusion protein:cellular polypeptide complex. In certain embodiments, the fusion protein is recombinantly expressed. In a particular embodiment, the fusion protein is recombinantly expressed by the cell of step (a).

In yet another embodiment of the aforementioned methods, the method further comprises identifying a cell type that comprises a cellular polypeptide to which a viral polypeptide that exhibits at least one virulence trait binds comprising (i) contacting the fusion protein and a biological sample comprising at least one cell, or a fraction of the cell or a supernatant of the cell, under conditions and for a time sufficient to permit the viral polypeptide moiety of the fusion protein to interact with the at least one cell, or the cell fraction or the cell supernatant; (ii) determining the presence or absence of binding of the fusion protein to the at least one cell, or the fraction or the supernatant thereof; (iii) isolating the cell to which the fusion protein binds; and (iv) characterizing the cell, and therefrom determining the cell type that comprises a cellular polypeptide to which the viral polypeptide binds.

In another embodiment, a method is provided for identifying a cellular polypeptide to which a viral polypeptide binds comprising (a) identifying in the genome of a virus, a polynucleotide sequence that encodes a viral polypeptide, which viral polypeptide comprises at least 40 amino acids; (b) producing a fusion protein comprising the viral polypeptide fused to an affinity tag sequence; (c) contacting the fusion protein and a cell, or a fraction or a supernatant of the cell, under conditions and for a time sufficient that permit the viral polypeptide moiety of the fusion protein to interact with a polypeptide associated with the cell, or the fraction or the supernatant thereof, to provide a fusion protein:cellular polypeptide complex; (d) isolating the fusion protein:cellular polypeptide complex; and (e) determining the amino acid sequence of all or a portion of the cellular polypeptide, and thereby identifying a cellular polypeptide to which a viral polypeptide binds. In a particular embodiment, the fusion protein is produced by the cell of step (c). In a particular embodiment, the viral polypeptide exhibits at least one virulence trait that comprises the trait that expression of a mutant viral polypeptide in a cell infected by the virus correlates with a decrease in virulence of the virus. In another particular embodiment, the at least one virulence trait comprises the trait that absence of expression of the viral polypeptide in a cell infected by the virus correlates with a decrease in virulence of the virus. In yet another particular embodiment, the viral polypeptide (i) is secreted by a cell infected with the virus, (ii) is associated with a cellular membrane, or (iii) is intracellular. In certain particular embodiments, the at least one virulence trait of the viral polypeptide comprises the trait that the viral polypeptide is secreted by a cell infected with the virus; in another certain embodiment, the at least one virulence trait comprises the trait that the viral polypeptide is associated with a cellular membrane of the cell infected by the virus. In another embodiment of the aforementioned method, the at least one virulence trait comprises the trait that the polynucleotide sequence in the virus genome is located in a genomic region that encodes at least one other viral polypeptide (i.e., a second viral polypeptide) that is a viral virulence factor, wherein the region is at the 5' terminal end or the 3' terminal end of the virus genome. In certain embodiments, the virus is a poxvirus. In certain embodiments, the virus comprises a DNA genome, a double-stranded RNA genome, or a single-stranded RNA genome. In a particular embodiment, the virus comprises a DNA genome, and the virus is a poxvirus, adenovirus, herpesvirus, or a hepatitis B virus. In another specific embodiment, the virus comprises an RNA genome and the virus is selected from a picornavirus, a retrovirus, a hemorrhagic fever virus, or a hepatitis C virus. In certain embodiments, prior to the step of contacting the fusion protein and a cell, or a fraction or a supernatant of the cell, the cell is subjected to at least one stimulus, and in certain embodiments, the cell is an immune cell and the at least one stimulus is selected from (a) an antibody that specifically binds to a cognate antigen expressed by the cell; (b) a phorbol ester; (c) concanavalin A; (d) a cytokine; (e) a chemokine; and (f) ionomycin. In other certain embodiments, the immune cell is subjected to at least two or to at least three of the aforementioned stimuli. In another embodiment, the fraction of the cell is selected from a cell lysate, a cell extract, or at least one isolated cell organelle. In a particular embodiment, the affinity tag comprises a detectable moiety, and in other particular embodiments, the affinity tag comprises a polypeptide tag and a detectable moiety. In a particular embodiment, the detectable moiety is selected from a fluorophore, a radionuclide, an enzyme, and biotin. In certain embodiments, the affinity tag comprises at least one polypeptide tag, and the polypeptide tag is selected from a hemagglutinin peptide, a calmodulin binding polypeptide, a streptavidin binding peptide, an immunoglobulin Fc polypeptide, an immunoglobulin mutein Fc polypeptide, a protein C-tag, an at least one immunoglobulin binding staphylococcal protein A domain, and Softag™. In another embodiment, the affinity tag comprises at least two, three, or four polypeptide tags, and each of the at least two, three, or four polypeptide tags is selected from hemagglutinin peptide, a calmodulin binding polypeptide, a streptavidin binding peptide, an immunoglobulin Fc polypeptide, an immunoglobulin mutein Fc polypeptide, a protein C-tag, an at least one immunoglobulin binding staphylococcal protein A domain, and Softag™. In a specific embodiment, the affinity tag further comprises at least one protease recognition sequence, wherein the at least one protease recognition sequence is either a tobacco etch virus protease recognition sequence or a Human Rhinovirus HRV3C protease recognition sequence. In yet another specific embodiment, the affinity tag further comprises at least two protease recognition sequences, wherein at least one protease recognition sequence is either a tobacco etch virus protease recognition sequence or a Human Rhinovirus HRV3C protease recognition sequence.

In one embodiment, a method is provided for identifying a cellular polypeptide to which a viral polypeptide binds, comprising (a) identifying in the genome of a virus, a polynucleotide sequence that encodes a viral polypeptide, which viral polypeptide comprises at least 40 amino acids; (b) introducing into a cell a recombinant expression construct comprising a promoter operatively linked to a polynucleotide encoding the viral polypeptide fused in frame with an affinity tag; (c) isolating from the cell, or from a fraction of the cell, or from a supernatant of the cell, a fusion protein:cellular polypeptide complex; (d) isolating the fusion protein:cellular polypeptide complex; and (e) determining the amino acid sequence of the cellular polypeptide or of at least one cellular polypeptide fragment comprising at least eight amino acids, and thereby identifying a cellular polypeptide to which a viral polypeptide binds. In a particular embodiment, the viral polypeptide comprises at least one virulence trait. In a specific embodiment, the at least one virulence trait comprises the trait that expression of a mutant viral polypeptide in a cell infected by the virus correlates with a decrease in virulence of the virus. In another particular embodiment, the at least one virulence trait comprises the trait that absence of expression of the viral polypeptide in a cell infected by the virus correlates with a decrease in virulence of the virus. In yet another particular embodiment, the viral polypeptide (i) is secreted by a cell infected with the virus, (ii) is associated with a cellular membrane, or (iii) is intracellular. In certain particular embodiments, the at least one virulence trait of the viral polypeptide comprises the trait that the viral polypeptide is secreted by a cell infected with the virus; in another certain embodiment, the at least one virulence trait comprises the trait that the viral polypeptide is associated with a cellular membrane of the cell infected by the virus. In another embodiment of the aforementioned method, the at least one virulence trait comprises the trait that the polynucleotide sequence in the virus genome is located in a genomic region that encodes at least one other viral polypeptide (i.e., a second viral polypeptide) that is a viral virulence factor, wherein the region is at the 5' terminal end or the 3' terminal end of the virus genome. In certain embodiments, the virus is a poxvirus. In certain embodiments, the virus comprises a DNA genome, a double-stranded RNA genome, or a single-stranded RNA genome. In a particular embodiment, the virus comprises a DNA genome, and the virus is a poxvirus, adenovirus, herpesvirus, or a hepatitis B virus. In another specific embodiment, the virus comprises an RNA genome and the virus is selected from a picornavirus, a retrovirus, a hemorrhagic fever virus, or a hepatitis C virus. In certain embodiments, the method further comprises prior to step (c) the cell is subjected to at least one stimulus, and in certain embodiments, the cell is an immune cell and the at least one stimulus is selected from (a) an antibody that specifically binds to a cognate antigen expressed by the cell; (b) a phorbol ester; (c) concanavalin A; (d) a cytokine; (e) a chemokine; and (f) ionomycin. In other certain embodiments, the immune cell is subjected to at least two or to at least three of the aforementioned stimuli. In another embodiment, the fraction of the cell is selected from a cell lysate, a cell extract, or at least one isolated cell organelle. In a particular embodiment, the affinity tag comprises a detectable moiety, and in other particular embodiments, the affinity tag comprises a polypeptide tag and a detectable moiety. In a particular embodiment, the detectable moiety is selected from a fluorophore, a radionuclide, an enzyme, and biotin. In certain embodiments, the affinity tag comprises at least one polypeptide tag, and the polypeptide tag is selected from a hemagglutinin peptide; a calmodulin binding polypeptide, a streptavidin binding peptide, an immunoglobulin Fc polypeptide, an immunoglobulin mutein Fc polypeptide, a protein C-tag, an at least one immunoglobulin binding staphylococcal protein A domain, and Softag™. In another embodiment, the affinity tag comprises at least two, three, or four polypeptide tags, and each of the at least two, three, or four polypeptide tags is selected from a hemagglutinin peptide; a calmodulin binding polypeptide, a streptavidin binding peptide, an immunoglobulin Fc polypeptide, an immunoglobulin mutein Fc polypeptide, a protein C-tag, an at least one immunoglobulin binding staphylococcal protein A domain, and Softag™. In a specific embodiment, the affinity tag further comprises at least one protease recognition sequence, wherein the at least one protease recognition sequence is either a tobacco etch virus protease recognition sequence or a Human Rhinovirus HRV3C protease recognition sequence. In yet another specific embodiment, the affinity tag further comprises at least two protease recognition sequences, wherein at least one protease recognition sequence is either a tobacco etch virus protease recognition sequence or a Human Rhinovirus HRV3C protease recognition sequence.

In yet another embodiment, a method is provided for identifying a cellular polypeptide to which a viral polypeptide binds comprising (a) contacting a cell, or a fraction or a supernatant of the cell, and a fusion protein comprising a viral polypeptide moiety fused to an affinity tag moiety, under conditions and for a time sufficient that permit the viral polypeptide moiety of the fusion protein to interact with a polypeptide associated with the cell, or the fraction or the supernatant of the cell, to provide a fusion protein:cellular polypeptide complex, wherein the viral polypeptide has at least one virulence trait, and wherein the affinity tag comprises at least a first polypeptide tag, a second polypeptide tag, and at least one protease recognition sequence; (b) isolating the fusion protein:cellular polypeptide complex, wherein said step of isolating comprises (i) contacting the fusion protein:cellular polypeptide complex with a first cognate ligand of the first polypeptide tag under conditions and for a time sufficient to permit the affinity tag moiety of the fusion protein to interact with the first cognate ligand to provide a first cognate ligand:fusion protein:cellular polypeptide complex; (ii) contacting the first cognate ligand:fusion protein:cellular polypeptide complex with a protease capable of cleaving the fusion protein at or near the protease recognition sequence to provide a cleaved fusion protein:cellular polypeptide complex; (iii) contacting the cleaved fusion protein:cellular polypeptide complex with a second cognate ligand that specifically binds to the second polypeptide tag, under conditions and for a time sufficient that permit the second cognate ligand and the cleaved fusion protein:cellular polypeptide complex to interact to form a second cognate ligand:cleaved fusion protein:cellular polypeptide complex; and (iv) isolating the cleaved fusion protein:cellular polypeptide complex from the second cognate ligand:cleaved fusion protein:cellular polypeptide complex; and (c) determining the amino acid sequence of the cellular polypeptide or of at least one polypeptide fragment of the cellular polypeptide, wherein the at least one polypeptide fragment comprises at least eight amino acids, and thereby identifying a cellular polypeptide to which a viral polypeptide binds. In a specific embodiment, the method further comprises prior to the step of contacting the cell, or a fraction or a supernatant of the cell, and a fusion protein the steps of (a) identifying in the genome of a virus, a polynucleotide sequence that encodes a viral polypeptide, which viral polypeptide comprises at least 40 amino acids; and (b) producing a fusion protein comprising the viral polypeptide fused to an affinity tag sequence. In a certain embodiment, prior to the step of contacting the cell, or a fraction or a supernatant of the cell, and a fusion protein further comprises (i) identifying in the genome of a virus, a polynucleotide sequence that encodes a viral polypeptide, which viral polypeptide comprises at least 40 amino acids; and (ii) producing a fusion protein comprising the viral polypeptide fused to an affinity tag sequence. In a particular embodiment, the viral polypeptide comprises at least one virulence trait. In a specific embodiment, the at least one virulence trait comprises the trait that expression of a mutant viral polypeptide in a cell infected by the virus correlates with a decrease in virulence of the virus. In another particular embodiment, the at least one virulence trait comprises the trait that absence of expression of the viral polypeptide in a cell infected by the virus correlates with a decrease in virulence of the virus. In yet another particular embodiment, the viral polypeptide (i) is secreted by a cell infected with the virus, (ii) is associated with a cellular membrane, or (iii) is intracellular. In certain particular embodiments, the at least one virulence trait of the viral polypeptide comprises the trait that the viral polypeptide is secreted by a cell infected with the virus; in another certain embodiment, the at least one virulence trait comprises the trait that the viral polypeptide is associated with a cellular membrane of the cell infected by the virus. In another embodiment of the aforementioned method, the at least one virulence trait comprises the trait that the polynucleotide sequence in the virus genome is located in a genomic region that encodes at least one other viral polypeptide (i.e., a second viral polypeptide) that is a viral virulence factor, wherein the region is at the 5' terminal end or the 3' terminal end of the virus genome. In certain embodiments, the virus is a poxvirus. In certain embodiments, the virus comprises a DNA genome, a double-stranded RNA genome, or a single-stranded RNA genome. In a particular embodiment, the virus comprises a DNA genome, and the virus is a poxvirus, adenovirus, herpesvirus, or a hepatitis B virus. In another specific embodiment, the virus comprises an RNA genome and the virus is selected from a picornavirus, a retrovirus, a hemorrhagic fever virus, or a hepatitis C virus. In certain embodiments, prior to step (a) the cell is subjected to at least one stimulus, and in certain embodiments, the cell is an immune cell and the at least one stimulus is selected from (a) an antibody that specifically binds to a cognate antigen expressed by the cell; (b) a phorbol ester; (c) concanavalin A; (d) a cytokine; (e) a chemokine; and (f) ionomycin. In other certain embodiments, the immune cell is subjected to at least two or to at least three of the aforementioned stimuli. In another embodiment, the fraction of the cell is selected from a cell lysate, a cell extract, or at least one isolated cell organelle. In a particular embodiment, the affinity tag comprises a detectable moiety, and in other particular embodiments, the affinity tag comprises a polypeptide tag and a detectable moiety. In a particular embodiment, the detectable moiety is selected from a fluorophore, a radionuclide, an enzyme, and biotin. In certain embodiments, the affinity tag comprises at least one polypeptide tag, and wherein the polypeptide tag is selected from a hemagglutinin peptide; a calmodulin binding polypeptide, a streptavidin binding peptide, an immunoglobulin Fc polypeptide, an immunoglobulin mutein Fc polypeptide, a protein C-tag, an at least one immunoglobulin binding staphylococcal protein A domain, and Softag™. In another embodiment, the affinity tag comprises at least two, three, or four polypeptide tags, and wherein each of the at least two, three, or four polypeptide tags is selected from hemagglutinin peptide, a calmodulin binding polypeptide, a streptavidin binding peptide, an immunoglobulin Fc polypeptide, an immunoglobulin mutein Fc polypeptide, a protein C-tag, an at least one immunoglobulin binding staphylococcal protein A domain, and Softag™. In a specific embodiment, the affinity tag further comprises at least one protease recognition sequence, wherein the at least one protease recognition sequence is either a tobacco etch virus protease recognition sequence or a Human Rhinovirus HRV3C protease recognition sequence. In yet another specific embodiment, the affinity tag further comprises at least two protease recognition sequences, wherein at least one protease recognition sequence is either a tobacco etch virus protease recognition sequence or a Human Rhinovirus HRV3C protease recognition sequence.

In another embodiment, a method for identifying a cellular polypeptide to which a viral polypeptide binds comprises (a) contacting an isolated viral polypeptide with a cell, or a fraction or supernatant of the cell, under conditions and for a time sufficient that permit the viral polypeptide moiety of the fusion protein to interact with a polypeptide associated with the cell, providing a viral polypeptide:cellular polypeptide complex, wherein the viral polypeptide comprises at least one virulence trait selected from (i) expression of a mutant of the viral polypeptide in a cell infected by a virus correlates with a decrease in virulence of the virus, wherein the virus comprises a genome that encodes the viral polypeptide; (ii) absence of expression of the viral polypeptide in a cell infected by a virus correlates with a decrease in virulence of the virus, wherein the virus comprises a genome that encodes the viral polypeptide; (iii) the viral polypeptide is secreted by a cell infected with a virus wherein the virus comprises a genome that encodes the viral polypeptide; (iv) the viral polypeptide is encoded by a polynucleotide sequence present in the genome of a virus, wherein the polynucleotide sequence is located at a genomic region that encodes at least one other viral polypeptide (i.e., a second viral polypeptide) that is a viral virulence factor; (v) the viral polypeptide is encoded by a polynucleotide sequence present in the genome of a virus, wherein the polynucleotide sequence is located at the 5' terminal end or the 3' terminal end of the viral genome; and (vi) the viral polypeptide comprises at least 40 amino acids; and (b) isolating the viral polypeptide:cellular polypeptide complex; and (c) determining the amino acid sequence of the cellular polypeptide or of at least one cellular polypeptide fragment comprising at least eight amino acids, and thereby identifying a cellular polypeptide to which a viral polypeptide binds. In another embodiment of the aforementioned method, the polynucleotide sequence in the virus genome is located in a genomic region that encodes at least one viral virulence factor, wherein the region is at the 5' terminal end or the 3' terminal end of the virus genome, and wherein in certain embodiments, the virus is a poxvirus. In certain embodiments, the virus comprises a DNA genome, a double-stranded RNA genome, or a single-stranded RNA genome. In a particular embodiment, the virus comprises a DNA genome, and the virus is a poxvirus, adenovirus, herpesvirus, or a hepatitis B virus. In another specific embodiment, the virus comprises an RNA genome and the virus is selected from a picornavirus, a retrovirus, a hemorrhagic fever virus, or a hepatitis C virus. In certain embodiments, prior to step (a) the cell is subjected to at least one stimulus, and in certain embodiments, the cell is an immune cell and the at least one stimulus is selected from (a) an antibody that specifically binds to a cognate antigen expressed by the cell; (b) a phorbol ester; (c) concanavalin A; (d) a cytokine; (e) a chemokine; and (f) ionomycin. In other certain embodiments, the immune cell is subjected to at least two or to at least three of the aforementioned stimuli. In another embodiment, the fraction of the cell is selected from a cell lysate, a cell extract, or at least one isolated cell organelle. In a particular embodiment, the affinity tag comprises a detectable moiety, and in other particular embodiments, the affinity tag comprises a polypeptide tag and a detectable moiety. In a particular embodiment, the detectable moiety is selected from a fluorophore, a radionuclide, an enzyme, and biotin. In certain embodiments, the affinity tag comprises at least one polypeptide tag, and the polypeptide tag is selected from a hemagglutinin peptide, a calmodulin binding polypeptide, a streptavidin binding peptide, an immunoglobulin Fc polypeptide, an immunoglobulin mutein Fc polypeptide, a protein C-tag, an at least one immunoglobulin binding staphylococcal protein A domain, and Softag™. In another embodiment, the affinity tag comprises at least two, three, or four polypeptide tags, and each of the at least two, three, or four polypeptide tags is selected from hemagglutinin peptide, a calmodulin binding polypeptide, a streptavidin binding peptide, an immunoglobulin Fc polypeptide, an immunoglobulin mutein Fc polypeptide, a protein C-tag, an at least one immunoglobulin binding staphylococcal protein A domain, and Softag™. In a specific embodiment, the affinity tag further comprises at least one protease recognition sequence, wherein the at least one protease recognition is either a tobacco etch virus protease recognition sequence or a Human Rhinovirus HRV3C protease recognition sequence. In yet another specific embodiment, the affinity tag further comprises at least one protease recognition sequence, wherein at least one protease recognition sequence is either a tobacco etch virus protease recognition sequence or a Human Rhinovirus HRV3C protease recognition sequence.

In another embodiment, a method of identifying a cellular polypeptide to which a viral polypeptide binds, comprises (a) identifying in the genome of a virus, a polynucleotide sequence that encodes a viral polypeptide, wherein the viral polypeptide comprises at least 40 amino acids; (b) producing a fusion protein comprising the viral polypeptide fused to an affinity tag sequence, wherein the affinity tag sequence comprises a first polypeptide tag sequence, a second polypeptide tag sequence, and a protease recognition sequence located between the first and second polypeptide tag sequences; (c) contacting the fusion protein and a cell, or a fraction or a supernatant of the cell, under conditions and for a time sufficient that permit the viral polypeptide moiety of the fusion protein to interact with a polypeptide associated with the cell, or the fraction or the supernatant thereof, to provide a fusion protein:cellular polypeptide complex; (d) isolating the fusion protein:cellular polypeptide complex, wherein said step of isolating comprises (i) contacting the fusion protein:cellular polypeptide complex with a first cognate ligand of the first polypeptide tag under conditions and for a time sufficient to permit the affinity tag moiety of the fusion protein to interact with the first cognate ligand to provide a first cognate ligand: fusion protein:cellular polypeptide complex; (ii) contacting the first cognate ligand:fusion protein:cellular polypeptide complex with a protease capable of cleaving the fusion protein at or near the protease recognition sequence to provide a cleaved fusion protein:cellular polypeptide complex; (iii) contacting the cleaved fusion protein:cellular polypeptide complex with a second cognate ligand that specifically binds to the second polypeptide tag, under conditions and for a time sufficient that permit the second cognate ligand and the cleaved fusion protein:cellular polypeptide complex to interact to form a second cognate ligand:cleaved fusion protein: cellular polypeptide complex; and (iv) isolating the cleaved fusion protein:cellular polypeptide complex; and (e) determining the amino acid sequence of the cellular polypeptide or of at least one cellular polypeptide fragment comprising at least eight amino acids, and therefrom identifying a cellular polypeptide to which a viral polypeptide binds. In a particular embodiment, the viral polypeptide comprises at least one virulence trait. In a specific embodiment, the at least one virulence trait comprises the trait that expression of a mutant viral polypeptide in a cell infected by the virus correlates with a decrease in virulence of the virus. In another particular embodiment, the at least one virulence trait comprises the trait that absence of expression of the viral polypeptide in a cell infected by the virus correlates with a decrease in virulence of the virus. In yet another particular embodiment, the viral polypeptide (i) is secreted by a cell infected with the virus, (ii) is associated with a cellular membrane, or (iii) is intracellular. In certain particular embodiments, the at least one virulence trait of the viral polypeptide comprises the trait that the viral polypeptide is secreted by a cell infected with the virus; in another certain embodiment, the at least one virulence trait comprises the trait that the viral polypeptide is associated with a cellular membrane of the cell infected by the virus. In another embodiment of the aforementioned method, the at least one virulence trait comprises the trait that the polynucleotide sequence in the virus genome is located in a genomic region that encodes at least one other viral polypeptide (i.e., a second viral polypeptide) that is a viral virulence factor, wherein the region is at the 5' terminal end or the 3' terminal end of the virus genome. In certain embodiments, the virus is a poxvirus. In certain embodiments, the virus comprises a DNA genome, a double-stranded RNA genome, or a single-stranded RNA genome. In a particular embodiment, the virus comprises a DNA genome, and the virus is a poxvirus, adenovirus, herpesvirus, or a hepatitis B virus. In another specific embodiment, the virus comprises an RNA genome and the virus is selected from a picornavirus, a retrovirus, a hemorrhagic fever virus, or a hepatitis C virus. In certain embodiments, prior to step (c) the cell is subjected to at least one stimulus, and in certain embodiments, the cell is an immune cell and the at least one stimulus is selected from (a) an antibody that specifically binds to a cognate antigen expressed by the cell; (b) a phorbol ester; (c) concanavalin A; (d) a cytokine; (e) a chemokine; and (f) ionomycin. In other certain embodiments, the immune cell is subjected to at least two or to at least three of the aforementioned stimuli. In another embodiment, the fraction of the cell is selected from a cell lysate, a cell extract, or at least one isolated cell organelle. In a particular embodiment, the affinity tag further comprises a detectable moiety. In a particular embodiment, the detectable moiety is selected from a fluorophore, a radionuclide, an enzyme, and biotin. In certain embodiments, the at least two polypeptide tags that comprise the affinity tag, are each selected from a hemagglutinin peptide; a calmodulin binding polypeptide, a streptavidin binding peptide, an immunoglobulin Fc polypeptide, an immunoglobulin mutein Fc polypeptide, a protein C-tag, an at least one immunoglobulin binding staphylococcal protein A domain, and Softag™. In another embodiment, the affinity tag comprises at least three or four polypeptide tags, and each of the at least three or four polypeptide tags is selected from hemagglutinin peptide; a calmodulin binding polypeptide, a streptavidin binding peptide, an immunoglobulin Fc polypeptide, an immunoglobulin mutein Fc polypeptide, a protein C-tag, an at least one immunoglobulin binding staphylococcal protein A domain, and Softag™. In a specific embodiment, the affinity tag further comprises at least one second protease recognition sequence, wherein the at least one second protease recognition sequence is either a tobacco etch virus protease recognition sequence or a Human Rhinovirus HRV3C protease recognition sequence.

Also provided herein is a viral virulence factor comprising a viral polypeptide that binds to a host cell wherein the viral polypeptide comprises at least one trait selected from (a) expression of a mutant of the viral polypeptide in a cell infected by a virus correlates with a decrease in virulence of the virus, wherein the virus comprises a genome that encodes the viral polypeptide; (b) absence of expression of the viral polypeptide in a cell infected by a virus correlates with a decrease in virulence of the virus, wherein the virus comprises a genome encodes the viral polypeptide; (c) the viral polypeptide is secreted by a cell infected with a virus wherein the virus comprises a genome that encodes the viral polypeptide; (d) the viral polypeptide is encoded by a polynucleotide sequence present in the genome of a virus, wherein the polynucleotide sequence is located at a genomic region that encodes a second viral polypeptide that is a viral virulence factor; (e) the viral polypeptide is encoded by a polynucleotide sequence present in the genome of a virus, wherein the polynucleotide sequence is located at the 5' terminal end or the 3' terminal end of the viral genome; and (f) the viral polypeptide comprises at least 40 amino acids; and wherein binding of the viral polypeptide to a host cell alters at least one biological activity of the host cell such that the host exhibits an increased susceptibility to infection by a virus that comprises a genome encoding the viral polypeptide. In certain embodiments, the virus comprises a DNA genome, a double-stranded RNA genome, or a single-stranded RNA genome. In a particular embodiment the virus comprises a DNA genome, wherein the virus is a poxvirus, an adenovirus, a hepatitis B virus, or a herpesvirus. In another particular embodiment, the virus comprises an RNA genome and the virus is selected from a picornavirus, a retrovirus, a hemorrhagic fever virus, or a hepatitis C virus.

In another embodiment, provided herein is an isolated polypeptide comprising a cellular polypeptide that binds to a viral polypeptide, wherein the cellular polypeptide is isolated according to a method comprising (a) identifying in the genome of a virus, a polynucleotide sequence that encodes a viral polypeptide, which viral polypeptide comprises at least 40 amino acids; (b) producing a fusion protein comprising the viral polypeptide fused to an affinity tag sequence; (c) contacting the fusion protein and a cell, or a fraction of the cell or a supernatant of the cell, under conditions and for a time sufficient that permit the viral polypeptide moiety of the fusion protein to interact with a polypeptide present in the cell, or the fraction of the cell or the supernatant of the cell, to provide a fusion protein:cellular polypeptide complex; (d) isolating the fusion protein:cellular polypeptide complex; and (e) determining the amino acid sequence of the cellular polypeptide or of at least one cellular polypeptide fragment comprising at least eight amino acids, and thereby identifying a cellular polypeptide to which a viral polypeptide binds. In certain embodiments, the virus comprises a DNA genome, a double-stranded RNA genome, or a single-stranded RNA genome. In a particular embodiment the virus comprises a DNA genome, wherein the virus is a poxvirus, an adenovirus, a hepatitis B virus, or a herpesvirus. In another particular embodiment, the virus comprises an RNA genome and the virus is selected from a picornavirus, a retrovirus, a hemorrhagic fever virus, or a hepatitis C virus. In certain embodiments, the viral polypeptide is a viral virulence factor comprising a viral polypeptide that binds to a host cell wherein the viral polypeptide comprises at least one virulence trait as described above.

Also provided herein is a method of identifying an agent for treating an immunological disease or disorder comprising (a) identifying a cellular polypeptide to which a viral polypeptide binds according to any of the aforementioned methods for identifying a cellular polypeptide, wherein interaction between the cellular polypeptide and the viral polypeptide alters immunoresponsiveness of an immune cell; (b) contacting (i) the cellular polypeptide, or a cell comprising the cellular polypeptide; (ii) the viral polypeptide; (iii) and a candidate agent, under conditions and for a time sufficient that permit the cellular polypeptide and the viral polypeptide to interact; (c) determining the level of binding of the viral polypeptide to the cellular polypeptide in the presence of the candidate agent to the level of binding of the viral polypeptide to the cellular polypeptide in the absence of the candidate agent, wherein a decrease in the level of binding of the viral polypeptide to the cellular polypeptide in the presence of the candidate agent compared with the level of binding of the viral polypeptide to the cellular polypeptide in the absence of the candidate agent thereby identifies an agent for treating an immunological disease or disorder. In certain embodiments, the agent is selected from (a) an antibody, or antigen-binding fragment thereof, (b) a viral polypeptide/Fc polypeptide fusion protein; (c) a peptide/Fc polypeptide fusion protein; (d) a small molecule; (e) a small interfering RNA (siRNA); (f) an antisense polynucleotide; and (g) an aptamer.

In another embodiment, antibody, or antigen-binding fragment thereof, is provided that specifically binds to the cellular polypeptide, which cellular polypeptide binds to a viral polypeptide as described above and herein, and which cellular polypeptide is identified according to any one of the methods described above or herein. In certain embodiments, the antibody is a polyclonal antibody. In certain other embodiments, the antibody is a monoclonal antibody, wherein the monoclonal antibody is selected from a mouse monoclonal antibody, a human monoclonal antibody, a rat monoclonal antibody, and a hamster monoclonal antibody. In other embodiments, the antibody is a humanized antibody or a chimeric antibody. Also provided herein is a host cell that expresses the antibody, and in certain embodiments, the host cell is a hybridoma cell. In a specific embodiment, the antigen-binding fragment is selected from $F(ab')_2$, Fab', Fab, Fd, and Fv; and in other specific embodiments, the antigen-binding fragment is of human, mouse, chicken, or rabbit origin. In another specific embodiment, the antigen-binding fragment is a single chain Fv (scFv). In another embodiment, a method is provided for treating a disease or disorder comprising administering to a subject in need thereof (a) a pharmaceutically suitable carrier; and (b) the antibody, or an antigen binding fragment thereof. In particular embodiments, the disease or disorder is an immunological disease or disorder, a cardiovascular disease or disorder, a metabolic disease or disorder, or a proliferative disease or disorder. In a specific embodiment, the immunological disease or disorder is an autoimmune disease or an inflammatory disease. In yet other specific embodiments, the immunological disease or disorder is multiple sclerosis, rheumatoid arthritis, systemic lupus erythematosus, graft versus host disease, sepsis, diabetes, psoriasis, atherosclerosis, Sjogren's syndrome, progressive systemic sclerosis, scleroderma, acute coronary syndrome, ischemic reperfusion, Crohn's Disease, endometriosis, glomerulonephritis, myasthenia gravis, idiopathic pulmonary fibrosis, asthma, acute respiratory distress syndrome (ARDS), vasculitis, or inflammatory autoimmune myositis. In another specific embodiment, the disease or disorder is a cardiovascular disease or disorder, wherein the cardiovascular disease or disorder is atherosclerosis, endocarditis, hypertension, or peripheral ischemic disease.

In another embodiment, a method is provided for treating an immunological disease or disorder in a subject, which method comprises administering to the subject an antibody, or antigen-binding fragment thereof, that inhibits binding of a cellular polypeptide with a viral polypeptide that exhibits at least one virulence trait, as described above and herein. In yet another embodiment, a method is provided for treating a disease or disorder comprising administering to a subject in need thereof (a) a pharmaceutically suitable carrier; and (b) a cellular polypeptide that binds to a viral polypeptide that exhibits at least one virulence trait as described above and herein, or that binds to the cellular polypeptide identified according to any one of the methods described above or herein, or an extracellular domain thereof. In certain embodiments, the cellular polypeptide or at least one extracellular domain of the cellular polypeptide is fused to a second polypeptide sequence. In a specific embodiment, the second polypeptide sequence is an immunoglobulin Fc polypeptide or an immunoglobulin mutein Fc polypeptide. In particular embodiments, the disease or disorder is an immunological disease or disorder, a cardiovascular disease or disorder, a metabolic disease or disorder, or a proliferative disease or disorder. In a specific embodiment, the immunological disease or disorder is an autoimmune disease or an inflammatory disease. In yet other specific embodiments, the immunological disease or disorder is multiple sclerosis, rheumatoid arthritis, systemic lupus erythematosus, graft versus host disease, sepsis, diabetes, psoriasis, atherosclerosis, Sjogren's syndrome, progressive systemic sclerosis, scleroderma, acute coronary syndrome, ischemic reperfusion, Crohn's Disease, endometriosis, glomerulonephritis, myasthenia gravis, idiopathic pulmonary fibrosis, asthma, acute respiratory distress syndrome (ARDS), vasculitis, or inflammatory autoimmune myositis. In another specific embodiment, the disease or disorder is a cardiovascular disease or disorder, wherein the cardiovascular disease or disorder is atherosclerosis, endocarditis, hypertension, or peripheral ischemic disease.

Also provided is a method of treating a disease or disorder comprising administering to a subject in need thereof (a) a pharmaceutically suitable carrier; and (b) an agent identified according to method comprising (a) identifying a cellular polypeptide to which a viral polypeptide binds according to any of the aforementioned methods for identifying a cellular polypeptide, wherein interaction between the cellular polypeptide and the viral polypeptide alters immunoresponsiveness of an immune cell; (b) contacting (i) the cellular polypeptide, or a cell comprising the cellular polypeptide; (ii) the viral polypeptide; (iii) and a candidate agent, under conditions and for a time sufficient that permit the cellular polypeptide and the viral polypeptide to interact; (c) determining a level of binding of the viral polypeptide to the cellular polypeptide in the presence of the candidate agent to a level of binding of the viral polypeptide to the cellular polypeptide in the absence of the candidate agent, wherein a decrease in the level of binding of the viral polypeptide to the cellular polypeptide in the presence of the candidate agent compared with the level of binding of the viral polypeptide to the cellular polypeptide in the absence of the candidate agent thereby identifies an agent for treating an immunological disease or disorder. In particular embodiments, the disease or disorder is an immunological disease or disorder, a cardiovascular disease or disorder, a metabolic disease or disorder, or a proliferative disease or disorder. In a specific embodiment, the immunological disease or disorder is an autoimmune disease or an inflammatory disease. In yet other specific embodiments, the immunological disease or disorder is multiple sclerosis, rheumatoid arthritis, systemic lupus erythematosus, graft versus host disease, sepsis, diabetes, psoriasis, atherosclerosis, Sjogren's syndrome, progressive systemic sclerosis, scleroderma, acute coronary syndrome, ischemic reperfusion, Crohn's Disease, endometriosis, glomerulonephritis, myasthenia gravis, idiopathic pulmonary fibrosis, asthma, acute respiratory distress syndrome (ARDS), vasculitis, or inflammatory autoimmune myositis. In another specific embodiment, the disease or disorder is a cardiovascular disease or disorder, wherein the cardiovascular disease or disorder is atherosclerosis, endocarditis, hypertension, or peripheral ischemic disease.

The invention further provides a business method comprising (a) identifying a viral polypeptide that is a viral virulence factor; (b) identifying a cellular polypeptide to which the viral virulence factor binds, wherein binding of the viral virulence factor to the cellular polypeptide alters at least one biological activity of a cell; (c) identifying an agent that inhibits binding of the viral virulence factor to the cellular polypeptide, thereby identifying an agent that alters the at least one biological activity of the cell; and (d) designing and executing at least one pre-clinical study to determine whether altering the at least one biological activity of the cell by the agent indicates that the agent is useful for treating a disease or medical disorder in a human subject. In a particular embodiment, the business method further comprises designing and executing at least one clinical study to evaluate the safety of the agent in a human subject, which in certain embodiments further comprises designing and executing at least one clinical study to evaluate the efficacy of the agent in a human subject in need of the agent, and in still certain other embodiments, further comprises selling the agent. In specific embodiments, the business method comprises a step of licensing of the viral polypeptide from a licensing organization to an acquiring company. In another specific embodiment, comprises a step of licensing of the cellular polypeptide from a licensing organization to an acquiring company. In yet another specific embodiment, the method comprises a step of licensing of the agent from a licensing organization to an acquiring company, wherein, in certain embodiments, the licensing organization is a biopharmaceutical company. In other certain embodiments, the acquiring company is a biopharmaceutical company. In one particular embodiment, the biopharmaceutical company performs experiments to identify the cellular polypeptide. In other particular embodiments, a biopharmaceutical company performs experiments to identify the agent. In still another embodiment, the business method further comprises licensing the right from a biopharmaceutical company to a selling company to sell the agent. In another specific embodiment, the business method further comprises collecting a royalty fee from the selling company by a biopharmaceutical company. In one embodiment, the agent is selected from (a) an antibody, or antigen-binding fragment thereof, (b) a viral polypeptide/Fc polypeptide fusion protein; (c) a peptide/Fc polypeptide fusion protein; (d) a domain of the cellular polypeptide, or a fragment thereof comprising at least eight amino acids, fused to an Fc polypeptide; (e) a small molecule; (f) a small interfering RNA (siRNA); (g) an antisense polynucleotide; and (h) an aptamer. In another certain embodiment, the at least one biological activity of the cell is immunoresponsiveness and the cell is an immune cell. In specific embodiments, the disease or disorder is an immunological disease or disorder, a cardiovascular disease or disorder, a metabolic disease or disorder, or a proliferative disease or disorder. In a specific embodiment, the immunological disease or disorder is an autoimmune disease or an inflammatory disease. In yet other specific embodiments, the immunological disease or disorder is multiple sclerosis, rheumatoid arthritis, systemic lupus erythematosus, graft versus host disease, sepsis, diabetes, psoriasis, atherosclerosis, Sjogren's syndrome, progressive systemic sclerosis, scleroderma, acute coronary syndrome, ischemic reperfusion, Crohn's Disease, endometriosis, glomerulonephritis, myasthenia gravis, idiopathic pulmonary fibrosis, asthma, acute respiratory distress syndrome (ARDS), vasculitis, or inflammatory autoimmune myositis. In another specific embodiment, the disease or disorder is a cardiovascular disease or disorder, wherein the cardiovascular disease or disorder is atherosclerosis, endocarditis, hypertension, or peripheral ischemic disease.

In another embodiment, a method is provided for guiding the selection of a therapeutic agent for treating a disease or medical disorder, comprising (a) identifying a viral polypeptide that increases the virulence of a virus in a host infected with the virus; (b) identifying a cellular polypeptide to which the viral polypeptide binds, wherein binding of the viral polypeptide to the cellular polypeptide alters at least one biological activity of a cell; (c) identifying one or more agents that inhibit binding of the viral polypeptide to the cellular polypeptide; (d) categorizing the capability of the one or more agents identified in step (c) to alter at least one biological effect of a cell, wherein altering the at least one biological effect reduces the risk of developing a disease or medical disorder or reduces at least one symptom of a disease or medical disorder in a host; and (e) selected at least one agent for testing in a preclinical and/or a clinical method, and therefrom guiding the selection of a therapeutic agent for treating a disease or disorder. In another certain embodiment, the at least one biological activity of the cell is immunoresponsiveness and the cell is an immune cell. In specific embodiments, the disease or disorder is an immunological disease or disorder, a cardiovascular disease or disorder, a metabolic disease or disorder, or a proliferative disease or disorder. In a specific embodiment, the immunological disease or disorder is an autoimmune disease or an inflammatory disease. In yet other specific embodiments, the immunological disease or disorder is multiple sclerosis, rheumatoid arthritis, systemic lupus erythematosus, graft versus host disease, sepsis, diabetes, psoriasis, atherosclerosis, Sjogren's syndrome, progressive systemic sclerosis, scleroderma, acute coronary syndrome, ischemic reperfusion, Crohn's Disease, endometriosis, glomerulonephritis, myasthenia gravis, idiopathic pulmonary fibrosis, asthma, acute respiratory distress syndrome (ARDS), vasculitis, or inflammatory autoimmune myositis. In another specific embodiment, the disease or disorder is a cardiovascular disease or disorder, wherein the cardiovascular disease or disorder is atherosclerosis, endocarditis, hypertension, or peripheral ischemic disease. In another specific embodiment, step (a) is performed using a computer device comprising (i) a first knowledge base comprising a plurality of different polynucleotide sequences encoding a plurality of viral polypeptides; and (ii) a second knowledge base comprising a plurality of rules for evaluating and selecting a viral polypeptide that is a viral virulence factor, wherein the viral polypeptide is identified from information received in step (i).

In another embodiment, provided herein is a business method for selling a therapeutic agent to treat a disease or disorder, comprising (a) receiving information regarding a viral polypeptide that increases the virulence of a virus in a host infected with the virus; (b) identifying a cellular polypeptide to which the viral polypeptide binds, wherein binding of the viral polypeptide to the cellular polypeptide alters at least one biological activity of a cell; (c) identifying one or more agents that inhibit binding of the viral polypeptide to the cellular polypeptide and that alter the at least one biological activity of the cell, wherein altering the at least one biological effect reduces the risk of developing an disease or disorder or reduces at least one symptom of an disease or medical disorder in a host; and (d) selling an agent identified in step (c) to a medical professional or patient for treatment of the disease or medical disorder. In a specific embodiment, the immunological disease or disorder is an autoimmune disease or an inflammatory disease. In yet other specific embodiments, the immunological disease or disorder is multiple sclerosis, rheumatoid arthritis, systemic lupus erythematosus, graft versus host disease, sepsis, diabetes, psoriasis, atherosclerosis, Sjogren's syndrome, progressive systemic sclerosis, scleroderma, acute coronary syndrome, ischemic reperfusion, Crohn's Disease, endometriosis, glomerulonephritis, myasthenia gravis, idiopathic pulmonary fibrosis, asthma, acute respiratory distress syndrome (ARDS), vasculitis, or inflammatory autoimmune myositis. In another specific embodiment, the disease or disorder is a cardiovascular disease or disorder, wherein the cardiovascular disease or disorder is atherosclerosis, endocarditis, hypertension, or peripheral ischemic disease. In another specific embodiment, step (a) is performed using a computer device comprising (i) a first knowledge base comprising a plurality of different polynucleotide sequences encoding a plurality of viral polypeptides; and (ii) a second knowledge base comprising a plurality of rules for evaluating and selecting a viral polypeptide that is a viral virulence factor, wherein the viral polypeptide is identified from information received in step (i).

Also provided herein is a system for guiding the selection of a viral polypeptide to achieve a desired result, comprising (a) a computing device comprising (i) a first knowledge base comprising a plurality of polynucleotide sequences encoding a plurality of viral polypeptides; and (ii) a second knowledge base comprising a plurality of rules for evaluating and selecting a viral polypeptide that is a viral virulence factor based upon information received in step (i); (b) means for providing information regarding a target viral virulence factor and a desired result to said computing device; and (c) means in said computing device for identifying and categorizing or ranking at least one polynucleotide sequence encoding a viral polypeptide that may be used to identify a cellular polypeptide with which the viral polypeptide binds, wherein binding of the viral polypeptide to the cellular polypeptide alters at least one biological activity of a cell.

In another embodiment, a computer program product is provided for guiding the selection of a viral polypeptide to achieve a desired result, said computer program product comprising a computer usable storage medium having computer readable program code means embodied in the medium, the computer readable program code means comprising (a) computer readable program code means for generating (i) a first knowledge base comprising a plurality of polynucleotide sequences encoding a plurality of viral polypeptides; and (ii) a second knowledge base comprising a plurality of rules for evaluating and selecting a viral polypeptide that is a viral virulence factor based upon information received in step (i); (b) a computer readable program code means for providing information regarding a target viral virulence factor and a desired result to said computing device; and (c) computer readable program code means for identifying and categorizing or ranking a target viral virulence factor that may be used to identify a cellular polypeptide to which the viral polypeptide binds, wherein binding of the viral polypeptide to the cellular polypeptide alters at least one biological activity of a cell.

In another embodiment is provided a method of manufacture for producing a cellular polypeptide that binds to a viral polypeptide comprising (a) identifying a cellular polypeptide to which a viral polypeptide binds according to the methods described above and herein; (b) determining a nucleotide sequence that encodes the cellular polypeptide; (c) preparing a recombinant expression vector comprising a promoter operatively linked to the nucleotide sequence that encodes the cellular polypeptide; (d) transfecting or transforming a host cell with the recombinant expression vector prepared in step (c); (e) culturing the host cell of step (d) under conditions that permit expression of the cellular polypeptide; and (f) isolating the cellular polypeptide from the host cell culture.

In another embodiment, method of manufacture is provided for producing an agent for treating an immunological disease or disorder comprising (a) identifying an agent for treating an immunological disease or disorder, wherein the step of identifying comprises (i) identifying a cellular polypeptide to which a viral polypeptide binds according to any of the methods described above or herein, wherein interaction between the cellular polypeptide and the viral polypeptide alters immunoresponsiveness of an immune cell; (ii)

contacting (A) the cellular polypeptide, or a cell comprising the cellular polypeptide; (B) the viral polypeptide; (C) and a candidate agent, under conditions and for a time sufficient that permit the cellular polypeptide and the viral polypeptide to interact; (iii) determining a level of binding of the viral polypeptide to the cellular polypeptide in the presence of the candidate agent to a level of binding of the viral polypeptide to the cellular polypeptide in the absence of the candidate agent, thereby identifying an agent for treating an immunological disease or disorder; and (b) producing the agent identified in step (a). In a specific embodiment, the agent is selected from (a) an antibody, or antigen-binding fragment thereof, (b) a viral polypeptide/Fc polypeptide fusion protein; (c) a peptide/Fc polypeptide fusion protein; (d) a domain of the cellular polypeptide, or a fragment thereof comprising at least eight amino acids, fused to an Fc polypeptide; (e) a small molecule; (f) a small interfering RNA (siRNA); (g) an antisense polynucleotide; and (h) an aptamer.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells and equivalents thereof known to those skilled in the art, and so forth. The term "comprising" (and related terms such as "comprise" or "comprises" or "having" or "including") is not intended to exclude that, for example, any composition of matter, composition, method, or process, or the like, described herein may "consist of" or "consist essentially of" the described features.

All U.S. patents, U.S. patent application publications, U.S. patent applications, foreign patents, foreign patent applications, and non-patent publications referred to in this application and/or listed in the Application Data Sheet, are incorporated herein by reference, in their entireties.

BRIEF DESCRIPTION OF THE DRAWINGS

FIG. 1 presents a schematic of an A41L fusion polypeptide encoded by a recombinant expression construct (A41LCRFC) for expression of the fusion polypeptide used for tandem affinity purification (TAP). The encoded fusion polypeptide includes mature A41L from Cowpox virus that was fused at its amino terminal end to the carboxy terminus of the human growth hormone leader peptide (GH Leader). The tandem affinity tag (CRFC) was fused to the carboxy terminus of A41L and included a human influenza virus hemagglutinin (HA) epitope (YPYDVDYA, SEQ ID NO:1) in frame with a Protein C-TAG (EDQVDPRLIDGK (SEQ ID NO:4), derived from the heavy chain of human Protein C); human rhinovirus HRV3C protease site (HRV3C cleavage site) (LEVLFQGP (SEQ ID NO:16); and a mutein derivative of the Fc portion of a human IgG immunoglobulin (Mutein FC).

FIG. 2 presents a schematic of the TAP procedure for identifying cellular polypeptides that bind to A41L.

FIG. 3 illustrates peptides of LAR, RPTP-δ, and RPTP-σ identified by tandem affinity purification (TAP) and LC/MS/MS analysis. FIG. 3A illustrates the sequences of peptides (bold typeface) within LAR (SEQ ID NO:43) that were identified by LC/MS/MS after TAP. FIG. 3B illustrates the sequences of peptides (bold typeface) within RPTP-σ (SEQ ID NO:18) that were identified by LC/MS/MS after TAP. FIG. 3C illustrates the sequences of peptides (bold typeface) within RPTP-δ (SEQ ID NO:19) that were identified by LC/MS/MS after TAP.

FIG. 4 provides a schematic of various fusion protein constructs that may be used for tandem affinity purification procedures. A human growth hormone (GH) signal peptide is shown at the amino terminal end of each construct. ORF (open reading frame) refers to an encoded viral virulence factor, which may be the full-length polypeptide or a portion thereof. The affinity tag polypeptides include HA (human influenza virus hemagglutinin peptide (also called hemagglutinin epitope)); CBP, calmodulin binding protein; SBP, streptavidin binding protein; 2XSBP, tandem repeat of streptavidin binding protein; mutein Fc, mutein immunoglobulin Fc polypeptide; C-TAG, protein C-tag derived from the heavy chain of human protein C; Softag™ peptide; and ZZ, an IgG-binding ZZ polypeptide. Protease sites include Rhino, human rhinovirus 3C (HRV3C) protease site; and TEV, tobacco etch virus protease site.

FIG. 5 presents a schematic of tandem affinity purification using a CRFC affinity tag fused in frame to a viral virulence factor open reading frame (Viral ORF). The CRFC Tag includes from the amino terminal end, HA (hemagglutinin peptide (also called hemagglutinin epitope); C-TAG; HRV3C protease site; and immunoglobulin Fc polypeptide, which can be either a wildtype Fc polypeptide or a mutein Fc polypeptide.

FIG. 6 presents an amino acid sequence alignment between (i) an A41L/Fc fusion polypeptide comprising an A41L signal peptide sequence, an A41L polypeptide, and a human IgG1 Fc polypeptide (A41L/Fc) (SEQ ID NO:32) and (ii) an A41L/mutein Fc fusion polypeptide comprising a human growth hormone signal peptide sequence, an A41L polypeptide variant, and a mutein Fc polypeptide (A41L/mutein Fc) (SEQ ID NO:31). The consensus sequence (SEQ ID NO:44) is also shown. The vertical dotted lines indicate the amino terminal and carboxy terminal ends of the A41L polypeptide.

DETAILED DESCRIPTION OF THE INVENTION

The present invention relates to methods for rapidly identifying cellular targets that are important in modulating the human immune system, and then identifying the counter-structures that will bind and modulate those targets. The method described herein comprises identifying viral virulence genes using bioinformatics and expressing the virulence genes, or portions (or fragments) thereof, that encode a viral virulence polypeptide, or a fragment thereof (such as a fragment that binds to a cellular polypeptide). The expressed viral virulence polypeptides may further comprise one or more sequence tags for detection and isolation. The expressed, tagged virulence gene products are used to screen cells (for example by fluorescence-activated cell sorting) or to screen isolated cell membranes (such as by BIAcore) to identify a cellular target molecule that interacts with the virulence gene product. The cellular target can then be isolated and identified, for example by, determining its amino acid sequence.

Methods described herein comprise contacting a cell, a fraction of a cell, or a supernatant of a cell, with a viral polypeptide that is a viral virulence factor (also called a viral virulence polypeptide) and then identifying the cellular target to which the viral virulence polypeptide binds. Viral virulence genes and the polypeptides encoded by the virulence genes are identified, for example, by bioinformatics methods. Fusion proteins may be prepared that comprise the viral virulence polypeptide (or a fragment or portion thereof that interacts with a cellular polypeptide) and an affinity tag (also called an epitope tag). In certain embodiments, the methods comprise a modification of a tandem affinity purification (TAP) tag procedure for isolating the cellular polypeptide target, including a cellular polypeptide target that is secreted by a cell.

Viruses have evolved numerous mechanisms to evade detection and elimination by the immune system of an infected host by encoding proteins that are viral homologues of cell cytokines, cell chemokines or the receptor(s) of a cytokine or chemokine. For example, the genomes of poxviruses encode a soluble viral tumor necrosis factor (TNF) receptor, which binds to and inhibits the inflammation-inducing cytokine, TNF. Other cellular polypeptides targeted by viral polypeptides include interleukin 1, various chemokines, and CD30.

Viruses have evolved to withstand mechanisms that an infected host has developed to limit infection and to adversely affect the replication cycle of the virus. Viruses comprise genes encoding proteins that have properties, characteristics, and/or functions that enable the virus to evade or modulate the immune response of the host. In addition, viruses have the ability to acquire genes from the host and/or to evolve viral homologues of host genes and/or to evolve viral modulators of host genes. Accordingly, a virus, which has the capability to evolve and/or the capability to acquire genes from the host, comprises a genome that encodes proteins called virulence factors (also called herein a viral virulence polypeptide) that modulate an immune response of the host to the virus. A cellular component in the host that is a ligand for a viral virulence factor may be, therefore, an important immunomodulatory target.

In particular, identification of cellular polypeptides, including cell surface polypeptides, secreted polypeptides, and intracellular polypeptides that are expressed by immune cells and that interact with a viral virulence factor (i.e., a viral virulence polypeptide or a viral polypeptide that exhibits at least one viral virulence trait) will be useful and beneficial for identifying agents that may be used for treating immunological disorders, such as, for example, inflammatory diseases and autoimmune diseases, including multiple sclerosis, rheumatoid arthritis, and systemic lupus erythematosus (SLE). In another embodiment, identification of a viral virulence factor is useful for identifying agents that are used to treat and/or prevent a viral infection that is caused by the virus (or a related virus) that encodes the virulence factor. A need exists to identify and develop compositions that can be used for treatment and prophylaxis of such immunological diseases and disorders and viral infections.

Methods for Identifying a Cellular Polypeptide Therapeutic Target

Methods described herein for identifying cellular polypeptides that are suitable targets for altering a cellular activity or function include methods for identifying a cellular polypeptide to which a viral polypeptide (e.g., a viral virulence polypeptide or virulence factor) binds. Such methods comprise contacting a cell, or a fraction or a supernatant of the cell, with a fusion protein. The fusion protein comprises the viral virulence polypeptide that is fused to an affinity tag. The fusion protein and cell (or a cell fraction, cell culture supernatant, cell lysate, cell extract, or extracellular supernatant comprising the cognate cellular polypeptide(s)) are permitted to interact under conditions and for a time sufficient to permit the viral polypeptide moiety of the fusion protein to interact with a polypeptide associated with the cell, a fraction of the cell, or a supernatant of the cell, and form a fusion protein/cellular polypeptide complex. The complex may be isolated via the affinity tag, which is permitted to bind to a cognate ligand of the tag. The identity of the cellular polypeptide may be determined according to methods described herein and practiced in the art, including but not limited to LC-MS/MS, MALDI-TOF, immunoassays, peptide mapping, and amino acid analyses, including amino terminal end analysis (e.g., Edman degradation).

An exemplary method for affinity isolation of a target cellular polypeptide is tandem affinity purification (TAP) (also called TAP tag) (see, e.g., Rigaut et al. *Nat. Biotech.* 17:1030-32 (1999); Puig et al., *Methods* 24:218-29 (2001); Knuesel et al. *Mol. Cell. Proteomics* 2:1225-33 (2003)). The TAP method permits identification of components present in biological complexes. Purification may be rapid and is performed under conditions that in general do not require denaturation of any components or of the biological complex. Typically, a TAP tag (or affinity tag) is fused to the amino terminal or carboxy terminal end of a polypeptide of interest (in this instance, a viral virulence polypeptide, or a portion thereof encoded by an open reading frame of the viral genome), which is contacted with a cell or a cell fraction to permit interaction between the polypeptide of interest and the cellular polypeptide such that a complex is formed between the polypeptide of interest and the cellular polypeptide. The complex is then isolated by exploiting the binding properties of the affinity tag. Subsequent to TAP procedures, in certain embodiments the identity of the target cellular polypeptide is determined by liquid chromatograph tandem mass spectrometry, referred to as LC-MS/MS, which is described in greater detail herein.

Viral Polypeptides

Viral polypeptides that are useful in methods for identifying a cellular polypeptide that is a therapeutic target include viral polypeptides that maintain or increase the ability of a virus to cause disease in a host, that is, that affect the virulence of the virus. Such viral polypeptides are referred to herein as a viral virulence polypeptide, which is a viral polypeptide that exhibits at least one virulence trait. In a certain embodiment, a method for identifying a cellular polypeptide to which a viral virulence polypeptide binds and to which therapeutic agents may be targeted, further comprises identifying in the genome of a virus, a polynucleotide sequence that encodes a viral polypeptide (e.g., for example, identifying a polynucleotide sequence that encodes for at least 20, 30, or 40 contiguous amino acids) that has one or more virulence traits. The identified viral polypeptide is then fused to an affinity tag, which is described in further detail herein.

Virulence or the ability of a virus to cause disease includes the extent to which the virus has the capability to overcome or minimize one or more host defense mechanisms. Components of microorganisms, including viruses, that maintain or increase the virulence of the microorganism are also called virulence factors. A viral polypeptide that is a viral virulence factor (or viral virulence polypeptide) has the capability to evade or modulate the immune response of the host. As described herein, virulence of a virus is maintained in part by evolution of the genetic information contained within a virus and by the ability of a virus to acquire genes from the host and/or to evolve viral homologues of host genes and/or to evolve viral modulators of host genes. Viral polypeptides that are viral virulence factors include polypeptides that when bound to cellular polypeptides affect (i.e., modulate or alter) a biological function or activity of the cellular polypeptide, which alters the ability of the host to effect an immune response that will prevent, minimize, reduce, suppress, or inhibit infection by the virus and that will prevent, minimize, reduce, suppress, or inhibit the sequelae of the disease associated therewith.

The genome of a virus that encodes one or more viral polypeptides that are viral virulence factors may be a single-stranded DNA genome, double-stranded DNA genome, double-stranded RNA genome, or single-stranded RNA genome (sense or anti-sense). Exemplary DNA viruses include, but are not limited to, large DNA genome (double-stranded DNA) viruses, such as herpesviruses, adenoviruses, and poxviruses. Other viruses that encode polypeptides that contribute to the virulence of a virus include but are not limited to picornaviruses (RNA containing viruses e.g., an enterovirus, rhinoviruses, hepatovirus (Hepatitis A virus), cardiovirus, aphthovirus, parechovirus, erbovirus, kobuvirus, and teschovirus); hemorrhagic fever viruses (RNA containing viruses e.g., arenaviruses, filoviruses, bunyviruses, flaviviruses); influenza viruses (single stranded RNA viruses); retroviruses (e.g., oncoviruses and lentiviruses (RNA containing viruses, for example, HIV-1, HIV-2, HTLV-1, HTLV-2)); hepatitis B virus (DNA containing virus); hepatitis C virus (RNA containing virus); and coronaviruses. An antisense RNA virus is also referred to in the art as negative RNA-stranded virus and includes, for example, measles virus, mumps virus, influenza virus, Ebola virus, and respiratory syncytial virus. Positive-stranded RNA viruses, also referred to as sense RNA viruses include, for example, polioviruses, rhinoviruses, coronaviruses, rubella, yellow fever virus, West Nile virus, dengue fever viruses, hepatitis A and hepatitis C viruses.

Poxviruses form a group of double-stranded DNA viruses that replicate in the cytoplasm of a cell and have adapted to replicate in numerous different hosts. An adaptive mechanism of many poxviruses involves the acquisition of host genes that allow the viruses to evade the host's immune system and/or facilitate viral replication (Smith et al., *Science* 248:1019 (1990); Bugert and Darai, *Virus Genes* 21:111 (2000); Alcami et al., *Semin. Virol.* 8:419 (1998); McFadden and Barry, *Semin. Virol.* 8:429 (1998)). This process is facilitated by the relatively large size and complexity of the poxvirus genome. Poxviruses include, for example, orthopox viruses such as vaccinia, monkeypox, cowpox, and variola viruses (e.g., smallpox virus), leporipoxviruses, such as myxoma and Shope fibroma virus, molluscipox (e.g., *Molluscum contagiosum*), yatapoxvirus (such as Yaba-like disease virus), parapoxvirus (e.g., ORF virus). By way of example, vaccinia virus, a prototype poxvirus widely used as a smallpox vaccine, has a genome of approximately 190 kilobases, which could potentially encode more than 200 proteins (Goebel et al., *Virology* 179:247 (1990)). Even though the entire genome of Vaccinia virus and other poxviruses have been sequenced, the function of many of the potential open reading frames (ORFs), and the existence of polypeptides encoded by the ORFs, remains unknown.

Expeditious inspection of polynucleotide sequences within a viral genome to identify those sequences that encode a viral virulence factor among the many ORFs of a viral genome, for example, a large DNA genome-containing virus such as a poxvirus, is useful for the methods described herein for identifying a cellular polypeptide that is a therapeutic target. In certain embodiments, a genome of a virus, such as a poxvirus, is analyzed to identify polynucleotide sequences within the viral genome that encode viral polypeptides that contribute to the virulence of the virus. Such viral polypeptides exhibit at least one (i.e., one or more) virulence characteristics or virulence traits.

Exemplary virulence traits of a viral virulence factor include traits that may be observed in a host infected with the virus that expresses the viral virulence factor or may be observed in cells propagated in tissue culture. A viral polypeptide that contributes to virulence of the virus includes a polypeptide that when it is altered such as when it comprises a mutation (at least one substitution, insertion, or deletion of an amino acid either as a consequence of natural selection or by any number of different mutagenesis techniques practiced by persons skilled in the molecular biology art) that alters (such as decreases in a statistically significant or biologically significant manner) a biological activity of the viral polypeptide. When such a viral polypeptide mutant (or altered viral polypeptide) is expressed in a cell infected by the virus comprising the genome that encodes the mutant (or altered) viral polypeptide, the expression of the mutant (or altered) viral polypeptide correlates with a decrease in virulence of the virus.

Also, a virulence trait of a viral polypeptide that is a viral virulence factor is indicated by the correlation between the absence of expression of the viral polypeptide in a cell infected by a virus with a decrease in virulence of the virus. The correlation between lack of expression of a viral polypeptide and decreased virulence may be observed by infecting cells with a recombinant virus in which the gene encoding the viral polypeptide is deleted, silenced (e.g., by treating a cell infected with the virus with an antisense polynucleotide or by RNA interference using a small interfering RNA (siRNA)), or knocked out. In tissue culture, passage of cells may not be adversely affected when the cells are infected with a virus that expresses a mutant of the particular viral polypeptide of interest or that fails to express the viral polypeptide. In a host, a viral polypeptide that exhibits at least one virulence trait includes a viral polypeptide that when its expression is altered (for example, by introduction of at least one mutation that alters a biological activity of the viral polypeptide or by reduced expression or lack of expression), the altered expression correlates with decreased virulence, that is, a decreased ability of the virus to cause disease, and/or an increase in inflammation, and/or an increase in other types of immune responses. That is, the host has increased immunoresponsiveness to the virus comprising a genome that encodes a mutant viral polypeptide or that does not contain a polynucleotide sequence that encodes the polypeptide.

A virulence trait also relates to the cellular or extracellular location of the viral polypeptide after it is expressed in a cell infected with a virus that comprises the genome encoding the viral polypeptide. After expression in an infected cell, the viral polypeptide may remain at an intracellular location, may be a membrane spanning polypeptide having extracellular domains, or may be secreted by the infected cell. A viral polypeptide that is secreted by an infected cell or that has extracellular domains contributes to the virulence of the virus by interacting with other cells of the host or with other molecules associated with or secreted by other cells of the host. Such molecules include, but are not limited to, cell surface antigens, cytokines, chemokines, hormones, and other molecules that contribute to host defense.

Viral polypeptides that contribute to viral virulence are typically encoded by polynucleotide sequences that are located within proximity of each other in the viral genome. Accordingly, a virulence trait of a viral polypeptide includes that the polypeptide is encoded by a polynucleotide sequence that is located at a genomic region that encodes at least one other polypeptide that is either known in the art to be a viral virulence polypeptide or is determined to be a viral virulence polypeptide according to methods described herein and practiced in the art. For example in poxviruses, a polynucleotide sequence present in the viral genome that encodes a viral polypeptide that is a virulence viral polypeptide is located toward the 5' terminal end or toward the 3' terminal end of the viral genome. In certain instances a polynucleotide sequence encoding a viral polypeptide that is a virulence factor may be found within about one-third or within about one-quarter of the 5' terminal end or the 3' terminal end of the genome (i.e., such a polynucleotide sequence comprises nucleotides that are located within at least 20%, 25%, 30%, 33%, or at least 35% of either the 5' terminal end or the 3' terminal end of the viral genome).

Accordingly, also provided herein are viral virulence factors that are viral virulence polypeptides that bind to a host cell. Such a virus virulence factor is a viral polypeptide that comprises at least one trait (virulence trait) such as (a) expression of a mutant of the viral polypeptide (or an altered viral polypeptide) in a cell infected by a virus, which correlates with a decrease in virulence of the virus, wherein the virus comprises a genome that encodes the viral polypeptide; (b) absence of expression of the viral polypeptide in a cell infected by a virus correlates with a decrease in virulence of the virus, wherein the virus comprises a genome that encodes the viral polypeptide; (c) the viral polypeptide is secreted by a cell infected with a virus wherein the virus comprises a genome that encodes the viral polypeptide; (d) the viral polypeptide is encoded by a polynucleotide sequence present in the genome of a virus, wherein the polynucleotide sequence is located at a genomic region that encodes at least one viral virulence factor; (e) the viral polypeptide is encoded by a polynucleotide sequence present in the genome of a virus, wherein the polynucleotide sequence is located at the 5' terminal end or the 3' terminal end of the viral genome; and (f) the viral polypeptide comprises at least 40 amino acids (which may include a signal peptide sequence). When a viral polypeptide that is a virulence factor interacts with a cell (including specifically binding to a cellular polypeptide that is intracellular, located in a cellular membrane, or is secreted), the viral polypeptide alters at least one biological activity of the host cell such that the host exhibits an increased susceptibility to infection (or a decreased capability to resist infection) by the virus that comprises a genome encoding the viral polypeptide.

A viral virulence polypeptide (or a variant, derivative, or fragment thereof) may also be used as a therapeutic agent. In one embodiment, a viral virulence polypeptide or a fusion polypeptide comprising the virulence polypeptide may be used for treating a patient or subject in need thereof. In a specific embodiment, the subject presents an acute immune response, such as, by way of nonlimiting example, a subject who presents an acute respiratory distress syndrome (ARDS). To reduce or minimize the possibility or the extent of an immune response by the subject that is specific for a viral virulence polypeptide (or a variant, derivative, or fragment thereof) the viral polypeptide may be administered in a limited number of doses, may be produced or derived in a manner that alters a post-translational modification of the viral polypeptide and thus decreases the immunogenicity of the viral polypeptide, and may be administered under conditions that reduce or minimize antigenicity of the viral polypeptide. For example, a viral virulence polypeptide may be administered prior to, concurrently with, or subsequent to the administration in the subject of a second composition that suppresses an immune response, particularly a response that is specific for the viral polypeptide. In addition, persons skilled in the art are familiar with methods for increasing the half-life and/or improving the pharmacokinetic properties of a polypeptide, such as by pegylating the polypeptide, which may increase the effectiveness of a therapeutic agent, including agents that are not administered multiple times.

Viral polypeptides that are known to contribute to virulence of the virus are typically at least 20, 30, or 40 amino acids in length or at least 50, 60, 70, 80, 90, 100, 120, 140, 160, 180, 200, 250, 300, or 400 or more amino acids in length. To identify a polynucleotide sequences in a viral genome that may encode a polypeptide that is a virulence factor, the sequence of the genome is inspected to identify regions containing open reading frames for at least 20, 30, 40, 50 or more amino acids (i.e., 20, 30, 40, or 50 contiguous amino acids). In certain embodiments, the polynucleotide sequence comprises an open reading frame that encodes a polypeptide comprising at least 40 amino acids. The viral polypeptide encoded by the open reading frame identified in the methods described herein may be a full-length viral polypeptide or may be a portion or fragment of a full-length polypeptide. In particular embodiments, the fragment of a viral virulence polypeptide is a fragment that comprises at least 10, 15, 20, 25, 30, 40, 50 or more, consecutive (or contiguous) amino acids of the full-length polypeptide and that is capable of binding to a cellular polypeptide.

The polynucleotide sequence may include nucleotides that encode a signal peptide sequence and the mature polypeptide or a portion of a full-length, mature polypeptide. Signal peptides, which facilitate translocation of secretory proteins and cell-surface proteins across intracellular membranes and to final localization, are located at the N-terminus of such proteins and are typically 13-40 amino acids in length. A polypeptide comprising a signal peptide sequence is also called a pre-protein. The signal peptide is normally cleaved from the pre-protein to provide the mature protein. Signal peptides exhibit certain sequence characteristics and other properties such that the signal peptide sequence can be distinguished from the mature polypeptide sequence; computer programs may be used to aid determining the amino acid sequence of the signal polypeptide (Zhang et al., *Protein Sci.* 13:2819-24 (2004)).

Inspection of polynucleotide sequences that encode viral polypeptides may be accomplished by scanning the polynucleotide sequence of a viral genome or putative viral genome, or any portion or fraction thereof, for example, by using a computer and applicable software programs. The polynucleotide sequence of a viral genome or a portion of the viral genome can be translated into six open reading frames (three forward and three reverse) using readily available computer programs. Software programs include programs that are available commercially and include programs that may be custom designed and prepared. The six open reading frames may then be inspected, with or without the aid of additional computer software programs, to identify locations in the viral genome that contain open reading frames that encode for at least 20, 30, or 40 amino acids.

A viral polypeptide encoded by the open reading frame may be a full-length viral virulence polypeptide, or a fragment or portion of the viral virulence polypeptide, as described herein, and may be used for identifying a cellular polypeptide, which is a therapeutic target. A fragment or portion of a viral polypeptide that comprises at least 20 consecutive (or contiguous) amino acids, at least 30 or at least 40 amino acids or at least 50, 60, 70, 80, 90, 100, 120, 140, 160, 180, 200 amino acids, or more (or any integer between the ranges described) may be attached to or fused to and affinity tag. A fragment or a portion of a viral polypeptide useful for the methods described herein includes an extracellular portion of a viral polypeptide that is a membrane polypeptide or includes a portion of the viral polypeptide that comprises at least one binding domain.

A protein (or polypeptide) domain for any of the viral virulence polypeptides or cellular polypeptides or other polypeptides described herein refers to a region of a polypeptide or protein that can be defined or described structurally and/or functionally. For example, a domain of a polypeptide may represent an enzymatic motif or region, a binding domain (for a ligand or a specifically-binding antibody), a location (e.g., an extracellular domain or intracellular domain), and independently folding structural unit, and other definitions understood in the art. The presence of a domain in a polypeptide may be determined by inspection of the primary sequence to determine sequence homology with a known or similar domain or may be determined (or the likelihood of the presence of domain determined) with computer programs such as PROSITE, BLOCKS, PRINTS, DOMAK, and PFAM that are readily available (see also, e.g., Siddiqui et al., *Protein Science* 4:872-884 (1995)).

A viral polypeptide described herein also includes a viral polypeptide variant. A viral polypeptide variant includes a viral strain variant or other variant. Variants may result from natural polymorphisms or may be synthesized by recombinant methodology (e.g., to obtain codon optimization for expression in a particular host or to introduce an amino acid mutation) or chemical synthesis, and may differ from wildtype polypeptides by one or more amino acid substitutions, insertions, deletions. A variant of a viral polypeptide identified as described herein has at least 70% to 100% amino acid identity (that is, at least 70%, 75%, 80%, 85%, 90%, 95%, or 99% identity) to the amino acid sequence encoded by the viral genome. Preferably a variant viral polypeptide that comprises at least one substitution, deletion, or insertion of an amino acid retains the same biological activity, including the capability to bind to at least one cellular polypeptide. A viral polypeptide variant that comprises one or more substitutions preferably comprises conservative substitution(s) compared with the wildtype polypeptide sequence.

A conservative substitution is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Examples of conservative substitutions include substituting one aliphatic amino acid for another, such as isoleucine, valine, leucine, or alanine, or substituting one polar residue for another, such as between lysine and arginine, glutamic acid and aspartic acid, or glutamine and asparagine. A similar amino acid or a conservative amino acid substitution is also one in which an amino acid residue is replaced with an amino acid residue having a similar side chain, which include amino acids with basic side chains (e.g., lysine, arginine, histidine); acidic side chains (e.g., aspartic acid, glutamic acid); uncharged polar side chains (e.g., glycine, asparagine, glutamine, serine, threonine, tyrosine, cysteine, histidine); nonpolar side chains (e.g., alanine, valine, leucine, isoleucine, proline, phenylalanine, methionine, tryptophan); beta-branched side chains (e.g., threonine, valine, isoleucine), and aromatic side chains (e.g., tyrosine, phenylalanine, tryptophan). Proline, which is considered more difficult to classify, shares properties with amino acids that have aliphatic side chains (e.g., Leu, Val, Ile, and Ala). In certain circumstances, substitution of glutamine for glutamic acid or asparagine for aspartic acid may be considered a similar substitution in that glutamine and asparagine are amide derivatives of glutamic acid and aspartic acid, respectively. A variant may also, or alternatively, contain nonconservative changes that do not adversely alter the properties, including the binding properties, of the viral polypeptide.

Variants may also (or alternatively) be modified by, for example, the deletion or addition of amino acids that have minimal influence on the activity of the polypeptide. In particular, variants may contain additional amino acid sequences at the amino and/or carboxy termini. Such sequences may be used, for example, to facilitate purification or detection of the polypeptide.

A polynucleotide sequence that encodes the viral virulence polypeptide, fragment, portion, or variant thereof, includes the polynucleotide sequence identified in the viral genome and also includes a polynucleotide variant that differs from the genomic sequence due to degeneracy of the genetic code. A polynucleotide variant also includes a polynucleotide sequence that encodes a viral virulence polypeptide variant as described herein.

Persons skilled in the art may readily introduce mutations into a polynucleotide sequence for preparing a polypeptide variant using any one of a variety of mutagenesis techniques routinely used by a person skilled in the art. Mutations may be introduced at particular loci by synthesizing oligonucleotides that contain a mutant sequence that are flanked by restriction sites, enabling ligation to fragments of the native sequence. Following ligation, the resulting reconstructed sequence encodes a derivative or variant having the desired amino acid insertion, substitution, or deletion.

Alternatively, oligonucleotide-directed site-specific (or segment specific) mutagenesis procedures may be employed to provide an altered polynucleotide having particular codons altered according to the substitution, deletion, or insertion. Exemplary methods of making the alterations set forth above are disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods*, Plenum Press, 1981); and Sambrook et al. (supra). Deletion or truncation derivatives of a viral virulence polypeptide (e.g., a soluble extracellular portion) may also be constructed by using convenient restriction endonuclease sites adjacent to the desired deletion. Subsequent to restriction, overhangs may be filled in and the DNA religated. Exemplary methods of making the alterations set forth above are disclosed by Sambrook et al. (*Molecular Cloning: A Laboratory Manual,* 3d Ed., Cold Spring Harbor Laboratory Press (2001)).

Mutations that are made in a polynucleotide preferably preserve the reading frame of the coding sequences. Furthermore, the mutations will preferably not create complementary regions that when transcribed could hybridize to produce secondary mRNA structures, such as loops or hairpins, which would adversely affect translation of the mRNA. Although a mutation site may be predetermined, the nature of the mutation need not per se be predetermined. For example, random mutagenesis may be conducted at the target codon and the expressed mutants screened for gain, loss, or retention of biological activity. Alternatively, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion. Nucleic acid molecules that encode viral virulence polypeptides or fusion proteins as described herein may also be constructed using techniques such as polymerase chain reaction (PCR) mutagenesis, chemical mutagenesis (Drinkwater and Klinedinst, *Proc. Natl. Acad. Sci. USA* 83:3402-3406, 1986); forced nucleotide misincorporation (e.g., Liao and Wise *Gene* 88:107-111, 1990); or use of randomly mutagenized oligonucleotides (Horwitz et al., *Genome* 3:112-117, 1989).

Nucleotide sequences and amino acid sequences of two or more viral polynucleotides and the encoded polypeptides and variants thereof, respectively, can be compared using any standard software program, such as BLAST, tBLAST, pBLAST, or MegAlign. Still others include those provided in the Lasergene bioinformatics computing suite, which is produced by DNASTAR® (Madison, Wis.); CLUSTALW program (Thompson et al., *Nucleic Acids Res.* 22:4673-80 (1991)); and "GeneDoc" (Nicholas et al., *EMBNEW News* 4:14 (1991)). References for algorithms such as ALIGN or BLAST may be found in, for example, Altschul, *J. Mol. Biol.* 219:555-565, 1991; or Henikoff and Henikoff, *Proc. Natl. Acad. Sci. USA* 89:10915-10919, 1992. BLAST is available at the NCBI website. Such algorithms include Align or the BLAST algorithm (see, e.g., Altschul, *J. Mol. Biol.* 219:555-565, 1991; Henikoff and Henikoff, *Proc. Natl. Acad. Sci. USA* 89:10915-10919, 1992), which are available at the NCBI website (see [online] Internet at ncbi.nlm.nih.gov/cgi-bin/BLAST). Default parameters may be used. Other methods for comparing two nucleotide or amino acid sequences by determining optimal alignment are practiced by those having skill in the art (see, for example, Peruski and Peruski, *The Internet and the New Biology: Tools for Genomic and Molecular Research* (ASM Press, Inc. 1997); Wu et al. (eds.), "Information Superhighway and Computer Databases of Nucleic Acids and Proteins," in *Methods in Gene Biotechnology*, pages 123-151 (CRC Press, Inc. 1997); and Bishop (ed.), *Guide to Human Genome Computing*, 2nd Ed. (Academic Press, Inc. 1998)).

As used herein, "percent identity" is the percent value returned by comparing a viral polypeptide (i.e., a viral virulence polypeptide that is a viral polypeptide that exhibits at least one virulence trait), fragment, or variant thereof, sequence to a test sequence using a computer implemented algorithm, typically with default parameters. A variant polypeptide could be made to include one or more of a variety of mutations, such as point mutations, frameshift mutations, missense mutations, additions, deletions, and the like, or the variants can be a result of modifications, such as by certain chemical substituents, including glycosylation, alkylation, etc. As used herein, "similarity" between two peptides or polypeptides is generally determined by comparing the amino acid sequence of one peptide or polypeptide to the amino acid sequence and conserved amino acid substitutes thereto of a second peptide or polypeptide.

A viral polypeptide, including a viral virulence polypeptide, may be prepared by chemically synthesizing the polypeptide according to chemical synthesis methods practiced in the art, including synthesis by automated procedure. Equipment for automated synthesis of polypeptides is commercially available from suppliers such as Perkin-Elmer, Inc., Applied BioSystems Division (Foster City, Calif.), and may be operated according to the manufacturer's instructions. Such polypeptides may be synthesized using any of the commercially available solid-phase techniques, such as the Merrifield solid-phase synthesis method, by which amino acids are sequentially added to a growing amino acid chain (see, e.g., Merrifield, *J. Am. Chem. Soc.* 85:2149 (1963)). For example, polypeptides may be synthesized using N-alpha-(9-fluorenylmethyloxycarbonyl (Fmoc) or tert-butoxycarbonyl (tBoc)-protection strategies with 2-(1H-7-Azabenzotriazol-1-yl)-1,1,3,3-tetramethyl uronium hexafluorophosphate (HATU) or 2-(1H-Benzotriazol-1-yl)-1,1,3,3-tetramethyluronium hexafluorophosphate (HBTU) as the coupling agent (see, e.g., Schnölzer, et al. *Int. Pept. Protein Res.* 40, 180-193 (1992); Hackeng et al., *Proc. Natl. Acad. Sci. USA* 94:7845-50 (1997)). The crude polypeptide may be further purified using preparative reverse phase chromatography. Other purification methods, such as partition chromatography, gel filtration, gel electrophoresis, or ion-exchange chromatography may be used. In addition, any naturally occurring amino acid or derivative thereof may be used, including D-amino acids or L-amino acids, and combinations thereof. In certain embodiments, a synthetic viral polypeptide has an amino acid sequence that is identical to, or at least 80% identical (which includes at least 85%, 90%, or 95% or any percent in between 80% and 100%) to the amino acid sequence encoded by the viral genome.

Alternatively, the viral virulence polypeptide may be prepared by recombinant expression methods described herein and/or practiced routinely in the art, wherein the viral polypeptide, or fusion protein comprising the viral polypeptide, is expressed from a polynucleotide that is operatively linked to an expression control sequence (e.g., a promoter, enhancer, transcription initiation site) in a nucleic acid expression construct. A viral polypeptide and a fusion polypeptide comprising a viral polypeptide as described in greater detail herein may be expressed using vectors and constructs, particularly recombinant expression constructs, that include any polynucleotide encoding such polypeptides. Host cells are genetically engineered with vectors and/or constructs to produce these polypeptides and fusion proteins, or fragments or variants thereof, by recombinant techniques. Each of the polypeptides and fusion polypeptides described herein can be expressed in mammalian cells, yeast, bacteria, or other cells under the control of appropriate promoters. Cell-free translation systems can also be employed to produce such proteins using RNAs derived from DNA constructs. Appropriate cloning and expression vectors for use with prokaryotic and eukaryotic hosts are described, for example, by Sambrook, et al., *Molecular Cloning: A Laboratory Manual*, Third Edition, Cold Spring Harbor, N.Y., (2001).

Cells and Cellular Polypeptides

Described herein are methods for identifying cellular polypeptides that in some manner are affected by or are effectors of a disease process. By altering (increasing or decreasing in a statistically significant or biologically significant manner) at least one (i.e., one or more) biological activity of a cellular polypeptide, the disease process may be inhibited, abrogated, slowed, or interfered with such that the disease or disorder in an affected host is treated and/or prevented, and/or at least one symptom of the disease or disorder is inhibited, reduced, or abrogated.

As described herein viruses, such as poxviruses, encode proteins that are expressed during infection that contribute to the capability of the virus to evade a host's immune system and/or to suppress the host's immune system by interacting with one or more cellular molecules. These viral polypeptides interact with cellular polypeptides that include, but are not limited to, cell surface antigens, cell surface receptors, cytokines, chemokines, cytokine or chemokine binding proteins, intracellular signaling polypeptides, or substrates of cell surface receptors or signaling molecules, and other immunoregulatory molecules that affect and regulate an immune response (see, e.g., U.S. Pat. No. 5,359,039; U.S. Pat. No. 6,852,486; U.S. Pat. No. 5,871,740; U.S. Pat. No. 6,843,991; U.S. Pat. No. 6,355,252).

Cellular polypeptides may be identified according to the methods described herein using a biological sample that comprises an intact cell, a cell fraction, and/or a cell supernatant. A "biological sample" as used herein refers in certain embodiments to a sample containing at least one cell or a fraction of a cell or a supernatant of a cell. A biological sample may be a blood sample (from which serum or plasma may be prepared), biopsy specimen, body fluids (e.g., lung lavage, ascites, mucosal washings, synovial fluid), bone marrow, lymph nodes, tissue explant, organ culture, or any other tissue or cell preparation from a subject or a biological source.

The subject or biological source may be a human or non-human animal, a primary cell culture (e.g., immune cells, virus infected cells), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiable cell lines, transformed cell lines, and the like. A variety of normal cells and tumor cell types may be used to identify cellular polypeptides that bind to or interact with a viral virulence polypeptide, including B cells and T cells (activated or non-activated), macrophages, epithelial cells, fibroblasts, and cell lines such as Raji (B cell lymphoma), THP-1 (acute monocytic leukemia), and Jurkat (T cell leukemia). Cells useful for the methods described herein are immune cells, including T cells, B cells, natural killer cells, macrophages, etc. The immune cell may be present in or isolated from a biological sample as described herein. For example, the immune cell or any other cell may be obtained from a primary or long-term cell culture or may be present in or isolated from a biological sample obtained from a subject (human or non-human animal).

A sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication, or combination thereof, or any other means for processing a sample derived from a subject or biological source. Such a cell preparation includes a cell fraction such as a cell lysate or cell extract that may be used in the methods described herein. A cell fraction also includes a preparation of one or more isolated organdies from a cell. A cell organelle includes but is not limited to nucleus, mitochondrion, nucleolus, centriole, centrosome, Golgi, cytoskeleton, cytosol, secretory vesicle, lysosome, peroxisome, vacuole, cell membrane, and endoplasmic reticulum. A cell fraction also includes complex multi-molecular structures such as lipid rafts and other trafficking and transport complexes. A cell fraction and an isolated cell organelle may be prepared according to methods routinely practiced in the art.

As described herein, a cellular polypeptide to which a viral virulence polypeptide binds includes a cellular polypeptide that is secreted by a cell. Accordingly, a cell supernatant, which includes, for example, cellular washes, cell culture media, or conditioned media (i.e., media from cells in culture that have been propagated for a period of time sufficient for the cells to secrete such cellular polypeptides), or any other extracellular preparation may be used in the methods described herein. A biological sample, such as blood, serum, or plasma, cerebral spinal fluid, or other body fluids described herein, may also contain one or more cellular polypeptides to which a viral polypeptide binds and be used as a source for detecting the presence of the cellular polypeptide that is secreted by a cell or that is released by a cell via other processes including normal or abnormal cell death.

In certain embodiments, a cell is stimulated prior to, at the same time, or after, a cell, or a fraction or a supernatant of the cell, is contacted with a fusion protein comprising a viral polypeptide fused to an affinity tag, as described in detail herein. A cell may be stimulated with at least one stimulus, at least two stimuli, or more than two different stimuli. Exemplary stimuli include an antibody that specifically binds to a cognate antigen (e.g., a cell surface marker antigen or cell surface receptor) expressed by the cell; a phorbol ester (which modulate gene expression, reorganize the cytoskeleton, and/or stimulate bulk protein synthesis) (e.g., Phorbol 12-myristate 13-acetate (PMA)), and other mitogens (e.g., concanavalin A and other lectins; lipospolysaccharide, phytohemagglutinin (PHA), pokeweed mitogen (PWM), insulin, polypeptide growth factors); a cytokine; a chemokine; and ionomycin. In certain embodiments, a cell may be exposed to a combination of at least two agents, for example, PMA and ionomycin or PWM and insulin.

Detection of a Viral Polypeptide/Cellular Polypeptide Complex

As described herein, methods are provided for identifying a cellular polypeptide to which a viral virulence polypeptide binds by contacting (mixing, combining, or in some manner permitting interaction) a source of the cellular polypeptide (e.g., a cell, cell fraction, or cell supernatant) and a viral polypeptide under conditions and for a time sufficient for the viral polypeptide and the cellular polypeptide to form a complex. The viral polypeptide/cellular polypeptide complex may then be detected and/or isolated. In certain embodiments, the viral polypeptide is fused to an affinity tag to form a fusion protein. Such fusion proteins may be used in methods such as tandem affinity purification for purification and/or isolation of the cellular polypeptide. The identity of the cellular polypeptide may be determined according to a variety of methods practiced in the art and described herein, such as LC-MS/MS.

Fusion Proteins: Viral Polypeptide Fused to an Affinity Tag

In one embodiment, the viral virulence polypeptide (or fragment thereof) is fused to an affinity tag, which may be used in methods described herein for identifying a cellular polypeptide. The affinity tag may comprise at least one polypeptide tag and/or at least one detectable moiety (or label or reporter molecule) such as an enzyme, cytotoxicity agent, or other reporter molecule, including a dye, radionuclide, luminescent group, fluorescent group, or biotin, or the like according to methods practiced in the art. Techniques for radiolabeling of polypeptides are known in the art (see, e.g., Adams, *In Vivo* 12:11-21 (1998); Hiltunen, *Acta Oncol.* 32:83'-9 (1993)). The detectable moiety may be attached to the viral polypeptide or the polypeptide tag, such as through any available amino acid side-chain, terminal amino acid, or carbohydrate functional group located in the polypeptide, provided that the attachment or attachment process does not adversely affect the binding properties such that the usefulness of the molecule is abrogated. Particular functional groups include, for example, any free amino, imino, thiol, hydroxyl, carboxyl, or aldehyde group. Attachment of the polypeptide (either the viral polypeptide or a polypeptide tag portion of the affinity tag) and the detectable moiety may be achieved via such groups and an appropriate functional group in the detectable moiety. The linkage may be direct or indirect through spacing or bridging groups (see, e.g., International Patent Application Publication Nos. WO 93/06231, WO 92/22583, WO 90/091195, and WO 89/01476; see also, e.g., commercial vendors such as Pierce Biotechnology, Rockford, Ill.).

An affinity tag comprising a polypeptide tag may be attached to the viral polypeptide by any of a variety of techniques with which those skilled in the art will be familiar. A fusion protein comprising a viral polypeptide and an affinity tag may be detected, identified, or isolated when bound to a cellular polypeptide according to methods and techniques including, for example, interaction of the polypeptide tag to a detectable cognate binding molecule (i.e., cognate ligand), direct covalent modification of a fusion protein with a detectable moiety (e.g., a labeling moiety), non-covalent binding of the fusion protein to a specific labeled reporter molecule, enzymatic modification of a detectable substrate by a fusion protein that includes a portion having enzyme activity, or immobilization (covalent or non-covalent) of the fusion protein on a solid-phase support. A cognate ligand of an affinity tag, which includes a cognate ligand of a polypeptide tag is a molecule with which a polypeptide tag is capable of interacting to form a complex. Examples of cognate ligands include but are not limited to an antibody (or a fragment or derivative thereof) that specifically binds to the polypeptide tag, a small molecule, a polypeptide, peptide, carbohydrate, hormone, cell receptor polypeptide (or fragment or domain thereof), cell surface antigen, or other cellular molecule to which the polypeptide tag binds. A viral polypeptide may be fused to another polypeptide such as a peptide tag having desirable affinity properties according to methods described in the art and routinely practiced by skilled artisans (see, e.g., U.S. Pat. No. 5,100,788; WO 89/03422; U.S. Pat. No. 5,489,528; U.S. Pat. No. 5,672,691; WO 93/24631; U.S. Pat. No. 5,168,049; U.S. Pat. No. 5,272,254; EP 511,747).

In certain embodiments, the affinity tag that is attached to a viral virulence polypeptide comprises at least one polypeptide tag; in certain other embodiments, the affinity tag comprises at least two, three, or four, or more polypeptide tags. Examples of polypeptide tags include but are not limited to an immunoglobulin Fc polypeptide, an immunoglobulin mutein Fc polypeptide, a hemagglutinin peptide, a calmodulin binding polypeptide (or a domain or peptide thereof), a protein C-tag, a streptavidin binding peptide (or fragments thereof), a protein A fragment (e.g., an IgG-binding ZZ polypeptide), and a Softag™ peptide. Additional affinity tags include polyhistidine tag (his tag) or FLAG® epitope tag (DYKDDDDK, SEQ ID NO:20), beta-galactosidase, alkaline phosphatase, GST, or the XPRESS™ epitope tag (DLYDDDDK, SEQ ID NO:21; (Invitrogen Corp., Carlsbad, Calif.) and the like (see, e.g., U.S. Pat. No. 5,011,912; Hopp et al., *Bio/Technology* 6:1204 (1988)). The affinity sequence may be supplied by a vector, such as, for example, a hexa-histidine tag that is provided in pBAD/His (Invitrogen). Alternatively, the affinity sequence may be added either synthetically or engineered into the primers used to recombinantly generate the nucleic acid coding sequence (e.g., using the polymerase chain reaction).

In one embodiment, at least one polypeptide tag is an Fc polypeptide. In a particular embodiment, the Fc polypeptide is of human origin and may be from any of the immunoglobulin classes, such as human IgG1, IgG2, IgG3, IgG4, or IgA. In a certain embodiment, the Fc polypeptide is derived from a human IgG1 immunoglobulin, (see Kabat et al., in *Sequences of Proteins of immunological Interest,* 4th ed., (U.S. Dept. of Health and Human Services, U.S. Government Printing Office, 1991)). In another embodiment, the Fc polypeptide comprises an amino acid sequence of an Fc polypeptide from a non-human animal, for example, but not limited to, a mouse, rat, rabbit, or hamster. Binding partners (or cognate ligands) of an Fc polypeptide include, for example, protein A (or at least one domain of protein A that binds to an immunoglobulin Fc polypeptide); protein G; an antibody (or fragment or derivative thereof) that specifically binds to the Fc polypeptide from a particular species (e.g., an antibody that specifically binds to an Fc polypeptide of a particular class or isotype and from a particular species, such as an antibody that specifically binds to a human IgG1 Fc polypeptide). A fusion protein that comprises an affinity tag comprising an Fc polypeptide may be identified, detected, or isolated, for example, when the fusion protein has formed a complex with a cellular polypeptide by contacting the complex with any one of the Fc polypeptide binding partners or ligands described herein or known in the art.

The amino acid sequences of Fc polypeptides of human origin and of a variety of species are available in the art, for example, in Kabat et al. (in *Sequences of Proteins of Immunological Interest,* 4th ed. (U.S. Dept. of Health and Human Services, U.S. Government Printing Office, 1991)). By way of example, the Fc polypeptide tag of a fusion protein described herein may comprise the amino acid sequence of all or a portion of the hinge region, CH2 domain, and CH3 domain of a human immunoglobulin, for example, an IgG1. An Fc polypeptide is capable of interacting with a second Fc polypeptide to form a dimer via covalent, such as disulfide bond formation, and noncovalent interactions.

An Fc polypeptide as described herein also includes Fc polypeptide variants. One such Fc polypeptide variant has one or more cysteine residues (such as one or more cysteine residues in the hinge region) that forms an interchain disulfide bond substituted with another amino acid, such as serine, to reduce the number of interchain disulfide bonds that can form between the two heavy chain constant region polypeptides that form an Fc polypeptide. In addition, or alternatively, the most amino terminal cysteine residue of the hinge region that typically forms a disulfide bond with a light chain constant region in an immunoglobulin molecule may be deleted or substituted, for example, substituted with a serine residue. Another example of an Fc polypeptide variant is a variant that has one or more amino acids involved in an effector function substituted or deleted such that the Fc polypeptide has a reduced level of an effector function. For example, amino acids in the Fc region may be substituted to reduce or abrogate binding of a component of the complement cascade (see, e.g., Duncan et al., *Nature* 332:563-64 (1988); Morgan et al., *Immunology* 86:319-24 (1995)) or to reduce or abrogate the ability of the Fc fragment to bind to an IgG Fc receptor expressed by an immune cell (Wines et al., *J. Immunol.* 164: 5313-18 (2000); Chappel et al., *Proc. Natl. Acad. Sci. USA* 88:9036 (1991); Canfield et al., *J. Exp. Med.* 173:1483 (1991); Duncan et al., supra); or to alter antibody-dependent cellular cytotoxicity. Such an Fc polypeptide variant that differs from the wildtype Fc polypeptide is also called herein a mutein Fc polypeptide.

In one embodiment, a viral virulence polypeptide (or fragment or variant thereof) is fused in frame with an Fc polypeptide that comprises at least one substitution of a residue that in the wildtype Fc region polypeptide contributes to binding of an Fc polypeptide or immunoglobulin to one or more IgG Fc receptors expressed on certain immune cells. Such a mutein Fc polypeptide comprises at least one substitution of an amino acid residue in the CH2 domain of the mutein Fc polypeptide, such that the capability of the fusion polypeptide to bind to an IgG Fc receptor, such as an IgG Fc receptor present on the surface of an immune cell, is reduced.

By way of background, on human leukocytes three distinct types of Fc IgG-receptors are expressed that are distinguishable by structural and functional properties, as well as by antigenic structures, which differences are detected by CD specific monoclonal antibodies. The IgG Fc receptors are designated FcγRI (CD64), FcγRII (CD32), and FcγRIII (CD16) and are differentially expressed on overlapping subsets of leukocytes.

FcγRI (CD64), a high-affinity receptor expressed on monocytes, macrophages, neutrophils, myeloid precursors, and dendritic cells, comprises isoforms Ia and Ib. FcγRII (CD32), comprised of isoforms IIa, IIb1, IIb2, IIb3, and IIc, is a low-affinity receptor that is the most widely distributed human FcγR type; it is expressed on most types of blood leukocytes, as well as on Langerhans cells, dendritic cells, and platelets. FcγRIII (CD16) has two isoforms, both of which are capable of binding to human IgG1 and IgG3. The FcγRIIIa isoform has an intermediate affinity for IgG and is expressed on macrophages, monocytes, natural killer (NK) cells, and subsets of T cells. FcγRIIIb is a low-affinity receptor for IgG and is selectively expressed on neutrophils.

Residues in the amino terminal portion of the CH2 domain that contribute to IgG Fc receptor binding include residues at positions Leu234-Ser239 (Leu-Leu-Gly-Gly-Pro-Ser (SEQ ID NO:22) (EU numbering system, Kabat et al., supra) (see, e.g., Morgan et al., *Immunology* 86:319-24 (1995), and references cited therein). These positions correspond to positions 15-20 of the amino acid sequence of an exemplary human IgG1 Fc polypeptide (SEQ ID NO:25). Substitution of the amino acid at one or more of these six positions (i.e., one, two, three, four, five, or all six) in the CH2 domain results in a reduction of the capability of the Fc polypeptide to bind to one or more of the IgG Fc receptors (or isoforms thereof) (see, e.g., Burton et al., *Adv. Immunol.* 51:1 (1992); Hulett et al., *Adv. Immunol.* 57:1 (1994); Jefferis et al., *Immunol. Rev.* 163:59 (1998); Lund et al., *J. Immunol.* 147:2657 (1991); Sarmay et al., *Mol. Immunol.* 29:633 (1992); Lund et al., *Mol. Immunol.* 29:53 (1992); Morgan et al., supra). In addition to substitution of one or more amino acids at EU positions 234-239, one, two, or three or more amino acids adjacent to this region (either to the carboxy terminal side of position 239 or to the amino terminal side of position 234) may also be substituted.

By way of example, substitution of the leucine residue at position 235 (which corresponds to position 16 of SEQ ID NO:25) with a glutamic acid residue or an alanine residue abolishes or reduces, respectively, the affinity of an immunoglobulin (such as human IgG3) for FcγRI (Lund et al., 1991, supra; Canfield et al., supra; Morgan et al., supra). As another example, replacement of the leucine residues at positions 234 and 235 (which correspond to positions 15 and 16 of SEQ ID NO:25), for example, with alanine residues, abrogates binding of an immunoglobulin to FcγRIIa (see, e.g., Wines et al., supra). Alternatively, leucine at position 234 (corresponding to position 15 of SEQ ID NO:25), leucine at position 235 (corresponding to position 16 of SEQ ID NO:25), and glycine at position 237 (corresponding to position 18 of SEQ ID NO:25), each may be substituted with a different amino acid, such as leucine at position 234 may be substituted with an alanine residue (L234A), leucine at 235 may be substituted with an alanine residue (L235A) or with a glutamic acid residue (L235E), and the glycine residue at position 237 may be substituted with another amino acid, for example an alanine residue (G237A).

In one embodiment, a mutein Fc polypeptide that is fused in frame to a viral virulence polypeptide (or variant or fragment thereof) comprises one, two, three, four, five, or six mutations at positions 15-20 of SEQ ID NO:25 that correspond to positions 234-239 of a human IgG1 CH2 domain (EU numbering system) as described herein. An exemplary mutein Fc polypeptide comprises the amino acid sequence set forth in SEQ ID NO:23 in which substitutions corresponding to (L234A), (L235E), and (G237A) may be found at positions 13, 14, and 16 of SEQ ID NO:23.

In another embodiment, a mutein Fc polypeptide comprises a mutation of a cysteine residue in the hinge region of an Fc polypeptide. In one embodiment, the cysteine residue most proximal to the amino terminus of the hinge region of an Fc polypeptide that in a whole immunoglobulin molecule forms a disulfide bond with a cysteine in the constant region of the light chain (e.g., for example, the cysteine residue most proximal to the amino terminus of the hinge region of the Fc portion of a wildtype IgG1 immunoglobulin) is deleted or substituted with another amino acid. That is, by way of illustration, the cysteine residue that corresponds to the cysteine at position 1 of the exemplary Fc polypeptide having the sequence set forth in SEQ ID NO:25, is deleted, or the cysteine residue at this position is substituted with another amino acid that is incapable of forming a disulfide bond, for example, a serine residue. In another embodiment, a mutein Fc polypeptide comprises a deletion or substitution of the cysteine residue most proximal to the amino terminus of the hinge region of an Fc polypeptide further comprises deletion or substitution of the adjacent C-terminal amino acid. In a certain embodiment, this cysteine residue and the adjacent C-terminal residue are both deleted from the hinge region of a mutein Fc polypeptide. In a specific embodiment, a mutein Fc polypeptide comprises an amino acid sequence wherein the cysteine residue at a position corresponding to position 1 of SEQ ID NO:25 and the aspartic acid at a position corresponding to position 2 of SEQ ID NO:25 are deleted. Fc polypeptides that comprise deletion of these cysteine and aspartic acid residues in the hinge region may be efficiently expressed in a host cell, and in certain instances, may be more efficiently expressed in a cell than an Fc polypeptide that retains the wildtype cysteine and aspartate residues.

In a specific embodiment, a mutein Fc polypeptide comprises the amino acid sequence set forth in SEQ ID NO:23, which differs from the wildtype Fc polypeptide (SEQ ID NO:25) wherein the cysteine residue at position 1 of SEQ ID NO:25 is deleted and the aspartic acid at position 2 of SEQ ID NO:25 is deleted and the leucine reside at position 15 of SEQ ID NO:25 is substituted with an alanine residue (i.e., position 13 of SEQ ID NO:23), the leucine residue at position 16 is substituted with a glutamic acid residue (i.e., position 14 of SEQ ID NO:23), and the glycine at position 18 is substituted with an alanine residue (i.e., position 16 of SEQ ID NO:23) (see FIG. 6; SEQ ID NO:23). Thus, an exemplary mutein Fc polypeptide comprises an amino acid sequence at its amino terminal portion of KTHTCPPCPAPEAEGAPS (SEQ ID NO:26) (see SEQ ID NO:23, an exemplary Fc mutein sequence).

Other Fc variants encompass similar amino acid sequences of known Fc polypeptide sequences that have only minor changes, for example by way of illustration and not limitation, covalent chemical modifications, insertions, deletions and/or substitutions, which may further include conservative substitutions. Amino acid sequences that are similar to one another may share substantial regions of sequence homology. Similarly, nucleotide sequences that encode the Fc variants may encompass substantially similar nucleotide sequences and have only minor changes, for example by way of illustration and not limitation, covalent chemical modifications, insertions, deletions, and/or substitutions, which may further include silent mutations owing to degeneracy of the genetic code. Nucleotide sequences that are similar to one another may share substantial regions of sequence homology.

Another polypeptide tag that may be used as an affinity tag, either alone or with at least one additional polypeptide tag, includes a hemagglutinin peptide, which in certain embodiments is a human influenza hemagglutinin peptide. The amino acid sequence of an exemplary hemagglutinin peptide comprises YPYDVDYA (SEQ ID NO:1). Antibodies that specifically bind to the hemagglutinin peptide are examples of cognate ligands for a hemagglutinin peptide and are available commercially (e.g., Roche Diagnostics Corp., Roche Applied Science, Indianapolis, Ind.; Vector Laboratories, Burlingame, Calif.).

In another embodiment, a calmodulin binding polypeptide (CBP) derived from cAMP kinase or a CBP domain or CBP peptide may be used as at least one polypeptide tag (see, e.g., Puig et al., *Methods* 24:218-29 (2001)). The CBP moiety, which may be a peptide or domain of the CBP full-length polypeptide is capable of binding to calmodulin (i.e., a cognate ligand) in the presence of calcium ($Ca^{2+}$). An exemplary CBP peptide comprises the sequence set forth in SEQ ID NO:3 (KRRWKKNFIAVSAANRFKKISSSGAL), which may have at least one, two, three, four, five, six, seven, or more amino acids at either the amino terminus or carboxy terminus that are the adjacent amino acids of the calmodulin binding protein or that represent a spacer peptide. The interaction between the CBP moiety and calmodulin may be disrupted by the addition of a chelating agent, such as EGTA or EDTA. In certain instances, endogenous calmodulin is present in the cell, cell fraction, or cell supernatant that is used in the methods described herein for identifying a cellular polypeptide to which a viral virulence polypeptide may bind. Binding of the fusion protein that comprises a CBP moiety to endogenous calmodulin may be prevented or significantly reduced by adding a chelating agent prior to exposure of a fusion protein:cellular polypeptide complex (or other complex formed according to the methods described herein) to an exogenous source of calmodulin.

An affinity tag may also comprise a protein C-tag as a polypeptide tag. A protein C-tag comprises the amino acid sequence EDQVDPRLIDGK (SEQ ID NO:4), derived from the heavy chain of human protein C (vitamin K-dependent serine protease). Antibodies are commercially available that may be used to detect the protein C-tag polypeptide tag or to isolate a complex or fusion protein that comprises the protein C-tag polypeptide tag (see, e.g., Roche Applied Science; Delta BioLabs, Gilroy, Calif.; Abcam Inc., Cambridge, Mass.; Immunology Consultants Laboratory, Inc., Newburg, Oreg.). Binding of the C-tag peptide to an antibody called HPC4 (Roche Applied Science) is calcium dependent, wherein the calcium binding domain resides on the antibody. A fusion polypeptide comprising the protein C tag as a polypeptide tag that is bound to a calcium-dependent specific antibody may be eluted (i.e., the binding interaction between the protein C tag and the antibody is disrupted) by using a chelating agent such as EDTA.

An affinity tag may also comprise a streptavidin binding peptide (SBP) (or fragments thereof). The amino acid sequence of SBP comprises, for example, MDEKTTGWRGGHVVEGLAGELEQLRARLEHHPQGQREP (SEQ ID NO:6; encoded by the nucleotide sequence set forth in SEQ ID NO:9). An affinity tag may comprise one SBP moiety or may comprise two SBP moieties (i.e., in tandem) (e.g., SEQ ID NO:8, encoded by the nucleotide sequence set forth in SEQ ID NO:10), which increases the affinity of the interaction between streptavidin binding peptide and streptavidin, its cognate ligand. In certain embodiments, a lower affinity interaction between streptavidin and a SBP peptide tag may be desirable. Accordingly, a SBP peptide comprising 15 amino acids (DVEAWLDERVPLVET; SEQ ID NO:7), may be used (see also, e.g., Lamla, *Protein Expr. Purif.* 33:39-47 (2004)). Binding of an SBP polypeptide to streptavidin can be disrupted by addition of biotin, which will compete with SBP for binding to streptavidin.

Another polypeptide tag that may be incorporated into the affinity tag portion of the viral polypeptide fusion protein is a staphylococcal protein A binding domain that binds to the Fc portion of certain classes and isotypes of immunoglobulins, which accordingly serve as cognate ligands for a staphylococcal protein A binding domain tag. The affinity tag may comprise at least two staphylococcal protein A binding domains. In one embodiment, the staphylococcal protein A binding domain comprises an IgG-binding protein ZZ, which binds to the Fc portion of immunoglobulins (see, e.g., Nizard et al., *Protein Eng.* 14:439-446 (2001); Nizard et al., *FEBS Lett.* 433:83-88 (1998)). The ZZ polypeptide is prepared by duplicating a mutated B domain of staphylococcal protein A, the polypeptide and encoding nucleotide sequences of which are long known in the art (see, e.g., Nizard et al., (2001), supra; Nilsson et al., *Protein Eng.* 1:107-13 (1987); Ljungberg et al., *Mol. Immunol.* 30:1279-85 (1993); Jansson et al., FEMS *Immunol. Med. Microbiol.* 20:69-78 (1998); see also, e.g., GenBank Accession Nos. M74186 (Jun. 21, 1993) and M74187 (May 23, 1996)).

An affinity tag may comprise a polypeptide tag that is a Softag™ peptide, which comprises the amino acid sequence SLAELLNAGLGGS (SEQ ID NO:11) (an epitope of *Escherichia coli* RNA polymerase) (NeoClone, Madison, Wis.). This peptide tag specifically binds to an antibody called NT73, which is an example of a cognate ligand for Softag™ (Thompson et al., *Biochemistry* 31:7003-7008 (1992); Anthony et al., *J. Biol. Chem.* 277:46433-41 (2002)). A binding interaction between Softag™ and NT73 may be disrupted in the presence of a low molecular weight polyhydroxylated compound (polyol) and a non-chaotropic salt (see Thompson et al., supra).

As described herein, in certain embodiments, a fusion protein comprising a viral virulence polypeptide and an affinity tag is used in methods described herein for identifying a cellular polypeptide that may be a suitable target for a therapeutic agent and may be used in methods for identifying a cell type that expresses such a cellular polypeptide. The affinity tag, in certain embodiments, comprises at least one polypeptide tag, and in certain other embodiments, the affinity tag may comprise at least two, three, or four polypeptide tags. The fusion protein may be constructed using synthetic biochemical and organic chemical methods that are described herein and routinely practiced in the art. The fusion protein may also be constructed recombinantly using molecular biology techniques and procedures, also described herein and routinely practiced in the molecular biology art, and then expressed in eukaryotic or prokaryotic cells as a recombinant protein.

As used herein, a fusion protein that comprises a viral polypeptide and an affinity tag may further comprise spacer peptide sequences between moieties of the fusion polypeptide. For example, a spacer peptide may be located between the viral polypeptide and the affinity tag, or when the affinity tag comprises at least two polypeptide tags, an amino acid spacer sequence may also be between the polypeptide tags. The spacer peptide may be at least one, two, three, four, five, six, or seven or more amino acids. Spacer peptides may be incorporated into a fusion protein to enable or ensure or facilitate proper folding of each moiety of the fusion protein. In addition, or alternatively, when the fusion protein is prepared recombinantly, the spacer peptide may be the translational product (i.e. encoded amino acid sequence) of a polynucleotide restriction site that is incorporated into the nucleotide sequence of a recombinant construct and that is useful for cloning purposes. In certain other embodiments one, two, or three amino acids at the amino terminal end or carboxy terminal end of a polypeptide tag (Such as those described herein) may be deleted or substituted, which may be useful for accommodating a restriction site sequence or a spacer sequence.

An affinity tag may further comprise at least one protease recognition sequence. A protease recognition sequence refers to a consecutive amino acid sequence that is recognized and required for proteolytic cleavage by a particular protease. A protease recognition sequence may be coincident with the protease cleavage site, that is, cleavage occurs at the protease recognition sequence. The protease recognition sequence may include one or more amino acids on either side of the peptide bond to be hydrolyzed by the protease. Alternatively, the protease recognition sequence may be one, two, or more amino acids distal, toward the amino or carboxy terminus, to the cleavage site of the protease. Accordingly, the protease cleaves the polypeptide comprising the protease recognition sequence at or near the protease recognition sequence.

In one embodiment, a protease recognition sequence comprises the protease cleavage site of tobacco etch virus (TEV) protease. TEV protease recognizes a linear epitope of the general formula E-X-X-Y-X-Q-(G/S) (SEQ ID NO:28), wherein X refers to any amino acid. In a particular embodiment, a fusion protein comprises a TEV protease recognition sequence having the amino acid sequence ENLYFQS (SEQ ID NO:29). Another commonly used TEV protease recognition sequence comprises the amino acids ENLYFQG (SEQ ID NO:30). Incorporation of certain other amino acids at the variable amino acid positions results in a peptide sequence that is less efficiently cleaved by the TEV protease, which in certain specific embodiments, may be desirable. The protease cleaves between the glutamine and glycine or serine residues (-Q-(G/S)).

In certain embodiments, the affinity tag may comprise a human rhinovirus 3C (HRV3C) protease site. The protease recognition sequence comprises the amino acids LEVLFQGP (SEQ ID NO:16). In certain other embodiments, the affinity tag may comprise at least two protease recognition sequences, such as the TEV protease recognition sequence and the human rhinovirus HRV3C protease recognition sequence.

In certain embodiments, the affinity tag comprises at least two polypeptide tags. In other certain embodiments, the affinity tag may comprise at least two protease recognition sequences. For example, the affinity tag may comprise at least three polypeptide tags, and one protease recognition sequence may be between a first and a second polypeptide tag and a second protease recognition sequence may be located between the second polypeptide tag and a third polypeptide tag. Alternatively, a fusion protein that comprises at least two protease recognition sequences may comprise a first protease recognition sequence between the viral polypeptide and the affinity tag and may comprise a second protease recognition sequence between any of two polypeptide tags present in the affinity tag. Persons skilled in the art will appreciate that a protease recognition sequence in the fusion proteins and affinity tags described herein may be located between any two polypeptide tags of the affinity tag or may be located between the viral polypeptide and the affinity tag.

An affinity tag may be located at the amino terminal end of the viral polypeptide or may be located at the carboxy terminal end of the viral polypeptide of a fusion protein. When a fusion protein is expressed recombinantly, a person skilled in the art using standard molecular biology and recombinant expression methods and procedures will be able to determine readily if locating an affinity tag at either terminal end of the viral polypeptide adversely affects expression, that is, any one of translation, folding, and/or transport of the fusion protein. The recombinant vector can then be constructed accordingly so that expression of the fusion protein is not significantly adversely affected.

In one embodiment, the affinity tag comprises one polypeptide tag, such as a mutein Fc polypeptide. In another embodiment, an affinity tag comprises at least two, at least three, at least four, or at least five or six polypeptide tags described herein, including but not limited to an immunoglobulin Fc polypeptide, an immunoglobulin mutein Fc polypeptide, a hemagglutinin peptide, a calmodulin binding peptide or a calmodulin domain, a protein C-tag, a streptavidin binding peptide (or fragments thereof), a His tag, a protein A fragment (e.g., an IgG-binding ZZ polypeptide), and a Softag™ peptide. In certain embodiments, one or more of the polypeptide tags is repeated, that is, at least two amino acid sequences of the same polypeptide tag are repeated in the affinity tag. The repeated polypeptide tags may be immediately adjacent to each other or separated by at least one different polypeptide tag.

In a specific embodiment, the affinity tag comprises a hemagglutinin peptide, a C-tag peptide, and a Softag™ peptide. In another certain embodiment, the affinity tag comprises a hemagglutinin peptide, a C-tag peptide, and a mutein Fc polypeptide tag. In another specific embodiment, the affinity tag comprises a hemagglutinin peptide, a C-tag peptide, and a protein A fragment, such as an IgG-binding ZZ polypeptide. In another embodiment, the affinity tag comprises a hemagglutinin peptide, a calmodulin binding peptide or domain, a streptavidin binding peptide (SBP) (or a fragment thereof). In another embodiment, the affinity tag comprises a hemagglutinin peptide, a C-tag peptide, and a SBP or fragment thereof. In a particular embodiment, the SBP peptide, or fragment thereof, is repeated at least two times. In another embodiment, the affinity tag comprises a hemagglutinin peptide, a calmodulin binding peptide or domain, a SBP (or a fragment thereof), and a mutein Fc polypeptide. In still other embodiments as described herein, an affinity tag, including the specific embodiments described herein, further comprises at least one protease recognition sequence. By way of non-limiting example, an affinity tag that comprises a hemagglutinin peptide, a calmodulin binding peptide or domain, a SBP (or a fragment thereof), and a mutein Fc polypeptide may further comprise a protease recognition sequence, for example, a TEV protease recognition sequence or a HRV3C protease sequence, between any two polypeptide tags. Affinity tags comprising one polypeptide tag, such as mutein Fc polypeptide, may also further comprise a protease recognition sequence between the viral polypeptide sequence and the mutein Fc polypeptide.

Recombinant Expression Constructs

In certain embodiments, a fusion protein comprising a viral virulence polypeptide and an affinity tag is recombinantly expressed. According to the methods described herein, a fusion protein may be used as a probe to identify a cellular polypeptide that binds to a viral polypeptide or to identify a cell type with which the cellular polypeptide is associated. In other embodiments, the fusion protein is used to identify and to isolate a cellular polypeptide to which a viral virulence polypeptide binds, using methods described in further detail herein, which may include steps similar to a tandem affinity purification (TAP) tag method, wherein the fusion protein is expressed recombinantly in a cell with which a target cellular polypeptide is associated (see, e.g., Rigaut et al., *Nat. Biotech.* 17:1030-32 (1999); Puig et al., supra; Tasto et al., *Yeast* 18:657-62 (2001); Gould et al., *Methods* 33:239-44 (2004)). Fusion proteins comprising the affinity tags described herein are particularly useful for isolating and purifying a cellular polypeptide to which a viral polypeptide binds.

A fusion protein comprising a viral virulence polypeptide and an affinity tag may be prepared by recombinant expression methods described herein and/or described in the art, wherein the fusion protein comprising the viral polypeptide, is expressed from a polynucleotide that is operatively linked to an expression control sequence (e.g., a promoter, enhancer, transcription initiation site) in a nucleic acid expression construct. The fusion protein as described in greater detail herein may be expressed using vectors and constructs, particularly recombinant expression constructs, that include any polynucleotide encoding such polypeptides. The nucleotide sequence of such polynucleotides that encode the viral polypeptides and polypeptide tags can be readily determined by a person skilled in the molecular biology art on the basis of the amino acid sequence of the viral polypeptides and polypeptide tags disclosed herein and known in the art, given the art accepted and well characterized genetic code. Host cells may be transfected, transformed, or transduced with vectors and/or constructs to produce these polypeptides and fusion proteins, or fragments or variants thereof, by recombinant techniques. Each of the polypeptides and fusion polypeptides described herein can be expressed in mammalian cells, yeast, bacteria, or other cells under the control of appropriate promoters. Appropriate cloning and expression vectors for use with prokaryotic and eukaryotic hosts are described, for example, by Sambrook, et al., *Molecular Cloning: A Laboratory Manual*, Third Edition, Cold Spring Harbor, N.Y., (2001). In particular embodiments, the host cell is a eukaryotic cell, which is a mammalian cell, including, for example, a CV1/EBNA cell, HEK293 cell, HEK2931 cell, COS-7 cell, a CHO cell, and the like.

A polynucleotide, nucleic acid, or nucleic acid molecule refers to any of single-stranded or double-stranded deoxyribonucleic acid (DNA) or ribonucleic acid (RNA) polynucleotide, oligonucleotide, or fragment thereof. Polynucleotides may be isolated from a biological source and/or may be generated and amplified by standard molecular biology methods practiced in the art, for cloning and amplification (such as the polymerase chain reaction (PCR)). Polynucleotide fragments may be obtained from a PCR product or from an isolated polynucleotide by any of ligation, scission, endonuclease, and/or exonuclease activity. Nucleic acids may be composed of monomers that are naturally occurring nucleotides (such as deoxyribonucleotides and ribonucleotides), analogs of naturally occurring nucleotides (e.g., α-enantiomeric forms of naturally-occurring nucleotides), or a combination of both. Modified nucleotides can have modifications in sugar moieties and/or in pyrimidine or purine base moieties.

In one embodiment, recombinant expression constructs comprise a polynucleotide sequence that encodes a fusion protein comprising a viral polypeptide that is fused in frame with an affinity tag. As described herein the affinity tag may comprise at least one, two, three, four, or more polypeptide tags and may further comprise at least one or at least two protease recognition sequences. As described herein, the recombinant expression constructs also contain nucleotide sequences that encode spacer peptides. When the amino acid sequence of a polypeptide is known, such as the polypeptide tag sequences disclosed herein and used in the art, a polynucleotide sequence that encodes such a polypeptide may readily be designed and prepared according to standard molecular biology knowledge (e.g., sequences of codons for each amino acid) and methods routinely practiced by a person skilled in the art.

A recombinant construct may further comprise a signal peptide sequence operatively linked and fused in frame with the fusion protein. A signal peptide may be incorporated into the recombinant expression construct to facilitate translocation of the fusion protein as a secretory protein or a cell-surface protein across intracellular membranes and to final localization. The signal peptide sequence is located at the N-terminus of a fusion protein and is typically 13-40 amino acids in length. Accordingly, a signal peptide may be located at the amino terminus of the viral polypeptide when the affinity tag is attached or fused to the carboxy terminal end of the viral polypeptide, or the signal peptide may be located at the amino terminus of the affinity tag of the fusion polypeptide when the affinity tag is attached or fused to the amino terminal end of the viral polypeptide.

An example of a signal peptide sequence that is fused in frame to the fusion protein is a human growth hormone signal peptide sequence. The recombinant construct therefore comprises a nucleotide sequence that encodes the amino acid sequence MATGSRTSLLLAFGLLCLPWLQEGSA (SEQ ID NO:12). The signal peptide sequence may further comprise amino acids that are encoded by the nucleotide sequences of restriction sites. The restriction sites may be useful for cloning and subcloning of the different polynucleotide sequences to construct a polynucleotide sequence that encodes the fusion polypeptide. Depending on the site at which a cellular enzyme cleaves the signal peptide from the mature fusion protein, the amino acids encoded by the restriction site nucleotide sequences may in whole or in part be attached at the amino terminal end of the fusion protein. In certain embodiments, the recombinant construct comprises a polynucleotide that has a nucleotide sequence that corresponds to the restriction site of the restriction enzyme Spe1 or Asp718, which nucleotide sequences encode the amino acids Thr-Ser and Gly-Thr, respectively. Accordingly, a human growth hormone signal peptide sequence further comprising nucleotides corresponding to a Spe1 and an Asp718 restriction site comprises the amino acid sequence MATGSRTSLLLAFGLLCLPWLQEGSATSGT (SEQ ID NO:13). A person skilled in the art can readily determine which restriction site nucleotide sequences encode amino acids and may incorporate additional restriction sites or alternative restriction sites at the carboxy terminal end of a signal sequence. Restriction site nucleotide sequences may also be incorporated between the viral polypeptide and the affinity tag and/or between polypeptide tags of the affinity tag.

Generally, recombinant expression vectors include origins of replication, selectable markers permitting transformation of the host cell, for example, the ampicillin resistance gene of *E. coli* and *S. cerevisiae* TRP1 gene, and a promoter derived from a highly expressed gene to direct transcription of a downstream structural sequence. Promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Vectors that may be used and modified for expression of the fusion polypeptides described herein that comprises a viral virulence polypeptide and an affinity tag are available from commercial sources and include, for example, pcDNA™3.1 and related vectors (Invitrogen), adenovirus vectors and adeno associated virus vectors (e.g., pAAV vectors, Stratagene, La Jolla, Calif.) and retroviral vectors including a Lentiviral vector system (e.g., pSL9).

Host cells containing the described recombinant expression constructs may be genetically engineered either by stably introducing or transiently introducing (transducing, transforming, or transfecting) the vectors and/or expression constructs (for example, a cloning vector, a shuttle vector, or an expression construct). Vector constructs comprising cloned polynucleotide sequences encoding a fusion protein described herein can be introduced into cultured mammalian cells by, for example, liposome-mediated transfection, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841-845, 1982), or DEAE-dextran mediated transfection (Ausubel et al. (eds.), *Current Protocols in Molecular Biology*, John Wiley and Sons, Inc., NY, 1987); retroviral, adenoviral and protoplast fusion-mediated transfection (see Sambrook et al., supra). To identify cells that have been stably transfected with the vector containing the cloned DNA, a selectable marker is generally introduced into the cells along with the polynucleotide of interest. Preferred selectable markers for use in cultured mammalian cells include genes that confer resistance to drugs, such as neomycin, hygromycin, and methotrexate. The selectable marker may be an amplifiable selectable marker. Preferred amplifiable selectable markers are the DHFR gene and the neomycin resistance gene. Selectable markers are reviewed by Thilly (*Mammalian Cell Technology*, Butterworth Publishers, Stoneham, Mass.).

The vector or construct may be in the form of a plasmid, a viral particle, a phage, etc. The engineered host cells can be cultured in conventional nutrient media modified as appropriate for activating promoters, selecting transformants, or amplifying particular genes or encoding-nucleotide sequences. Selection and maintenance of culture conditions for particular host cells, such as temperature, pH and the like, will be readily apparent to the ordinarily skilled artisan. Preferably the host cell can be adapted to sustained propagation in culture to yield a cell line according to art-established methodologies. In certain embodiments, the cell line is an immortal cell line, which refers to a cell line that can be repeatedly (at least ten times while remaining viable) passaged in culture following log-phase growth. In other embodiments the host cell used to generate a cell line is a cell that is capable of unregulated growth, such as a cancer cell, or a transformed cell, or a malignant cell.

Useful bacterial expression constructs for expressing a viral virulence polypeptide or fusion protein comprising the viral polypeptide are constructed by inserting into an expression vector a structural DNA sequence encoding a desired protein together with suitable translation initiation and termination signals in operable reading phase with a functional promoter. The construct may comprise one or more phenotypic selectable markers and an origin of replication to ensure maintenance of the vector construct and, if desirable, to provide amplification within the host. Suitable prokaryotic hosts for transformation include *E. coli, Bacillus subtilis, Salmonella lyphimurium* and various species within the genera *Pseudomonas, Streptomyces*, and *Staphylococcus*, although others may also be employed as a matter of choice. Any other plasmid or vector may be used as long as they are replicable and viable in the host. Thus, for example, the polynucleotides as described herein may be included in any one of a variety of expression vector constructs as a recombinant expression construct for expressing a polypeptide. Such vectors and constructs include chromosomal, nonchromosomal, and synthetic DNA sequences, e.g., bacterial plasmids; phage DNA; baculovirus; yeast plasmids; vectors derived from combinations of plasmids and phage DNA; viral DNA, such as vaccinia, adenovirus, fowl pox virus, and pseudorabies. However, any other vector may be used for preparation of a recombinant expression construct as long as it is replicable and viable in the host.

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. Numerous standard techniques are described, for example, in Ausubel et al. (*Current Protocols in Molecular Biology* (Greene Publ. Assoc. Inc. & John Wiley & Sons, Inc., 1993)); Sambrook et al. (*Molecular Cloning: A Laboratory Manual,* 3rd Ed., (Cold Spring Harbor Laboratory 2001)); Maniatis et al. (*Molecular Cloning*, (Cold Spring Harbor Laboratory 1982)), and elsewhere.

The polynucleotide sequence encoding a polypeptide in the expression vector is operatively linked to at least one appropriate expression control sequences (e.g., a promoter or a regulated promoter) to direct mRNA synthesis. Representative examples of such expression control sequences include LTR or SV40 promoter, the *E. coli* lac or trp, the phage lambda $P_L$ promoter, and other promoters known to control expression of genes in prokaryotic or eukaryotic cells or their viruses. Promoter regions can be selected from any desired gene using CAT (chloramphenicol transferase) vectors or other vectors with selectable markers. Particular bacterial promoters include lac, lacZ, T3, T5, T7, gpt, lambda $P_R$, $P_L$, and trp. Eukaryotic promoters include CMV immediate early, HSV thymidine kinase, early and late SV40, LTRs from retroviruses, and mouse metallothionein-1. Selection of the appropriate vector and promoter and preparation of certain recombinant expression constructs comprising at least one promoter or regulated promoter operatively linked to a polynucleotide described herein is well within the level of ordinary skill in the art.

Design and selection of inducible, regulated promoters and/or tightly regulated promoters are known in the art and will depend on the particular host cell and expression system. The pBAD Expression System (Invitrogen Life Technologies, Carlsbad, Calif.) is an example of a tightly regulated expression system that uses the *E. coli* arabinose operon ($P_{BAD}$ or $P_{ARA}$) (see Guzman et al., *J. Bacteriology* 177:4121-30 (1995); Smith et al., *J. Biol. Chem.* 253:6931-33 (1978); Hirsh et al., *Cell* 11:545-50 (1977)), which controls the arabinose metabolic pathway. A variety of vectors employing this system are commercially available. Other examples of tightly regulated promoter-driven expression systems include PET Expression Systems (see U.S. Pat. No. 4,952,496) available from Stratagene (La Jolla, Calif.) or tet-regulated expression systems (Gossen et al., *Proc. Natl. Acad. Sci. USA* 89:5547-51 (1992); Gossen et al., *Science* 268:1766-69 (1995)). The pLP-TRE2 Acceptor Vector (BD Biosciences Clontech, Palo Alto, Calif.) is designed for use with CLONTECH's Creator™ Cloning Kits to rapidly generate a tetracycline-regulated expression construct for tightly controlled, inducible expression of a gene of interest using the site-specific Cre-lox recombination system (see, e.g., Sauer, *Methods* 14:381-92 (1998); Furth, *J. Mamm. Gland Biol.*

*Neoplas.* 2:373 (1997)), which may also be employed for host cell immortalization (see, e.g., Cascio, *Artif. Organs* 25:529 (2001)).

The vector may be a viral vector such as a retroviral vector. For example, retroviruses from which the retroviral plasmid vectors may be derived include, but are not limited to, Moloney Murine Leukemia Virus, spleen necrosis virus, Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus. A viral vector also includes one or more promoters. Suitable promoters that may be employed include, but are not limited to, the retroviral LTR; the SV40 promoter; and the human cytomegalovirus (CMV) promoter described in Miller et al., *Biotechniques* 7:980-990 (1989), or any other promoter (e.g., eukaryotic cellular promoters including, for example, the histone, pol III, and β-actin promoters). Other viral promoters that may be employed include, but are not limited to, adenovirus promoters, thymidine kinase (TK) promoters, and B19 parvovirus promoters.

The retroviral plasmid vector is employed to transduce packaging cell lines (e.g., PE501, PA317, ψ-2, ψ-AM, PA12, T19-14X, VT-19-17-H2, ψCRE, ψCRIP, GP+E-86, GP+en-vAm12, DAN; see also, e.g., Miller, *Human Gene Therapy*, 1:5-14 (1990)) to form producer cell lines. The vector may transduce the packaging cells through any means known in the art, such as, for example, electroporation, the use of liposomes, and calcium phosphate precipitation. The producer cell line generates infectious retroviral vector particles that include the nucleic acid sequence(s) encoding the polypeptides or fusion proteins described herein. Such retroviral vector particles then may be employed, to transduce eukaryotic cells, either in vitro or in vivo. Eukaryotic cells that may be transduced include, for example, embryonic stem cells, embryonic carcinoma cells, hematopoietic stem cells, hepatocytes, fibroblasts, myoblasts, keratinocytes, endothelial cells, bronchial epithelial cells, and other culture-adapted cell lines.

As another example, host cells transduced by a recombinant viral construct directing the expression of polypeptides or fusion proteins may produce viral particles containing expressed polypeptides or fusion proteins that are derived from portions of a host cell membrane incorporated by the viral particles during viral budding. The polypeptide-encoding nucleic acid sequences may be cloned into a baculovirus shuttle vector, which is then recombined with a baculovirus to generate a recombinant baculovirus expression construct that is used to infect, for example, Sf9 host cells (see, e.g., *Baculovirus Expression Protocols, Methods in Molecular Biology* Vol. 39, Richardson, Ed. (Human Press 1995); Piwnica-Worms, "Expression of Proteins in Insect Cells Using Baculoviral Vectors," Section II, Chapter 16 in *Short Protocols in Molecular Biology*, 2$^{nd}$ Ed., Ausubel et al., eds., (John Wiley & Sons 1992), pages 16-32 to 16-48).

Methods for Identifying a Target Cellular Polypeptide

In one embodiment, a method is provided for identifying a cellular polypeptide to which a viral virulence polypeptide binds comprising contacting a cell, or a fraction or a supernatant of the cell, and a fusion protein comprising a viral polypeptide fused to an affinity tag, under conditions and for a time Sufficient that permit a viral polypeptide moiety of the fusion protein to interact with a polypeptide associated with the cell, or the fraction or the supernatant of the cell, to provide a fusion protein:cellular polypeptide complex, wherein the viral polypeptide has at least one virulence trait. The step of contacting (i.e., mixing, combining, or in some manner permitting interaction between the cell and fusion protein) may be performed in any suitable reaction vessel used in the art. The fusion protein:cellular polypeptide complex is then isolated, and the amino acid sequence of the cellular polypeptide determined by determining the amino acid sequence of the entire polypeptide or of at least one cellular polypeptide fragment (or a plurality of fragments), wherein each fragment comprises at least eight amino acids (which includes any polypeptide fragment having eight or more amino acids in any whole integer amount), and thereby identifying a cellular polypeptide to which a viral polypeptide binds. An exemplary technique or combination of techniques and methods for identifying a cellular polypeptide include tandem affinity purification (TAP) followed by LC-MS/MS (liquid chromatography-tandem mass spectrometry), which are practiced in the art and described herein.

As described herein, the viral virulence polypeptide is a polypeptide from a virus that contributes to the virulence of the virus in an infected host. At least one virulence trait of a viral polypeptide may be known in the art. Alternatively, the methods described herein may further comprise determining whether a viral polypeptide has at least one trait that is a virulence trait as described in detail herein. The polypeptide sequence of the viral polypeptide may also be known in the art or may be determined, for example, according to the methods described herein. Similarly, a trait of a viral polypeptide that is described herein as a virulence trait may be known in the art and that the trait relates to the virulence of the virus, may or may not be apparent to a person skilled in the art. Procedures and techniques for determining whether a viral polypeptide has one or more virulence traits may be performed according to methods described herein and with which a skilled artisan will be familiar. For example, prior to the step of contacting a cell, a cell supernatant, or a cell fraction, the polynucleotide sequence of a viral genome may be inspected or scanned as described herein to identify at least one open reading frame encoding at least forty amino acids (which may include a signal peptide sequence). Alternatively, or in addition, the method may further comprise any one or more of the following: determining that expression of a mutant viral polypeptide in a cell infected by the virus correlates with a decrease in virulence of the virus; determining that absence of expression of the viral polypeptide in a cell infected by the virus correlates with a decrease in virulence of the virus; determining that the viral polypeptide is secreted by a cell infected with the virus, is associated with a cellular membrane, or is intracellular; and determining that the polynucleotide sequence in the virus genome is located in a genomic region that encodes at least one other viral polypeptide that is a viral virulence factor, wherein the region is at the 5' terminal end or the 3' terminal end of the virus genome.

A fusion protein comprising the viral polypeptide and an affinity tag may be prepared synthetically or recombinantly according to methods described herein. Contacting the fusion protein with a cell, a fraction of the cell, or a supernatant of the cell, includes permitting the cell or fraction or supernatant to interact, such as mixing or combining together in some manner the cell, cell fraction, or cell supernatant and the fusion polypeptide. A cellular polypeptide of a cell, which may be expressed on the cell surface of a cell or is secreted from the cell, and thus can be obtained in a cell supernatant, may be contacted with a fusion protein described herein. In a specific embodiment, a cell supernatant, such as conditioned media (i.e., media collected from a plurality of cells that have been cultured for a time sufficient such that a cellular polypeptide is secreted, or in some manner released, by the cell), is contacted with a fusion polypeptide.

Contacting the cell, cell fraction, or cell supernatant and the fusion polypeptide also includes contact when the fusion protein is introduced into the cell. For example, a recombinant expression construct comprising a polynucleotide sequence that encodes the fusion protein may be introduced into the cell by a transfection, transformation, or other method described herein and practiced in the art such that the fusion protein is expressed by the cell. Thus, the fusion protein is permitted to interact with a cellular polypeptide that is intracellular, associated with a membrane (either a membrane of a cellular organelle or the cellular membrane), or that is secreted by the cell (and which may be located in the supernatant of the cell). A polynucleotide encoding the fusion protein may also be introduced into a cell as a "naked" polynucleotide as described, for example, in Ulmer et al., *Science* 259:1745-49 (1993) and reviewed by Cohen, *Science* 259: 1691-92 (1993). The uptake of a naked polynucleotide may be increased by coating the polynucleotide onto biodegradable beads, which are efficiently transported into the cells.

In particular embodiments, the fusion protein comprises a signal peptide sequence such as the human growth hormone signal peptide sequence that facilitates secretion of the fusion protein, which more readily permits interaction between the fusion protein and a cellular polypeptide that is a secreted cellular polypeptide. Accordingly, for identifying a cellular polypeptide including a polypeptide that is a secreted cellular polypeptide, the fusion protein may comprise, for example, a growth hormone signal peptide sequence fused in frame with the viral polypeptide, which is in turn fused in frame with the affinity tag. In a specific embodiment, the affinity tag comprises from the amino terminal end of the affinity tag toward the carboxy terminal end, a hemagglutinin peptide (e.g., YPYDVDYA (SEQ ID NO:1)), a calmodulin binding polypeptide (e.g., KRRWKKNFIAVSAANRFKKISSSGAL (SEQ ID NO:3)), a TEV protease recognition sequence, a streptavidin binding peptide, and an immunoglobulin mutein Fc polypeptide (e.g., a human IgG mutein Fc polypeptide). In another specific embodiment, the affinity tag of the fusion protein comprises a hemagglutinin peptide (e.g., YPYDVDYA (SEQ ID NO:1)), a calmodulin binding polypeptide (e.g., KRRWKKNFIAVSAANRFKKISSSGAL (SEQ ID NO:3)), a human rhinovirus 3C protease recognition sequence, and a streptavidin binding peptide, and a second repeat of the streptavidin binding peptide.

In certain embodiments, a cell is stimulated prior to, at the same time, or after, a cell, a cell fraction or a cell supernatant, is contacted with a fusion protein. As described herein, a stimulus includes, for example, an antibody that specifically binds to a cognate antigen (e.g., a cell surface marker antigen or cell surface receptor) expressed by the cell; a phorbol ester (e.g., PMA), and other mitogens; a cytokine; a chemokine; and ionomycin; or a combination of at least two agents (for example, PMA and ionomycin; PWM (pokeweed mitogen) and insulin).

Also as described herein, a cell fraction such as a cell lysate or cell extract that may be used in the methods described herein. A cell fraction also includes a preparation of one or more isolated organelles from a cell, which are described herein, and also includes complex multi-molecular structures such as lipid rafts and other trafficking and transport complexes. Cell fractions, cell lysates, cell extracts, and isolated cell organelles may be prepared according to methods and techniques appropriate for a particular cell and may include one or a combination of mechanical, physical, and chemical techniques with which a skilled artisan is familiar. A cell supernatant, which includes, for example, cellular washes, cell culture media, or conditioned media (i.e., media from cells in culture that have been propagated for a period of time sufficient for the cells to secrete a cellular polypeptide to which a viral polypeptide binds), or any other extracellular preparation, including a biological sample, may be used in the methods described herein. As described herein, a cell fraction or cell supernatant of a cell may be contacted with a fusion polypeptide that is expressed by the cell. Alternatively, a cell supernatant or cell fraction may be obtained and then contacted with a fusion polypeptide.

Interaction of the fusion protein and the cell, cell supernatant, or cell fraction permits the viral polypeptide moiety of the fusion protein to interact with or bind to a cellular polypeptide, which is a cellular polypeptide that the viral polypeptide interacts with during infection of a host by the virus that encodes and expresses the viral polypeptide. The interaction occurs under suitable conditions (e.g., temperature, atmosphere, nutrients, buffers, pH, etc.) and for a time sufficient to permit formation of a fusion protein:cellular polypeptide complex that can be isolated. As described herein, the fusion protein comprises an affinity tag, which comprises a detectable moiety and/or at least one polypeptide tag.

In one embodiment, the fusion protein:cellular polypeptide complex may be isolated from the cell, cell fraction, or from a cell supernatant by contacting the complex with a cognate ligand of at least one polypeptide tag of the affinity tag. Examples of polypeptide tags and cognate ligands are described in detail herein. The cognate ligand may be bound to a solid support, such as a plastic, glass, or metal surface, including but not limited to a slide, bead, plate (including a multi-well plate), nanoparticle, or other matrix, including polymeric matrices, negatively charged matrices, and positively charged matrices. For isolating the fusion protein:cellular polypeptide complex from the cell, cell fraction, or cell supernatant, the complex is permitted to interact with the cognate ligand under suitable conditions and for a time sufficient for a polypeptide tag and its cognate ligand to bind, thus forming a cognate ligand:fusion protein:cellular polypeptide complex. The fusion protein:cellular polypeptide complex may then be isolated by disrupting the interaction between the cognate ligand and the polypeptide tag and separating the complex from the cognate ligand. Persons skilled in the art can readily determine the suitable conditions for forming a complex formation and for disrupting a complex (e.g., pH; buffer; absence or presence of ions, salts, cations, or chelating agents; etc.) and time sufficient for formation of a complex between the cognate ligand and the polypeptide tag.

Alternatively, when the affinity tag comprises a protease recognition sequence, the respective protease may be contacted with the cognate ligand:fusion protein:cellular polypeptide complex under conditions and for a time sufficient for the protease to cleave the fusion polypeptide to release a cleaved fusion protein:cellular polypeptide complex. Certain polypeptide tags exhibit a high affinity for the respective cognate ligand (e.g., SBP peptide (SEQ ID NO:6) or tandem SBP tags (SEQ ID NO:8); Fc polypeptide-cognate ligand interactions; or certain antibody-polypeptide tag specific binding) such that disruption of the interaction between the polypeptide tag and cognate ligand requires conditions (e.g., low pH, chaotropic agents, high salt, etc.) that could (but not necessarily) adversely affect the structure of the cellular polypeptide or disrupt the interaction between the viral polypeptide and cellular polypeptide. Incorporation of at least one protease recognition sequence into the affinity tag provides the capability to separate and isolate the fusion protein (or a portion thereof):cellular polypeptide complex, thus minimizing possible adverse alteration of the cellular polypeptide and/or the viral polypeptide:cellular polypeptide interaction. In addition, incorporation of at least one protease recognition sequence into the affinity tag and subsequent proteolytic cleavage of a portion of the affinity tag from the fusion protein:cellular polypeptide complex increases the mass ratio of the cellular polypeptide to fusion protein and thus increases the sensitivity of detection and analysis of the cellular polypeptide by methods described herein, such as LC-MS/MS (liquid chromatography followed by tandem mass spectrometry). A cellular polypeptide:fusion protein complex may be identified and detected by methods described in further detail herein and known in the art including, for example, surface plasmon resonance (SPR); Fluorescence Activated Cell Sorting (FACS) (e.g., for identifying a cell surface expressed polypeptide); and kinetic protein interaction measuring devices such as a KinExA™ device (e.g., Sapidyne Instruments, Inc., Boise, Id.) (e.g., for identifying a cellular polypeptide in a cell supernatant such as conditioned media), which methods may further comprise use of radioactive labeling (e.g., $S^{35}$, $P^{32}$, and the like).

Subsequent to isolation of a fusion protein:cellular polypeptide complex from the cell, cell fraction, or cell supernatant, the cellular polypeptide is identified. In certain embodiments, the identity of the cellular polypeptide may be determined by analyzing the full-length polypeptide, for example, as described herein, by performing immunoassays using antibodies that have been characterized by their ability to specifically bind to a particular cellular polypeptide. The identity of the cellular polypeptide (either in the complex or isolated from the complex) can be determined by methods, for example, immunochemical methods, such as immunoblotting, immunoassay (e.g., an ELISA), radioimmunoassay, competition assays, and other assays practiced in the art. An immunoassay may be performed in a matrix or multi-plex or high throughput method in which the cellular polypeptide is contacted with numerous antibodies with specificities for different cellular polypeptides. Other exemplary procedures for identifying longer cellular polypeptide fragments or full-length polypeptides include MALDI-TOF, which is routinely practiced in the art and described herein. As described herein, such methods may be used for analyzing the full-length cellular polypeptide or fragments thereof, which may be fragments at least 6 amino acids or at least any number of amino acids between 6 amino acids and the number of amino acids that comprises the full-length of the polypeptide.

In other embodiments, the amino acid sequence of the cellular polypeptide or of at least one peptide thereof, can be determined. In certain embodiments, the cellular polypeptide may be isolated from the complex. The amino acid sequence of the cellular polypeptide or a peptide thereof may be determined by any one of a number of methods practiced by a person skilled in the art and described herein. For example, partial hydrolysis of a cellular polypeptide will generate peptides for which the amino acid sequence can be determined. Partial hydrolysis may be performed by chemical methods or by enzymatic methods. Compounds used for partial chemical hydrolysis of proteins include mild acid (e.g., formic acid at 40° C.) (specificity: Asp-Pro); hydroxylamine (specificity: Asn:Gly); cyanogens bromide (specificity: carboxyl side of Met); iodosobenzoic acid (specificity: carboxyl side of Trp); and 2-nitro-5-thiocyanobenzoate followed by alkali treatment (specificity: amine side of Cys). Proteolytic enzymes that are useful for generating peptide fragments that can be sequenced include for example, trypsin (specificity: carboxyl side of Arg and Lys); chymotrypsin (specificity: carboxyl side of Tyr, Phe, and Trp); elastase (specificity: carboxyl side of Ala and Gly); ficin (specificity: uncharged, aromatic amino acids); papain (carboxyl side of Arg, Lys, and Phe); pepsin (specificity: carboxyl side of Phe and Leu; non-polar pairs); thermolysin (specificity: amine side of Leu and Phe; non-polar residues); and thrombin (specificity: carboxyl side of Arg). Proteases that are particularly useful to generate peptides that will be subjected to mass spectrometry for amino acid sequence analysis include trypsin, and also include proteases called Asp-N (specificity: amine side of Asp and Cys), Glu-C (specificity: carboxyl side of Glu and Asp), Lys-C (specificity: carboxyl side of Lys), and Arg-C (specificity: carboxyl side of Arg), which are available commercially (see, e.g., Sigma Aldrich, St. Louis, Mo.). The three-letter and single letter nomenclature for amino acids that is used herein conforms to the art accepted standard for such abbreviations.

In certain embodiments, a cellular polypeptide is identified by contacting the cellular polypeptide (or cellular polypeptide:fusion protein complex) with a protease to generate peptide fragments of at least 8-20 (and any integer between the specifically named length range, e.g., 8, 10, 12, 14, 16, 18, or 20 amino acids) in length or longer. The cellular peptide fragments may then be separated or isolated so that individual fragments may be subjected to amino acid analysis. Separation methods include, for example, any of a variety of liquid chromatography (LC) techniques (high performance liquid chromatography, fast protein liquid chromatography), including two-dimensional LC, other chromatography methods (e.g., affinity, ion exchange, thin layer, gel chromatography, etc.), and various electrophoresis techniques that persons skilled in the art routinely use. The amino acid sequence of the peptides that are obtained, for example, from the LC step, may then be determined by a variety of sequencing methods practiced in the art, for example, mass spectrometry, which includes tandem mass spectrometry (MS/MS) that provides ion spectra identification, which may further comprise induced fragmentation of the parental peptide ions. The mass spectrometry data may then be analyzed by software programs (e.g., SEQUEST (Sequest Technologies, Inc. Lisle, Ill.); MASCOT (Matrix Science Ltd., London, UK); or X!TANDEM (open source software, Global Proteome Machine Organization); see also, e.g., Clauser et al., *Anal. Chem.* 71:2871 (1999)) that compare the data with information in databases regarding known polypeptides. Ion spectra may also be identified by comparing to databases of spectra that are associated with high confidence to specific peptides using software packages such as X!HUNTER.

Mass spectrometry methods include electrospray ionization, which provides high sensitivity and is directly applicable to the analysis of peptides and proteins. Multiple charging through the use of electrospray ionization is sample dependent, but can extend the upper mass limit that can be analyzed using a triple quadrupole instrument into the 50-80 kDa range for some proteins. For mass spectral analysis of peptides and proteins, preferably the sample is soluble in dilute acid. In many instances, the sample undergoes at least one round of HPLC. A variety of information about the polypeptide/peptides can be obtained through the use of electrospray-mass spectrometry on a triple quadrupole instrument. These include molecular mass measurement, assessment of chemical modifications through mass increases, daughter ion scans (for sequence analysis), precursor ion scans, constant mass difference scans and selected ion monitoring.

For analysis of peptides, triple quadrupole technology is used for performing collision-induced dissociation (CID) of the ion for sequence/structural information. The maximum number of residues that can be sequenced is usually about 20 amino acids. Sequence analysis from larger peptides/proteins usually requires a protease digestion step before analysis.

For example, LC-MS/MS may be performed using an ion trap mass spectrometer (such as LC/MS/MS LCQ Deca XP (ThermoFinnigan, Thermo Electron Corp., Waltham, Mass.); QSTAR® Elite LC/MS/MS System, Applied Biosystems/ MDS Sciex) to identify a target cellular polypeptide on the basis of the amino acid sequence of fragments of the polypeptide (MS/MS sequence). The mass spectrometer can be linked to an LC system, such as an HPLC system. Subsequent to protease digestion of the target cellular polypeptide, for example, after digestion with trypsin, the peptides are injected onto a reversed phase column and separated based on their hydrophobicity. Peptides desorbed from the column are eluted directly into the mass spectrometer. In the ion trap, the mass of the intact peptides is measured. Each peptide is then in turn isolated in the trap, and the collision energy is increased, which fragments the peptide, providing an MS/MS spectrum that represents the sequence of the peptide. The MS/MS spectra are subjected to search against a database (protein, DNA, or EST) to identify a peptide with the corresponding intact mass and fragment masses. Typically, protein identification software assigns a score for the match between the measured MS/MS mass spectrum and the theoretical peptide mass spectrum calculated from proteins in the database as described above. Other exemplary methods are described in U.S. Pat. No. 6,829,539 and U.S. Pat. No. 6,908,740. See also, for example, Lin et al., *J. Biomol. Techniques* 14:149-55 (2003); Tomlinson et al., *Rapid Commun. Mass Spectrom.* 17:909-16 (2003); Yi et al., *Rapid Commun. Mass Spectrom.* 17:2093-98 (2003)).

Other mass spectrometry methods that may be used for determining the identity of a target cellular polypeptide include matrix-assisted laser desorption ionization time-of-flight (MALDI-TOF), MALDI-TOF-MS. Procedures are available in the art for analyzing peptides from proteins that are subjected to protease digest and sodium dodecyl sulfate (SDS) gel electrophoresis (see, e.g., Egelhofer et al., *Anal. Chem.* 74:1760-71 (2002); Cohen et al., *Anal. Biochem.* 247:257-67 (1997); Cottrell et al., *Protein and peptide analysis by mass spectrometry*. C. J. R. Chapman. Totowa, N.J., Humana Press. 61:67-82 (1996); Fernandez et al., *Electrophoresis* 19:1036-45 (1998) Jensen et al., *Proteins Suppl.* 2: 74-79 (1998)). See also, for example, Andersen et al., *Nat. Biotechnol.* 14: 449-57 (1996); Chapman, *Protein and peptide analysis by mass spectrometry* C. J. R. Totowa, N.J., Humana Press. 61:9-28 (1996); Gillece-Castro et al., *Methods Enzymol.* 271: 427-48 (1996); Hillenkamp et al., *Methods Enzymol.* 193: 280-95 (1990); Katta et al., *Anal. Chem.* 70:4410-6 (1998); Patterson et al., *Anal. Chem.* 67:3971-78 (1995); Wang et al., *Protein and peptide analysis by mass spectrometry* J. R. Chapman. Totowa, N.J., Humana Press. 61:161-70 (1996); Oliver et al., *Methods Mol. Biol.* 61:295-309 (1996); Covey, *Methods Mol. Biol.* 61:83-99 (1996); Ducret et al., *Protein Sci.* 7:706-19 (1998); Fearnley et al., *Biochem. Soc. Trans.* 24:912-7 (1996); Yates, *Methods Enzymol.* 271:351-77 (1996)).

Additional methods known in the art for determining the amino acids sequence of a polypeptide or a peptide thereof may be used. Such methods include, for example, N-terminal group analysis using Edmund degradation that may be used in conjunction with aminopeptidase M cleavage; C-terminal analysis; and enzymatic C-terminal amino acid cleavage using any one of several carboxypeptidase enzymes (e.g., carboxypeptidase C, carboxypeptidase Y).

In certain embodiments, methods for identifying a cellular polypeptide to which a viral polypeptide (i.e., a viral virulence polypeptide that is a viral polypeptide that exhibits at least one virulence trait) interacts and which cellular polypeptide may be useful as a therapeutic target further comprise identifying a cell type that comprises the cellular polypeptide. A fusion protein comprising a viral polypeptide and an affinity tag can be contacted with a biological sample that comprises at least one cell, or a fraction of the cell or a supernatant of a cell, under conditions and for a time sufficient to permit the viral polypeptide moiety of the fusion protein to interact with the at least one cell, or the cell fraction or the cell supernatant. The level of binding of the fusion protein to the cell (or cell fraction or cell supernatant) can be determined, which indicates the presence or absence of binding of the fusion protein to the biological sample. The cell may then be isolated and characterized, thus identifying at least one cell type that comprises a cellular polypeptide to which the viral polypeptide binds. In certain embodiments, the affinity tag comprises a detectable moiety, for example, a fluorophore, a radionuclide, an enzyme, or biotin that is useful for isolating the fusion protein:cell complex and/or characterizing a cell type.

A biological sample, such as for example, blood, bone marrow, various tissue samples, may comprise different types of cells. A type of cell (or cell type) as referred to herein includes cells of different lineages, such as a hematopoietic cell and a neuronal cell, for example, and also refers to different types of cells that are more highly related, for example, the various types of immune cells (T cells, B cells, natural killer cells, macrophages, etc.). Types of cells may be distinguished and characterized according to cell surface antigen expression, morphology, response to stimuli and other features, which can be readily accomplished using standard reagents and methods (e.g., immunoassays, microscopy, and bioactivity assays).

In one embodiment, a method is provided for identifying a cellular polypeptide to which a viral virulence polypeptide binds that comprises contacting (mixing, combining, or in some manner permitting interaction, including expression of the fusion protein in the cell) a cell, or a fraction or a supernatant of the cell, and a fusion protein comprising a viral polypeptide (that has at least one virulence trait) fused to an affinity tag, under conditions and for a time sufficient that permit a viral polypeptide moiety of the fusion protein to interact with a polypeptide associated with the cell, or the fraction or the supernatant of the cell, to provide a fusion protein:cellular polypeptide complex. In certain embodiments, the affinity tag comprises at least a first polypeptide tag and a second polypeptide tag, and may further comprise at least one or two additional polypeptide tags, and also comprises at least one protease recognition sequence. The fusion protein:cellular polypeptide complex may then be isolated by contacting the fusion protein:cellular polypeptide complex and a first cognate ligand of the first polypeptide tag under conditions and for a time sufficient to permit the affinity tag moiety of the fusion protein to interact with the first cognate ligand to provide a first cognate ligand:fusion protein:cellular polypeptide complex. The first cognate ligand:fusion protein: cellular polypeptide complex may then be contacted, mixed, or combined with a protease capable of cleaving the fusion protein at or near the protease recognition sequence to provide a cleaved fusion protein:cellular polypeptide complex. In a subsequent step, the cleaved fusion protein:cellular polypeptide complex is contacted (mixed, combined, or in some manner permitted to interact) with a second cognate ligand that specifically binds to the second polypeptide tag, under conditions and for a time sufficient that permit the second cognate ligand and the cleaved fusion protein:cellular polypeptide complex to interact to form a second cognate ligand:cleaved fusion protein:cellular polypeptide complex. The cleaved fusion protein:cellular polypeptide complex may then be isolated from the second cognate ligand:cleaved fusion protein:cellular polypeptide complex, and the amino acid sequence of the cellular polypeptide or of at least one polypeptide fragment of the cellular polypeptide, wherein the at least one polypeptide fragment comprises at least eight amino acids (or at least 10, 12, 14, 16, 18, or 20 amino acids in length or longer) is determined.

Cellular Polypeptides and Agents

Also provided herein are cellular polypeptides that bind to viral polypeptides. As described herein a cellular polypeptide can be isolated according to a method comprising identifying in the genome of a virus, a polynucleotide sequence that encodes a viral polypeptide, which viral polypeptide exhibits at least one virulence trait as described herein, including comprising at least 40 amino acids (which may include a signal peptide sequence. In certain embodiments, a fusion protein comprising the viral polypeptide fused or in some manner attached to an affinity tag sequence is produced and then contacted with a cell, or a fraction of the cell or a supernatant of the cell, under conditions and for a time sufficient that permit the viral polypeptide moiety of the fusion protein to interact with a polypeptide present in the cell, or the fraction of the cell or the supernatant of the cell, to provide a fusion protein:cellular polypeptide complex. As described in detail herein the fusion protein:cellular polypeptide complex is isolated and the amino acid sequence of the cellular polypeptide or of at least one fragment of the polypeptide, wherein the fragment comprises at least eight amino acids (or at least 10, 12, 14, 16, 18, or 20 amino acids in length or longer) is determined according to the methods described herein. As described herein, the viral polypeptide may be encoded by the genome (RNA or DNA) of a virus, including large DNA genome viruses, such as poxviruses, adenoviruses, and herpesviruses, and including the genome of any other virus described herein or known in the art or a genome that becomes known or available.

Cellular polypeptides that are identified by the methods described herein include but are not limited to cell surface antigens, cell surface receptors, cytokines, chemokines, cytokine or chemokine binding proteins, intracellular signaling polypeptides, or substrates of cell surface receptors or signaling molecules. Exemplary cellular polypeptides that bind to a viral polypeptide include receptor-like protein tyrosine phosphatases (RPTP) (e.g., leukocyte common antigen related protein (LAR), RPTP-σ, and RPTP-δ) (see, e.g., U.S. Pat. No. 6,852,486; International Patent Application Publication WO 98/37217; Ng et al., *J. Gen. Virol.* 82:2095-105 (2001); U.S. Ser. No. 60/721,876). The viral polypeptide A41L that binds to the RPTPs is present in several different poxviruses, including Cowpox virus (CPV), vaccinia virus (strains Copenhagen, Ankara, Tian Tan and WR) and variola virus (including strains Harvey, India-1967 and Garcia-1966). Binding of A41L to LAR, RPTP-δ, and/or RPTP-σ alters at least one biological function of these phosphatases, and as described herein the interaction between A41L and LAR, RPTP-δ, and/or RPTP-σ expressed on the cell surface of an immune cell alters (e.g., suppresses or enhances) the immunoresponsiveness of the cell.

Alteration of a biological activity of a cell as a result of the interaction between a viral polypeptide and a cellular polypeptide (for example, interaction between the viral polypeptide A41L and a cellular RPTP, which alters the immunoresponsiveness of an immune cell) may also be effected by a bioactive agent (compound or molecule) in a manner similar to the viral polypeptide. Bioactive agents include, for example, small molecules, nucleic acids (such as aptamers, siRNAs, antisense nucleic acids), antibodies and fragments thereof, and fusion proteins (such as peptide-Fc fusion proteins and cell polypeptide domains or fragments (at least 8, 10, 12, 14, 16, 18, 20, 25, or 30 amino acids) that are fused to other moieties such as an immunoglobulin Fc polypeptide). An agent may interact with and bind to at least one cellular polypeptide at a location on the cellular polypeptide that is the same location or proximal to the same location as where the viral polypeptide binds. Alternatively, alteration of at least one biological function by an agent in a manner similar to the effect of a viral polypeptide may result from binding or interaction of the agent with the cellular polypeptide at a location distal from that at which the viral polypeptide binds. Binding studies, including competitive binding assays, and functional assays, which indicate the level of immunoresponsiveness of a cell, may be performed according to methods described herein and practiced in the art to determine and compare the capability and level with which an agent binds to and affects the immunoresponsiveness of an immune cell.

Provided herein are methods for identifying an agent for treating a disease or disorder, such as a cardiovascular disease or disorder, metabolic disease or disorder, or proliferative disease or disorder, or immunological disease or disorder. An agent that is useful for treating such diseases or disorders is capable of altering at least one biological function of a cellular polypeptide. The method comprises contacting (i.e., mixing, combining, or in some manner permitting interaction) among (i) the cellular polypeptide, or a cell comprising the cellular polypeptide, or a cell supernatant or cell fraction; (ii) the viral polypeptide (i.e., a viral polypeptide that is a viral virulence polypeptide and that exhibits at least one virulence trait as described herein); (iii) and a candidate agent, under conditions and for a time sufficient that permit the cellular polypeptide and the viral polypeptide to interact. The cellular polypeptide, or a cell supernatant or cell fraction comprising the cellular polypeptide is contacted (i.e., combined etc.) in a reaction vessel with and without the candidate agent. The level of binding of the cellular polypeptide to the viral polypeptide in the presence of the candidate agent (a first level of binding) is then determined and compared with the level of binding of the cellular polypeptide to the viral polypeptide in the absence of the candidate agent (a second level of binding) according to methods routinely practiced by persons skilled in the art and described herein. The level of binding of the viral polypeptide and cellular polypeptide without a candidate agent may be determined at the same time as the level of binding in the presence of the agent, or the level of binding of the viral polypeptide and cellular polypeptide in the absence of the candidate agent may be historically determined. A decrease in the level of binding of the viral polypeptide to the cellular polypeptide in the presence of the candidate agent compared to the level of binding of the viral polypeptide to the cellular polypeptide in the absence of the candidate agent indicates that the agent inhibits (partially or in total) binding of the viral polypeptide to the cellular polypeptide, thus identifying an agent that is useful for treating the disease or disorder. Binding of the agent to the cellular polypeptide thus affects at least one or more of the biological functions (e.g., the immunoresponsiveness of an immune cell) of the cellular polypeptide that is affected by binding of the viral polypeptide to the cellular polypeptide. Methods for identifying such an agent include any additional appropriate controls with which a person skilled in the art is familiar.

In a specific embodiment, a method is provided for identifying an agent for treating an immunological disease or disorder, comprising identifying a cellular polypeptide to which a viral polypeptide binds according to the methods described herein, wherein interaction between the cellular polypeptide and the viral polypeptide (i.e., a viral polypeptide that is a viral virulence polypeptide and that exhibits at least one virulence trait as described herein) alters (i.e., increases or decreases in a statistically significant or biologically significant manner) immunoresponsiveness of an immune cell. The method comprises contacting (i.e., mixing, combining, or in some manner permitting interaction) among (i) the cellular polypeptide, or a cell comprising the cellular polypeptide, or a cell supernatant or cell fraction; (ii) the viral polypeptide; (iii) and a candidate agent, under conditions and for a time sufficient that permit the cellular polypeptide and the viral polypeptide to interact. As described above, the level of binding of the viral polypeptide to the cellular polypeptide in the presence of the candidate agent is compared to a level of binding of the viral polypeptide to the cellular polypeptide in the absence of the candidate agent. If the level of binding of the viral polypeptide to the cellular polypeptide in the presence of the candidate agent is decreased compared with the level of binding of the of the viral polypeptide to the cellular polypeptide in the absence of the agent, the agent may be useful for treating an immunological disease or disorder. A candidate agent that inhibits (or prevents, reduces, minimizes, or abrogates) binding of the viral polypeptide to the cellular polypeptide may mimic or act in the same manner as the viral polypeptide, and thus affect at least one biological activity of the cellular polypeptide. Such a biological activity includes but is not limited to, altering immunoresponsiveness of an immune cell (e.g., in certain embodiments, to suppress the immunoresponsiveness of the immune cell and in certain other embodiments, to enhance immunoresponsiveness of the immune cell) that comprises the cellular polypeptide. Accordingly, such an agent is useful for treating an immunological disease or disorder.

Immunoresponsiveness may be determined according to methods practiced by a person skilled in the art such as measuring levels of cytokines, proliferation, and stimulation. Immunoresponsiveness of an immune cell may also be determined by evaluating changes in cell adhesion and cell migration and by examining the tyrosine phosphorylation pattern of cellular proteins, including but not limited to cytoskeletal proteins and other proteins that affect cell adhesion and migration.

The agents described herein may be useful for treating or preventing, inhibiting, slowing the progression of, or reducing the symptoms associated with, an immunological disease or disorder, a cardiovascular disease or disorder, a metabolic disease or disorder, or a proliferative disease or disorder. An immunological disorder includes an inflammatory disease or disorder and an autoimmune disease or disorder. While inflammation or an inflammatory response is a host's normal and protective response to an injury, inflammation can cause undesired damage. For example, atherosclerosis is, at least in part, a pathological response to arterial injury and the consequent inflammatory cascade.

An agent or cellular polypeptide (or fragment thereof) is useful for treating a subject who has or who is suspected of having a disorder or disease as described herein, such as an immunological disease or disorder. A subject in need of such treatment may be a human or may be a non-human primate or other animal (i.e., veterinary use) who has developed symptoms of an immunological disease or who is at risk for developing an immunological disease. Examples of non-human primates and other animals include but are not limited to farm animals, pets, and zoo animals (e.g., horses, cows, buffalo, llamas, goats, rabbits, cats, dogs, chimpanzees, orangutans, gorillas, monkeys, elephants, bears, large cats, etc.).

Examples of immunological disorders that may be treated with an antibody or antigen-binding fragment thereof described herein include but are not limited to multiple sclerosis, rheumatoid arthritis, systemic lupus erythematosus (SLE), graft versus host disease (GVHD), sepsis, diabetes, psoriasis, atherosclerosis, Sjogren's syndrome, progressive systemic sclerosis, scleroderma, acute coronary syndrome, ischemic reperfusion, Crohn's Disease, endometriosis, glomerulonephritis, myasthenia gravis, idiopathic pulmonary fibrosis, asthma, acute respiratory distress syndrome (ARDS), vasculitis, or inflammatory autoimmune myositis and other inflammatory and muscle degenerative diseases (e.g., dermatomyositis, polymyositis, juvenile dermatomyositis, inclusion body myositis). ARDS, which may develop in adults and in children, often follows a direct pulmonary or systemic insult (for example, sepsis, pneumonia, aspiration) that injures the alveolar-capillary unit. Several cytokines are associated with development of the syndrome, including, for example, tumor necrosis factor-alpha (TNF-$\alpha$), interleukin-beta (IL-$\beta$), IL-10, and soluble intercellular adhesion molecule 1 (sICAM-1). The increased or decreased level of these factors and cytokines in a biological sample may be readily determined by methods and assays described herein and practiced routinely in the art to monitor the acute state and to monitor the effect of treatment.

A cardiovascular disease or disorder that may be treated, which may include a disease and disorder that is also considered an immunological disease/disorder, includes for example, atherosclerosis, endocarditis, hypertension, or peripheral ischemic disease. A metabolic disease or disorder includes diabetes, obesity, and diseases and disorders associated with abnormal or altered mitochondrial function.

As described herein an agent may be a compound referred to as a small molecule. A small molecule agent may be provided as a member of a "library" or collection of compounds, compositions, or molecules. Small molecules typically have molecular weights less than $10^5$ daltons, less than $10^4$ daltons, or less than $10^3$ daltons. For example, members of a library of test compounds can be administered to a plurality of samples, each containing at least one cellular polypeptide or source of a cellular polypeptide as provided herein, and then the samples are assayed for their capability to enhance or inhibit a biological activity of the cellular polypeptide or for the capability to inhibit or enhance interaction between a viral polypeptide and a cellular polypeptide.

A bioactive agent that is used for altering the biological function of a cell, such as immunoresponsiveness of an immune cell, and that may be used for treating a disease or disorder is a peptide-immunoglobulin (Ig) constant region fusion polypeptide, which includes a peptide-IgFc fusion polypeptide. The peptide may be any naturally occurring or recombinantly prepared molecule. A peptide-Ig constant region fusion polypeptide, such as a peptide-IgFc fusion polypeptide (also referred to in the art as a peptibody (see, e.g., U.S. Pat. No. 6,660,843)), comprises a biologically active peptide or polypeptide capable of altering the activity of a protein of interest. The Fc polypeptide may also be a mutein Fc polypeptide as described herein. Peptides that alter a biological function of a cell, such as the immunoresponsiveness of an immune cell, may be identified and isolated from combinatorial libraries (see, e.g., International Patent Application Nos. PCT/US91/08694 and PCT/US91/04666) and from phage display peptide libraries (see, e.g., Scott et al., Science 249:386 (1990); Devlin et al., Science 249:404 (1990); Cwirla et al., Science 276: 1696-99 (1997); U.S. Pat. No. 5,223,409; U.S. Pat. No. 5,733,731; U.S. Pat. No. 5,498, 530; U.S. Pat. No. 5,432,018; U.S. Pat. No. 5,338,665; 1994; U.S. Pat. No. 5,922,545; International Application Publication Nos. WO 96/40987 and WO 98/15833).

In certain embodiments, polynucleotides and oligonucleotides are provided that are complementary to at least a portion of a sequence encoding a cellular polypeptide of interest (e.g., a short interfering nucleic acid, an antisense polynucleotide, a ribozyme, or a peptide nucleic acid) and that may be used to alter gene and/or protein expression. As described herein, these polynucleotides that specifically bind to or hybridize to nucleic acid molecules that encode a cellular polypeptide may be prepared using the nucleotide sequences available in the art. In another embodiment, nucleic acid molecules such as aptamers that are not sequence-specific may also be used to alter gene and/or protein expression.

Antisense polynucleotides bind in a sequence-specific manner to nucleic acids such as mRNA or DNA. Identification of oligonucleotides and ribozymes for use as antisense agents and identification of DNA encoding the genes for targeted delivery involve methods well known in the art. For example, the desirable properties, lengths, and other characteristics of such oligonucleotides are well known. Antisense technology can be used to control gene expression through interference with binding of polymerases, transcription factors, or other regulatory molecules (see Gee et al., In Huber and Carr, *Molecular and Immunologic Approaches*, Futura Publishing Co. (Mt. Kisco, N.Y.; 1994)).

Short interfering RNAs may be used for modulating (decreasing or inhibiting) the expression of a gene encoding a cellular polypeptide of interest. The disclosure herein relates to compounds, compositions, and methods useful for modulating the expression and activity of genes by RNA interference using small nucleic acid molecules. In particular, small nucleic acid molecules, such as short interfering RNA (siRNA), micro-RNA (miRNA), and short hairpin RNA (shRNA) molecules may be used according to the methods described herein to modulate the expression of a cellular polypeptide of interest. A siRNA polynucleotide preferably comprises a double-stranded RNA (dsRNA) but may comprise a single-stranded RNA (see, e.g., Martinez et al. *Cell* 110:563-74 (2002)). A siRNA polynucleotide may comprise other naturally occurring, recombinant, or synthetic single-stranded or double-stranded polymers of nucleotides (ribonucleotides or deoxyribonucleotides or a combination of both) and/or nucleotide analogues as provided herein and known and used by persons skilled in the art.

At least one strand of a double-stranded siRNA polynucleotide has at least one, and preferably two nucleotides that "overhang" (i.e., that do not base pair with a complementary base in the opposing strand) at the 3' end of either strand, or preferably both strands, of the siRNA polynucleotide. Typically, each strand of the siRNA polynucleotide duplex has a two-nucleotide overhang at the 3' end. The two-nucleotide overhang may be a thymidine dinucleotide (TT) or may comprise other bases, for example, a TC dinucleotide or a TG dinucleotide, or any other dinucleotide (see, e.g., International Patent Application Publication No. WO 01/75164). Alternatively, the siRNA polynucleotide may have blunt ends, that is, each nucleotide in one strand of the duplex is perfectly complementary (e.g., by Watson-Crick base-pairing) with a nucleotide of the opposite strand.

In another embodiment, peptide nucleic acids (PNAs) can be prepared by modifying the deoxyribose phosphate backbone of a polynucleotide (or a portion thereof) that encodes a cellular polypeptide of interest (see, e.g., Hyrup B. et al., *Bioorganic & Medicinal Chemistry* 4:5-23) (1996)). The terms "peptide nucleic acid" or "PNA" refers to a nucleic acid mimic, for example, a DNA mimic, in which the deoxyribose phosphate backbone is replaced by a pseudopeptide backbone wherein only the four natural nucleobases are retained. The neutral backbone of a PNA has been shown to allow for specific hybridization to DNA and RNA under conditions of low ionic strength. The synthesis of PNA oligomers can be performed using standard solid phase peptide synthesis protocols (see, e.g., Hyrup B., supra; Perry-O'Keefe et al., *Proc. Natl. Acad. Sci. USA* 93:14670-75 (1996)). A PNA molecule that is specific for a cellular polypeptide can be used as an antisense or anti-gene agent for sequence-specific modulation of gene expression for example, by inducing transcription or translation arrest or by inhibiting replication.

Aptamers are DNA or RNA molecules, generally single-stranded, that have been selected from random pools based on their ability to bind other molecules, including nucleic acids, proteins, lipids, etc. Unlike antisense polynucleotides, short interfering RNA (siRNA), or ribozymes that bind to a polynucleotide that comprises a sequence that encodes a polypeptide of interest and that alter transcription or translation, aptamers can target and bind to polypeptides. Aptamers may be selected from random or unmodified oligonucleotide libraries by their ability to bind to specific targets (see, e.g., U.S. Pat. No. 6,867,289; U.S. Pat. No. 5,567,588). Aptamers have capacity to form a variety of two- and three-dimensional structures and have sufficient chemical versatility available within their monomers to act as ligands (i.e., to form specific binding pairs) with virtually any chemical compound, whether monomeric or polymeric. Molecules of any size or composition can serve as targets. An iterative process of in vitro selection may be used to enrich the library for species with high affinity to the target. This process involves repetitive cycles of incubation of the library with a desired target, separation of free oligonucleotides from those bound to the target, and amplification of the bound oligonucleotide subset, such as by using the polymerase chain reaction (PCR). From the selected sub-population of sequences that have high affinity for the target, a sub-population may be subcloned and particular aptamers examined in further detail to identify aptamers that alter a biological function of the target (see, e.g., U.S. Pat. No. 6,699,843).

Aptamers may comprise any deoxyribonucleotide or ribonucleotide or modifications of these bases, such as deoxythiophosphate (or phosphorothioate), which have sulfur in place of oxygen as one of the non-bridging ligands bound to the phosphorus. Monothiophosphates αS have one sulfur atom and are thus chiral around the phosphorus center. Dithiophosphates are substituted at both oxygens and are thus achiral. Phosphorothioate nucleotides are commercially available or can be synthesized by several different methods known in the art.

An agent includes an antibody, or antigen binding fragment thereof, that specifically binds to a cellular polypeptide of interest. These specific antibodies may be polyclonal or monoclonal, prepared by immunization of animals and subsequent isolation of the antibody, or the antibodies may be recombinant antibodies.

As used herein, an antibody is said to be "immunospecific," "specific for" or to "specifically bind" to a cellular polypeptide of interest if it reacts at a detectable level with the cellular polypeptide, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ M$^{-1}$. Affinity of an antibody for its cognate antigen is also commonly expressed as a dissociation constant $K_D$, and an anti-cellular polypeptide antibody specifically binds to a cellular polypeptide if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M. These definitions are also applicable to other antigen-antibody interactions described herein, for example, polypeptide tags and their cognate ligands.

Affinities of binding partners or antibodies can be readily determined using conventional techniques, for example, those described by Scatchard et al. (*Ann. N.Y. Acad. Sci. USA* 51:660 (1949)) and by surface plasmon resonance (SPR; BIAcore™, Biosensor, Piscataway, N.J.). For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the surface plasmon resonance signal can be analyzed to yield apparent rate constants for the association and dissociation phases of the binding reaction. The ratio of these values gives the apparent equilibrium constant (affinity) (see, e.g., Wolff et al., *Cancer Res.* 53:2560-2565 (1993)).

Binding properties of an antibody to a cellular polypeptide described herein may generally be determined and assessed using immunodetection methods including, for example, an enzyme-linked immunosorbent assay (ELISA), immunoprecipitation, immunoblotting, countercurrent immunoelectrophoresis, radioimmunoassays, dot blot assays, inhibition or competition assays, and the like, which may be readily performed by those having ordinary skill in the art (see, e.g., U.S. Pat. Nos. 4,376,110 and 4,486,530; Harlow et al., *Antibodies: A Laboratory Manual*, Cold Spring Harbor Laboratory (1988)). Immunoassay methods may include controls and procedures to determine whether antibodies bind specifically to the cellular polypeptide and do not recognize or cross-react with other cellular polypeptides.

An antibody according may belong to any immunoglobulin class, for example IgG, IgE, IgM, IgD, or IgA. It may be obtained from or derived from an animal, for example, fowl (e.g., chicken) and mammals, which include but are not limited to a mouse, rat, hamster, rabbit, or other rodent, a cow, horse, sheep, goat, camel, human, or other primate. The antibody may be an internalising antibody. In one such technique, an animal is immunized with a cellular polypeptide or fragment thereof (at least 6 amino acids) as described herein as an antigen to generate polyclonal antisera. Suitable animals include, for example, rabbits, sheep, goats, pigs, cattle, and may also include smaller mammalian species, such as mice, rats, and hamsters, or other species.

Antibodies may generally be prepared by any of a variety of techniques known to persons having ordinary skill in the art. See, e.g., Harlow et al., *Antibodies: A Laboratory Manual*, Cold Spring Harbor Laboratory (1988); Peterson, *ILAR J.* 46:314-19 (2005)). Polyclonal antibodies that bind specifically to a cellular polypeptide can be prepared using methods described and practiced by persons skilled in the art (see, for example, Green et al., "Production of Polyclonal Antisera," in *Immunochemical Protocols* (Manson, ed.), pages 1-5 (Humana Press 1992); Harlow et al., *Antibodies: A Laboratory Manual*, Cold Spring Harbor Laboratory (1988); Williams et al., "Expression of foreign proteins in *E. coli* using plasmid vectors and purification of specific polyclonal antibodies," in *DNA Cloning 2: Expression Systems, 2nd Edition*, Glover et al. (eds.), page 15 (Oxford University Press 1995)). Although polyclonal antibodies are typically raised in animals such as rats, mice, rabbits, goats, cattle, or sheep, an anti-cellular polypeptide antibody may also be obtained from a subhuman primate. General techniques for raising diagnostically and therapeutically useful antibodies in baboons may be found, for example, in International Patent Application Publication No. WO 91/11465 (1991) and in Losman et al., *Int. J. Cancer* 46:310, 1990.

Monoclonal antibodies that specifically bind to a cellular polypeptide of interest and hybridomas, which are examples of immortal eukaryotic cell lines, that produce monoclonal antibodies having the desired binding specificity, may also be prepared, for example, using the technique of Kohler and Milstein (*Nature*, 256:495-97 (1976), *Eur. J. Immunol.* 6:511-19 (1975)) and improvements thereto (see, e.g., Coligan et al. (eds.), *Current Protocols in Immunology*, 1:2.5.1-2.6.7 (John Wiley & Sons 1991); U.S. Pat. Nos. 4,902,614, 4,543,439, and 4,411,993; *Monoclonal Antibodies, Hybridomas: A New Dimension in Biological Analyses*, Plenum Press, Kennett et al. (eds.) (1980); and *Antibodies: A Laboratory Manual*, Harlow and Lane (eds.), Cold Spring Harbor Laboratory Press (1988); see also, e.g., Brand et al., *Planta Med.* 70:986-92 (2004); Pasqualini et al., *Proc. Natl. Acad. Sci. USA* 101:257-59 (2004)). An animal, for example, a rat, hamster, or more commonly, a mouse, is immunized with a cellular polypeptide immunogen prepared according to methods practiced in the art. The presence of specific antibody production may be monitored after the initial injection (injections may be administered by any one of several routes as described herein for generation of polyclonal antibodies) and/or after a booster injection by obtaining a serum sample and detecting the presence of an antibody that binds to the cellular polypeptide using any one of several immunodetection methods known in the art and described herein.

An antibody that specifically binds to a cellular polypeptide may be a human monoclonal antibody. Human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes) (see, e.g., U.S. Pat. No. 4,464,456; see also, e.g., Glasky et al., *Hybridoma* 8:377-89 (1989)); in vitro immunization of human B cells (see, e.g., Boerner et al., *J. Immunol.* 147:86-95 (1991)); fusion of spleen cells from immunized transgenic mice carrying inserted human immunoglobulin genes (see, e.g., Green et al., *Nature Genet.* 7:13 (1994); Lonberg et al., *Nature* 368:856 (1994); Taylor et al., *Int. Immun.* 6:579 (1994); U.S. Pat. No. 5,877,397; Bruggemann et al., *Curr. Opin. Biolechnol.* 8:455-58 (1997); Jakobovits et al., *Ann. N.Y. Acad. Sci.* 764:525-35 (1995)); isolation from human immunoglobulin V region phage libraries; cloning the light chain and heavy chain variable regions from a B cell that is producing an anti-cellular polypeptide antibody (WO 92/02551; U.S. Pat. No. 5,627,052; Babcook et al., *Proc. Natl. Acad. Sci. USA* 93:7843-48 (1996)); or other procedures as known in the art and based on the disclosure herein.

Chimeric antibodies, specific for a cellular polypeptide of interest, including humanized antibodies, may also be generated according to the present invention. A chimeric antibody has at least one constant region domain derived from a first mammalian species and at least one variable region domain derived from a second, distinct mammalian species. See, e.g., Morrison et al., *Proc. Natl. Acad. Sci. USA*, 81:6851-55 (1984). In one embodiment, a chimeric antibody may be constructed by cloning the polynucleotide sequence that encodes at least one variable region domain derived from a non-human monoclonal antibody, such as the variable region derived from a murine, rat, or hamster monoclonal antibody, into a vector containing a nucleic acid sequence that encodes at least one human constant region (see, e.g., Shin et al., *Methods Enzymol.* 178:459-76 (1989); Walls et al., *Nucleic Acids Res.* 21:2921-29 (1993)).

A non-human/human chimeric antibody may be further genetically engineered to create a "humanized" antibody. Such a humanized antibody may comprise a plurality of CDRs derived from an immunoglobulin of a nonhuman mammalian species, at least one human variable framework region, and at least one human immunoglobulin constant region. Useful strategies for designing humanized antibodies may therefore include, for example by way of illustration and not limitation, identification of human variable framework regions that are most homologous to the non-human framework regions of the chimeric antibody (see, e.g., Jones et al., *Nature* 321:522-25 (1986); Riechmann et al., *Nature* 332:323-27 (1988)).

Designing a humanized antibody may therefore include determining CDR loop conformations and structural determinants of the non-human variable regions, for example, by computer modeling, and then comparing the CDR loops and determinants to known human CDR loop structures and determinants (see, e.g., Padlan et al., *FASEB* 9:133-39 (1995); Chothia et al., *Nature,* 342:377-83 (1989)). Computer modeling may also be used to compare human structural templates selected by sequence homology with the non-human variable regions (see, e.g., Bajorath et al., *Ther. Immunol.* 2:95-103 (1995); EP-0578515-A3; Davies et al., *Ann. Rev. Biochem.* 59:439-73, (1990)). If humanization of the non-human CDRs results in a decrease in binding affinity, computer modeling may aid in identifying specific amino acid residues that could be changed by site-directed or other mutagenesis techniques to partially, completely, or supra-optimally (i.e., increase to a level greater than that of the non-humanized antibody) restore affinity. Those having ordinary skill in the art are familiar with these techniques and will readily appreciate numerous variations and modifications to such design strategies.

For particular uses, antigen-binding fragments of antibodies may be desired. Antibody fragments, $F(ab')_2$, Fab, Fab', Fv, and Fd, can be obtained, for example, by proteolytic hydrolysis of the antibody, for example, pepsin or papain digestion of whole antibodies according to conventional methods. As an illustration, antibody fragments can be produced by enzymatic cleavage of antibodies with pepsin to provide a fragment denoted $F(ab')_2$. This fragment can be further cleaved using a thiol reducing agent to produce an Fab' monovalent fragment. Optionally, the cleavage reaction can be performed using a blocking group for the sulfhydryl groups that result from cleavage of disulfide linkages. As an alternative, an enzymatic cleavage of an antibody using papain produces two monovalent Fab fragments and an Fc fragment (see, e.g., U.S. Pat. No. 4,331,647; Nisonoff et al., *Arch. Biochem. Biophys.* 89:230 (1960); Porter, *Biochem. J.* 73:119 (1959); Edelman et al., in *Methods in Enzymology* 1:422 (Academic Press 1967); Weir, *Handhook of Experimental Immunology*, Blackwell Scientific, Boston (1986)). The antigen binding fragments may be separated from the Fc fragments by affinity chromatography, for example, using immobilized protein A, protein G, an Fc specific antibody, or immobilized cellular polypeptide or a fragment thereof. Other methods for cleaving antibodies, such as separating heavy chains to form monovalent light-heavy chain fragments (Fd), further cleaving of fragments, or other enzymatic, chemical, or genetic techniques may also be used, so long as the fragments bind to the cellular polypeptide that is recognized by the intact antibody.

An antibody fragment may also be any synthetic or genetically engineered protein that acts like an antibody in that it binds to a specific antigen to form a complex. For example, antibody fragments include isolated fragments consisting of the light chain variable region, Fv fragments consisting of the variable regions of the heavy and light chains, recombinant single chain polypeptide molecules in which light and heavy variable regions are connected by a peptide linker (scFv proteins), and minimal recognition units consisting of the amino acid residues that mimic the hypervariable region. The antibody of the present invention preferably comprises at least one variable region domain. The variable region domain may be of any size or amino acid composition and will generally comprise at least one hypervariable amino acid sequence responsible for antigen binding and which is adjacent to or in frame with one or more framework sequences. In general terms, the variable (V) region domain may be any suitable arrangement of immuoglobulin heavy ($V_H$) and/or light ($V_L$) chain variable domains. Thus, for example, the V region domain may be monomeric and be a $V_H$ or $V_L$ domain, which is capable of independently binding antigen with acceptable affinity. Alternatively, the V region domain may be dimeric and contain $V_H$-$V_H$, $V_H$-$V_L$, or $V_L$-$V_L$, dimers. Preferably, the V region dimer comprises at least one $V_H$ and at least one $V_L$ chain that are non-covalently associated (hereinafter referred to as $F_v$). If desired, the chains may be covalently coupled either directly, for example via a disulfide bond between the two variable domains, or through a linker, for example a peptide linker, to form a single chain Fv ($scF_v$).

A minimal recognition unit is an antibody fragment comprising a single complementarity-determining region (CDR). Such CDR peptides can be obtained by constructing polynucleotides that encode the CDR of an antibody of interest. The polynucleotides are prepared, for example, by using the polymerase chain reaction to synthesize the variable region using mRNA isolated from or contained within antibody-producing cells as a template according to methods practiced by persons skilled in the art (see, for example, Larrick et al., *Methods: A Companion to Methods in Enzymology* 2:106, (1991); Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995); and Ward et al., "Genetic Manipulation and Expression of Antibodies," in *Monoclonal Antibodies: Principles and Applications*, Birch et al., (eds.), page 137 (Wiley-Liss, Inc. 1995)). Alternatively, such CDR peptides and other antibody fragment can be synthesized using an automated peptide synthesizer.

According to certain embodiments, non-human, human, or humanized heavy chain and light chain variable regions of any of the Ig molecules described herein may be constructed as scFv polypeptide fragments (single chain antibodies). See, e.g., Bird et al., *Science* 242:423-426 (1988); Huston et al., *Proc. Natl. Acad. Sci. USA* 85:5879-83 (1988)). Multi-functional scFv fusion proteins may be generated by linking a polynucleotide sequence encoding an scFv polypeptide in-frame with at least one polynucleotide sequence encoding any of a variety of known effector proteins. These methods are known in the art, and are disclosed, for example, in EP-B1-0318554, U.S. Pat. No. 5,132,405, U.S. Pat. No. 5,091,513, and U.S. Pat. No. 5,476,786. By way of example, effector proteins may include immunoglobulin constant region sequences. See, e.g., Hollenbaugh et al., *J. Immunol. Methods* 188:1-7 (1995). Other examples of effector proteins are enzymes. As a non-limiting example, such an enzyme may provide a biological activity for therapeutic purposes (see, e.g., Siemers et al., *Bioconjug. Chem.* 8:510-19 (1997)), or may provide a detectable activity, such as horseradish peroxidase-catalyzed conversion of any of a number of well-known substrates into a detectable product, for diagnostic uses.

Antibodies may also be identified and isolated from human immunoglobulin phage libraries, from rabbit immunoglobulin phage libraries, from mouse immunoglobulin phage libraries, and/or from chicken immunoglobulin phage libraries (see, e.g., Winter et al., *Annu. Rev. Immunol.* 12:433-55 (1994); Burton et al., *Adv. Immunol.* 57:191-280 (1994); U.S. Pat. No. 5,223,409; Huse et al., *Science* 246:1275-81 (1989); Schlebusch et al., *Hybridoma* 16:47-52 (1997) and references cited therein; Rader et al., *J. Biol. Chem.* 275:13668-76 (2000); Popkov et al., *J. Mol. Biol.* 325:325-35 (2003); Andris-Widhopf et al., *J. Immunol. Methods* 242:159-31 (2000)). Antibodies isolated from non-human species or non-human immunoglobulin libraries may be genetically engineered according to methods described herein and known in the art to "humanize" the antibody or fragment thereof. Immunoglobulin variable region gene combinatorial libraries may be created in phage vectors that can be screened to select Ig fragments (Fab, Fv, scFv, or multimers thereof) that bind specifically to a cellular polypeptide of interest (see, e.g., U.S. Pat. No. 5,223,409; Huse et al., *Science* 246:1275-81 (1989); Sastry et al., *Proc. Natl. Acad. Sci. USA* 86:5728-32 (1989); Alting-Mees et al., *Strategies in Molecular Biology* 3:1-9 (1990); Kang et al., *Proc. Natl. Acad. Sci. USA* 88:4363-66 (1991); Hoogenboom et al., *J. Molec. Biol.* 227:381-388 (1992); Schlebusch et al., *Hybridoma* 16:47-52 (1997) and references cited therein; U.S. Pat. No. 6,703,015).

In certain other embodiments, cellular polypeptide-specific antibodies are multimeric antibody fragments. Useful methodologies are described generally, for example in Hayden et al., *Curr Opin. Immunol.* 9:201-12 (1997) and Coloma et al., *Nat. Biotechnol.* 15:159-63 (1997). For example, multimeric antibody fragments may be created by phage techniques to form miniantibodies (U.S. Pat. No. 5,910,573) or diabodies (Holliger et al., *Cancer Immunol. Immunother.* 45:128-30 (1997)). Multimeric fragments may be generated that are multimers of a cellular polypeptide-specific Fv. Multimeric antibodies include bispecific and bifunctional antibodies comprising a first Fv specific for an antigen associated with a second Fv having a different antigen specificity (see, e.g., Drakeman et al., *Expert Opin. Investig. Drugs* 6:1169-78 (1997); Koelemij et al., *J. Immunother.* 22:514-24 (1999); Marvin et al., *Acta Phammacol. Sin.* 26:649-58 (2005); Das et al., *Methods Mol. Med.* 109:329-46 (2005)).

A minimal recognition unit is an antibody fragment comprising a single complementarity-determining region (CDR). Such CDR peptides can be obtained by constructing polynucleotides that encode the CDR of an antibody of interest. The polynucleotides are prepared, for example, by using the polymerase chain reaction to synthesize the variable region using mRNA isolated from or contained within antibody-producing cells as a template according to methods practiced by persons skilled in the art (see, for example, Larrick et al., *Methods: A Companion to Methods in Enzymology* 2:106, (1991); Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995); and Ward et al., "Genetic Manipulation and Expression of Antibodies," in *Monoclonal Antibodies: Principles and Applications*, Birch et al., (eds.), page 137 (Wiley-Liss, Inc. 1995)). Alternatively, such CDR peptides and other antibody fragment can be synthesized using an automated peptide synthesizer.

In other embodiments, a minimal recognition unit may be identified from a peptide library. Such peptides may be identified and isolated from combinatorial libraries (see, e.g., International Patent Application Nos. PCT/US91/08694 and PCT/US91/04666) and from phage display peptide libraries (see, e.g., Scott et al., *Science* 249:386 (1990); Devlin et al., *Science* 249:404 (1990); Cwirla et al., *Science* 276: 1696-99 (1997); U.S. Pat. No. 5,223,409; U.S. Pat. No. 5,733,731; U.S. Pat. No. 5,498,530; U.S. Pat. No. 5,432,018; U.S. Pat. No. 5,338,665; 1994; U.S. Pat. No. 5,922,545; International Application Publication Nos. WO 96/40987 and WO 98/15833). In phage display peptide libraries, random peptide sequences are fused to a phage coat protein such that the peptides are displayed on the external surface of a filamentous phage particle.

A peptide that is a minimal recognition unit or a CDR (i.e., any one or more of three CDRs present in a heavy chain variable region and/or one or more of three CDRs present in a light chain variable region) may be identified by computer modeling techniques, which can be used for comparing and predicting a peptide sequence that will specifically bind to a cellular polypeptide as described herein (see, e.g., Bradley et al., *Science* 309:1868 (2005); Schueler-Furman et al., *Science* 310:638 (2005)). Such computer-assisted predictive modeling techniques may also be useful for altering the binding affinity of an antibody that binds to a cellular polypeptide. By comparing the predicted three-dimensional structure of a minimal recognition unit and/or of one or more CDRs with the predicted three-dimensional structure of a viral polypeptide that specifically binds the cellular polypeptide, the modeling techniques provide a method to identify residues within the minimal recognition unit and/or of one or more CDRs that can be substituted and that will more closely approximate the binding interaction between the cellular polypeptide and the viral polypeptide. Amino acid substitutions may be readily accomplished using any one of a number of mutagenesis techniques described herein and used routinely in the art for making polynucleotide and polypeptide variants.

In certain embodiments, anti-idiotype antibodies that recognize and bind specifically to an antibody (or antigen-binding fragment thereof) that specifically binds to a cellular polypeptide of interest are provided. Anti-idiotype antibodies may be generated as polyclonal antibodies or as monoclonal antibodies by the methods described herein, using an antibody (or antigen-binding fragment thereof) that specifically binds to the cellular polypeptide as immunogen. Anti-idiotype antibodies or antigen-binding fragments thereof may also be generated by any of the recombinant genetic engineering methods described above or by phage display selection. Anti-idiotype antibodies may be further engineered to provide a chimeric or humanized anti-idiotype antibody, according to the description provided in detail herein and according to methods routinely practiced in the art. An anti-idiotype antibody may bind specifically to the antigen-binding site of the anti-cellular polypeptide antibody such that binding of the antibody to the cellular polypeptide is competitively inhibited. Alternatively, an anti-idiotype antibody as provided herein may not competitively inhibit binding of an anti-cellular polypeptide antibody to the cellular polypeptide.

An agent also includes a peptide-immunoglobulin (Ig) constant region fusion polypeptide, which includes a peptide-IgFc fusion polypeptide. The peptide may be any naturally occurring or recombinantly prepared molecule. A peptide-Ig constant region fusion polypeptide, such as a peptide-IgFc fusion polypeptide (also referred to in the art as a peptibody (see, e.g., U.S. Pat. No. 6,660,843)), comprises a biologically active peptide or polypeptide capable of altering the activity of a cellular polypeptide of interest that is fused in-frame with a portion, at least one constant region domain (e.g., CH1, CH2, CH3, and/or CH4), or the Fc portion (CH2-CH3) of an immunoglobulin. The Fc portion is also referred to herein as the Fc region.

In one embodiment, the peptide portion of the fusion polypeptide is capable of interacting with or binding to the cellular polypeptide to which the viral polypeptide binds and effecting the same biological activity as the viral polypeptide when it binds to the cellular polypeptide. In certain embodiments, binding of the peptide-Fc fusion polypeptide suppresses (inhibits, prevents, decreases, or abrogates) the immunoresponsiveness of an immune cell that expresses the cellular polypeptide. For example, such a peptide may be identified by determining its capability to inhibit or block binding of the viral polypeptide to a cell that expresses the cellular polypeptide. Alternatively, a candidate peptide may be permitted to contact or interact with a cell that expresses the cellular polypeptide, and the capability of the candidate peptide to suppress or enhance at least one biological function of the cell can be measured according to methods described herein and practiced in the art.

Candidate peptides may be provided as members of a combinatorial library, which includes synthetic peptides prepared according to a plurality of predetermined chemical reactions performed in a plurality of reaction vessels. For example, various starting peptides may be prepared according to standard peptide synthesis techniques with which a skilled artisan will be familiar.

Peptides that alter at least one biological activity of a cell may be identified and isolated from combinatorial libraries (see, e.g., International Patent Application Nos. PCT/US91/08694 and PCT/US91/04666) and from phage display peptide libraries (see, e.g., Scott et al., *Science* 249:386 (1990); Devlin et al., *Science* 249:404 (1990); Cwirla et al., *Science* 276: 1696-99 (1997); U.S. Pat. No. 5,223,409; U.S. Pat. No. 5,733,731; U.S. Pat. No. 5,498,530; U.S. Pat. No. 5,432,018; U.S. Pat. No. 5,338,665; 1994; U.S. Pat. No. 5,922,545; International Application Publication Nos. WO 96/40987 and WO 98/15833). In phage display peptide libraries, random peptide sequences are fused to a phage coat protein such that the peptides are displayed on the external surface of a filamentous phage particle. Typically, the displayed peptides are contacted with a ligand or binding molecule of interest to permit interaction between the peptide and the ligand or binding molecule, unbound phage are removed, and the bound phage are eluted and subsequently enriched by successive rounds of affinity purification and repropagation. The peptides with the greatest affinity for the ligand or binding molecule or target molecule of interest (e.g., the cellular polypeptides identified and described herein) may be sequenced to identify key residues, which may identify peptides within one or more structurally related families of peptides. Comparison of sequences of peptides may also indicate which residues in such peptides may be safely substituted or deleted by mutagenesis. These peptides may then be incorporated into additional peptide libraries that can be screened, and peptides with optimized affinity can be identified.

Additional methods for identifying peptides that may alter at least one biological activity of a cell and thus be useful for treating and/or preventing an immunological disease or disorder or a viral infection include, but are not limited to, (1) structural analysis of protein-protein interaction such as analyzing the crystal structure of the cellular polypeptide target (see, e.g., Jia, *Biochem. Cell Biol.* 75:17-26 (1997)) to identity and to determine the orientation of critical residues of the cellular polypeptide, which will be useful for designing a peptide (see, e.g., Takasaki et al., *Nature Biotech.* 15: 1266-70 (1997)); (2) a peptide library comprising peptides fused to a peptidoglycan-associated lipoprotein and displayed on the outer surface of bacteria such as *E. coli*; (3) generating a library of peptides by disrupting translation of polypeptides to generate RNA-associated peptides; and (4) generating peptides by digesting polypeptides with one or more proteases. (See also, e.g., U.S. Pat. Nos. 6,660,843; 5,773,569; 5,869,451; 5,932,946; 5,608,035; 5,786,331; 5,880,096). A peptide may comprise any number of amino acids between 3 and 75 amino acids, 3 and 60 amino acids, 3 and 50 amino acids, 3 and 40 amino acids, 3 and 30 amino acids, 3 and 20 amino acids, or 3 and 10 amino acids. A peptide that has the capability of alter a biological activity of a cell, such as for example, alter immunoresponsiveness of an immune cell (e.g., in certain embodiments, to suppress the immunoresponsiveness of the immune cell and in certain other embodiments, to enhance immunoresponsiveness of the immune cell) may also be further derivatized to add or insert amino acids that are useful for constructing a peptide-Ig constant region fusion protein (such as amino acids that are linking sequences or that are spacer sequences).

A peptide that may be used to construct a peptide-Ig constant region fusion polypeptide (including a peptide-IgFc fusion polypeptide) may be derived from the viral polypeptide that binds to the cellular polypeptide. Peptides may be randomly generated from the viral polypeptide by proteolytic digestion using any one or more of various proteases, isolated, and then analyzed for their capability to alter at least one biological activity of a cell. Peptides of a viral polypeptide may also be generated using recombinant methods described herein and practiced in the art. Randomly generated peptides may also be used to prepare peptide combinatorial libraries or phage libraries as described herein and in the art. Alternatively, the amino acid sequences of portions of a viral polypeptide that interact with the cellular polypeptide may be determined by computer modeling of the cellular polypeptide, or of a portion of the polypeptide, for example, the extracellular portion, and/or x-ray crystallography (which may include preparation and analysis of crystals of the cellular polypeptide (or a fragment thereof) only or of the cellular polypeptide-viral polypeptide (or fragments of the cellular polypeptide and/or the viral polypeptide complex).

As described in detail herein, an Fc polypeptide (or portion or region) of an immunoglobulin comprises the heavy chain CH2 domain and CH3 domain and a portion of or the entire hinge region that is located between CH1 and CH2. Historically, an Fc fragment was derived by papain digestion of an immunoglobulin and included the hinge region of the immunoglobulin. An Fc region or Fc polypeptide referred to herein is a monomeric polypeptide that may be linked or associated to form dimeric or multimeric forms by covalent (e.g., particularly disulfide bonds) and non-covalent association. The number of intermolecular disulfide bonds between monomeric subunits of Fc polypeptides varies depending on the immunoglobulin class (e.g., IgG, IgA, IgE) or subclass (e.g., human IgG1, IgG2, IgG3, IgG4, IgA1, IgA2). The Fc portion of the immunoglobulin mediates certain effector functions of an immunoglobulin. Three general categories of effector functions associated with the Fc region include (1) activation of the classical complement cascade, (2) interaction with effector cells, and (3) compartmentalization of immunoglobulins. Presently, an Fc polypeptide, and any one or more constant region domains, and fusion proteins comprising at least one immunoglobulin constant region domain can be readily prepared according to recombinant molecular biology techniques with which a skilled artisan is quite familiar.

The Fc polypeptide is preferably prepared using the nucleotide and the encoded amino acid sequences derived from the animal species for whose use the peptide-IgFc fusion polypeptide is intended. In one embodiment, the Fc fragment is of human origin and may be from any of the immunoglobulin classes, such as human IgG1 and IgG2.

An Fc polypeptide as described herein also includes Fc polypeptide variants. One such Fc polypeptide variant has one or more cysteine residues (such as one or more cysteine residues in the hinge region) that forms a disulfide bond with another Fc polypeptide substituted with another amino acid, such as serine, to reduce the number of disulfide bonds formed between two Fc polypeptides. Another example of an Fc polypeptide variant is a variant that has one or more amino acids involved in an effector function substituted such that the Fc polypeptide has a reduced level of an effector function. For example, amino acids in the Fc region may be substituted to reduce or abrogate binding of a component of the complement cascade (see, e.g., Duncan et al., *Nature* 332:563-64 (1988); Morgan et al., *Immunology* 86:319-24 (1995)); to reduce or abrogate the ability of the Fc polypeptide to bind to an Fc receptor expressed by an immune cell; or to alter antibody-dependent cellular cytotoxicity.

Other Fc variants encompass similar amino acid sequences of known Fc polypeptide sequences that have only minor changes, for example by way of illustration and not limitation, covalent chemical modifications, insertions, deletions and/or substitutions, which may further include conservative substitutions. Amino acid sequences that are similar to one another may share substantial regions of sequence homology. Similarly, nucleotide sequences that encode the Fc variants may encompass substantially similar nucleotide sequences and have only minor changes, for example by way of illustration and not limitation, covalent chemical modifications, insertions, deletions, and/or substitutions, which may further include silent mutations owing to degeneracy of the genetic code. Nucleotide sequences that are similar to one another may share substantial regions of sequence homology.

An Fc polypeptide or at least one immunoglobulin constant region, or portion thereof, when fused to a peptide or polypeptide of interest acts, at least in part, as a vehicle or carrier moiety that prevents degradation and/or increases half-life, reduces toxicity, reduces immunogenicity, and/or increases biological activity of the peptide such as by forming dimers or other multimers (see, e.g., U.S. Pat. Nos. 6,018,026; 6,291,646; 6,323,323; 6,300,099; 5,843,725). (See also, e.g., U.S. Pat. No. 5,428,130; U.S. Pat. No. 6,660,843; U.S. Patent Application Publication Nos. 2003/064480; 2001/053539; 2004/087778; 2004/077022; 2004/071712; 2004/057953; 2004/053845; 2004/044188; 2004/001853; 2004/082039). Alternative moieties to an immunoglobulin constant region such as an Fc polypeptide that may be linked or fused to a peptide that binds to a viral polypeptide and/or that alters at least one biological activity of a cell include, for example, a linear polymer (e.g., polyethylene glycol, polylysine, dextran, etc.; see, for example, U.S. Pat. No. 4,289,872; International Patent Application Publication No. WO 93/21259); a lipid; a cholesterol group (such as a steroid); a carbohydrate or oligosaccharide.

Provided herein are methods of manufacture for producing a cellular polypeptide to which a viral polypeptide (particularly a viral polypeptide that has at least one virulence trait described herein). For example a process (or method) for manufacturing a cellular polypeptide comprises identifying a cellular polypeptide to which a viral polypeptide binds according to any one of the method described herein. After the amino acid sequence of the cellular polypeptide is determined, a nucleotide sequence that encodes the cellular polypeptide may be determining according to principles based on the genetic code. Alternatively, the nucleotide sequence of the genomic DNA or mRNA of a cell that encodes the cellular polypeptide may be determined by using standard molecular biology techniques, including primer design, hybridization, nucleic acid isolation, cloning, and amplification, and sequencing. A polynucleotide comprising a nucleotide sequence encoding the cellular polypeptide may be incorporated into a recombinant expression construct (i.e., vector) according to well known methods and principles known in the molecular biology art and described herein for preparing a recombinant expression vector. The vector also includes a promoter operatively linked to the nucleotide sequence that encodes the cellular polypeptide as well as other regulatory elements (e.g., enhancer or transcription initiation site) with which a skilled artisan is familiar. The vector may then be introduced into a host cell (e.g., a prokaryotic, eukaryotic, insect, yeast, or other suitable host cell) such as by transfecting or transforming the host cell with the recombinant expression vector. After culturing the host cell under conditions and for a time sufficient that permit expression of the cellular polypeptide, the cellular polypeptide may be isolated from the host cell culture or from the host cells.

The nucleic acid molecules encoding the cellular polypeptide that specifically binds to the viral polypeptide, as described herein, may be propagated and expressed according to any of a variety of well-known procedures for nucleic acid excision, ligation, transformation, and transfection. Thus, in certain embodiments expression of the cellular polypeptide may be preferred in a prokaryotic host cell, such as *Escherichia coli* (see, e.g., Pluckthun et al., *Methods Enzymol.* 178:497-515 (1989)). In certain other embodiments, expression of the cellular polypeptide may be preferred in a eukaryotic host cell, including yeast (e.g., *Saccharomyces cerevisiae, Schizosaccharomyces pombe*, and *Pichia pastoris*); animal cells (including mammalian cells); or plant cells. Examples of suitable animal cells include, but are not limited to, myeloma, HEK293, COS, or CHO cells. Examples of plant cells include tobacco, corn, soybean, and rice cells. By methods known to those having ordinary skill in the art and based on the present disclosure, a nucleic acid vector may be designed for expressing foreign sequences in a particular host system, and then polynucleotide sequences encoding the cellular polypeptide may be inserted. The regulatory elements will vary according to the particular host.

Also provided herein are methods of manufacture for producing an agent that is useful for treating a subject who has or who is at risk of developing a disease or disorder as described herein, including an immunological disease or disorder, or who is has a viral infection or who is at risk for developing a viral infection. In one embodiment, such a method of manufacture comprises (a) identifying an agent for treating a disease or disorder, such as an immunological disease or disorder or a viral infection according to methods described herein and practiced in the art. For example, identifying an agent comprises identifying a cellular polypeptide to which a viral polypeptide binds according to the methods described herein, wherein interaction between the cellular polypeptide and the viral polypeptide alters immunoresponsiveness of an immune cell. The method for identifying an agent comprises contacting the cellular polypeptide, or a cell comprising the cellular polypeptide; the viral polypeptide; and a candidate agent, which agents are described herein in detail, under conditions and for a time sufficient that permit the cellular polypeptide and the viral polypeptide to interact. The level of binding of the viral polypeptide to the cellular polypeptide in the presence of the candidate agent is then determined and compared with the level of binding of the viral polypeptide to the cellular polypeptide in the absence of the candidate agent. A candidate agent that inhibits (or prevents, reduces, minimizes, or abrogates) binding of the viral polypeptide to the cellular polypeptide may mimic or act in the same manner as the viral polypeptide, and thus affect at least one biological activity of the cellular polypeptide. Such a biological activity includes but is not limited to, altering immunoresponsiveness of an immune cell (e.g., in certain embodiments, to suppress the immunoresponsiveness of the immune cell and in certain other embodiments, to enhance immunoresponsiveness of the immune cell) that comprises the cellular polypeptide. Accordingly, such an agent is useful for treating an immunological disease or disorder. The agent is then produced according to methods known in the art for producing the agent.

The agent may be any agent described herein, such as, for example, an antibody, or antigen-binding fragment thereof; a small molecule; an aptamer; an antisense polynucleotide; a small interfering RNA (siRNA); and a peptide-IgFc fusion polypeptide. In a particular embodiment, the agent is an antibody, or antigen-binding fragment thereof, which may be produced according to methods described herein and that are adapted for large-scale manufacture. For example, production methods include batch cell culture, which is monitored and controlled to maintain appropriate culture conditions. Purification of the antibody, or antigen-binding fragment thereof, may be performed according to methods described herein and known in the art and that comport with guidelines of domestic and foreign regulatory agencies.

An agent (such as, but not limited to, an antibody, or antigen-binding fragment thereof that binds to a target cellular polypeptide) identified according to the methods described herein that may be useful for treating or preventing a disease or disorder, including a cardiovascular disease or disorder, a metabolic disease or disorder, a proliferative disease or disorder, or an immunological disease or disorder may be combined (i.e., formulated) with a pharmaceutically (i.e., physiologically) suitable excipient for administration to a subject. A pharmaceutical composition may be a sterile aqueous or non-aqueous solution, suspension or emulsion, which additionally comprises a physiologically acceptable excipient (pharmaceutically acceptable or suitable excipient or carrier) (i.e., a non-toxic material that does not interfere with the activity of the active ingredient). Such compositions may be in the form of a solid, liquid, or gas (aerosol). Alternatively, compositions described herein may be formulated as a lyophilizate, or compounds may be encapsulated within liposomes using technology known in the art. Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable excipient or carrier known to those of ordinary skill in the art for use in pharmaceutical compositions may be employed in the compositions described herein. Excipients for therapeutic use are well known, and are described, for example, in *Remingtons Pharmaceutical Sciences*, Mack Publishing Co. (A. R. Gennaro ed. 1985). In general, the type of excipient is selected based on the mode of administration. Pharmaceutical compositions may be formulated for any appropriate manner of administration.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a disease such as an immunological disease or disorder.

Optimal doses may generally be determined using experimental models and/or clinical trials. The optimal dose may depend upon the body mass, weight, or blood volume of the patient. In general, the amount of a polypeptide, such as an antibody or antigen-binding fragment thereof, as described herein, present in a dose, or produced in situ by DNA present in a dose, ranges from about 0.01 µg to about 1000 µg per kg of subject. The use of the minimum dosage that is sufficient to provide effective therapy is usually preferred. Patients may generally be monitored for therapeutic or prophylactic effectiveness using assays suitable for the condition being treated or prevented, which assays will be familiar to those having ordinary skill in the art. Suitable dose sizes will vary with the size of the patient, but will typically range from about 1 ml to about 500 ml for a 10-60 kg subject.

Business Methods

Provided herein are methods and systems for identifying agents that may be used as therapeutic bioactive agents for treating diseases and disorders, including immunological diseases and disorders, testing and evaluating the agents in preclinical and clinical trials, and then selling the agents to health care professionals. Systems and methods for selling a therapeutic agent include, but are not limited to, (1) scientific methods, which may include computer systems and methods, for identifying and analyzing a viral polypeptide that is a viral virulence factor; (2) scientific methods for identifying a cellular polypeptide that binds to the viral virulence factor and which cellular polypeptide is therefore a target for a therapeutic agent; (3) scientific methods for identifying and analyzing an agent that inhibits binding of the viral polypeptide to the cellular polypeptide, and thus alters at least one biological activity of the cellular polypeptide; (4) methods and systems for clinical development of the agent; (5) selling the agent to health care professionals for treatment of patients in need of the agent.

In one embodiment, a business method is provided that comprises identifying a viral polypeptide that is a viral virulence factor; identifying a cellular polypeptide to which a viral virulence factor binds, wherein binding of the viral virulence factor to the cellular polypeptide alters at least one biological activity of the cell with which the cellular polypeptide is associated; identifying an agent that inhibits binding of the cellular polypeptide and the viral polypeptide, thereby identifying an agent that alters at least one biological activity of the cell; and designing and executing at least one preclinical study. In certain other embodiments, the business method further comprises designing and executing at least one clinical trial in human subjects to determine the safety profile of the agent in humans. The business method may also further comprises the design and execution of at least one clinical trial for evaluating the efficacy of the agent in human subjects who are in need of such an agent for treatment (which includes prevention) of a disease or medical disorder. The method may still further comprise selling the agent to a health care professional or to a distributing entity that provides the agent to a health care professional.

In a specific embodiment, the at least one biological effect is immunoresponsiveness and the cell is an immune cell, and the agent alters immunoresponsiveness of the immune cell. The agent that inhibits binding between the viral and cellular polypeptides is, thus, also capable of altering immunoresponsiveness of an immune cell. As described in detail herein, the agent includes, but is not limited to, (a) an antibody, or antigen-binding fragment thereof, (b) a viral polypeptide/Fc polypeptide fusion protein; (c) a peptide/Fc polypeptide fusion protein; (d) a domain of the cellular polypeptide, or a fragment thereof comprising at least eight amino acids, fused to an Fc polypeptide; (e) a small molecule; (f) a small interfering RNA (siRNA); (g) an antisense polynucleotide; and (h) an aptamer.

As described herein, the business method comprises designing and executing at least one pre-clinical study to determine whether altering the at least one biological activity of the cell by the agent indicates that the agent is useful for treating a disease or medical disorder in a human subject. Preclinical studies include experiments that contribute to the determination of the therapeutic window of the agent (i.e., the relationship between the efficacy and safety of the agent). Procedures may be designed and performed or executed in cell culture studies to determine the level of the agent that induces at least one toxic effect in a cell. A toxic effect is understood to mean an undesirable effect in a cell. For example, if the agent is being tested for its capability to enhance or prolong survival of a cell or to maintain a normal biological activity or function, a toxic effect would include induction of apoptosis, an abnormal change in structural cell morphology or integrity, or induction and maintenance of any cellular pathway that is not considered normal for that particular cell type or that alters the capability of the cell to thrive. If the agent were being tested for its capability to treat a cancer or malignancy and/or act as an anti-proliferative agent, induction of apoptosis and cell death are desirable effects and such analyses would indicate potential efficacy of the agent. Preclinical studies that may be designed and executed for toxicity analysis include studies in animals. Examples of other preclinical studies that may be conducted using cell culture methods and/or animal models include determining teratotagenicity; effects on male and female reproductive systems, including effects of the agent on the birth of offspring; pharmacokinetic analyses; and stability studies.

Preclinical studies also include cell culture and animal studies that indicate and evaluate the efficacy of the agent. Agents that are useful for treating an immunological disease or disorder, such as an autoimmune disease or inflammatory disease or disorder, cardiovascular disease or disorder, a metabolic disease or disorder, or a proliferative disease or disorder, may be determined and evaluated in any one of a number of animal models described herein and used by persons skilled in the art (see, e.g., reviews by Taneja et al., *Nat. Immunol.* 2:781-84 (2001); Lam-Tse et al., *Springer Semin. Immunopathol.* 24:297-321 (2002)). For example, mice that have three genes, Tyro3, Mer, and Axl that encode receptor tyrosine kinases, knocked out exhibit several symptoms of autoimmune diseases, including rheumatoid arthritis and SLE (Lu et al., *Science* 293:228-29 (2001)). A murine model of spontaneous lupus-like disease has been described using NZB/WF1 hybrid mice (see, e.g., Drake et al., *Immunol. Rev.* 144:51-74 (1995)). An animal model for type I diabetes that permits testing of agents and molecules that affect onset, modulation, and/or protection of the animal from disease uses MHC transgenic (Tg) mice. Mice that express the HLA-DQ8 transgene (HLA-DQ8 is the predominant predisposing gene in human type I diabetes) and the HLA-DQ6 transgene (which is diabetes protective) were crossed with RIP(rat insulin promoter).B7-1-Tg mice to provide HLA-DQ8 RIP.B7-1 transgenic mice that develop spontaneous diabetes (see Wakeland et al., *Curr. Opin. Immunol.* 11:701-707 (1999); Wen et al., *J. Exp. Med.* 191:97-104 (2000)). (See also Brondum et al., *Horm. Metab. Res.* 37 Suppl 1:56-60 (2005)).

Animal models that may be used for characterizing agents that are useful for treating rheumatoid arthritis include a collagen-induced arthritis model (see, e.g., Kakimoto, *Chin. Med. Sci. J.* 6:78-83 (1991); Myers et al., *Life Sci.* 61:1861-78 (1997)) and an anti-collagen antibody-induced arthritis model (see, e.g., Kakimoto, supra). Other applicable animal models for immunological diseases include an experimental autoimmune encephalomyelitis model (also called experimental allergic encephalomyelitis model), an animal model of multiple sclerosis; a psoriasis model that uses AGR129 mice that are deficient in type I and type II interferon receptors and deficient for the recombination activating gene 2 (Zenz et al., *Nature* 437:369-75 (2005); Boyman et al., *J. Exp. Med.* 199:731-36 (2004); published online Feb. 23, 2004); and a TNBS (2,4,6-trinitrobenzene sulphonic acid) mouse model for inflammatory bowel disease. Numerous animal models for cardiovascular disease are available and include models described in van Vlijmen et al., *J Clin. Invest.* 93:1403-10 (1994); Kiriazis et al., *Annu. Rev. Physiol.* 62:321-51 (2000); Babu et al., *Methods Mol. Med.* 112:365-77 (2005).

As described herein, the business method comprises designing and executing at least one clinical study to determine whether altering the at least one biological activity of the cell by the agent indicates that the agent is useful (i.e., safe and effective) for treating a disease or medical disorder in a human subject. Clinical studies are performed by persons skilled in the art and according to statutes and rules (see 21 U.S.C. (The Federal Food, Drug, and Cosmetics Act) and 21 C.F.R., particularly 21 C.F.R. §§312, 314, 316, 50, 54, 56, 58, and 201) and guidance documents provided by the Food and Drug Administration (FDA) for designing, executing, evaluating, and reporting the results of clinical studies. In certain embodiments, the business method comprises design and execution of at least one Phase I clinical trial, at least one Phase II clinical trial, and at least one Phase III clinical trial. In another embodiment, the method comprises design and execution of at least one Phase I clinical trial and at least one Phase II clinical trial, and in another embodiment the business method comprises design and execution of at least one Phase I clinical trial.

A Phase I clinical trial typically includes design and execution of studies to evaluate the safety of the agent in human subjects. A Phase I study or a second Phase I study may include dose escalation studies. In certain instances, the Phase I trial may be tested in a patient group that may gain some clinical benefit from receiving the agent. A Phase I study is designed to determine how an agent is absorbed, metabolized, and excreted in the human body and also to assess adverse effects. Designing a Phase I clinical trial including preparation of an Investigational New Drug (IND) Application and submission to the FDA for evaluation and approval. The content of an IND and the studies that are performed that are included in the content of the IND are determined, for example, by the agent, therapeutic indication, and the appropriate pre-clinical in vivo (i.e., animal studies) and in vitro (cell culture and other biological and chemical assays) studies that inform a clinician or other health care professional about the therapeutic agent.

A phase II study includes the early controlled clinical studies conducted to obtain some preliminary data on the effectiveness of the drug for a particular indication or indications in patients with the disease or condition. This phase of testing also helps determine the common short-term side effects and risks associated with the drug. Phase II studies are typically well-controlled, closely monitored, and conducted in a relatively small number of patients, usually involving several hundred people. Phase III studies are expanded controlled and uncontrolled trials. These studies are performed after preliminary evidence suggesting effectiveness of the drug has been obtained in Phase II, and are intended to gather the additional information about effectiveness and safety that is needed to evaluate the overall benefit-risk relationship of the drug. Phase III studies also provide an adequate basis for extrapolating the results to the general population and transmitting that information in the physician labeling. Phase III studies usually include several hundred to several thousand people.

Design and execution of each clinical study includes clinical study protocol design (including but not limited to inclusion and exclusion criteria, statistical design and analyses for primary and secondary endpoint determinations; adverse effect analysis and protocols for reporting an adverse event; background about the agent and the disease indication; patient information (background and monitoring); clinical administration protocol; etc.); study evaluation (including but not limited to statistical analyses of all measured parameters outlined in the clinical protocol; statistical analysis and categorization of adverse events; narratives for serious adverse events; and other summaries as required by the FDA); and conclusions. Design, results, and conclusions may be discussed with the FDA informally as well as formally, which is required by statute. Design and execution of clinical studies may include additional methods and systems with which persons skilled in the art of design and execution of clinical studies will be very familiar.

The business methods described herein may further comprise preparation of a New Drug Application (NDA) or Biological License Application (BLA) as appropriate for the particular agent and as provided in guidelines of FDA sub-agencies (CDER and CBER) and presentation to the FDA to obtain marketing approval of the drug. Accordingly, the business methods may further comprise selling the agent. The agent may be sold directly to a health care professional, including but not limited to, a physician or a pharmacist, or may be sold to a distributor of marketed drugs and biologics, which then sells the drug to the health care professional. In certain circumstances, the drug may be sold directly over the counter by retail and wholesale entities to the consumer.

The business methods described herein may comprise licensing by a pharmaceutical company to another biopharmaceutical company, research or medical institution, large pharmaceutical company, or a generic drug manufacturing company the rights to make and use the viral polypeptide, the cellular polypeptide to which the viral polypeptide binds, and/or the agent. The rights to make and use each of the aforementioned viral polypeptide, cellular polypeptide, and agent may include a sale or assignment of the rights or licensing of the rights. The entity that sells or licenses the viral polypeptide, cellular polypeptide, and/or agent to another party is referred to as the selling company or licensing organization, respectively, and the party to which the viral polypeptide, cellular polypeptide, and/or agent is sold or licensed to is referred to as the acquiring company. The term "company" refers to any business entity or government institution or other public institution that may be legally formed within a country or within a state or province of the country, which may be a for profit or a non-profit entity.

In certain particular embodiments, the business arrangement between the acquiring company and the licensing organization may provide for the acquiring company to acquire intellectual property to the viral polypeptide, cellular polypeptide, and/or agent, and also to acquire certain associated technical information and know-how. The acquiring company may pay the licensing organization a combination of any one of upfront fees, ongoing research and development costs, royalties, milestone payments (for example, payment upon the acquiring company initiating and/or completing one or more stages of clinical development, revenue creation, and technical success milestones), in addition to other consideration agreed to by the acquiring company and the licensing organization. The payments may be in the form of cash, equity, and/or traded assets (including rights to other agents, viral polypeptides, and/or cellular polypeptides), or other agreed upon payment. In return, the licensing organization may grant to the acquiring company exclusive or non-exclusive licenses to the intellectual property rights associated with the viral polypeptide, cellular polypeptide, and/or agent, or assign the intellectual property rights associated with the viral polypeptide, cellular polypeptide, and/or agent. The rights may be granted in total or in specific fields (e.g., use of the agent for a particular disease indication) or in specific territories.

In a particular embodiment, the licensing organization is a biopharmaceutical company and in other particular embodiments, the acquiring organization is a biopharmaceutical company. In other embodiments, the biopharmaceutical company performs experiments to identify the viral polypeptide, the cellular polypeptide to which the viral polypeptide binds, and/or to identify the agent that alters at least one biological activity of a cell. In certain embodiments, the agent alters immunoresponsiveness of an immune cell.

Also provided herein is a method for guiding the selection of a therapeutic agent for treating a disease or medical disorder. The method comprises receiving information regarding a viral polypeptide that increases the virulence of a virus in a host infected with the virus; identifying a cellular polypeptide to which the viral polypeptide binds, wherein binding of the viral polypeptide to the cellular polypeptide alters at least one biological activity of a cell; identifying one or more agents that inhibit binding of the viral polypeptide to the cellular polypeptide; categorizing the capability of the one or more agents to alter at least one biological effect of a cell, wherein altering the at least one biological effect reduces the risk of developing a disease or medical disorder or reduces at least one symptom of a disease or medical disorder in a host; and providing the categorization of the capability of the agent to alter at least one biological effect of a cell to a medical research professional to assist in selecting the agent for testing in preclinical and clinical methods, and therefrom guiding the selection of a therapeutic agent for treating a disease or disorder. In a particular embodiment the at least one biological effect is immunoresponsiveness and the cell is an immune cell.

The capability of at least one agent to reduce the risk of developing a disease include the capability of the at least one agent (or more than one agent) to increase or prolong the time between when a subject is suspected or having a disease or disorder or determined to be at risk for developing a disease or disorder to when the subject exhibits at least one symptom or sequelae of the disease or disorder. Reducing at least one symptom includes the capability of the agent to decrease, ameliorate, or otherwise minimize the intensity, development, or exacerbation of a symptom (or sequelae) of the disease or disorder. The agent may also prevent development of a disease or disorder.

As described herein the capability of the one or more agents to alter at least one biological effect of a cell, wherein altering the at least one biological effect reduces the risk of developing a disease or medical disorder or reduces at least one symptom of a disease or medical disorder in a host may be determined using experimental models and/or clinical trials. Pharmaceutical compositions may be administered in a manner appropriate to the disease to be treated (or prevented) as determined by persons skilled in the medical arts. An appropriate dose and a suitable duration and frequency of administration will be determined by such factors as the condition of the subject or host, the type and severity of the subject's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a symptom associated with a disease or medical disorder including an immunological disease or disorder.

In another embodiment, business method is provided for selling a therapeutic agent to treat a disease or disorder. The business method comprises receiving information regarding a viral polypeptide that increases the virulence of a virus in a host infected with the virus, and identifying a cellular polypeptide to which the viral polypeptide binds, wherein binding of the viral polypeptide to the cellular polypeptide alters at least one biological activity of a cell. In particular embodiments, the at least one biological activity is immunoresponsiveness and the cell is an immune cell. The method may further comprise identifying one or more agents that inhibit binding of the viral polypeptide to the cellular polypeptide and that alter the at least one biological activity of the cell. As described herein when at least one biological effect is altered, the risk of developing a disease or medical disorder is reduced or at least one symptom of the disease or medical disorder is reduced in a subject (or patient or host). Such methods may further comprise selling the agent to a medical professional or health caregiver, a distributor that sells the drug to the medical professional, or to a patient in need of the treatment for the disease or disorder.

Also provided herein is a system for guiding the selection of a viral polypeptide to achieve a desired result. The system comprises a computing device, which includes a knowledge base comprising a plurality of polynucleotide sequences encoding a plurality of viral polypeptides. The system also includes a second knowledge base that comprises a plurality of rules for evaluating and selecting a viral polypeptide that is a viral virulence factor based upon information received regarding polynucleotide sequences encoding viral polypeptides. The system further comprises means for providing information regarding a target viral virulence factor and a desired result to said computing device; and a means in the computing device for identifying and categorizing or ranking at least one polynucleotide sequence encoding a viral polypeptide that may be used to identify a cellular polypeptide with which the viral polypeptide binds.

Also contemplated is a computer program product for guiding the selection of a viral polypeptide to achieve a desired result. The computer program product includes a computer usable storage medium having computer readable program code means embodied in the medium. The computer readable program code means comprises computer readable program code means for generating one knowledge base comprising a plurality of polynucleotide sequences encoding a plurality of viral polypeptides, and a second knowledge base that comprises a plurality of rules for evaluating and selecting a viral polypeptide that is a viral virulence factor based upon information regarding polynucleotide sequences that encode viral polypeptides. A computer program product may also comprises a computer readable program code means for providing information regarding a target viral virulence factor and a desired result to the computing device; and computer readable program code means for identifying and categorizing or ranking a target viral virulence factor that may be used to identify a cellular polypeptide to which the viral polypeptide binds, and wherein binding of the viral polypeptide to the cellular polypeptide alters at least one biological activity of a cell.

Categorizing the capability of at least one agent that inhibits binding of a viral polypeptide that is a virulence factor to a cellular polypeptide comprises analyzing the output from scientific method analysis, chemical composition analysis, and/or biological comparison analysis, for various techniques and assays and sorting them according to their predicted effect (i.e., the capability to alter at least one biological activity in a cell). The results may include plotting of various assay results and data, assigning numerical scores or values to the various results and data, based upon one or more predicted effects, and ranking of various assay results and data based upon the desired effect or outcome. In addition, biological reaction analysis also includes designing appropriate assay controls and methods of efficacy measurement. A variety of charts, graphs, graphical models, and other documents related to categorizing results and data from the assays according to any of a variety of different factors, including predicted potency and specificity, may be generated and stored.

The methods and systems described herein may be practiced without the aid of computers or related software. However, in certain embodiments, the methods and systems described herein are practiced using computers and software to accomplish one or more of the analyses described. For example, computers and software may be used for receiving information regarding a viral polypeptide that increases the virulence of a virus in a host infected with the virus may be performed using a computer device. In certain embodiments, the device comprises at least one knowledge base. For example, one knowledge base comprises a plurality of different polynucleotide sequences that encode a plurality of viral polypeptides. Another knowledge base useful for the methods described herein comprises a plurality of rules for evaluating and selecting a viral polypeptide that is a viral virulence factor. The rules include whether a viral polypeptide identified from the plurality of polynucleotide sequences comprises at least one of the virulence traits of viral polypeptides, which are described in detail herein.

Receiving information may be embodied in many different forms, including, e.g., a method data processing system or computer program product. Furthermore, the methods and systems described herein may comprise an entirely hardware embodiment, an entirely software embodiment, or an embodiment combining software and hardware aspects. Furthermore, the methods may provide a computer program product on a computer-usable storage medium that has computer readable program code means embodied in the medium. Any suitable computer readable medium may be used including, but not limited to, hard disks, CD-ROMs, optical storage devices, and magnetic storage devices.

The business methods and methods for selecting a therapeutic agent described herein may further comprise cataloging and document creation, which comprises sorting, serializing, and/or storing all output from various sources and analysis for documentation and retrieval. In certain embodiments, the output is organized and rendered into a final document that is delivered to the medical professional, medical research professional, or other health caregiver. The documents may further comprise predictions, prediction models, designs, and serialized custom products. Thus, in certain embodiments, the methods and systems of the present invention include organizing results of one or more of the analyses described above into groups and serializing and cataloguing these results for each customer or user (i.e., medical professional, medical research professional, or caregiver or the like).

In particular embodiments, the computer or other programmable data processing apparatus contain one or more knowledge bases that include information and/or rules useful in performing analyses. In certain embodiments, the computer or other programmable data processing apparatus includes means for determining or obtaining a gene or polynucleotide sequence that encodes a viral polypeptide, based upon receiving information regarding said sequence in any of a variety of formats, including the entry of the sequence itself, the name of the gene and organism, or a sequence identifier number from any one of a number of available databases (either public or that may be purchased).

Figure 2:
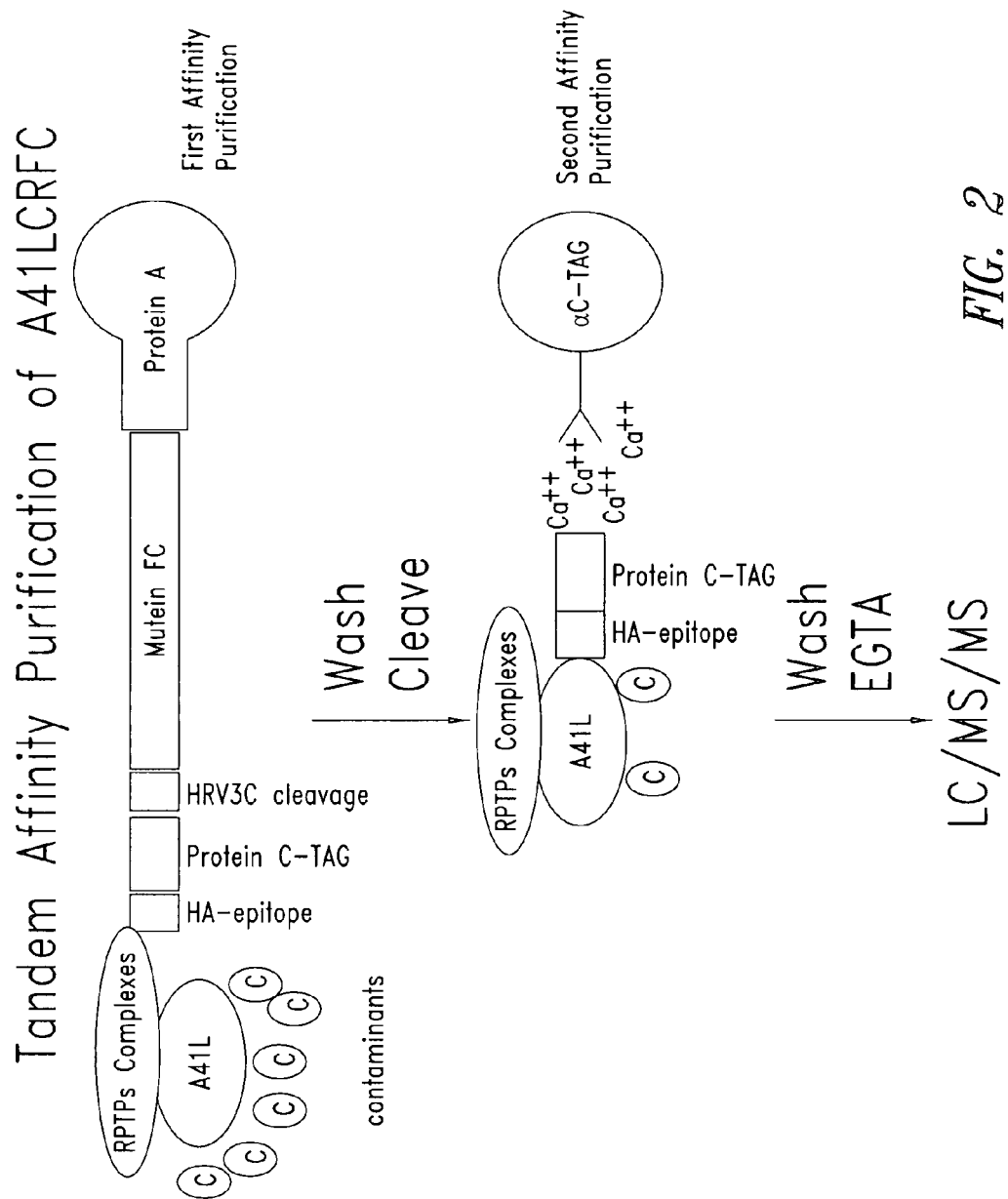

In another embodiment, a knowledge base includes a variety of different biological assays or information assigned for achieving different results, such as a group of assays suitable for determining levels of viral polypeptide expression, localization of the viral polypeptide after it is expressed by an infected cell, determining the effect on virulence of the virus by substituting, deleting or inserting one or more amino acids in the viral polypeptide, or information related to the location of the polynucleotide sequence encoding the viral polypeptide in the viral genome, and other assays and information. Such a knowledge base may further comprise expert rules for determining possible biological assays based upon user input regarding the desired result.

In other embodiments, a knowledge base comprises expert rules for determining structural characteristics of a polynucleotide sequence (e.g., a polynucleotide sequence that encodes a viral polypeptide as described herein), such as rules provided in the programs recited herein. In a related embodiment, a knowledge base comprises expert rules for comparing a polynucleotide sequence to another database, e.g., human genome database, to identify and/or predict biological interactions of a reagent in a cellular or genomic environment.

Thus, in one embodiment, information regarding a polynucleotide that encodes a viral virulence factor, a target cellular polypeptide, and an agent that alters the interaction between the viral virulence factor and the cellular polypeptide and desired result, e.g., altering a biological activity of a cell (e.g., immunoresponsiveness of an immune cell), is inputted into a computer comprising a knowledge base regarding agents, and the computer selects appropriate agents based upon the desired result. The computer then designs reagents agents suitable for treating a disease or medical disorder, based upon the identified viral polypeptide and cellular polypeptide target and agent, using expert rules for analyzing the chemical composition of potential agents, as well as analyzing potential interactions in a biological system, such as a cell or genomic environment. The agents are then ranked using several criteria, with related documentation produced.

As described herein a medical disease or disorder includes an immunological disease or disorder, a cardiovascular disease or disorder, a metabolic disease or disorder, or a proliferative disease or disorder. An immunological disorder or disease includes but is not limited to an autoimmune disease or an inflammatory disease. Exemplary immunological diseases and disorders include but are not limited to multiple sclerosis, rheumatoid arthritis, systemic lupus erythematosus, graft versus host disease, sepsis, diabetes, psoriasis, atherosclerosis, Sjogren's syndrome, progressive systemic sclerosis, scleroderma, acute coronary syndrome, ischemic reperfusion, Crohn's Disease, endometriosis, glomerulonephritis, myasthenia gravis, idiopathic pulmonary fibrosis, asthma, acute respiratory distress syndrome (ARDS), vasculitis, and inflammatory autoimmune myositis. Examples of cardiovascular diseases include atherosclerosis, endocarditis, hypertension, and peripheral ischemic disease.

The following Examples are offered for the purpose of illustrating the embodiments disclosed herein and are not to be construed to limit the scope of this invention.

EXAMPLES

Example 1

Identification of RPTPs Expressed on Immune Cells that Bind A41L

This Example describes a method for identifying cell surface polypeptides that bind to A41L.

A recombinant expression vector comprising a polynucleotide that encoded a Cowpox A41L fusion polypeptide was constructed for a tandem affinity purification (TAP) procedure (also called TAP tag procedure) (see also, e.g., Rigaut et al. *Nat. Biotech.* 17:1030-32 (1999); Puig et al., *Methods* 24:218-29 (2001); Knuesel et al. *Mol. Cell. Proteomics* 2:1225-33 (2003)). The construct called A41LCRFC was prepared and the fusion polypeptide expressed and isolated according to standard molecular biology and affinity purification techniques and methods. A schematic of the construct is provided in FIG. 1. The A41 LCRFC construct included a nucleotide sequence that encoded a mature A41L coding sequence from Cowpox virus fused to the C-terminus of the human growth hormone leader peptide. The CRFC tandem affinity tag was fused to the C-terminus of A41L. The CRFC tag included a human influenza virus hemagglutinin peptide, the HA epitope, amino acids YPYDVDYA (SEQ ID NO:1, which is encoded by the nucleotide sequence set forth in SEQ ID NO:2), for which antibodies are commercially available, permitting detection of the expression fusion polypeptide by immunochemistry methods, such as fluorescence activated cell sorting (FACS) or immunoblotting. Fused to the carboxyl terminal end of the HA epitope was a Protein C-tag, amino acids EDQVDPRLIDGK (SEQ ID NO:4, which is encoded by the nucleotide sequence set forth in SEQ ID NO:5), which is derived from the heavy chain of human Protein C. To the carboxyl end of the Protein C-tag was fused a Human Rhinovirus HRV3C protease site, amino acids LEVLFQGP (SEQ ID NO:16, which is encoded by the nucleotide sequence set forth in SEQ ID NO:17); and to the carboxyl end of the HRV3C protease site was fused a mutein derivative of the Fc portion of a human IgG.

A schematic illustrating the TAP tag procedure is presented in FIG. 2. Ten μg of the A41LCRFC fusion polypeptide that was bound to Protein A was incubated with cell lysates prepared from $5 \times 10^6$ monocytes. A variety of normal cells and tumor cell types may be used to identify cellular polypeptides that bind to or interact with A41L, including B cells and T cells (activated or non-activated), macrophages, epithelial cells, fibroblasts, and cell lines such as Raji (B cell lymphoma), THP-1 (acute monocytic leukemia), and Jurkat (T cell leukemia).

The A41LCRFC/cell lysate complexes were washed and then subjected to cleavage by the HRV3C protease, which released A41L and associated proteins. Calcium chloride (1 M) was added to the released A41L/cell lysate complexes, which were then applied to an anti-protein C-Tag affinity resin. Calcium chloride is required for the interaction of anti-C-tag and the C-tag epitope. The complexes bound to the anti-protein C-Tag affinity resin were washed in a buffer containing calcium chloride and then eluted by calcium chelation using EGTA. The subsequent eluent was digested with trypsin and the digested A41L complexes were subjected to direct tandem mass spectrometry to identify A41L and its associated proteins.

The sequences of the trypsin-generated peptides were identified by mass spectrometry. The peptides were identified as portions of the receptor-like protein tyrosine phosphatases, LAR, RPTP-σ, and RPTP-δ as shown in FIGS. 3A, 3B, and 3C, respectively.

Example 2

Preparation of A41L-Fc Fusion Polypeptides

This example describes preparation of recombinant expression vectors for expression of an A41L-Fc fusion polypeptide and an A41L-mutein Fc fusion polypeptide.

Figure 6:
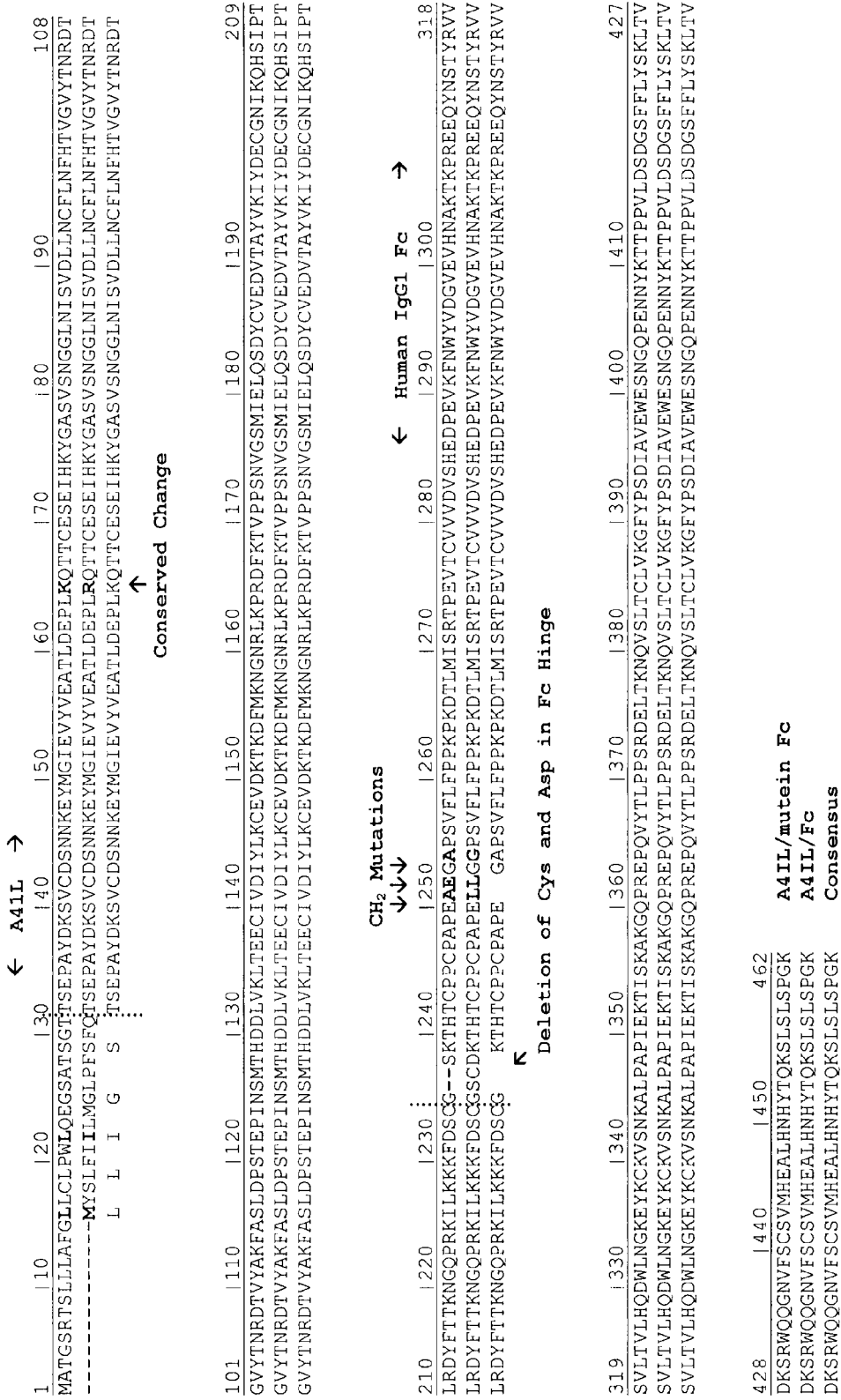

Recombinant expression vectors were prepared according to methods routinely practiced by a person skilled in the molecular biology art. A polynucleotide encoding A41L-Fc and a polynucleotide encoding A41L-mutein Fc were cloned into the multiple cloning site of the vector, pDC409 (SEQ ID NO:41) (see, e.g., U.S. Pat. No. 6,512,095 and U.S. Pat. No. 6,680,840, and references cited therein). The amino acid sequence of the A41L-Fc polypeptide is set forth in SEQ ID NO:32, and the amino acid sequence of the A41L-mutein Fc polypeptide is set forth in SEQ ID NO: 31 (see FIG. 6). The nucleotide sequence that encodes the mutein Fc (human IgG1) polypeptide (SEQ ID NO:23) is set forth in SEQ ID NO:24. Ten to twenty micrograms of each expression plasmid were transfected into a HEK293T cells or COS-7 cells (American Type Tissue Collection (ATCC), Manassas, Va.) that were grown in 10 cm diameter standard tissue culture plates to approximately 80% confluency. Transfection was performed using Lipofectamine™ Plus™ (Invitrogen Corp., Carlsbad, Calif.). The transfected cells were cultured for 48 hours, and then supernatant from the cell cultures was harvested. The A41L fusion proteins were purified by Protein A sepharose affinity chromatography according to standard procedures.

Example 3

Preparation of Affinity Tags for Fusion Polypeptides

This example describes preparation of recombinant expression vectors for expression of various affinity tags.

Fusion proteins, such as a fusion protein comprising a virulence factor polypeptide, or portion thereof, encoded by a viral virulence gene are fused in frame to an affinity tag for detection and/or isolation, for example, by tandem affinity purification (TAP). The fusion polypeptide may comprise more than one affinity tag. Recombinant expression vectors that comprise polynucleotide sequences encoding fusion proteins are prepared according to methods and techniques well known and routinely used by a person skilled in the molecular biology art (see also Example 2). As described herein, a fusion protein may further comprise at least one protease site. The polynucleotides encoding the fusion proteins may be inserted into any number of recombinant expression vectors available from commercial vendors and manufacturers. The vectors may be further adapted for insertion of polynucleotides described herein, for example, to introduce or remove a restriction site or to introduce or remove a regulatory element. Exemplary vectors include but are not limited to pCDNA™3.1 that contains the CMV promoter (SEQ ID NO:39) (Invitrogen) (see, e.g., U.S. Pat. Nos. 5,168,062 and 5,385,839); pSL9, a lentiviral expression plasmid (SEQ ID NO:40); pDC409 (SEQ ID NO:41); and pAAV, an adeno-associated virus expression plasmid (see, e.g., Stratagene, La Jolla, Calif.) (for example, SEQ ID NO:42).

Figure 4:
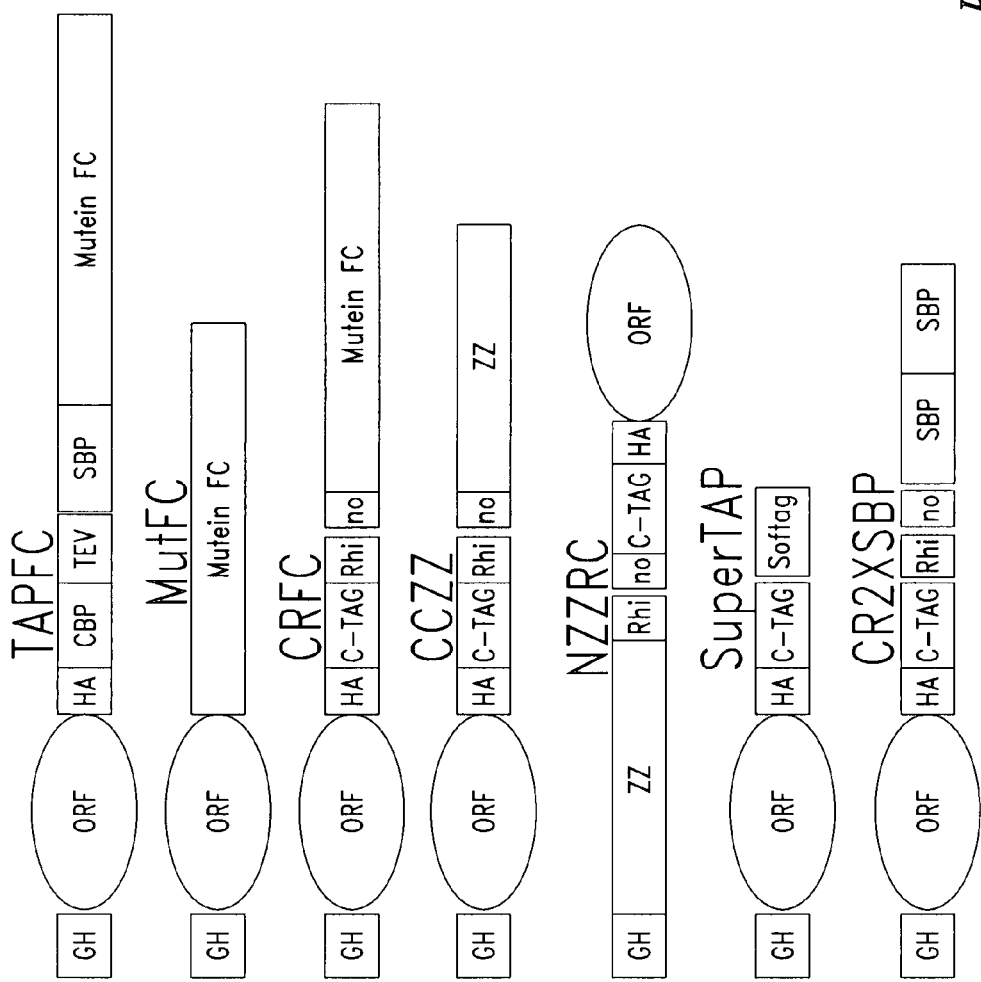
Figure 5:
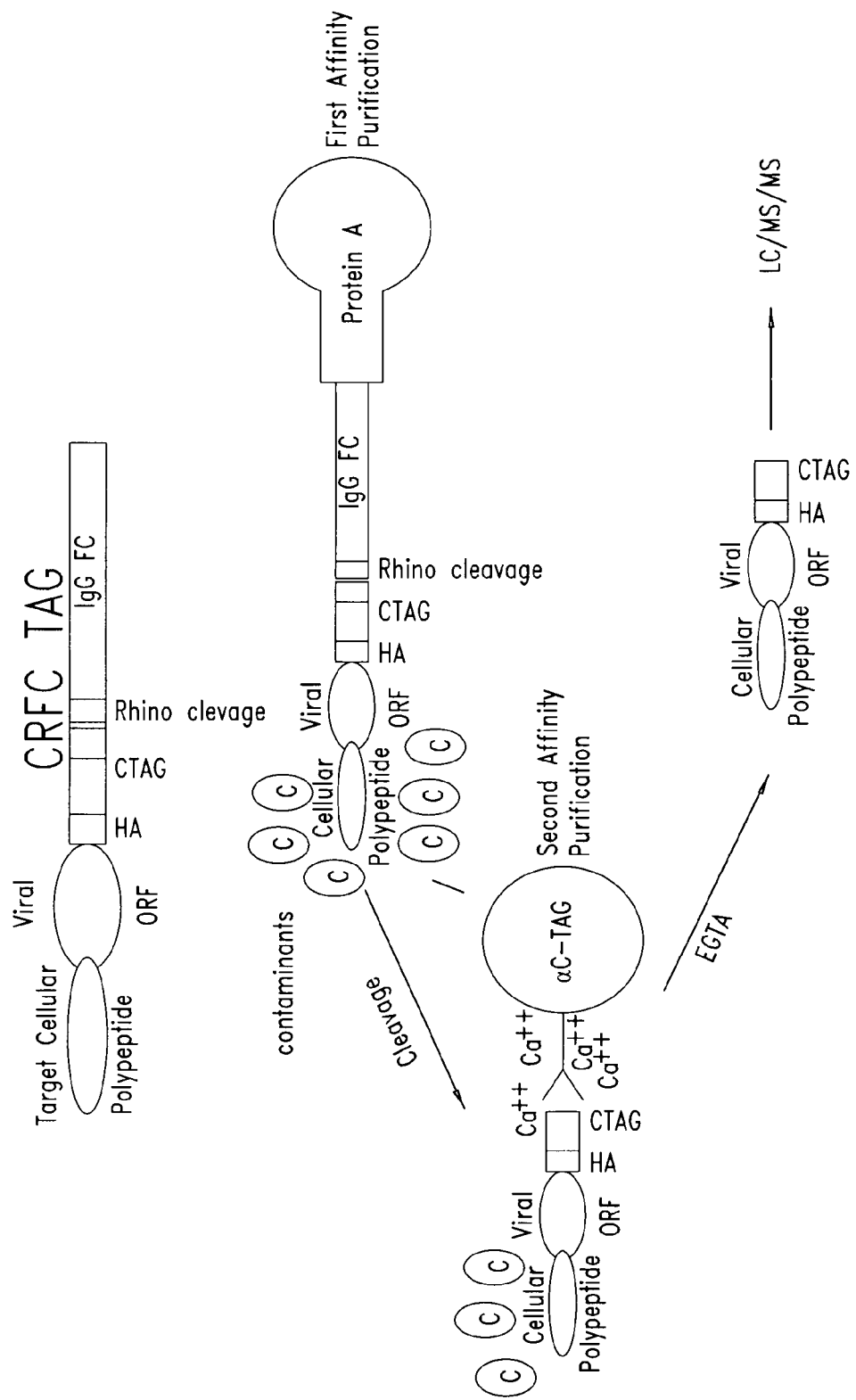

Examples of polypeptide and peptide sequences that may be included in a fusion protein are presented in FIG. 4. The expression constructs comprise a growth hormone (GH) signal peptide sequence (SEQ ID NO:12) (encoded by the polynucleotide set forth in SEQ ID NO:14). In certain embodiments, the sequence includes restriction sites, for example, SpeI and Asp718 are added to the C-terminus of the signal peptide (SEQ ID NO:13) to permit a polypeptide moiety to be fused to the signal peptide sequence (nucleotide sequence encoding GH with restriction sites: SEQ ID NO:15).

As described herein, fusion polypeptides comprise one, two, three, four, or more affinity tags and one or more protease sites. Peptide spacer sequences may be included between any two polypeptide moieties, such as between two affinity tags or between and affinity tag and a protease site, or between a virulence factor polypeptide open reading frame (ORF) and an affinity tag or protease site. The peptide spacer sequences may be, but not necessarily be, encoded by a nucleotide sequence that is a cleavage site or recognition site for a restriction enzyme. An example of an affinity tag includes an affinity tag combination that has more than one polypeptide. For instance, an HAC tag comprises an HA-epitope tag, C-TAG, and 2XSBP, which may be present in a fusion protein in any order (see, e.g., SEQ ID NO:35 sets forth the amino acid sequence of the HAC tag, wherein the HA epitope is located at the amino terminal end of the affinity tag fused to a C-TAG, which is fused to 2XSBP; SEQ ID NO:36 provides the nucleotide sequence encoding this HAC tag).

Another affinity tag that is an affinity tag combination is called herein a CRFC tag (see Example 1). A CRFC tag is a combination of an HA-epitope tag, a C-TAG, a human Rhinovirus HRV3C protease site, and an Fc polypeptide. An exemplary polypeptide sequence is provided in SEQ ID NO:37 and the nucleotide sequence encoding the CRFC tag is set forth in SEQ ID NO:38. The fusion polypeptides comprising any of the affinity tags described herein, which include affinity tag combinations, are used for tandem affinity purification of target cellular polypeptides that interact with a viral virulence factor, or a portion thereof.

From the foregoing it will be appreciated that, although specific embodiments of the invention have been described herein for purposes of illustration, various modifications may be made without deviating from the spirit and scope of the invention. Those skilled in the art will recognize, or be able to ascertain, using no more than routine experimentation, many equivalents to the specific embodiments of the invention described herein. Such equivalents are intended to be encompassed by the following claims.

We claim the following:

1. A method of identifying a cellular polypeptide to which a viral polypeptide binds, said method comprising:
   (a) contacting (i) a fraction or a supernatant obtained from a plurality of cells, and (ii) a fusion protein comprising a viral virulence polypeptide moiety fused to an affinity tag moiety, to permit the viral virulence polypeptide moiety to interact with a polypeptide associated with the cell fraction or the cell supernatant, to provide a fusion protein:cellular polypeptide complex, wherein the affinity tag moiety comprises a first polypeptide tag and a second polypeptide tag wherein the first polypeptide tag comprises a protein C-tag and the second polypeptide tag comprises a streptavidin binding peptide;
   (b) contacting the fusion protein:cellular polypeptide complex with a cognate ligand capable of interacting with the affinity tag, to permit formation of a cognate ligand:fusion protein:cellular polypeptide complex;
   (c) isolating the fusion protein:cellular polypeptide complex from the cognate ligand:fusion protein:cellular polypeptide complex by affinity purification;
   (d) subsequent to affinity purification,
      (A) determining the amino acid sequence of the cellular polypeptide or
      (B) determining the amino acid sequence of at least one fragment of the cellular polypeptide, comprising:
         (i) cleaving the fusion protein:cellular polypeptide complex of step (c) with a protease to generate a plurality of polypeptide fragments of the cellular polypeptide;
         (ii) determining the amino acid sequence of at least one polypeptide fragment of the cellular polypeptide, wherein the fragment comprises at least eight amino acids; and
         (iii) comparing the amino acid sequence of the at least one polypeptide fragment with the amino acid sequence of a known cellular polypeptide; and
   (e) identifying the cell type of a cell that comprises the cellular polypeptide to which the viral virulence polypeptide binds, said step comprising:
      (i) contacting the fusion protein and a biological sample comprising a plurality of cells, to permit the viral virulence polypeptide moiety of the fusion protein to interact with the cells;
      (ii) determining the presence or absence of binding of the fusion protein to the cells;
      (iii) isolating the cells to which the fusion protein binds; and
      (iv) characterizing the cells, and therefrom determining the cell type of the cell that comprises a cellular polypeptide to which the viral virulence polypeptide binds.

2. The method of claim 1 wherein the amino acid sequence of the cellular polypeptide or the at least one fragment of the cellular polypeptide is determined by a method comprising liquid chromatography and mass spectrometry.

3. The method of claim 1 wherein the affinity tag comprises at least the first polypeptide tag, the second polypeptide tag, and at least one protease recognition sequence, and wherein the step of isolating the fusion protein:cellular polypeptide complex by affinity purification comprises:
   (i) contacting the fusion protein:cellular polypeptide complex with a first cognate ligand that interacts with the protein C tag of the first polypeptide tag permitting the affinity tag moiety of the fusion protein to interact with the first cognate ligand to provide a first cognate ligand: fusion protein:cellular polypeptide complex;
   (ii) contacting the first cognate ligand:fusion protein:cellular polypeptide complex with a protease capable of cleaving the fusion protein at or near the protease recognition sequence to provide a cleaved fusion protein:cellular polypeptide complex;
   (iii) contacting the cleaved fusion protein:cellular polypeptide complex with a second cognate ligand that specifically binds to the streptavidin binding peptide of the second polypeptide tag, to permit the second cognate ligand and the cleaved fusion protein:cellular polypeptide complex to interact to form a second cognate ligand: cleaved fusion protein:cellular polypeptide complex; and
   (iv) isolating the cleaved fusion protein:cellular polypeptide complex from the second cognate ligand:cleaved fusion protein:cellular polypeptide complex.

4. A method of identifying a cellular polypeptide to which a viral polypeptide binds, said method comprising
   (a) identifying in the genome of a virus by using bioinformatics a polynucleotide sequence that encodes a viral virulence polypeptide, which viral virulence polypeptide comprises at least 20 amino acids;
   (b) producing a fusion protein comprising the viral virulence polypeptide fused to an affinity tag sequence, wherein the affinity tag sequence comprises a first polypeptide tag and a second polypeptide tag;
   (c) subsequent to step (b), contacting (i) a plurality of immune cells, or a fraction or a supernatant thereof, wherein the plurality of immune cells is subjected to at least one stimulus and (ii) the fusion protein comprising the viral virulence polypeptide fused to the affinity tag, under conditions and for a time sufficient that permit the viral virulence polypeptide moiety of the fusion protein to interact with a polypeptide associated with the plurality of immune cells, or with the fraction or the supernatant thereof, to provide a fusion protein: cellular polypeptide complex;
   (d) isolating the fusion protein: cellular polypeptide complex by tandem affinity purification; and
   (e) determining the amino acid sequence of the cellular polypeptide or of at least one cellular polypeptide fragment comprising at least eight amino acids; and
   (f) comparing the amino acid sequence of the cellular polypeptide or of the at least one cellular polypeptide fragment with the amino acid sequence of a known cellular polypeptide.

5. The method of claim 1 wherein absence of expression of the viral virulence polypeptide in a virus-infected cell correlates with a decrease in virulence of the virus.

6. The method of claim 1 wherein when the viral virulence polypeptide is expressed in a virus-infected cell comprising a genome encoding the viral virulence polypeptide, the viral virulence polypeptide (A) is secreted by the virus-infected cell, (B) is associated with a cellular membrane, or (C) is intracellular.

7. The method of claim 1 wherein the viral virulence polypeptide is secreted by a virus-infected cell or the viral virulence polypeptide is associated with a cellular membrane of the virus-infected cell.

8. The method according to claim 1 wherein prior to step (a), the plurality of cells is subjected to at least one stimulus, wherein the at least one stimulus is selected from (a) an antibody that specifically binds to a cognate antigen expressed by the cell; (b) a phorbol ester; (c) concanavalin A; (d) a cytokine; (e) a chemokine; and (f) ionomycin.

9. The method according to claim 1 wherein the affinity tag further comprises a detectable moiety.

10. The method according to claim 1 wherein the affinity tag moiety further comprises a protease recognition sequence.

11. The method according to claim 1 wherein the second polypeptide tag comprises two streptavidin binding peptides.

12. The method according to claim 10 wherein the protease recognition sequence is located between the first polypeptide tag and the second polypeptide tag.

13. The method according to claim 1 wherein the affinity tag moiety further comprises a third polypeptide tag.

14. The method according to claim 13 wherein the third polypeptide tag is selected from a hemagglutinin peptide and a peptide comprising the amino acid sequence set forth in SEQ ID NO:11.

15. The method according to claim 14 wherein the third polypeptide tag is a hemagglutinin peptide.

16. The method according to claim 14 wherein the affinity tag moiety comprises at least one protease recognition sequence.

17. The method according to claim 16 wherein the at least one protease recognition sequence is located between the first polypeptide tag and the second polypeptide tag, or wherein the protease recognition sequence is located between the second polypeptide tag and the third polypeptide tag.

18. The method according to claim 13 wherein the affinity tag moiety further comprises a fourth polypeptide tag.

19. The method according to claim 18 wherein the fourth polypeptide tag is a peptide comprising the amino acid sequence set forth in SEQ ID NO:11.

20. The method according to claim 10 wherein the protease recognition sequence is a Human Rhinovirus HRV3C protease recognition sequence or a tobacco etch virus protease recognition sequence.

21. The method according to claim 16 wherein the at least one protease recognition sequence is a Human Rhinovirus HRV3C protease recognition sequence or a tobacco etch virus protease recognition sequence.

22. The method according to either claim 10 or claim 16 wherein the affinity tag further comprises a second protease recognition sequence.

23. The method according to claim 4, wherein the amino acid sequence is determined by a method comprising liquid chromatography and mass spectrometry.

24. The method according to claim 4, wherein the virus comprises a DNA genome and the virus is a poxvirus, adenovirus, herpesvirus, or a hepatitis B virus; or the virus comprises an RNA genome and the virus is a picornavirus, a retrovirus, a hemorrhagic fever virus, or a hepatitis C virus.

25. The method according to claim 4, wherein the at least one stimulus is selected from (a) an antibody that specifically binds to a cognate antigen expressed by the immune cell; (b) a phorbol ester; (c) concanavalin A; (d) a cytokine; (e) a chemokine; and (f) ionomycin.

26. The method according to claim 4, wherein the fraction of the plurality of immune cells is selected from a cell lysate, a cell extract, or at least one isolated cell organelle.

27. The method according to claim 4, wherein the affinity tag further comprises a detectable moiety.

28. The method according to claim 27, wherein the detectable moiety is selected from a fluorophore, a radionuclide, an enzyme, and biotin.

29. The method according to claim 4, wherein the affinity tag further comprises at least one protease recognition sequence.

30. The method according to claim 4, wherein the affinity tag further comprises a third polypeptide tag.

31. The method according to claim 30, wherein the first, second, and third, polypeptide tags are each independently selected from a hemagglutinin peptide, a calmodulin binding polypeptide, a streptavidin binding peptide, an immunoglobulin Fc polypeptide, an immunoglobulin mutein Fc polypeptide, a protein C-tag, an at least one immunoglobulin binding staphylococcal protein A domain, and a peptide comprising the amino acid sequence set forth in SEQ ID NO:11.

32. The method according to claim 30, wherein (a) the first polypeptide tag is a hemagglutinin peptide; the second polypeptide tag is a protein C-tag; and the third polypeptide tag is a peptide comprising the amino acid sequence set forth in SEQ ID NO:11; or (b) the first polypeptide tag is a hemagglutinin peptide; the second polypeptide tag is a protein C-tag; and the third polypeptide tag is a streptavidin binding protein.

33. The method according to claim 30, wherein the affinity tag further comprises a fourth polypeptide tag.

34. The method according to claim 33, wherein the fourth polypeptide tag is the same as the first, second, or third polypeptide tag.

35. The method according to claim 34, wherein the first polypeptide tag is the hemagglutinin polypeptide; the second polypeptide tag is the protein C-tag; the third polypeptide tag is the streptavidin binding peptide; and the fourth polypeptide tag is a repeat of the third polypeptide tag.

36. The method according to claim 30, wherein the affinity tag further comprises a second protease recognition sequence.

37. The method according to claim 4, wherein the fusion protein further comprises a signal peptide sequence.

38. The method according to claim 37, wherein the signal peptide sequence comprises the amino acid sequence MATGSRTSLLLAFGLLCLPWLQEGSA (SEQ ID NO:12).

* * * * *

SEQUENCE LISTING

<160> NUMBER OF SEQ ID NOS: 44

<210> SEQ ID NO 1
<211> LENGTH: 8
<212> TYPE: PRT
<213> ORGANISM: Artificial Sequence
<220> FEATURE:
<223> OTHER INFORMATION: hemagglutinin peptide sequence

<400> SEQUENCE: 1

Tyr Pro Tyr Asp Val Asp Tyr Ala
 1               5

<210> SEQ ID NO 2
<211> LENGTH: 27
<212> TYPE: DNA
<213> ORGANISM: Artificial Sequence
<220> FEATURE:
<223> OTHER INFORMATION: hemagglutinin nucleotide sequence

<400> SEQUENCE: 2
tacccctacg acgtgcccga ctacgcc                                           27

<210> SEQ ID NO 3
<211> LENGTH: 26
<212> TYPE: PRT
<213> ORGANISM: Artificial Sequence
<220> FEATURE:
<223> OTHER INFORMATION: calmodulin binding polypeptide sequence

<400> SEQUENCE: 3

Lys Arg Arg Trp Lys Lys Asn Phe Ile Ala Val Ser Ala Ala Asn Arg
 1               5                  10                  15

Phe Lys Lys Ile Ser Ser Ser Gly Ala Leu
             20                  25

<210> SEQ ID NO 4
<211> LENGTH: 12
<212> TYPE: PRT
<213> ORGANISM: Artificial Sequence
<220> FEATURE:
<223> OTHER INFORMATION: Protein C-tag peptide sequence

<400> SEQUENCE: 4

Glu Asp Gln Val Asp Pro Arg Leu Ile Asp Gly Lys
 1               5                  10

<210> SEQ ID NO 5
<211> LENGTH: 36
<212> TYPE: DNA
<213> ORGANISM: Artificial Sequence
<220> FEATURE:
<223> OTHER INFORMATION: Protein C-tag nucleotide sequence

<400> SEQUENCE: 5
gaggaccagg tggacccccg gctgatcgac ggcaag                                 36

<210> SEQ ID NO 6
<211> LENGTH: 38
<212> TYPE: PRT
<213> ORGANISM: Artificial Sequence
<220> FEATURE:
<223> OTHER INFORMATION: Streptavidin binding protein sequence

<400> SEQUENCE: 6

```
Met Asp Glu Lys Thr Thr Gly Trp Arg Gly Gly His Val Val Glu Gly
 1               5                  10                  15

Leu Ala Gly Glu Leu Glu Gln Leu Arg Ala Arg Leu Glu His His Pro
             20                  25                  30

Gln Gly Gln Arg Glu Pro
         35

<210> SEQ ID NO 7
<211> LENGTH: 15
<212> TYPE: PRT
<213> ORGANISM: Artificial Sequence
<220> FEATURE:
<223> OTHER INFORMATION: Low affinity streptavidin binding protein
      sequence

<400> SEQUENCE: 7

Asp Val Glu Ala Trp Leu Asp Glu Arg Val Pro Leu Val Glu Thr
 1               5                  10                  15

<210> SEQ ID NO 8
<211> LENGTH: 79
<212> TYPE: PRT
<213> ORGANISM: Artificial Sequence
<220> FEATURE:
<223> OTHER INFORMATION: Tandem streptavidin binding protein sequence

<400> SEQUENCE: 8

Met Asp Glu Lys Thr Thr Gly Trp Arg Gly Gly His Val Val Glu Gly
 1               5                  10                  15

Leu Ala Gly Glu Leu Glu Gln Leu Arg Ala Arg Leu Glu His His Pro
             20                  25                  30

Gln Gly Gln Arg Glu Pro Gly Ser Gly Met Asp Glu Lys Thr Thr Gly
         35                  40                  45

Trp Arg Gly Gly His Val Val Glu Gly Leu Ala Gly Glu Leu Glu Gln
     50                  55                  60

Leu Arg Ala Arg Leu Glu His His Pro Gln Gly Gln Arg Glu Pro
65                  70                  75

<210> SEQ ID NO 9
<211> LENGTH: 114
<212> TYPE: DNA
<213> ORGANISM: Artificial Sequence
<220> FEATURE:
<223> OTHER INFORMATION: Low affinity streptavidin binding nucleotide
      sequence

<400> SEQUENCE: 9
atggacgaga agaccaccgg ctggcggggc ggccacgtgg tggagggcct ggccggcgag    60
ctggagcagc tgcgggcccg gctggagcac caccccagg gccagcggga gccc          114

<210> SEQ ID NO 10
<211> LENGTH: 240
<212> TYPE: DNA
<213> ORGANISM: Artificial Sequence
<220> FEATURE:
<223> OTHER INFORMATION: Tandem streptavidin binding nucleotide sequence

<400> SEQUENCE: 10
atggacgaga agaccaccgg ctggcggggc ggccacgtgg tggagggcct ggccggcgag    60
ctggagcagc tgcgggcccg gctggagcac caccccagg gccagcggga gcccggaagc    120
ggtatggatg aaaaaactac tggttggaga ggggacatg tagtcgaagg tctggccggc    180
gagttagaac aattaagagc tagattggaa catcatccac aaggtcaaag agaaccttag   240
```

<210> SEQ ID NO 11
<211> LENGTH: 13
<212> TYPE: PRT
<213> ORGANISM: Artificial Sequence
<220> FEATURE:
<223> OTHER INFORMATION: SoftagTM peptide sequence

<400> SEQUENCE: 11

Ser Leu Ala Glu Leu Leu Asn Ala Gly Leu Gly Gly Ser
 1               5                  10

<210> SEQ ID NO 12
<211> LENGTH: 26
<212> TYPE: PRT
<213> ORGANISM: Homo sapiens

<400> SEQUENCE: 12

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala
            20                  25

<210> SEQ ID NO 13
<211> LENGTH: 30
<212> TYPE: PRT
<213> ORGANISM: Artificial Sequence
<220> FEATURE:
<223> OTHER INFORMATION: Synthesized human growth hormone peptide with
      restriction sites

<400> SEQUENCE: 13

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Thr Ser Gly Thr
            20                  25                  30

<210> SEQ ID NO 14
<211> LENGTH: 78
<212> TYPE: DNA
<213> ORGANISM: Homo sapiens

<400> SEQUENCE: 14
atggctacag gctcccggac gtccctgctc ctggcttttg gcctgctctg cctgccctgg      60
cttcaagagg gcagtgca                                                   78

<210> SEQ ID NO 15
<211> LENGTH: 90
<212> TYPE: DNA
<213> ORGANISM: Artificial Sequence
<220> FEATURE:
<223> OTHER INFORMATION: Human growth hormone nucleotide with
      restriction sites

<400> SEQUENCE: 15
atggctacag gctcccggac gtccctgctc ctggcttttg gcctgctctg cctgccctgg      60
cttcaagagg gcagtgcaac tagtggtacc                                      90

<210> SEQ ID NO 16
<211> LENGTH: 8
<212> TYPE: PRT
<213> ORGANISM: Human rhinovirus

<400> SEQUENCE: 16

```
Leu Glu Val Leu Phe Gln Gly Pro
 1               5
```

<210> SEQ ID NO 17
<211> LENGTH: 24
<212> TYPE: DNA
<213> ORGANISM: Human rhinovirus

<400> SEQUENCE: 17
ctggaggtgc tgttccaggg cccc                                          24

<210> SEQ ID NO 18
<211> LENGTH: 1948
<212> TYPE: PRT
<213> ORGANISM: Homo sapiens

<400> SEQUENCE: 18

```
Met Ala Pro Thr Trp Gly Pro Gly Met Val Ser Val Gly Pro Met
 1               5                  10                  15

Gly Leu Leu Val Val Leu Val Gly Gly Cys Ala Ala Glu Glu Pro
                20                  25                  30

Pro Arg Phe Ile Lys Glu Pro Lys Asp Gln Ile Gly Val Ser Gly
                35                  40                  45

Val Ala Ser Phe Val Cys Gln Ala Thr Gly Asp Pro Lys Pro Arg Val
50                      55                      60

Thr Trp Asn Lys Lys Gly Lys Lys Val Asn Ser Gln Arg Phe Glu Thr
65                  70                  75                      80

Ile Glu Phe Asp Glu Ser Ala Gly Ala Val Leu Arg Ile Gln Pro Leu
                85                  90                      95

Arg Thr Pro Arg Asp Glu Asn Val Tyr Glu Cys Val Ala Gln Asn Ser
                100                 105                 110

Val Gly Glu Ile Thr Val His Ala Lys Leu Thr Val Leu Arg Glu Asp
            115                 120                 125

Gln Leu Pro Ser Gly Phe Pro Asn Ile Asp Met Gly Pro Gln Leu Lys
            130                 135                 140

Val Val Glu Arg Thr Arg Thr Ala Thr Met Leu Cys Ala Ala Ser Gly
145                 150                 155                 160

Asn Pro Asp Pro Glu Ile Thr Trp Phe Lys Asp Phe Leu Pro Val Asp
                165                 170                 175

Pro Ser Ala Ser Asn Gly Arg Ile Lys Gln Leu Arg Ser Asp Gln Ala
                180                 185                 190

Phe Ser His Leu Pro Thr Gly Ala Leu Gln Ile Glu Ser Ser Glu Glu
                195                 200                 205

Thr Asp Gln Gly Lys Tyr Glu Cys Val Ala Thr Asn Ser Ala Gly Val
            210                 215                 220

Arg Tyr Ser Ser Pro Ala Asn Leu Tyr Val Arg Ala Leu Leu Lys Leu
225                 230                 235                 240

Arg Arg Val Ala Pro Arg Phe Ser Ile Leu Pro Met Ser His Glu Ile
                245                 250                 255

Met Pro Gly Gly Asn Val Asn Ile Thr Cys Val Ala Val Gly Ser Pro
                260                 265                 270

Met Pro Tyr Val Lys Trp Met Gln Gly Ala Glu Asp Leu Thr Pro Glu
                275                 280                 285

Asp Asp Met Pro Val Gly Arg Asn Val Leu Glu Leu Thr Asp Val Lys
            290                 295                 300

Asp Ser Ala Asn Tyr Thr Cys Val Ala Met Ser Ser Leu Gly Val Ile
305                 310                 315                 320
```

```
Glu Ala Val Ala Gln Ile Thr Val Lys Ser Leu Pro Lys Ala Pro Gly
                325                 330                 335

Thr Pro Met Val Thr Glu Asn Thr Ala Thr Ser Ile Thr Ile Thr Trp
            340                 345                 350

Asp Ser Gly Asn Pro Asp Pro Val Ser Tyr Tyr Val Ile Glu Tyr Lys
        355                 360                 365

Ser Lys Ser Gln Asp Gly Pro Tyr Gln Ile Lys Glu Asp Ile Thr Thr
370                 375                 380

Thr Arg Tyr Ser Ile Gly Gly Leu Ser Pro Asn Ser Glu Tyr Glu Ile
385                 390                 395                 400

Trp Val Ser Ala Val Asn Ser Ile Gly Gln Gly Pro Pro Ser Glu Ser
                405                 410                 415

Val Val Thr Arg Thr Gly Glu Gln Ala Pro Ala Ser Ala Pro Arg Asn
            420                 425                 430

Val Gln Ala Arg Met Leu Ser Ala Thr Thr Met Ile Val Gln Trp Glu
        435                 440                 445

Glu Pro Val Glu Pro Asn Gly Leu Ile Arg Gly Tyr Arg Val Tyr Tyr
450                 455                 460

Thr Met Glu Pro Glu His Pro Val Gly Asn Trp Gln Lys His Asn Val
465                 470                 475                 480

Asp Asp Ser Leu Leu Thr Thr Val Gly Ser Leu Leu Glu Asp Glu Thr
                485                 490                 495

Tyr Thr Val Arg Val Leu Ala Phe Thr Ser Val Gly Asp Gly Pro Leu
            500                 505                 510

Ser Asp Pro Ile Gln Val Lys Thr Gln Gln Gly Val Pro Gly Gln Pro
        515                 520                 525

Met Asn Leu Arg Ala Glu Ala Arg Ser Glu Thr Ser Ile Thr Leu Ser
530                 535                 540

Trp Ser Pro Pro Arg Gln Glu Ser Ile Ile Lys Tyr Glu Leu Leu Phe
545                 550                 555                 560

Arg Glu Gly Asp His Gly Arg Glu Val Gly Arg Thr Phe Asp Pro Thr
                565                 570                 575

Thr Ser Tyr Val Val Glu Asp Leu Lys Pro Asn Thr Glu Tyr Ala Phe
            580                 585                 590

Arg Leu Ala Ala Arg Ser Pro Gln Gly Leu Gly Ala Phe Thr Pro Val
        595                 600                 605

Val Arg Gln Arg Thr Leu Gln Ser Lys Pro Ser Ala Pro Pro Gln Asp
610                 615                 620

Val Lys Cys Val Ser Val Arg Ser Thr Ala Ile Leu Val Ser Trp Arg
625                 630                 635                 640

Pro Pro Pro Pro Glu Thr His Asn Gly Ala Leu Val Gly Tyr Ser Val
                645                 650                 655

Arg Tyr Arg Pro Leu Gly Ser Glu Asp Pro Glu Pro Lys Glu Val Asn
            660                 665                 670

Gly Ile Pro Pro Thr Thr Thr Gln Ile Leu Leu Glu Ala Leu Glu Lys
        675                 680                 685

Trp Thr Gln Tyr Arg Ile Thr Thr Val Ala His Thr Glu Val Gly Pro
690                 695                 700

Gly Pro Glu Ser Ser Pro Val Val Val Arg Thr Asp Glu Asp Val Pro
705                 710                 715                 720

Ser Ala Pro Pro Arg Lys Val Glu Ala Glu Ala Leu Asn Ala Thr Ala
                725                 730                 735

Ile Arg Val Leu Trp Arg Ser Pro Ala Pro Gly Arg Gln His Gly Gln
```

-continued

```
                    740                 745                 750
Ile Arg Gly Tyr Gln Val His Tyr Val Arg Met Glu Gly Ala Glu Ala
            755                 760                 765
Arg Gly Pro Pro Arg Ile Lys Asp Val Met Leu Ala Asp Ala Gln Trp
    770                 775                 780
Glu Thr Asp Asp Thr Ala Glu Tyr Glu Met Val Ile Thr Asn Leu Gln
785                 790                 795                 800
Pro Glu Thr Ala Tyr Ser Ile Thr Val Ala Ala Tyr Thr Met Lys Gly
                805                 810                 815
Asp Gly Ala Arg Ser Lys Pro Lys Val Val Thr Lys Gly Ala Val
            820                 825                 830
Leu Gly Arg Pro Thr Leu Ser Val Gln Gln Thr Pro Glu Gly Ser Leu
    835                 840                 845
Leu Ala Arg Trp Glu Pro Pro Ala Gly Thr Ala Glu Asp Gln Val Leu
    850                 855                 860
Gly Tyr Arg Leu Gln Phe Gly Arg Glu Asp Ser Thr Pro Leu Ala Thr
865                 870                 875                 880
Leu Glu Phe Pro Pro Ser Glu Asp Arg Tyr Thr Ala Ser Gly Val His
                885                 890                 895
Lys Gly Ala Thr Tyr Val Phe Arg Leu Ala Ala Arg Ser Arg Gly Gly
                900                 905                 910
Leu Gly Glu Glu Ala Ala Glu Val Leu Ser Ile Pro Glu Asp Thr Pro
            915                 920                 925
Arg Gly His Pro Gln Ile Leu Glu Ala Ala Gly Asn Ala Ser Ala Gly
        930                 935                 940
Thr Val Leu Leu Arg Trp Leu Pro Pro Val Pro Ala Glu Arg Asn Gly
945                 950                 955                 960
Ala Ile Val Lys Tyr Thr Val Ala Val Arg Glu Ala Gly Ala Leu Gly
                965                 970                 975
Pro Ala Arg Glu Thr Glu Leu Pro Ala Ala Ala Glu Pro Gly Ala Glu
            980                 985                 990
Asn Ala Leu Thr Leu Gln Gly Leu Lys Pro Asp Thr Ala Tyr Asp Leu
        995                 1000                1005
Gln Val Arg Ala His Thr Arg Arg Gly Pro Gly Pro Phe Ser Pro Pro
    1010                1015                1020
Val Arg Tyr Arg Thr Phe Leu Arg Asp Gln Val Ser Pro Lys Asn Phe
1025                1030                1035                1040
Lys Val Lys Met Ile Met Lys Thr Ser Val Leu Leu Ser Trp Glu Phe
                1045                1050                1055
Pro Asp Asn Tyr Asn Ser Pro Thr Pro Tyr Lys Ile Gln Tyr Asn Gly
                1060                1065                1070
Leu Thr Leu Asp Val Asp Gly Arg Thr Thr Lys Lys Leu Ile Thr His
            1075                1080                1085
Leu Lys Pro His Thr Phe Tyr Asn Phe Val Leu Thr Asn Arg Gly Ser
        1090                1095                1100
Ser Leu Gly Gly Leu Gln Gln Thr Val Thr Ala Trp Thr Ala Phe Asn
1105                1110                1115                1120
Leu Leu Asn Gly Lys Pro Ser Val Ala Pro Lys Pro Asp Ala Asp Gly
                1125                1130                1135
Phe Ile Met Val Tyr Leu Pro Asp Gly Gln Ser Pro Val Pro Val Gln
            1140                1145                1150
Ser Tyr Phe Ile Val Met Val Pro Leu Arg Lys Ser Arg Gly Gly Gln
        1155                1160                1165
```

-continued

Phe Leu Thr Pro Leu Gly Ser Pro Glu Asp Met Asp Leu Glu Glu Leu
    1170                1175                1180

Ile Gln Asp Ile Ser Arg Leu Gln Arg Arg Ser Leu Arg His Ser Arg
1185                1190                1195                1200

Gln Leu Glu Val Pro Arg Pro Tyr Ile Ala Ala Arg Phe Ser Val Leu
                1205                1210                1215

Pro Pro Thr Phe His Pro Gly Asp Gln Lys Gln Tyr Gly Gly Phe Asp
                1220                1225                1230

Asn Arg Gly Leu Glu Pro Gly His Arg Tyr Val Leu Phe Val Leu Ala
                1235                1240                1245

Val Leu Gln Lys Ser Glu Pro Thr Phe Ala Ala Ser Pro Phe Ser Asp
                1250                1255                1260

Pro Phe Gln Leu Asp Asn Pro Asp Pro Gln Pro Ile Val Asp Gly Glu
1265                1270                1275                1280

Glu Gly Leu Ile Trp Val Ile Gly Pro Val Leu Ala Val Val Phe Ile
                1285                1290                1295

Ile Cys Ile Val Ile Ala Ile Leu Leu Tyr Lys Asn Lys Pro Asp Ser
                1300                1305                1310

Lys Arg Lys Asp Ser Glu Pro Arg Thr Lys Cys Leu Leu Asn Asn Ala
                1315                1320                1325

Asp Leu Ala Pro His His Pro Lys Asp Pro Val Glu Met Arg Arg Ile
                1330                1335                1340

Asn Phe Gln Thr Pro Asp Ser Gly Leu Arg Ser Pro Leu Arg Glu Pro
1345                1350                1355                1360

Gly Phe His Phe Glu Ser Met Leu Ser His Pro Pro Ile Pro Ile Ala
                1365                1370                1375

Asp Met Ala Glu His Thr Glu Arg Leu Lys Ala Asn Asp Ser Leu Lys
                1380                1385                1390

Leu Ser Gln Glu Tyr Glu Ser Ile Asp Pro Gly Gln Gln Phe Thr Trp
                1395                1400                1405

Glu His Ser Asn Leu Glu Val Asn Lys Pro Lys Asn Arg Tyr Ala Asn
    1410                1415                1420

Val Ile Ala Tyr Asp His Ser Arg Val Ile Leu Gln Pro Ile Glu Gly
1425                1430                1435                1440

Ile Met Gly Ser Asp Tyr Ile Asn Ala Asn Tyr Val Asp Gly Tyr Arg
                1445                1450                1455

Cys Gln Asn Ala Tyr Ile Ala Thr Gln Gly Pro Leu Pro Glu Thr Phe
                1460                1465                1470

Gly Asp Phe Trp Arg Met Val Trp Glu Gln Arg Ser Ala Thr Ile Val
                1475                1480                1485

Met Met Thr Arg Leu Glu Glu Lys Ser Arg Ile Lys Cys Asp Gln Tyr
    1490                1495                1500

Trp Pro Asn Arg Gly Thr Glu Thr Tyr Gly Phe Ile Gln Val Thr Leu
1505                1510                1515                1520

Leu Asp Thr Ile Glu Leu Ala Thr Phe Cys Val Arg Thr Phe Ser Leu
                1525                1530                1535

His Lys Asn Gly Ser Ser Glu Lys Arg Glu Val Arg Gln Phe Gln Phe
                1540                1545                1550

Thr Ala Trp Pro Asp His Gly Val Pro Glu Tyr Pro Thr Pro Phe Leu
                1555                1560                1565

Ala Phe Leu Arg Arg Val Lys Thr Cys Asn Pro Pro Asp Ala Gly Pro
                1570                1575                1580

Ile Val Val His Cys Ser Ala Gly Val Gly Arg Thr Gly Cys Phe Ile
1585                1590                1595                1600

Val Ile Asp Ala Met Leu Glu Arg Ile Lys Pro Glu Lys Thr Val Asp
             1605                1610                1615

Val Tyr Gly His Val Thr Leu Met Arg Ser Gln Arg Asn Tyr Met Val
             1620                1625                1630

Gln Thr Glu Asp Gln Tyr Ser Phe Ile His Glu Ala Leu Leu Glu Ala
             1635                1640                1645

Val Gly Cys Gly Asn Thr Glu Val Pro Ala Arg Ser Leu Tyr Ala Tyr
             1650                1655                1660

Ile Gln Lys Leu Ala Gln Val Glu Pro Gly Glu His Val Thr Gly Met
1665             1670                1675                1680

Glu Leu Glu Phe Lys Arg Leu Ala Asn Ser Lys Ala His Thr Ser Arg
             1685                1690                1695

Phe Ile Ser Ala Asn Leu Pro Cys Asn Lys Phe Lys Asn Arg Leu Val
             1700                1705                1710

Asn Ile Met Pro Tyr Glu Ser Thr Arg Val Cys Leu Gln Pro Ile Arg
             1715                1720                1725

Gly Val Glu Gly Ser Asp Tyr Ile Asn Ala Ser Phe Ile Asp Gly Tyr
             1730                1735                1740

Arg Gln Gln Lys Ala Tyr Ile Ala Thr Gln Gly Pro Leu Ala Glu Thr
1745             1750                1755                1760

Thr Glu Asp Phe Trp Arg Met Leu Trp Glu Asn Asn Ser Thr Ile Val
             1765                1770                1775

Val Met Leu Thr Lys Leu Arg Glu Met Gly Arg Glu Lys Cys His Gln
             1780                1785                1790

Tyr Trp Pro Ala Glu Arg Ser Ala Arg Tyr Gln Tyr Phe Val Val Asp
             1795                1800                1805

Pro Met Ala Glu Tyr Asn Met Pro Gln Tyr Ile Leu Arg Glu Phe Lys
             1810                1815                1820

Val Thr Asp Ala Arg Asp Gly Gln Ser Arg Thr Val Arg Gln Phe Gln
1825             1830                1835                1840

Phe Thr Asp Trp Pro Glu Gln Gly Val Pro Lys Ser Gly Glu Gly Phe
             1845                1850                1855

Ile Asp Phe Ile Gly Gln Val His Lys Thr Lys Glu Gln Phe Gly Gln
             1860                1865                1870

Asp Gly Pro Ile Ser Val His Cys Ser Ala Gly Val Gly Arg Thr Gly
             1875                1880                1885

Val Phe Ile Thr Leu Ser Ile Val Leu Glu Arg Met Arg Tyr Glu Gly
             1890                1895                1900

Val Val Asp Ile Phe Gln Thr Val Lys Met Leu Arg Thr Gln Arg Pro
1905             1910                1915                1920

Ala Met Val Gln Thr Glu Asp Glu Tyr Gln Phe Cys Tyr Gln Ala Ala
             1925                1930                1935

Leu Glu Tyr Leu Gly Ser Phe Asp His Tyr Ala Thr
             1940                1945

<210> SEQ ID NO 19
<211> LENGTH: 1913
<212> TYPE: PRT
<213> ORGANISM: Homo sapiens

<400> SEQUENCE: 19

Met Val His Val Ala Arg Leu Leu Leu Leu Leu Thr Phe Phe Leu
1               5                   10                  15

Arg Thr Asp Ala Glu Thr Pro Pro Arg Phe Thr Arg Thr Pro Val Asp
                20                  25                  30

-continued

Gln Thr Gly Val Ser Gly Val Ala Ser Phe Ile Cys Gln Ala Thr
                35                  40                  45

Gly Asp Pro Arg Pro Lys Ile Val Trp Asn Lys Lys Gly Lys Lys Val
 50                  55                  60

Ser Asn Gln Arg Phe Glu Val Ile Glu Phe Asp Asp Gly Ser Gly Ser
 65                  70                  75                  80

Val Leu Arg Ile Gln Pro Leu Arg Thr Pro Arg Asp Glu Ala Ile Tyr
                85                  90                  95

Glu Cys Val Ala Ser Asn Asn Val Gly Glu Ile Ser Val Ser Thr Arg
                100                 105                 110

Leu Thr Val Leu Arg Glu Asp Gln Ile Pro Arg Gly Phe Pro Thr Ile
                115                 120                 125

Asp Met Gly Pro Gln Leu Lys Val Val Glu Arg Thr Arg Thr Ala Thr
                130                 135                 140

Met Leu Cys Ala Ala Ser Gly Asn Pro Asp Pro Glu Ile Thr Trp Phe
145                 150                 155                 160

Lys Asp Phe Leu Pro Val Asp Thr Ser Asn Asn Asn Gly Arg Ile Lys
                165                 170                 175

Gln Leu Arg Ser Gly Arg Val Phe Lys Arg Leu Asn Arg Arg Ala Leu
                180                 185                 190

Gln Ile Glu Gln Ser Glu Glu Ser Asp Gln Gly Lys Tyr Glu Cys Val
                195                 200                 205

Ala Thr Asn Ser Ala Gly Thr Arg Tyr Ser Ala Pro Ala Asn Leu Tyr
                210                 215                 220

Val Arg Val Glu Thr Pro Gln Val Arg Arg Val Pro Pro Arg Phe Ser
225                 230                 235                 240

Ile Pro Pro Thr Asn His Glu Ile Met Pro Gly Gly Ser Val Asn Ile
                245                 250                 255

Thr Cys Val Ala Val Gly Ser Pro Met Pro Tyr Val Lys Trp Met Leu
                260                 265                 270

Gly Ala Glu Asp Leu Thr Pro Glu Asp Asp Met Pro Ile Gly Arg Asn
                275                 280                 285

Val Leu Glu Leu Asn Asp Val Arg Gln Ser Ala Asn Tyr Thr Cys Val
                290                 295                 300

Ala Met Ser Thr Leu Gly Val Ile Glu Ala Ile Ala Gln Ile Thr Val
305                 310                 315                 320

Lys Ala Leu Pro Lys Pro Pro Gly Thr Pro Val Val Thr Glu Ser Thr
                325                 330                 335

Ala Thr Ser Ile Thr Leu Thr Trp Asp Ser Gly Asn Pro Glu Pro Val
                340                 345                 350

Ser Tyr Tyr Ile Ile Gln His Lys Pro Lys Asn Ser Glu Glu Leu Tyr
                355                 360                 365

Lys Glu Ile Asp Gly Val Ala Thr Thr Arg Tyr Ser Val Ala Gly Leu
 370                 375                 380

Ser Pro Tyr Ser Asp Tyr Glu Phe Arg Val Val Ala Val Asn Asn Ile
385                 390                 395                 400

Gly Arg Gly Pro Pro Ser Glu Pro Val Leu Thr Gln Thr Ser Glu Gln
                405                 410                 415

Ala Pro Ser Ser Ala Pro Arg Asp Val Gln Ala Arg Met Leu Ser Ser
                420                 425                 430

Thr Thr Ile Leu Val Gln Trp Lys Glu Pro Glu Glu Pro Asn Gly Gln
                435                 440                 445

Ile Gln Gly Tyr Arg Val Tyr Tyr Thr Met Asp Pro Thr Gln His Val

-continued

```
                450                 455                 460
Asn Asn Trp Met Lys His Asn Val Ala Asp Ser Gln Ile Thr Thr Ile
465                 470                 475                 480

Gly Asn Leu Val Pro Gln Lys Thr Tyr Ser Val Lys Val Leu Ala Phe
                485                 490                 495

Thr Ser Ile Gly Asp Gly Pro Leu Ser Ser Asp Ile Gln Val Ile Thr
                500                 505                 510

Gln Thr Gly Val Pro Gly Gln Pro Leu Asn Phe Lys Ala Glu Pro Glu
                515                 520                 525

Ser Glu Thr Ser Ile Leu Leu Ser Trp Thr Pro Pro Arg Ser Asp Thr
530                 535                 540

Ile Ala Asn Tyr Glu Leu Val Tyr Lys Asp Gly Glu His Gly Glu Glu
545                 550                 555                 560

Gln Arg Ile Thr Ile Glu Pro Gly Thr Ser Tyr Arg Leu Gln Gly Leu
                565                 570                 575

Lys Pro Asn Ser Leu Tyr Tyr Phe Arg Leu Ala Ala Arg Ser Pro Gln
                580                 585                 590

Gly Leu Gly Ala Ser Thr Ala Glu Ile Ser Ala Arg Thr Met Gln Ser
                595                 600                 605

Lys Pro Ser Ala Pro Pro Gln Asp Ile Ser Cys Thr Ser Pro Ser Ser
610                 615                 620

Thr Ser Ile Leu Val Ser Trp Gln Pro Pro Val Glu Lys Gln Asn
625                 630                 635                 640

Gly Ile Ile Thr Glu Tyr Ser Ile Lys Tyr Thr Ala Val Asp Gly Glu
                645                 650                 655

Asp Asp Lys Pro His Glu Ile Leu Gly Ile Pro Ser Asp Thr Thr Lys
                660                 665                 670

Tyr Leu Leu Glu Gln Leu Glu Lys Trp Thr Glu Tyr Arg Ile Thr Val
                675                 680                 685

Thr Ala His Thr Asp Val Gly Pro Gly Pro Glu Ser Leu Ser Val Leu
                690                 695                 700

Ile Arg Thr Asn Glu Asp Val Pro Ser Gly Pro Pro Arg Lys Val Glu
705                 710                 715                 720

Val Glu Ala Val Asn Ser Thr Ser Val Lys Val Ser Trp Arg Ser Pro
                725                 730                 735

Val Pro Asn Lys Gln His Gly Gln Ile Arg Gly Tyr Gln Val His Tyr
                740                 745                 750

Val Arg Met Glu Asn Gly Glu Pro Lys Gly Gln Pro Met Leu Lys Asp
                755                 760                 765

Val Met Leu Ala Asp Ala Gln Trp Glu Phe Asp Asp Thr Thr Glu His
770                 775                 780

Asp Met Ile Ile Ser Gly Leu Gln Pro Glu Thr Ser Tyr Ser Leu Thr
785                 790                 795                 800

Val Thr Ala Tyr Thr Thr Lys Gly Asp Gly Ala Arg Ser Lys Pro Lys
                805                 810                 815

Leu Val Ser Thr Thr Gly Ala Val Pro Gly Lys Pro Arg Leu Val Ile
                820                 825                 830

Asn His Thr Gln Met Asn Thr Ala Leu Ile Gln Trp His Pro Pro Val
                835                 840                 845

Asp Thr Phe Gly Pro Leu Gln Gly Tyr Arg Leu Lys Phe Gly Arg Lys
                850                 855                 860

Asp Met Glu Pro Leu Thr Thr Leu Glu Phe Ser Glu Lys Glu Asp His
865                 870                 875                 880
```

-continued

Phe Thr Ala Thr Asp Ile His Lys Gly Ala Ser Tyr Val Phe Arg Leu
                885                 890                 895

Ser Ala Arg Asn Lys Val Gly Phe Gly Glu Glu Met Val Lys Glu Ile
            900                 905                 910

Ser Ile Pro Glu Glu Val Pro Thr Gly Phe Pro Gln Asn Leu His Ser
        915                 920                 925

Glu Gly Thr Thr Ser Thr Ser Val Gln Leu Ser Trp Gln Pro Pro Val
    930                 935                 940

Leu Ala Glu Arg Asn Gly Ile Ile Thr Lys Tyr Thr Leu Leu Tyr Arg
945                 950                 955                 960

Asp Ile Asn Ile Pro Leu Leu Pro Met Glu Gln Leu Ile Val Pro Ala
                965                 970                 975

Asp Thr Thr Met Thr Leu Thr Gly Leu Lys Pro Asp Thr Thr Tyr Asp
            980                 985                 990

Val Lys Val Arg Ala His Thr Ser Lys Gly Pro Gly Pro Tyr Ser Pro
        995                 1000                1005

Ser Val Gln Phe Arg Thr Leu Pro Val Asp Gln Val Phe Ala Lys Asn
    1010                1015                1020

Phe His Val Lys Ala Val Met Lys Thr Ser Val Leu Leu Ser Trp Glu
1025                1030                1035                1040

Ile Pro Glu Asn Tyr Asn Ser Ala Met Pro Phe Lys Ile Leu Tyr Asp
                1045                1050                1055

Asp Gly Lys Met Val Glu Val Asp Gly Arg Ala Thr Gln Lys Leu
            1060                1065                1070

Ile Val Asn Leu Lys Pro Glu Lys Ser Tyr Ser Phe Val Leu Thr Asn
        1075                1080                1085

Arg Gly Asn Ser Ala Gly Gly Leu Gln His Arg Val Thr Ala Lys Thr
    1090                1095                1100

Ala Pro Asp Val Leu Arg Thr Lys Pro Ala Phe Ile Gly Lys Thr Asn
1105                1110                1115                1120

Leu Asp Gly Met Ile Thr Val Gln Leu Pro Glu Val Pro Ala Asn Glu
                1125                1130                1135

Asn Ile Lys Gly Tyr Tyr Ile Ile Val Pro Leu Lys Lys Ser Arg
            1140                1145                1150

Gly Lys Phe Ile Lys Pro Trp Glu Ser Pro Asp Glu Met Glu Leu Asp
        1155                1160                1165

Glu Leu Leu Lys Glu Ile Ser Arg Lys Arg Arg Ser Ile Arg Tyr Gly
    1170                1175                1180

Arg Glu Val Glu Leu Lys Pro Tyr Ile Ala Ala His Phe Asp Val Leu
1185                1190                1195                1200

Pro Thr Glu Phe Thr Leu Gly Asp Asp Lys His Tyr Gly Gly Phe Thr
                1205                1210                1215

Asn Lys Gln Leu Gln Ser Gly Gln Glu Tyr Val Phe Phe Val Leu Ala
            1220                1225                1230

Val Met Glu His Ala Glu Ser Lys Met Tyr Ala Thr Ser Pro Tyr Ser
        1235                1240                1245

Asp Pro Val Val Ser Met Asp Leu Asp Pro Gln Pro Ile Thr Asp Glu
    1250                1255                1260

Glu Glu Gly Leu Ile Trp Val Val Gly Pro Val Leu Ala Val Val Phe
1265                1270                1275                1280

Ile Ile Cys Ile Val Ile Ala Ile Leu Leu Tyr Lys Arg Lys Arg Ala
                1285                1290                1295

Glu Ser Asp Ser Arg Lys Ser Ser Ile Pro Asn Asn Lys Glu Ile Pro
            1300                1305                1310

-continued

Ser His His Pro Thr Asp Pro Val Glu Leu Arg Arg Leu Asn Phe Gln
        1315                1320                1325

Thr Pro Gly Met Ala Ser His Pro Ile Pro Ile Leu Glu Leu Ala
    1330                1335                1340

Asp His Ile Glu Arg Leu Lys Ala Asn Asp Asn Leu Lys Phe Ser Gln
1345                1350                1355                1360

Glu Tyr Glu Ser Ile Asp Pro Gly Gln Gln Phe Thr Trp Glu His Ser
            1365                1370                1375

Asn Leu Glu Val Asn Lys Pro Lys Asn Arg Tyr Ala Asn Val Ile Ala
        1380                1385                1390

Tyr Asp His Ser Arg Val Leu Leu Ser Ala Ile Glu Gly Ile Pro Gly
        1395                1400                1405

Ser Asp Tyr Val Asn Ala Asn Tyr Ile Asp Gly Tyr Arg Lys Gln Asn
    1410                1415                1420

Ala Tyr Ile Ala Thr Gln Gly Ser Leu Pro Glu Thr Phe Gly Asp Phe
1425                1430                1435                1440

Trp Arg Met Ile Trp Glu Gln Arg Ser Ala Thr Val Val Met Met Thr
            1445                1450                1455

Lys Leu Glu Glu Arg Ser Arg Val Lys Cys Asp Gln Tyr Trp Pro Ser
        1460                1465                1470

Arg Gly Thr Glu Thr His Gly Leu Val Gln Val Thr Leu Leu Asp Thr
        1475                1480                1485

Val Glu Leu Ala Thr Tyr Cys Val Arg Thr Phe Ala Leu Tyr Lys Asn
    1490                1495                1500

Gly Ser Ser Glu Lys Arg Glu Val Arg Gln Phe Gln Phe Thr Ala Trp
1505                1510                1515                1520

Pro Asp His Gly Val Pro Glu His Pro Thr Pro Phe Leu Ala Phe Leu
            1525                1530                1535

Arg Arg Val Lys Thr Cys Asn Pro Pro Asp Ala Gly Pro Met Val Val
        1540                1545                1550

His Cys Ser Ala Gly Val Gly Arg Thr Gly Cys Phe Ile Val Ile Asp
            1555                1560                1565

Ala Met Leu Glu Arg Ile Lys His Glu Lys Thr Val Asp Ile Tyr Gly
        1570                1575                1580

His Val Thr Leu Met Arg Ala Gln Arg Asn Tyr Met Val Gln Thr Glu
1585                1590                1595                1600

Asp Gln Tyr Ile Phe Ile His Asp Ala Leu Leu Glu Ala Val Thr Cys
            1605                1610                1615

Gly Asn Thr Glu Val Pro Ala Arg Asn Leu Tyr Ala Tyr Ile Gln Lys
        1620                1625                1630

Leu Thr Gln Ile Glu Thr Gly Glu Asn Val Thr Gly Met Glu Leu Glu
        1635                1640                1645

Phe Lys Arg Leu Ala Ser Ser Lys Ala His Thr Ser Arg Phe Ile Ser
    1650                1655                1660

Ala Asn Leu Pro Cys Asn Lys Phe Lys Asn Arg Leu Val Asn Ile Met
1665                1670                1675                1680

Pro Tyr Glu Ser Thr Arg Val Cys Leu Gln Pro Ile Arg Gly Val Glu
            1685                1690                1695

Gly Ser Asp Tyr Ile Asn Ala Ser Phe Ile Asp Gly Tyr Arg Gln Gln
        1700                1705                1710

Lys Ala Tyr Ile Ala Thr Gln Gly Pro Leu Ala Glu Thr Thr Glu Asp
        1715                1720                1725

Phe Trp Arg Met Leu Trp Glu His Asn Ser Thr Ile Val Val Met Leu

```
                    1730                1735                1740
Thr Lys Leu Arg Glu Met Gly Arg Glu Lys Cys His Gln Tyr Trp Pro
1745                1750                1755                1760

Ala Glu Arg Ser Ala Arg Tyr Gln Tyr Phe Val Val Asp Pro Met Ala
                1765                1770                1775

Glu Tyr Asn Met Pro Gln Tyr Ile Leu Arg Glu Phe Lys Val Thr Asp
            1780                1785                1790

Ala Arg Asp Gly Gln Ser Arg Thr Val Arg Gln Phe Gln Phe Thr Asp
        1795                1800                1805

Trp Pro Glu Gln Gly Val Pro Lys Ser Gly Glu Gly Phe Ile Asp Phe
    1810                1815                1820

Ile Gly Gln Val His Lys Thr Lys Glu Gln Phe Gly Gln Asp Gly Pro
1825                1830                1835                1840

Ile Ser Val His Cys Ser Ala Gly Val Gly Arg Thr Gly Val Phe Ile
                1845                1850                1855

Thr Leu Ser Ile Val Leu Glu Arg Met Arg Tyr Glu Gly Val Val Asp
            1860                1865                1870

Ile Phe Gln Thr Val Lys Met Leu Arg Thr Gln Arg Pro Ala Met Val
        1875                1880                1885

Gln Thr Glu Asp Gln Tyr Gln Phe Ser Tyr Arg Ala Ala Leu Glu Tyr
    1890                1895                1900

Leu Gly Ser Phe Asp His Tyr Ala Thr
1905                1910

<210> SEQ ID NO 20
<211> LENGTH: 8
<212> TYPE: PRT
<213> ORGANISM: Artificial Sequence
<220> FEATURE:
<223> OTHER INFORMATION: FLAG epitope tag peptide

<400> SEQUENCE: 20

Asp Tyr Lys Asp Asp Asp Asp Lys
1               5

<210> SEQ ID NO 21
<211> LENGTH: 8
<212> TYPE: PRT
<213> ORGANISM: Artificial Sequence
<220> FEATURE:
<223> OTHER INFORMATION: XPRESS epitope tag peptide

<400> SEQUENCE: 21

Asp Leu Tyr Asp Asp Asp Asp Lys
1               5

<210> SEQ ID NO 22
<211> LENGTH: 6
<212> TYPE: PRT
<213> ORGANISM: Homo sapiens

<400> SEQUENCE: 22

Leu Leu Gly Gly Pro Ser
1               5

<210> SEQ ID NO 23
<211> LENGTH: 226
<212> TYPE: PRT
<213> ORGANISM: Artificial Sequence
<220> FEATURE:
<223> OTHER INFORMATION: Mutated human amino acid sequence (mutein Fc)
```

-continued

<400> SEQUENCE: 23

Lys Thr His Thr Cys Pro Pro Cys Pro Ala Pro Glu Ala Glu Gly Ala
1               5                   10                  15

Pro Ser Val Phe Leu Phe Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Arg Asp Glu Leu Thr Lys Asn Gln Val Ser Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys
225

<210> SEQ ID NO 24
<211> LENGTH: 678
<212> TYPE: DNA
<213> ORGANISM: Artificial Sequence
<220> FEATURE:
<223> OTHER INFORMATION: Mutated human oligonucleotide sequence (mutein Fc)

<400> SEQUENCE: 24
aaaactcaca catgcccacc gtgcccagca cctgaagccg agggcgcgcc gtcagtcttc      60
ctcttccccc caaaacccaa ggacaccctc atgatctccc ggacccctga ggtcacatgc     120
gtggtggtgg acgtgagcca cgaagaccct gaggtcaagt tcaactggta cgtggacggc     180
gtggaggtgc ataatgccaa gacaaagccg cgggaggagc agtacaacag cacgtaccgt     240
gtggtcagcg tcctcaccgt cctgcaccag gactggctga atggcaagga gtacaagtgc     300
aaggtctcca acaaagccct cccagccccc atcgagaaaa ccatctccaa agccaaaggg     360
cagccccgag aaccacaggt gtacaccctg cccccatccc gggatgagct gaccaagaac     420
caggtcagcc tgacctgcct ggtcaaaggc ttctatccca gcgacatcgc cgtggagtgg     480
gagagcaatg ggcagccgga gaacaactac aagaccacgc ctcccgtgct ggactccgac     540
ggctccttct tcctctatag caagctcacc gtggacaaga gcaggtggca gcaggggaac     600
gtcttctcat gctccgtgat gcatgaggct ctgcacaacc actacacgca gaagagcctc     660

<210> SEQ ID NO 25
<211> LENGTH: 228
<212> TYPE: PRT
<213> ORGANISM: Homo sapiens

<400> SEQUENCE: 25

```
Cys Asp Lys Thr His Thr Cys Pro Pro Cys Pro Ala Pro Glu Leu Leu
  1               5                  10                  15

Gly Gly Pro Ser Val Phe Leu Phe Pro Pro Lys Pro Lys Asp Thr Leu
             20                  25                  30

Met Ile Ser Arg Thr Pro Glu Val Thr Cys Val Val Val Asp Val Ser
         35                  40                  45

His Glu Asp Pro Glu Val Lys Phe Asn Trp Tyr Val Asp Gly Val Glu
     50                  55                  60

Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225
```

<210> SEQ ID NO 26
<211> LENGTH: 18
<212> TYPE: PRT
<213> ORGANISM: Artificial Sequence
<220> FEATURE:
<223> OTHER INFORMATION: Mutated human peptide sequence (NH2 end of mutein Fc)

<400> SEQUENCE: 26

```
Lys Thr His Thr Cys Pro Pro Cys Pro Ala Pro Glu Ala Glu Gly Ala
  1               5                  10                  15

Pro Ser
```

<210> SEQ ID NO 27
<211> LENGTH: 20
<212> TYPE: PRT
<213> ORGANISM: Artificial Sequence
<220> FEATURE:
<223> OTHER INFORMATION: Mutated human peptide sequence (NH2 end of mutein Fc with 2 amino acid spacer)

-continued

```
<400> SEQUENCE: 27

Gly Ser Lys Thr His Thr Cys Pro Pro Cys Pro Ala Pro Glu Ala Glu
1               5                   10                  15

Gly Ala Pro Ser
            20

<210> SEQ ID NO 28
<211> LENGTH: 7
<212> TYPE: PRT
<213> ORGANISM: Unknown
<220> FEATURE:
<223> OTHER INFORMATION: TEV motif
<220> FEATURE:
<221> NAME/KEY: VARIANT
<222> LOCATION: 2, 3, 5
<223> OTHER INFORMATION: Xaa = Any Amino Acid
<220> FEATURE:
<221> NAME/KEY: VARIANT
<222> LOCATION: 7
<223> OTHER INFORMATION: Xaa = Gly or Ser

<400> SEQUENCE: 28

Glu Xaa Xaa Tyr Xaa Gln Xaa
1               5

<210> SEQ ID NO 29
<211> LENGTH: 7
<212> TYPE: PRT
<213> ORGANISM: Tobacco etch virus

<400> SEQUENCE: 29

Glu Asn Leu Tyr Phe Gln Ser
1               5

<210> SEQ ID NO 30
<211> LENGTH: 7
<212> TYPE: PRT
<213> ORGANISM: Tobacco etch virus

<400> SEQUENCE: 30

Glu Asn Leu Tyr Phe Gln Gly
1               5

<210> SEQ ID NO 31
<211> LENGTH: 468
<212> TYPE: PRT
<213> ORGANISM: Artificial Sequence
<220> FEATURE:
<223> OTHER INFORMATION: Mutated human fusion peptide (A41L-Mutein Fc)

<400> SEQUENCE: 31

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Thr Ser Gly Thr Thr Ser
            20                  25                  30

Glu Pro Ala Tyr Asp Lys Ser Val Cys Asp Ser Asn Asn Lys Glu Tyr
        35                  40                  45

Met Gly Ile Glu Val Tyr Val Glu Ala Thr Leu Asp Glu Pro Leu Lys
    50                  55                  60

Gln Thr Thr Cys Glu Ser Glu Ile His Lys Tyr Gly Ala Ser Val Ser
65                  70                  75                  80

Asn Gly Gly Leu Asn Ile Ser Val Asp Leu Leu Asn Cys Phe Leu Asn
                85                  90                  95

Phe His Thr Val Gly Val Tyr Thr Asn Arg Asp Thr Gly Val Tyr Thr
```

```
                    100                 105                 110
Asn Arg Asp Thr Val Tyr Ala Lys Phe Ala Ser Leu Asp Pro Ser Thr
            115                 120                 125
Glu Pro Ile Asn Ser Met Thr His Asp Asp Leu Val Lys Leu Thr Glu
        130                 135                 140
Glu Cys Ile Val Asp Ile Tyr Leu Lys Cys Glu Val Asp Lys Thr Lys
145                 150                 155                 160
Asp Phe Met Lys Asn Gly Asn Arg Leu Lys Pro Arg Asp Phe Lys Thr
                165                 170                 175
Val Pro Pro Ser Asn Val Gly Ser Met Ile Glu Leu Gln Ser Asp Tyr
            180                 185                 190
Cys Val Glu Asp Val Thr Ala Tyr Val Lys Ile Tyr Asp Glu Cys Gly
        195                 200                 205
Asn Ile Lys Gln His Ser Ile Pro Thr Leu Arg Asp Tyr Phe Thr Thr
    210                 215                 220
Lys Asn Gly Gln Pro Arg Lys Ile Leu Lys Lys Phe Asp Ser Cys
225                 230                 235                 240
Gly Ser Lys Thr His Thr Cys Pro Pro Cys Pro Ala Pro Glu Ala Glu
                245                 250                 255
Gly Ala Pro Ser Val Phe Leu Phe Pro Pro Lys Pro Lys Asp Thr Leu
            260                 265                 270
Met Ile Ser Arg Thr Pro Glu Val Thr Cys Val Val Val Asp Val Ser
        275                 280                 285
His Glu Asp Pro Glu Val Lys Phe Asn Trp Tyr Val Asp Gly Val Glu
    290                 295                 300
Val His Asn Ala Lys Thr Lys Pro Arg Glu Glu Gln Tyr Asn Ser Thr
305                 310                 315                 320
Tyr Arg Val Val Ser Val Leu Thr Val Leu His Gln Asp Trp Leu Asn
                325                 330                 335
Gly Lys Glu Tyr Lys Cys Lys Val Ser Asn Lys Ala Leu Pro Ala Pro
            340                 345                 350
Ile Glu Lys Thr Ile Ser Lys Ala Lys Gly Gln Pro Arg Glu Pro Gln
        355                 360                 365
Val Tyr Thr Leu Pro Pro Ser Arg Asp Glu Leu Thr Lys Asn Gln Val
    370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Val Leu Asp Ser Asp Gly Ser Phe Phe Leu Tyr Ser Lys Leu Thr
            420                 425                 430
Val Asp Lys Ser Arg Trp Gln Gln Gly Asn Val Phe Ser Cys Ser Val
        435                 440                 445
Met His Glu Ala Leu His Asn His Tyr Thr Gln Lys Ser Leu Ser Leu
    450                 455                 460
Ser Pro Gly Lys
465

<210> SEQ ID NO 32
<211> LENGTH: 456
<212> TYPE: PRT
<213> ORGANISM: Artificial Sequence
<220> FEATURE:
<223> OTHER INFORMATION: Mutated human fusion peptide (A41L-wild type
      Fc)
```

-continued

```
<400> SEQUENCE: 32

Met Tyr Ser Leu Phe Ile Ile Leu Met Gly Leu Pro Phe Ser Phe Gln
 1               5                  10                  15

Thr Ser Glu Pro Ala Tyr Asp Lys Ser Val Cys Asp Ser Asn Asn Lys
            20                  25                  30

Glu Tyr Met Gly Ile Glu Val Tyr Val Glu Ala Thr Leu Asp Glu Pro
        35                  40                  45

Leu Arg Gln Thr Thr Cys Glu Ser Glu Ile His Lys Tyr Gly Ala Ser
 50                  55                  60

Val Ser Asn Gly Gly Leu Asn Ile Ser Val Asp Leu Leu Asn Cys Phe
 65                  70                  75                  80

Leu Asn Phe His Thr Val Gly Val Tyr Thr Asn Arg Asp Thr Gly Val
                85                  90                  95

Tyr Thr Asn Arg Asp Thr Val Tyr Ala Lys Phe Ala Ser Leu Asp Pro
            100                 105                 110

Ser Thr Glu Pro Ile Asn Ser Met Thr His Asp Leu Val Lys Leu
        115                 120                 125

Thr Glu Glu Cys Ile Val Asp Ile Tyr Leu Lys Cys Glu Val Asp Lys
130                 135                 140

Thr Lys Asp Phe Met Lys Asn Gly Asn Arg Leu Lys Pro Arg Asp Phe
145                 150                 155                 160

Lys Thr Val Pro Pro Ser Asn Val Gly Ser Met Ile Glu Leu Gln Ser
                165                 170                 175

Asp Tyr Cys Val Glu Asp Val Thr Ala Tyr Val Lys Ile Tyr Asp Glu
            180                 185                 190

Cys Gly Asn Ile Lys Gln His Ser Ile Pro Thr Leu Arg Asp Tyr Phe
        195                 200                 205

Thr Thr Lys Asn Gly Gln Pro Arg Lys Ile Leu Lys Lys Phe Asp
210                 215                 220

Ser Cys Gly Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415
```

```
Ser Lys Leu Thr Val Asp Lys Ser Arg Trp Gln Gln Gly Asn Val Phe
         420                 425                 430

Ser Cys Ser Val Met His Glu Ala Leu His Asn His Tyr Thr Gln Lys
         435                 440                 445

Ser Leu Ser Leu Ser Pro Gly Lys
         450                 455

<210> SEQ ID NO 33
<211> LENGTH: 210
<212> TYPE: PRT
<213> ORGANISM: Poxvirus (A41L)

<400> SEQUENCE: 33

Thr Ser Glu Pro Ala Tyr Asp Lys Ser Val Cys Asp Ser Asn Asn Lys
 1               5                  10                  15

Glu Tyr Met Gly Ile Glu Val Tyr Val Glu Ala Thr Leu Asp Glu Pro
             20                  25                  30

Leu Lys Gln Thr Thr Cys Glu Ser Glu Ile His Lys Tyr Gly Ala Ser
         35                  40                  45

Val Ser Asn Gly Gly Leu Asn Ile Ser Val Asp Leu Leu Asn Cys Phe
 50                  55                  60

Leu Asn Phe His Thr Val Gly Val Tyr Thr Asn Arg Asp Thr Gly Val
65                  70                  75                  80

Tyr Thr Asn Arg Asp Thr Val Tyr Ala Lys Phe Ala Ser Leu Asp Pro
                 85                  90                  95

Ser Thr Glu Pro Ile Asn Ser Met Thr His Asp Asp Leu Val Lys Leu
            100                 105                 110

Thr Glu Glu Cys Ile Val Asp Ile Tyr Leu Lys Cys Glu Val Asp Lys
        115                 120                 125

Thr Lys Asp Phe Met Lys Asn Gly Asn Arg Leu Lys Pro Arg Asp Phe
    130                 135                 140

Lys Thr Val Pro Pro Ser Asn Val Gly Ser Met Ile Glu Leu Gln Ser
145                 150                 155                 160

Asp Tyr Cys Val Glu Asp Val Thr Ala Tyr Val Lys Ile Tyr Asp Glu
                165                 170                 175

Cys Gly Asn Ile Lys Gln His Ser Ile Pro Thr Leu Arg Asp Tyr Phe
            180                 185                 190

Thr Thr Lys Asn Gly Gln Pro Arg Lys Ile Leu Lys Lys Lys Phe Asp
        195                 200                 205

Ser Cys
    210

<210> SEQ ID NO 34
<211> LENGTH: 226
<212> TYPE: PRT
<213> ORGANISM: Pox virus (A41L)

<400> SEQUENCE: 34

Met Tyr Ser Leu Phe Ile Ile Leu Met Gly Leu Pro Phe Ser Phe Gln
 1               5                  10                  15

Thr Ser Glu Pro Ala Tyr Asp Lys Ser Val Cys Asp Ser Asn Asn Lys
             20                  25                  30

Glu Tyr Met Gly Ile Glu Val Tyr Val Glu Ala Thr Leu Asp Glu Pro
         35                  40                  45

Leu Arg Gln Thr Thr Cys Glu Ser Glu Ile His Lys Tyr Gly Ala Ser
 50                  55                  60

Val Ser Asn Gly Gly Leu Asn Ile Ser Val Asp Leu Leu Asn Cys Phe
```

```
                65                  70                  75                  80
Leu Asn Phe His Thr Val Gly Val Tyr Thr Asn Arg Asp Thr Gly Val
                    85                  90                  95

Tyr Thr Asn Arg Asp Thr Val Tyr Ala Lys Phe Ala Ser Leu Asp Pro
            100                 105                 110

Ser Thr Glu Pro Ile Asn Ser Met Thr His Asp Asp Leu Val Lys Leu
        115                 120                 125

Thr Glu Glu Cys Ile Val Asp Ile Tyr Leu Lys Cys Glu Val Asp Lys
    130                 135                 140

Thr Lys Asp Phe Met Lys Asn Gly Asn Arg Leu Lys Pro Arg Asp Phe
145                 150                 155                 160

Lys Thr Val Pro Pro Ser Asn Val Gly Ser Met Ile Glu Leu Gln Ser
                165                 170                 175

Asp Tyr Cys Val Glu Asp Val Thr Ala Tyr Val Lys Ile Tyr Asp Glu
            180                 185                 190

Cys Gly Asn Ile Lys Gln His Ser Ile Pro Thr Leu Arg Asp Tyr Phe
        195                 200                 205

Thr Thr Lys Asn Gly Gln Pro Arg Lys Ile Leu Lys Lys Lys Phe Asp
    210                 215                 220

Ser Cys
225

<210> SEQ ID NO 35
<211> LENGTH: 106
<212> TYPE: PRT
<213> ORGANISM: Artificial Sequence
<220> FEATURE:
<223> OTHER INFORMATION: Peptide sequence of combined affinity tags

<400> SEQUENCE: 35

Ala Gly Gly Pro Gly Gly Tyr Pro Tyr Asp Val Pro Asp Tyr Ala Glu
1               5                   10                  15

Asp Gln Val Asp Pro Arg Leu Ile Asp Gly Lys Met Asp Glu Lys Thr
            20                  25                  30

Thr Gly Trp Arg Gly Gly His Val Val Glu Gly Leu Ala Gly Glu Leu
        35                  40                  45

Glu Gln Leu Arg Ala Arg Leu Glu His His Pro Gln Gly Gln Arg Glu
    50                  55                  60

Pro Gly Ser Gly Met Asp Glu Lys Thr Thr Gly Trp Arg Gly Gly His
65                  70                  75                  80

Val Val Glu Gly Leu Ala Gly Glu Leu Glu Gln Leu Arg Ala Arg Leu
                85                  90                  95

Glu His His Pro Gln Gly Gln Arg Glu Pro
            100                 105

<210> SEQ ID NO 36
<211> LENGTH: 327
<212> TYPE: DNA
<213> ORGANISM: Artificial Sequence
<220> FEATURE:
<223> OTHER INFORMATION: Nucleotide sequence of combined affinity tags

<400> SEQUENCE: 36
gcggccgctg gcggcccgg cggctacccc tacgacgtgc cgactacgc cgaggaccag      60 gtggaccccc ggctgatcga cggcaagatg gacgagaaga ccaccggctg gcggggcggc    120
cacgtggtgg agggcctggc cggcgagctg gagcagctgc gggcccggct ggagcaccac    180
ccccagggcc agcgggagcc cggaagcggt atggatgaaa aaactactgg ttggagaggg    240
```

```
ggacatgtag tcgaaggtct ggccggcgag ttagaacaat taagagctag attggaacat      300
catccacaag gtcaaagaga accttag                                          327

<210> SEQ ID NO 37
<211> LENGTH: 270
<212> TYPE: PRT
<213> ORGANISM: Artificial Sequence
<220> FEATURE:
<223> OTHER INFORMATION: Peptide sequence of combined affinity tags

<400> SEQUENCE: 37

Gly Gly Ser Gly Pro Gly Gly Tyr Pro Tyr Asp Val Pro Asp Tyr Ala
 1               5                  10                  15

Glu Asp Gln Val Asp Pro Arg Leu Ile Asp Gly Lys Leu Glu Val Leu
            20                  25                  30

Phe Gln Gly Pro Leu Glu Val Leu Phe Gln Gly Pro Lys Thr His Thr
        35                  40                  45

Cys Pro Pro Cys Pro Ala Pro Glu Ala Glu Gly Ala Pro Ser Val Phe
    50                  55                  60

Leu Phe Pro Pro Lys Pro Lys Asp Thr Leu Met Ile Ser Arg Thr Pro
65                  70                  75                  80

Glu Val Thr Cys Val Val Val Asp Val Ser His Glu Asp Pro Glu Val
                85                  90                  95

Lys Phe Asn Trp Tyr Val Asp Gly Val Glu Val His Asn Ala Lys Thr
            100                 105                 110

Lys Pro Arg Glu Glu Gln Tyr Asn Ser Thr Tyr Arg Val Val Ser Val
        115                 120                 125

Leu Thr Val Leu His Gln Asp Trp Leu Asn Gly Lys Glu Tyr Lys Cys
    130                 135                 140

Lys Val Ser Asn Lys Ala Leu Pro Ala Pro Ile Glu Lys Thr Ile Ser
145                 150                 155                 160

Lys Ala Lys Gly Gln Pro Arg Glu Pro Gln Val Tyr Thr Leu Pro Pro
                165                 170                 175

Ser Arg Asp Glu Leu Thr Lys Asn Gln Val Ser Leu Thr Cys Leu Val
            180                 185                 190

Lys Gly Phe Tyr Pro Ser Asp Ile Ala Val Glu Trp Glu Ser Asn Gly
        195                 200                 205

Gln Pro Glu Asn Asn Tyr Lys Thr Thr Pro Pro Val Leu Asp Ser Asp
    210                 215                 220

Gly Ser Phe Phe Leu Tyr Ser Lys Leu Thr Val Asp Lys Ser Arg Trp
225                 230                 235                 240

Gln Gln Gly Asn Val Phe Ser Cys Ser Val Met His Glu Ala Leu His
                245                 250                 255

Asn His Tyr Thr Gln Lys Ser Leu Ser Leu Ser Pro Gly Lys
            260                 265                 270

<210> SEQ ID NO 38
<211> LENGTH: 821
<212> TYPE: DNA
<213> ORGANISM: Artificial Sequence
<220> FEATURE:
<223> OTHER INFORMATION: Nucleotide sequence of combined affinity tags

<400> SEQUENCE: 38
gcggccgctg gcggcagcgg ccccggcggc taccccctaca cgtgcccgac tacgccgagg      60
accaggtgga ccccccggctg atcgacggca agctggaggt cctctttcaa gggccactgg    120
```

```
aagtcctgtt ccaaggacct aaaactcaca catgcccacc gtgcccagca cctgaagccg      180
agggcgcgcc gtcagtcttc ctcttccccc caaaacccaa ggacaccctc atgatctccc      240
ggacccctga ggtcacatgc gtggtggtgg acgtgagcca cgaagaccct gaggtcaagt      300
tcaactggta cgtggacggc gtggaggtgc ataatgccaa gacaaagccg cgggaggagc      360
agtacaacag cacgtaccgt gtggtcagcg tcctcaccgt cctgcaccag gactggctga      420
atggcaagga gtacaagtgc aaggtctcca acaaagccct cccagccccc atcgagaaaa      480
ccatctccaa agccaaaggg cagccccgag aaccacaggt gtacaccctg cccccatccc      540
gggatgagct gaccaagaac caggtcagcc tgacctgcct ggtcaaaggc ttctatccca      600
gcgacatcgc cgtggagtgg gagagcaatg ggcagccgga gaacaactac aagaccacgc      660
ctcccgtgct ggactccgac ggctccttct cctctatag caagctcacc gtggacaaga      720
gcaggtggca gcagggggaac gtcttctcat gctccgtgat gcatgaggct ctgcacaacc      780
actacacgca gaagagcctc tccctgtctc cgggtaaatg a                         821

<210> SEQ ID NO 39
<211> LENGTH: 5428
<212> TYPE: DNA
<213> ORGANISM: Artificial Sequence
<220> FEATURE:
<223> OTHER INFORMATION: Vector sequence (PCDNA3.1)

<400> SEQUENCE: 39
gacggatcgg gagatctccc gatccctat ggtgcactct cagtacaatc tgctctgatg        60
ccgcatagtt aagccagtat ctgctccctg cttgtgtgtt ggaggtcgct gagtagtgcg      120
cgagcaaaat ttaagctaca acaaggcaag gcttgaccga caattgcatg aagaatctgc      180
ttagggttag gcgttttgcg ctgcttcgcg atgtacgggc cagatatacg cgttgacatt      240
gattattgac tagttattaa tagtaatcaa ttacggggtc attagttcat agcccatata      300
tggagttccg cgttacataa cttacggtaa atggcccgcc tggctgaccg cccaacgacc      360
cccgcccatt gacgtcaata atgacgtatg ttcccatagt aacgccaata gggactttcc      420
attgacgtca atgggtggag tatttacggt aaactgccca cttggcagta catcaagtgt      480
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta acaactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gctggctagc      900
gtttaaactt aagcttggta ccgagctcgg atccactagt ccagtgtggt ggaattctgc      960
agatatccag cacagtggcg gccgctcgag tctagagggc ccgtttaaac ccgctgatca     1020
gcctcgactg tgccttctag ttgccagcca tctgttgttt gccctccccc gtgccttcc      1080 ttgaccctgg aaggtgccac tcccactgtc ctttcctaat aaaatgagga aattgcatcg     1140
cattgtctga gtaggtgtca ttctattctg ggggtgggg tggggcagga cagcaagggg      1200
gaggattggg aagacaatag caggcatgct ggggatgcgg tgggctctat ggcttctgag      1260
gcggaaagaa ccagctgggg ctctaggggg tatccccacg cgccctgtag cggcgcatta     1320
agcgcggcgg gtgtggtggt tacgcgcagc gtgaccgcta cacttgccag cgccctagcg     1380
```

```
cccgctcctt tcgctttctt cccttcctt ctcgccacgt tcgccggctt tccccgtcaa    1440
gctctaaatc gggggctccc tttagggttc cgatttagtg ctttacggca cctcgacccc    1500
aaaaaacttg attagggtga tggttcacgt agtgggccat cgccctgata gacggttttt    1560
cgcccttga cgttggagtc cacgttcttt aatagtggac tcttgttcca aactggaaca     1620
acactcaacc ctatctcggt ctattctttt gatttataag ggattttgcc gatttcggcc    1680
tattggttaa aaaatgagct gatttaacaa aaatttaacg cgaattaatt ctgtggaatg    1740
tgtgtcagtt agggtgtgga aagtccccag gctccccagc aggcagaagt atgcaaagca    1800
tgcatctcaa ttagtcagca accaggtgtg gaaagtcccc aggctcccca gcaggcagaa    1860
gtatgcaaag catgcatctc aattagtcag caaccatagt cccgccccta actccgccca    1920
tcccgcccct aactccgccc agttccgccc attctccgcc ccatggctga ctaattttt     1980
ttatttatgc agaggccgag gccgcctctg cctctgagct attccagaag tagtgaggag    2040
gcttttttgg aggcctaggc ttttgcaaaa agctcccggg agcttgtata tccattttcg    2100
gatctgatca agagacagga tgaggatcgt ttcgcatgat tgaacaagat ggattgcacg    2160
caggttctcc ggccgcttgg gtggagaggc tattcggcta tgactgggca acagacaa     2220
tcggctgctc tgatgccgcc gtgttccggc tgtcagcgca ggggcgcccg gttcttttg     2280
tcaagaccga cctgtccggt gccctgaatg aactgcagga cgaggcagcg cggctatcgt    2340
ggctggccac gacgggcgtt ccttgcgcag ctgtgctcga cgttgtcact gaagcgggaa    2400
gggactggct gctattgggc gaagtgccgg ggcaggatct cctgtcatct caccttgctc    2460
ctgccgagaa agtatccatc atggctgatg caatgcggcg gctgcatacg cttgatccgg    2520
ctacctgccc attcgaccac caagcgaaac atcgcatcga gcgagcacgt actcggatgg    2580
aagccggtct tgtcgatcag gatgatctgg acgaagagca tcaggggctc gcgccagccg    2640
aactgttcgc caggctcaag gcgcgcatgc ccgacggcga ggatctcgtc gtgacccatg    2700
gcgatgcctg cttgccgaat atcatggtgg aaaatggccg cttttctgga ttcatcgact    2760
gtggccggct gggtgtggcg gaccgctatc aggacatagc gttggctacc cgtgatattg    2820
ctgaagagct tggcggcgaa tgggctgacc gcttcctcgt gctttacggt atcgccgctc    2880
ccgattcgca gcgcatcgcc ttctatcgcc ttcttgacga gttcttctga gcgggactct    2940
ggggttcgaa atgaccgacc aagcgacgcc caacctgcca tcacgagatt tcgattccac    3000
cgccgccttc tatgaaaggt tgggcttcgg aatcgttttc cgggacgccg gctggatgat    3060
cctccagcgc ggggatctca tgctggagtt cttcgcccac cccaacttgt ttattgcagc    3120
ttataatggt tacaaataaa gcaatagcat cacaaatttc acaaataaag cattttttc     3180
actgcattct agttgtggtt tgtccaaact catcaatgta tcttatcatg tctgtatacc    3240
gtcgacctct agctagagct tggcgtaatc atggtcatag ctgtttcctg tgtgaaattg    3300
ttatccgctc acaattccac acaacatacg agccggaagc ataaagtgta aagcctgggg    3360
tgcctaatga gtgagctaac tcacattaat tgcgttgcgc tcactgcccg ctttccagtc    3420
gggaaacctg tcgtgccagc tgcattaatg aatcggccaa cgcgcgggga gaggcggttt    3480
gcgtattggg cgctcttccg cttcctcgct cactgactcg ctgcgctcgg tcgttcggct    3540
gcggcgagcg gtatcagctc actcaaaggc ggtaatacgg ttatccacag aatcaggga    3600
taacgcagga agaacatgt gagcaaaagg ccagcaaaag gccaggaacc gtaaaaaggc     3660
cgcgttgctg gcgtttttcc ataggctccg cccccctgac gagcatcaca aaaatcgacg    3720
ctcaagtcag aggtggcgaa acccgacagg actataaaga taccaggcgt ttccccctgg    3780
```

| | |
|---|---:|
| aagctccctc gtgcgctctc ctgttccgac cctgccgctt accggatacc tgtccgcctt | 3840 |
| tctcccttcg ggaagcgtgg cgctttctca tagctcacgc tgtaggtatc tcagttcggt | 3900 |
| gtaggtcgtt cgctccaagc tgggctgtgt gcacgaaccc cccgttcagc ccgaccgctg | 3960 |
| cgccttatcc ggtaactatc gtcttgagtc caacccggta agacacgact tatcgccact | 4020 |
| ggcagcagcc actggtaaca ggattagcag agcgaggtat gtaggcggtg ctacagagtt | 4080 |
| cttgaagtgg tggcctaact acggctacac tagaagaaca gtatttggta tctgcgctct | 4140 |
| gctgaagcca gttaccttcg gaaaaagagt tggtagctct tgatccggca aacaaaccac | 4200 |
| cgctggtagc ggtttttttg tttgcaagca gcagattacg cgcagaaaaa aaggatctca | 4260 |
| agaagatcct ttgatctttt ctacggggtc tgacgctcag tggaacgaaa actcacgtta | 4320 |
| agggattttg gtcatgagat tatcaaaaag gatcttcacc tagatccttt taaattaaaa | 4380 |
| atgaagtttt aaatcaatct aaagtatata tgagtaaact tggtctgaca gttaccaatg | 4440 |
| cttaatcagt gaggcaccta tctcagcgat ctgtctattt cgttcatcca tagttgcctg | 4500 |
| actccccgtc gtgtagataa ctacgatacg ggagggctta ccatctggcc ccagtgctgc | 4560 |
| aatgataccg cgagacccac gctcaccggc tccagattta tcagcaataa accagccagc | 4620 |
| cggaagggcc gagcgcagaa gtggtcctgc aactttatcc gcctccatcc agtctattaa | 4680 |
| ttgttgccgg gaagctagag taagtagttc gccagttaat agtttgcgca acgttgttgc | 4740 |
| cattgctaca ggcatcgtgg tgtcacgctc gtcgtttggt atggcttcat tcagctccgg | 4800 |
| ttcccaacga tcaaggcgag ttacatgatc ccccatgttg tgcaaaaaag cggttagctc | 4860 |
| cttcggtcct ccgatcgttg tcagaagtaa gttggccgca gtgttatcac tcatggttat | 4920 |
| ggcagcactg cataattctc ttactgtcat gccatccgta agatgctttt ctgtgactgg | 4980 |
| tgagtactca accaagtcat tctgagaata gtgtatgcgg cgaccgagtt gctcttgccc | 5040 |
| ggcgtcaata cgggataata ccgcgccaca tagcagaact ttaaaagtgc tcatcattgg | 5100 |
| aaaacgttct tcggggcgaa aactctcaag gatcttaccg ctgttgagat ccagttcgat | 5160 |
| gtaacccact cgtgcaccca actgatcttc agcatctttt actttcacca gcgtttctgg | 5220 |
| gtgagcaaaa acaggaaggc aaaatgccgc aaaaaaggga ataagggcga cacggaaatg | 5280 |
| ttgaatactc atactcttcc tttttcaata ttattgaagc atttatcagg gttattgtct | 5340 |
| catgagcgga tacatatttg aatgtattta gaaaaataaa caaataggggg ttccgcgcac | 5400 |
| atttccccga aaagtgccac ctgacgtc | 5428 |

<210> SEQ ID NO 40
<211> LENGTH: 6706
<212> TYPE: DNA
<213> ORGANISM: Artificial Sequence
<220> FEATURE:
<223> OTHER INFORMATION: Vector sequence pSL9

<400> SEQUENCE: 40

| | |
|---|---:|
| caggtggcac ttttcgggga aatgtgcgcg gaacccctat ttgtttattt ttctaaatac | 60 |
| attcaaatat gtatccgctc atgagacaat aaccctgata aatgcttcaa taatattgaa | 120 |
| aaaggaagag tatgagtatt caacatttcc gtgtcgccct tattcccttt tttgcggcat | 180 |
| tttgccttcc tgttttttgct cacccagaaa cgctggtgaa agtaaaagat gctgaagatc | 240 |
| agttgggtgc acgagtgggt tacatcgaac tggatctcaa cagcggtaag atccttgaga | 300 |
| gttttcgccc cgaagaacgt tttccaatga tgagcacttt taaagttctg ctatgtggcg | 360 |
| cggtattatc ccgtattgac gccgggcaag agcaactcgg tcgccgcata cactattctc | 420 |

```
agaatgactt ggttgagtac tcaccagtca cagaaaagca tcttacggat ggcatgacag    480
taagagaatt atgcagtgct gccataacca tgagtgataa cactgcggcc aacttacttc    540
tgacaacgat cggaggaccg aaggagctaa ccgcttttt gcacaacatg ggggatcatg     600
taactcgcct tgatcgttgg aaccggagc tgaatgaagc cataccaaac gacgagcgtg     660
acaccacgat gcctgtagca atggcaacaa cgttgcgcaa actattaact ggcgaactac    720
ttactctagc ttcccggcaa caattaatag actggatgga ggcggataaa gttgcaggac    780
cacttctgcg ctcggccctt ccggctggct ggtttattgc tgataaatct ggagccggtg    840
agcgtgggtc tcgcggtatc attgcagcac tggggccaga tggtaagccc tcccgtatcg    900
tagttatcta cacgacgggg agtcaggcaa ctatggatga acgaaataga cagatcgctg    960
agataggtgc ctcactgatt aagcattggt aactgtcaga ccaagtttac tcatatatac    1020
tttagattga tttaaaactt cattttttaat ttaaaaggat ctaggtgaag atccttttg    1080 ataatctcat gaccaaaatc ccttaacgtg agttttcgtt ccactgagcg tcagaccccg    1140
tagaaaagat caaaggatct tcttgagatc ctttttttct gcgcgtaatc tgctgcttgc    1200
aaacaaaaaa accaccgcta ccagcggtgg tttgtttgcc ggatcaagag ctaccaactc    1260
tttttccgaa ggtaactggc ttcagcagag cgcagatacc aaatactgtc cttctagtgt    1320
agccgtagtt aggccaccac ttcaagaact ctgtagcacc gcctacatac ctcgctctgc    1380
taatcctgtt accagtggct gctgccagtg gcgataagtc gtgtcttacc gggttggact    1440
caagacgata gttaccggat aaggcgcagc ggtcgggctg aacggggggt tcgtgcacac    1500
agcccagctt ggagcgaacg acctacaccg aactgagata cctacagcgt gagctatgag    1560
aaagcgccac gcttcccgaa gggagaaagg cggacaggta tccggtaagc ggcagggtcg    1620
gaacaggaga gcgcacgagg gagcttccag ggggaaacgc ctggtatctt tatagtcctg    1680
tcgggtttcg ccacctctga cttgagcgtc gattttgtg atgctcgtca gggggggcgga    1740 gcctatggaa aaacgccagc aacgcggcct ttttacggtt cctggccttt tgctggcctt    1800
ttgctcacat gttctttcct gcgttatccc ctgattctgt ggataaccgt attaccgcct    1860
ttgagtgagc tgataccgct cgccgcagcc gaacgaccga gcgcagcgag tcagtgagcg    1920
aggaagcgga agagcgccca atacgcaaac cgcctctccc cgcgcgttgg ccgattcatt    1980
aatgcagctg gcacgacagg tttcccgact ggaaagcggg cagtgagcgc aacgcaatta    2040
atgtgagtta gctcactcat taggcacccc aggctttaca ctttatgctt ccggctcgta    2100
tgttgtgtgg aattgtgagc ggataacaat ttcacacagg aaacagctat gaccatgatt    2160
acgccaagcg cgcaattaac cctcactaaa gggaacaaaa gctggagctg caagcttaat    2220
gtagtcttat gcaatactct tgtagtcttg caacatggta acgatgagtt agcaacatgc    2280
cttacaagga gagaaaagc accgtgcatg ccgattggtg gaagtaaggt ggtacgatcg    2340
tgccttatta ggaaggcaac agacgggtct gacatggatt ggacgaacca ctgaattgga    2400
ggcgtggcct gggcgggact ggggagtggc gagccctcag atcctgcata taagcagctg    2460 cttttttgcct gtactgggtc tctctggtta gaccagatct gagcctggga gctctctggc    2520
taactaggga acccactgct taagcctcaa taaagcttgc cttgagtgct tcaagtagtg    2580
tgtgcccgtc tgttgtgtga ctctggtaac tagagatccc tcagaccctt ttagtcagtg    2640
tggaaaatct ctagcagtgg cgcccgaaca gggacctgaa agcgaagggg aaaccagagc    2700
tctctcgacg caggactcgg cttgctgaag cgcgcacggc aagaggcgag gggcggcgac    2760
tggtgagtac gccaaaaatt ttgactagcg gaggctagaa ggagagagat gggtgcgaga    2820
```

```
gcgtcagtat taagcggggg agaattagat cgcgatggga aaaaattcgg ttaaggccag    2880
ggggaaagaa aaaatataaa ttaaaacata tagtatgggc aagcagggag ctagaacgat    2940
tcgcagttaa tcctggcctg ttagaaacat cagaaggctg tagacaaata ctgggacagc    3000
tacaaccatc ccttcagaca ggatcagaag aacttagatc attatataat acagtagcaa    3060
ccctctattg tgtgcatcaa aggatagaga taaaagacac caaggaagct ttagacaaga    3120
tagaggaaga gcaaaacaaa agtaagacca ccgcacagca agcggccgct gatcttcaga    3180
cctggaggag gagatatgag ggacaattgg agaagtgaat tatataaata taaagtagta    3240
aaaattgaac cattaggagt agcacccacc aaggcaaaga gaagagtggt gcagagagaa    3300
aaaagagcag tgggaatagg agctttgttc cttgggttct tgggagcagc aggaagcact    3360
atgggcgcag cctcaatgac gctgacggta caggccagac aattattgtc tggtatagtg    3420
cagcagcaga acaatttgct gagggctatt gaggcgcaac agcatctgtt gcaactcaca    3480 gtctgggggca tcaagcagct ccaggcaaga atcctggctg tggaaagata cctaaaggat    3540
caacagctcc tggggatttg ggttgctct ggaaaactca tttgcaccac tgctgtgcct    3600
tggaatgcta gttggagtaa taaatctctg aacagattg gaatcacacg acctggatgg    3660
agtgggacag agaaattaac aattacacaa gcttaataca ctccttaatt gaagaatcgc    3720
aaaaccagca agaaaagaat gaacaagaat tattggaatt agataaatgg gcaagtttgt    3780
ggaattggtt taacataaca aattggctgt ggtatataaa attattcata atgatagtag    3840
gaggcttggt aggtttaaga atagttttg ctgtactttc tatagtgaat agagttaggc    3900
agggatattc accattatcg tttcagaccc acctcccaac cccgagggga cccgacaggc    3960
ccgaaggaat agaagaagaa ggtggagaga gagacagaga cagatccatt cgattagtga    4020
acggatctcg acggtatcgg ttttaaaaga aaggggggga ttgggggggta cagtgcaggg    4080 gaaagaatag tagacataat agcaacagac atacaaacta agaattaca aaaacaaatt    4140 acaaaaattc aaaattttat cggggctgca ggaattcggc gcgccacgcg tccgcggact    4200
agtctcgagt taattaagct agcctagtgc catttgttca gtggttcgta ggctttccc    4260 ccactgtttg gctttcagtt atatggatga tgtggtattg ggggcaagt ctgtacagca    4320 tcttgagtcc cttttaccg ctgttaccaa ttttcttttg tctttgggta tacatttaaa    4380
ccctaacaaa acaagagat gggggttactc tctaaatttt atgggttatg tcattggatg    4440
ttatgggtcc ttgccacaag aacacatcat acaaaaaatc aaagaatgtt ttagaaaact    4500
tcctattaac aggcctattg attggaaagt atgtcaacga attgtgggtc ttttgggttt    4560
tgctgcccct tttacacaat gtggttatcc tgcgttgatg cctttgtatg catgtattca    4620
atctaagcag gctttcactt tctcgccaac ttacaaggcc tttctgtgta aacaataccct    4680 gaacctttac cccgttgccc ggcaacggcc acctctgtgc caagtgtttg ctgacgcaac    4740
ccccactggc tggggcttgg tcatgggcca tcagcgcatg cgtggaacct tttcggctcc    4800
tctgccgatc catactgcgg aactcctagc cgcttgtttt gctcgcagca ggtctggagc    4860
aaacattatc gggactgata actctgttgt cctatcccgc aaatatacat cgtttccatg    4920
gctgctaggc tgtgctgcca actggatcct gcgcgggacg tcctttgttt acgtcccgtc    4980
ggcgctgaat cctgcggacg acccttctcg ggtcgcttg ggactctctc gtcccttct    5040 ccgtctgccg ttccgaccga ccacggggcg cacctctctt tacgcggact cccgtctgt    5100 gccttctcat ctgccggacc gtgtgcactt cgcttcacct ctgcacgtcg catggagacc    5160
accgtgaacg cccaccaaat attgcccaag gtcttacata agaggactct tggactctca    5220
```

-continued

| | |
|---|---|
| gcaatgtcaa cgaccgacct tgaggcatac ttcaaagact gtttgtttaa agactgggag | 5280 |
| gagttggggg aggagattag gttaaaggtc tttgtactag gaggctgtag gcataaattg | 5340 |
| gtctgcgcac cagcaccatg tatcactaga gcggggtacc tttaagacca atgacttaca | 5400 |
| aggcagctgt agatcttagc cacttttaa aagaaaaggg gggacttgga agggctaatt | 5460 |
| cactcccaac gaagacaaga tctgcttttt gcttgtactg ggtctctctg gttagaccag | 5520 |
| atctgagcct gggagctctc tggctaacta gggaacccac tgcttaagcc tcaataaagc | 5580 |
| ttgccttgag tgcttcaagt agtgtgtgcc cgtctgttgt gtgactctgg taactagaga | 5640 |
| tccctcagac cctttagtc agtgtggaaa atctctagca gtagtagttc atgtcatctt | 5700 |
| attattcagt atttataact tgcaaagaaa tgaatatcag agagtgagag gaacttgttt | 5760 |
| attgcagctt ataatggtta caaataaagc aatagcatca caatttcac aaataaagca | 5820 |
| ttttttttcac tgcattctag ttgtggtttg tccaaactca tcaatgtatc ttatcatgtc | 5880 |
| tggctctagc tatcccgccc ctaactccgc ccagttccgc ccattctccg ccccatggct | 5940 |
| gactaatttt ttttatttat gcagaggccg aggccgcctc ggcctctgag ctattccaga | 6000 |
| agtagtgagg aggcttttt ggaggcctag gcttttgcgt cgagacgtac ccaattcgcc | 6060 |
| ctatagtgag tcgtattacg cgcgctcact ggccgtcgtt ttacaacgtc gtgactggga | 6120 |
| aaaccctggc gttacccaac ttaatcgcct tgcagcacat ccccctttcg ccagctggcg | 6180 |
| taatagcgaa gaggcccgca ccgatcgccc ttcccaacag ttgcgcagcc tgaatggcga | 6240 |
| atggcgcgac gcgccctgta gcggcgcatt aagcgcggcg ggtgtggtgg ttacgcgcag | 6300 |
| cgtgaccgct acacttgcca gcgccctagc gcccgctcct ttcgctttct tcccttcctt | 6360 |
| tctcgccacg ttcgccggct ttccccgtca agctctaaat cggggggctcc ctttagggtt | 6420 |
| ccgatttagt gctttacggc acctcgaccc caaaaaactt gattagggtg atggttcacg | 6480 |
| tagtgggcca tcgccctgat agacggtttt tcgccctttg acgttggagt ccacgttctt | 6540 |
| taatagtgga ctcttgttcc aaactggaac aacactcaac cctatctcgg tctattcttt | 6600 |
| tgatttataa gggattttgc cgatttcggc ctattggtta aaaaatgagc tgatttaaca | 6660 |
| aaaatttaac gcgaatttta acaaaatatt aacgtttaca atttcc | 6706 |

<210> SEQ ID NO 41
<211> LENGTH: 7749
<212> TYPE: DNA
<213> ORGANISM: Artificial Sequence
<220> FEATURE:
<223> OTHER INFORMATION: Vector sequence pDC409

<400> SEQUENCE: 41

| | |
|---|---|
| gggctgtgga atgtgtgtca gttagggtgt ggaaagtccc caggctcccc agcaggcaga | 60 |
| agtatgcaaa gcatgcatct caattagtca gcaaccaggt gtggaaagtc cccaggctcc | 120 |
| ccagcaggca gaagtatgca aagcatgcat ctcaattagt cagcaaccat agtcccgccc | 180 |
| ctaactccgc ccatcccgcc cctaactccg cccagttccg cccattctcc gccccatggc | 240 |
| tgactaattt ttttttattta tgcagaggcc gaggccgcct cggcctctga gctattccag | 300 |
| aagtagtgag gaggcttttt tggaggccta ggcttttgca aaaagctctc tagatcgatg | 360 |
| aattctcgag ccaccatgga gccagtgat cctagactag agccctggaa gcatccagga | 420 |
| agtcagccta aaactgcttg taccaattgc tattgtaaaa agtgttgctt tcattgccaa | 480 |
| gtttgtttca taacaaaggc cttaggcatc tcctacggcc gcaagaagcg agacagcga | 540 |
| cgaagacctc ctcaaggcag tcagactcat caagtttctc tatcaaagca acccacctcc | 600 |

```
caatcccgag gggacccgac aggcccgaag gaataggtac caagcttcta gaggatcttt    660
gtgaaggaac cttacttctg tggtgtgaca taattggaca aactacctac agagatttaa    720
agctctaagg taaatataaa attttttaagt gtataatgtg ttaaactact gattctaatt   780
gtttgtgtat tttagattcc aacctatgga actgatgaat gggagcagtg gtggaatgcc    840
tttaatgagg aaaacctgtt ttgctcagaa gaaatgccat ctagtgatga tgaggctact    900
gctgactctc aacattctac tcctccaaaa aagaagagaa aggtagaaga ccccaaggac    960
tttccttcag aattgctaag ttttttgagt catgctgtgt ttagtaatag aactcttgct   1020
tgctttgcta tttacaccac aaaggaaaaa gctgcactgc tatacaagaa aattatggaa   1080
aaatattctg taacctttat aagtaggcat aacagttata atcataacat actgtttttt   1140
cttactccac acaggcatag agtgtctgct attaataact atgctcaaaa attgtgtacc   1200
tttagctttt taatttgtaa aggggttaat aaggaatatt tgatgtatag tgccttgact   1260
agagatcata atcagccata ccacatttgt agaggtttta cttgctttaa aaaacctccc   1320
acacctcccc ctgaacctga acataaaat gaatgcaatt gttgttgtta acttgtttat    1380
tgcagcttat aatggttaca aataaagcaa tagcatcaca aatttcacaa ataaagcatt   1440
tttttcactg cattctagtt gtggtttgtc caaactcatc aatgtatctt atcatgtctg   1500
gatccgagct tatcgatggt accgcatcgg gagtacttca agaactgctg atatcgagct   1560
tgctacaagg gactttccgc tggggacttt ccagggaggc gtggcctggg cgggactggg   1620
gagtggcgag ccctcagatc ctgcatataa gcagctgctt tttgcctgta ctgggtctct   1680
gccattagag gtcatctgag cctgggagct ctgaccctag tggcggaacc cactgcttaa   1740
gcctcaatag gatcctcttc cgcatcgctg tctgcgaggg ccagctgttg ggctcgcggt   1800
tgaggacaaa ctcttcgcgg tctttccagt actcttggat cggaaacccg tcggcctccg   1860
aacggtactc cgccaccgag ggacctgagc gagtccgcat cgaccggatc ggaaaacctc   1920
tcgagggcca cgcgtttaaa cgtcgacggc ccgggcggcc gctacagatc tgtttaaact   1980
agttagctag gcgcacccta tagtgagtcg tattaggatc tacgcgattt gatgtatagt   2040
gccttgacta gagatcataa tcagccatac cacatttgta gaggttttac ttgctttaaa   2100
aaacctccca cacctccccc tgaacctgaa acataaaatg aatgcaattg ttgttgttaa   2160
cttgtttatt gcagcttata atggttacaa ataaagcaat agcatcacaa atttcacaaa   2220
taaagcattt ttttcactgc attctagttg tggtttgtcc aaactcatca atgtatctta   2280
tcatgtctgg atccgagctt atcgactcta gaggatcccc catggtcggg acgctctggc   2340
cggtgaggcg tgcgcagtcg ttgacgctct agaccgtgca aaaggagagc ctgtaagcgg   2400
gcactcttcc gtggtctggt ggataaattc gcaagggtat catggcggac gaccggggtt   2460
cgaaccccgg atccggccgt ccgccgtgat ccatgcggtt accgcccgcg tgtcgaaccc   2520
aggtgtgcga cgtcagacaa cgggggagcg ctcctttttgg cttccttcca ggcgcggcgg   2580
ctgctgcgct agcttttttg gccactggcc gcgcgcggcg taagcggtta ggctggaaag   2640
cgaaagcatt aagtggctcg ctcccctgtag ccggagggtt attttccaag ggttgagtcg   2700
caggaccccc ggttcgagtc tcgggccggc cggactgcgg cgaacggggg tttgcctccc   2760
cgtcatgcaa gaccccgctt gcaaattcct ccggaaacag ggacgagccc cttttttgct   2820
tttcccagat gcatccggtg ctgcggcaga tgcgcccccc tcctcagcag cggcaagagc   2880
aagagcagcg gcagacatgc agggcaccct cccccttctcc taccgcgtca ggaggggcaa   2940
catccgggta ccgagctcga attcttgaag acgaaagggc ctcgtgatac gcctattttt   3000
```

```
ataggttaat gtcatgataa taatggtttc ttagacgtca ggtggcactt tcggggaaa    3060
tgtgcgcgga accccta ttt gtttatttt ctaaatacat tcaaatatgt atccgctcat   3120
```



```
ataggttaat gtcatgataa taatggtttc ttagacgtca ggtggcactt tcggggaaa    3060
tgtgcgcgga acccctattt gtttattttt ctaaatacat tcaaatatgt atccgctcat    3120
gagacaataa ccctgataaa tgcttcaata atattgaaaa aggaagagta tgagtattca    3180
acatttccgt gtcgccctta ttcccttttt tgcggcattt tgccttcctg ttttgctca     3240
cccagaaacg ctggtgaaag taaaagatgc tgaagatcag ttgggtgcac gagtgggtta    3300
catcgaactg gatctcaaca gcggtaagat ccttgagagt tttcgccccg aagaacgttt    3360
tccaatgatg agcacttta aagttctgct atgtggcgcg gtattatccc gtgttgacgc     3420
cgggcaagag caactcggtc gccgcataca ctattctcag aatgacttgg ttgagtactc    3480
accagtcaca gaaaagcatc ttacggatgg catgacagta agagaattat gcagtgctgc    3540
cataaccatg agtgataaca ctgcggccaa cttacttctg acaacgatcg gaggaccgaa    3600
ggagctaacc gcttttttgc acaacatggg ggatcatgta actcgccttg atcgttggga    3660
accggagctg aatgaagcca taccaaacga cgagcgtgac accacgatgc ctgcagcaat    3720
ggcaacaacg ttgcgcaaac tattaactgg cgaactactt actctagctt cccggcaaca    3780
attaatagac tggatggagg cggataaagt tgcaggacca cttctgcgct cggcccttcc    3840
ggctggctgg tttattgctg ataaatctgg agccggtgag cgtgggtctc gcggtatcat    3900
tgcagcactg gggccagatg gtaagccctc ccgtatcgta gttatctaca cgacggggag    3960
tcaggcaact atggatgaac gaaatagaca gatcgctgag ataggtgcct cactgattaa    4020
gcattggtaa ctgtcagacc aagtttactc atatatactt tagattgatt taaaacttca    4080
ttttaattt aaaaggatct aggtgaagat cctttttgat aatctcatga ccaaaatccc     4140
ttaacgtgag ttttcgttcc actgagcgtc agacccgta gaaaagatca aaggatcttc     4200
ttgagatcct ttttttctgc gcgtaatctg ctgcttgcaa acaaaaaaac caccgctacc    4260
agcggtggtt tgtttgccgg atcaagagct accaactctt ttccgaagg taactggctt     4320
cagcagagcg cagataccaa atactgtcct tctagtgtag ccgtagttag gccaccactt    4380
caagaactct gtagcaccgc ctacatacct cgctctgcta atcctgttac cagtggctgc    4440
tgccagtggc gataagtcgt gtcttaccgg gttggactca agacgatagt taccggataa    4500
ggcgcagcgg tcgggctgaa cggggggttc gtgcacacag cccagcttgg agcgaacgac    4560
ctacaccgaa ctgagatacc tacagcgtga gcattgagaa agcgccacgc ttcccgaagg    4620
gagaaaggcg acaggtatc cggtaagcgg cagggtcgga acaggagagc gcacgaggga    4680
gcttccaggg ggaaacgcct ggtatcttta tagtcctgtc gggtttcgcc acctctgact    4740
tgagcgtcga ttttgtgat gctcgtcagg ggggcggagc ctatggaaaa acgccagcaa     4800
cgcggccttt ttacggttcc tggccttttg ctggccttt tgaagctgtc cctgatggtc     4860
gtcatctacc tgcctggaca gcatggcctg caacgcgggc atcccgatgc cgccggaagc    4920
gagaagaatc ataatgggga aggccatcca gcctcgcgtc gcgaacgcca gcaagacgta    4980
gcccagcgcg tcggccgcca tgccggcgat aatggcctgc ttctcgccga acgtttggt    5040
ggcgggacca gtgacgaagg cttgagcgag ggcgtgcaag attccgaata ccgcaagcga    5100
caggccgatc atcgtcgcgc tccagcgaaa gcggtcctcg ccgaaaatga cccagagcgc    5160
tgccggcacc tgtcctacga gttgcatgat aagaagaca gtcataagtg cggcgacgat    5220
agtcatgccc cgcgcccacc ggaaggagct gactgggttg aaggctctca agggcatcgg    5280
tcgatgcagg aaaaggacaa gcagcgaaaa ttcacgcccc cttgggaggt ggcggcatat    5340
gcaaaggata gcactcccac tctactactg ggtatcatat gctgactgta tatgcatgag    5400
```

```
gatagcatat gctacccgga tacagattag gatagcatat actacccaga tatagattag    5460
gatagcatat gctacccaga tatagattag gatagcctat gctacccaga tataaattag    5520
gatagcatat actacccaga tatagattag gatagcatat gctacccaga tatagattag    5580
gatagcctat gctacccaga tatagattag gatagcatat gctacccaga tatagattag    5640
gatagcatat gctatccaga tatttgggta gtatatgcta cccagatata aattaggata    5700
gcatatacta ccctaatctc tattaggata gcatatgcta cccggataca gattaggata    5760
gcatatacta cccagatata gattaggata gcatatgcta cccagatata gattaggata    5820
gcctatgcta cccagatata aattaggata gcatatacta cccagatata gattaggata    5880
gcatatgcta cccagatata gattaggata gcctatgcta cccagatata gattaggata    5940
gcatatgcta tccagatatt tgggtagtat atgctaccca tggcaacatt agcccaccgt    6000
gctctcagcg acctcgtgaa tatgaggacc aacaaccctg tgcttggcgc tcaggcgcaa    6060
gtgtgtgtaa tttgtcctcc agatcgcagc aatcgcgccc ctatcttggc ccgcccacct    6120
acttatgcag gtattccccg gggtgccatt agtggttttg tgggcaagtg gtttgaccgc    6180
agtggttagc ggggttacaa tcagccaagt tattacaccc ttattttaca gtccaaaacc    6240
gcagggcggc gtgtgggggc tgacgcgtgc ccccactcca caatttcaaa aaaaagagtg    6300
gccacttgtc tttgtttatg ggccccattg gcgtggagcc ccgtttaatt ttcggggtg     6360 ttagagacaa ccagtggagt ccgctgctgt cggcgtccac tctctttccc cttgttacaa    6420
atagagtgta acaacatggt tcacctgtct tggtccctgc ctgggacaca tcttaataac    6480
cccagtatca tattgcacta ggattatgtg ttgcccatag ccataaattc gtgtgagatg    6540
gacatccagt ctttacggct tgtccccacc ccatggattt ctattgttaa agatattcag    6600
aatgtttcat tcctacacta gtatttattg cccaaggggt ttgtgagggt tatattggtg    6660
tcatagcaca atgccaccac tgaaccccc gtccaaattt tattctgggg gcgtcacctg     6720
aaaccttgtt ttcgagcacc tcacatacac cttactgttc acaactcagc agttattcta    6780
ttagctaaac gaaggagaat gaagaagcag gcgaagattc aggagagttc actgcccgct    6840
ccttgatctt cagccactgc ccttgtgact aaaatggttc actaccctcg tggaatcctg    6900
accccatgta aataaaaccg tgacagctca tggggtggga gatatcgctg ttccttagga    6960 ccctttact aaccctaatt cgatagcata tgcttcccgt tgggtaacat atgctattga    7020
attagggtta gtctggatag tatatactac tacccgggaa gcatatgcta cccgtttagg    7080
gttaacaagg gggccttata aacactattg ctaatgccct cttgagggtc cgcttatcgg    7140
tagctacaca ggcccctctg attgacgttg gtgtagcctc ccgtagtctt cctgggcccc    7200
tgggaggtac atgtccccca gcattggtgt aagagcttca gccaagagtt acacataaag    7260
gcaatgttgt gttgcagtcc acagactgca aagtctgctc caggatgaaa gccactcagt    7320 gttgcaaat gtgcacatcc atttataagg atgtcaacta cagtcagaga accccttgt      7380 gtttggtccc cccccgtgtc acatgtggaa cagggcccag ttggcaagtt gtaccaacca    7440
actgaaggga ttacatgcac tgcccccctc gacgctctcc cttatgcgac tcctgcatta    7500
ggaagcagcc cagtagtagg ttgaggccgt tgagcaccgc cgccgcaagg aatggtgcat    7560
gcaaggagat ggcgcccaac agtccccgg ccacggggcc tgccaccata cccacgccga     7620
aacaagcgct catgagcccg aagtggcgag cccgatcttc cccatcggtg atgtcggcga    7680
tataggcgcc agcaaccgca cctgtggcgc cggtgatgcc ggccacgatg cgtccggcgt    7740
agaggatcc                                                           7749
```

<210> SEQ ID NO 42
<211> LENGTH: 4650
<212> TYPE: DNA
<213> ORGANISM: Artificial Sequence
<220> FEATURE:
<223> OTHER INFORMATION: Vector sequence pAAV

<400> SEQUENCE: 42

| | | | | | |
|---|---|---|---|---|---|
| cctgcaggca | gctgcgcgct | cgctcgctca | ctgaggccgc | ccgggcaaag | cccgggcgtc | 60 |
| gggcgacctt | tggtcgcccg | gcctcagtga | gcgagcgagc | gcgcagagag | ggagtggcca | 120 |
| actccatcac | taggggttcc | tgcggccgca | cgcgtggagc | tagttattaa | tagtaatcaa | 180 |
| ttacggggtc | attagttcat | agcccatata | tggagttccg | cgttacataa | cttacggtaa | 240 |
| atggcccgcc | tggctgaccg | cccaacgacc | cccgcccatt | gacgtcaata | atgacgtatg | 300 |
| ttcccatagt | aacgtcaata | gggactttcc | attgacgtca | atgggtggag | tatttacggt | 360 |
| aaactgccca | cttggcagta | catcaagtgt | atcatatgcc | aagtacgccc | cctattgacg | 420 |
| tcaatgacgg | taaatggccc | gcctggcatt | atgcccagta | catgacctta | tgggactttc | 480 |
| ctacttggca | gtacatctac | gtattagtca | tcgctattac | catggtgatg | cggttttggc | 540 |
| agtacatcaa | tgggcgtgga | tagcggtttg | actcacgggg | atttccaagt | ctccacccca | 600 |
| ttgacgtcaa | tgggagtttg | ttttgcacca | aaatcaacgg | gactttccaa | aatgtcgtaa | 660 |
| caactccgcc | ccattgacgc | aaatgggcgg | taggcgtgta | cggtgggagg | tctatataag | 720 |
| cagagctcgt | ttagtgaacc | gtcagatcgc | ctggagacgc | catccacgct | gttttgacct | 780 |
| ccatagaaga | caccgggacc | gatccagcct | ccgcggattc | gaatcccggc | cgggaacggt | 840 |
| gcattggaac | gcggattccc | cgtgccaaga | gtgacgtaag | taccgcctat | agagtctata | 900 |
| ggcccacaaa | aaatgctttc | ttcttttaat | atacttttt | gtttatctta | tttctaatac | 960 |
| tttccctaat | ctctttcttt | cagggcaata | atgatacaat | gtatcatgcc | tctttgcacc | 1020 |
| attctaaaga | ataacagtga | taatttctgg | gttaaggcaa | tagcaatatt | tctgcatata | 1080 |
| aatatttctg | catataaatt | gtaactgatg | taagaggttt | catattgcta | atagcagcta | 1140 |
| caatccagct | accattctgc | ttttatttta | tggttgggat | aaggctggat | tattctgagt | 1200 |
| ccaagctagg | cccttttgct | aatcatgttc | atacctctta | tcttcctccc | acagctcctg | 1260 |
| ggcaacgtgc | tggtctgtgt | gctggcccat | cactttggca | agaattggg | attcgaacat | 1320 |
| cgattgaatt | ccccggggat | cctctagagt | cgacctgcag | aagcttgcct | cgagcagcgc | 1380 |
| tgctcgagag | atctacgggt | ggcatccctg | tgacccctcc | ccagtgcctc | tcctggccct | 1440 |
| ggaagttgcc | actccagtgc | ccaccagcct | tgtcctaata | aaattaagtt | gcatcatttt | 1500 |
| gtctgactag | gtgtccttct | ataatattat | ggggtgaggg | gggtggtat | ggagcaaggg | 1560 |
| gcaagttggg | aagacaacct | gtagggcctg | cggggtctat | tgggaaccaa | gctggagtgc | 1620 |
| agtggcacaa | tcttggctca | ctgcaatctc | cgcctcctgg | gttcaagcga | ttctcctgcc | 1680 |
| tcagcctccc | gagttgttgg | gattccaggc | atgcatgacc | aggctcagct | aattttttgtt | 1740 |
| tttttggtag | agacggggtt | tcaccatatt | ggccaggctg | gtctccaact | cctaatctca | 1800 |
| ggtgatctac | ccaccttggc | ctcccaaatt | gctgggatta | caggcgtgaa | ccactgctcc | 1860 |
| cttccctgtc | cttctgattt | tgtaggtaac | cacgtgcgga | ccgagcggcc | gcaggaaccc | 1920 |
| ctagtgatgg | agttggccac | tccctctctg | cgcgctcgct | cgctcactga | ggccgggcga | 1980 |
| ccaaaggtcg | cccgacgccc | gggctttgcc | cgggcggcct | cagtgagcga | gcgagcgcgc | 2040 |
| agctgcctgc | aggggcgcct | gatgcggtat | tttctcctta | cgcatctgtg | cggtatttca | 2100 |

```
caccgcatac gtcaaagcaa ccatagtacg cgccctgtag cggcgcatta agcgcggcgg    2160
gtgtggtggt tacgcgcagc gtgaccgcta cacttgccag cgccctagcg cccgctcctt    2220
tcgctttctt cccttccttt ctcgccacgt tcgccggctt tccccgtcaa gctctaaatc    2280
gggggctccc tttagggttc cgatttagtg ctttacggca cctcgacccc aaaaaacttg    2340
atttgggtga tggttcacgt agtgggccat cgccctgata dacggttttt cgccctttga    2400
cgttggagtc cacgttcttt aatagtggac tcttgttcca aactggaaca acactcaacc    2460
ctatctcggg ctattctttt gatttataag ggattttgcc gatttcggcc tattggttaa    2520
aaaatgagct gatttaacaa aaatttaacg cgaattttaa caaaatatta acgtttacaa    2580
ttttatggtg cactctcagt acaatctgct ctgatgccgc atagttaagc cagccccgac    2640
acccgccaac acccgctgac gcgccctgac gggcttgtct gctcccggca tccgcttaca    2700
gacaagctgt gaccgtctcc gggagctgca tgtgtcagag gttttcaccg tcatcaccga    2760
aacgcgcgag acgaaagggc ctcgtgatac gcctattttt ataggttaat gtcatgataa    2820
taatggtttc ttagacgtca ggtggcactt ttcggggaaa tgtgcgcgga accnctattt    2880
gtttattttt ctaaatacat tcaaatatgt atccgctcat gagacaataa ccctgataaa    2940
tgcttcaata atattgaaaa aggaagagta tgagtattca acatttccgt gtcgcccttta    3000 ttccctttt tgcggcattt tgccttcctg ttttgctca cccagaaacg ctggtgaaag    3060 taaagatgc tgaagatcag ttgggtgcac gagtgggtta catcgaactg gatctcaaca    3120
gcggtaagat ccttgagagt tttcgccccg aagaacgttt tccaatgatg agcacttttta    3180 aagttctgct atgtggcgcg gtattatccc gtattgacgc cgggcaagag caactcggtc    3240
gccgcataca ctattctcag aatgacttgg ttgagtactc accagtcaca gaaaagcatc    3300
ttacggatgg catgacagta agagaattat gcagtgctgc cataaccatg agtgataaca    3360
ctgcggccaa cttacttctg acaacgatcg gaggaccgaa ggagctaacc gcttttttgc    3420
acaacatggg ggatcatgta actcgccttg atcgttggga accggagctg aatgaagcca    3480
taccaaacga cgagcgtgac accacgatgc ctgtagcaat ggcaacaacg ttgcgcaaac    3540
tattaactgg cgaactactt actctagctt cccggcaaca attaatagac tggatggagg    3600
cggataaagt tgcaggacca cttctgcgct cggcccttcc ggctggctgg tttattgctg    3660
ataaatctgg agccggtgag cgtgggtctc gcggtatcat tgcagcactg gggccagatg    3720
gtaagccctc ccgtatcgta gttatctaca cgacgggag tcaggcaact atggatgaac    3780
gaaatagaca gatcgctgag ataggtgcct cactgattaa gcattggtaa ctgtcagacc    3840
aagtttactc atatatactt tagattgatt taaaacttca ttttttaattt aaaaggatct    3900 aggtgaagat cctttttgat aatctcatga ccaaaatccc ttaacgtgag ttttcgttcc    3960
actgagcgtc agacccgta gaaaagatca aggatcttc ttgagatcct ttttttctgc    4020
gcgtaatctg ctgcttgcaa acaaaaaaac caccgctacc agcggtggtt tgtttgccgg    4080
atcaagagct accaactctt tttccgaagg taactggctt cagcagagcg cagataccaa    4140
atactgtcct tctagtgtag ccgtagttag gccaccactt caagaactct gtagcaccgc    4200
ctacatacct cgctctgcta atcctgttac cagtggctgc tgccagtggc gataagtcgt    4260
gtcttaccgg gttggactca agacgatagt taccggataa ggcgcagcgg tcgggctgaa    4320
cggggggttc gtgcacacag cccagcttgg agcgaacgac ctacaccgaa ctgagatacc    4380
tacagcgtga gctatgagaa agcgccacgc ttcccgaagg gagaaaggcg gacaggtatc    4440
cggtaagcgg cagggtcgga acaggagagc gcacgaggga gcttccaggg ggaaacgcct    4500
```

```
ggtatcttta tagtcctgtc gggtttcgcc acctctgact tgagcgtcga ttttgtgat    4560 gctcgtcagg ggggcggagc ctatggaaaa acgccagcaa cgcggccttt ttacggttcc    4620
tggccttttg ctggccttt gctcacatgt                                      4650
```

<210> SEQ ID NO 43
<211> LENGTH: 1897
<212> TYPE: PRT
<213> ORGANISM: Homo sapiens

<400> SEQUENCE: 43

```
Met Ala Pro Glu Pro Ala Pro Gly Arg Thr Met Val Pro Leu Val Pro
 1               5                  10                  15

Ala Leu Val Met Leu Gly Leu Val Ala Gly Ala His Gly Asp Ser Lys
            20                  25                  30

Pro Val Phe Ile Lys Val Pro Glu Asp Gln Thr Gly Leu Ser Gly Gly
        35                  40                  45

Val Ala Ser Phe Val Cys Gln Ala Thr Gly Glu Pro Lys Pro Arg Ile
    50                  55                  60

Thr Trp Met Lys Lys Gly Lys Lys Val Ser Ser Gln Arg Phe Glu Val
65                  70                  75                  80

Ile Glu Phe Asp Asp Gly Ala Gly Ser Val Leu Arg Ile Gln Pro Leu
                85                  90                  95

Arg Val Gln Arg Asp Glu Ala Ile Tyr Glu Cys Thr Ala Thr Asn Ser
           100                 105                 110

Leu Gly Glu Ile Asn Thr Ser Ala Lys Leu Ser Val Leu Glu Glu Glu
       115                 120                 125

Gln Leu Pro Pro Gly Phe Pro Ser Ile Asp Met Gly Pro Gln Leu Lys
   130                 135                 140

Val Val Glu Lys Ala Arg Thr Ala Thr Met Leu Cys Ala Ala Gly Gly
145                 150                 155                 160

Asn Pro Asp Pro Glu Ile Ser Trp Phe Lys Asp Phe Leu Pro Val Asp
                165                 170                 175

Pro Ala Thr Ser Asn Gly Arg Ile Lys Gln Leu Arg Ser Gly Ala Leu
           180                 185                 190

Gln Ile Glu Ser Ser Glu Glu Ser Asp Gln Gly Lys Tyr Glu Cys Val
       195                 200                 205

Ala Thr Asn Ser Ala Gly Thr Arg Tyr Ser Ala Pro Ala Asn Leu Tyr
   210                 215                 220

Val Arg Val Arg Arg Val Ala Pro Arg Phe Ser Ile Pro Pro Ser Ser
225                 230                 235                 240

Gln Glu Val Met Pro Gly Gly Ser Val Asn Leu Thr Cys Val Ala Val
                245                 250                 255

Gly Ala Pro Met Pro Tyr Val Lys Trp Met Met Gly Ala Glu Glu Leu
           260                 265                 270

Thr Lys Glu Asp Glu Met Pro Val Gly Arg Asn Val Leu Glu Leu Ser
       275                 280                 285

Asn Val Val Arg Ser Ala Asn Tyr Thr Cys Val Ala Ile Ser Ser Leu
   290                 295                 300

Gly Met Ile Glu Ala Thr Ala Gln Val Thr Val Lys Ala Leu Pro Lys
305                 310                 315                 320

Pro Pro Ile Asp Leu Val Val Thr Glu Thr Thr Ala Thr Ser Val Thr
                325                 330                 335

Leu Thr Trp Asp Ser Gly Asn Ser Glu Pro Val Thr Tyr Tyr Gly Ile
           340                 345                 350
```

-continued

```
Gln Tyr Arg Ala Ala Gly Thr Glu Gly Pro Phe Gln Glu Val Asp Gly
            355                 360                 365

Val Ala Thr Thr Arg Tyr Ser Ile Gly Gly Leu Ser Pro Phe Ser Glu
370                 375                 380

Tyr Ala Phe Arg Val Leu Ala Val Asn Ser Ile Gly Arg Gly Pro Pro
385                 390                 395                 400

Ser Glu Ala Val Arg Ala Arg Thr Gly Glu Gln Ala Pro Ser Ser Pro
                405                 410                 415

Pro Arg Arg Val Gln Ala Arg Met Leu Ser Ala Ser Thr Met Leu Val
                420                 425                 430

Gln Trp Glu Pro Pro Glu Pro Asn Gly Leu Val Arg Gly Tyr Arg
            435                 440                 445

Val Tyr Tyr Thr Pro Asp Ser Arg Arg Pro Pro Asn Ala Trp His Lys
450                 455                 460

His Asn Thr Asp Ala Gly Leu Leu Thr Thr Val Gly Ser Leu Leu Pro
465                 470                 475                 480

Gly Ile Thr Tyr Ser Leu Arg Val Leu Ala Phe Thr Ala Val Gly Asp
                485                 490                 495

Gly Pro Pro Ser Pro Thr Ile Gln Val Lys Thr Gln Gln Gly Val Pro
                500                 505                 510

Ala Gln Pro Ala Asp Phe Gln Ala Glu Val Glu Ser Asp Thr Arg Ile
            515                 520                 525

Gln Leu Ser Trp Leu Leu Pro Pro Gln Glu Arg Ile Ile Met Tyr Glu
530                 535                 540

Leu Val Tyr Trp Ala Ala Glu Asp Glu Asp Gln His Lys Val Thr
545                 550                 555                 560

Phe Asp Pro Thr Ser Ser Tyr Thr Leu Glu Asp Leu Lys Pro Asp Thr
                565                 570                 575

Leu Tyr Arg Phe Gln Leu Ala Ala Arg Ser Asp Met Gly Val Gly Val
                580                 585                 590

Phe Thr Pro Thr Ile Glu Ala Arg Thr Ala Gln Ser Thr Pro Ser Ala
            595                 600                 605

Pro Pro Gln Lys Val Met Cys Val Ser Met Gly Ser Thr Thr Val Arg
610                 615                 620

Val Ser Trp Val Pro Pro Ala Asp Ser Arg Asn Gly Val Ile Thr
625                 630                 635                 640

Gln Tyr Ser Val Ala Tyr Glu Ala Val Asp Gly Glu Asp Arg Gly Arg
                645                 650                 655

His Val Val Asp Gly Ile Ser Arg Glu His Ser Ser Trp Asp Leu Val
                660                 665                 670

Gly Leu Glu Lys Trp Thr Glu Tyr Arg Val Trp Val Arg Ala His Thr
            675                 680                 685

Asp Val Gly Pro Gly Pro Glu Ser Ser Pro Val Leu Val Arg Thr Asp
690                 695                 700

Glu Asp Val Pro Ser Gly Pro Pro Arg Lys Val Glu Val Glu Pro Leu
705                 710                 715                 720

Asn Ser Thr Ala Val His Val Tyr Trp Lys Leu Pro Val Pro Ser Lys
                725                 730                 735

Gln His Gly Gln Ile Arg Gly Tyr Gln Val Thr Tyr Val Arg Leu Glu
                740                 745                 750

Asn Gly Glu Pro Arg Gly Leu Pro Ile Ile Gln Asp Val Met Leu Ala
            755                 760                 765

Glu Ala Gln Glu Thr Thr Ile Ser Gly Leu Thr Pro Glu Thr Thr Tyr
770                 775                 780
```

```
Ser Val Thr Val Ala Ala Tyr Thr Thr Lys Gly Asp Gly Ala Arg Ser
785                 790                 795                 800

Lys Pro Lys Ile Val Thr Thr Gly Ala Val Pro Gly Arg Pro Thr
            805                 810                 815

Met Met Ile Ser Thr Thr Ala Met Asn Thr Ala Leu Leu Gln Trp His
                820                 825                 830

Pro Pro Lys Glu Leu Pro Gly Glu Leu Leu Gly Tyr Arg Leu Gln Tyr
            835                 840                 845

Cys Arg Ala Asp Glu Ala Arg Pro Asn Thr Ile Asp Phe Gly Lys Asp
            850                 855                 860

Asp Gln His Phe Thr Val Thr Gly Leu His Lys Gly Thr Thr Tyr Ile
865                 870                 875                 880

Phe Arg Leu Ala Ala Lys Asn Arg Ala Gly Leu Gly Glu Glu Phe Glu
                885                 890                 895

Lys Glu Ile Arg Thr Pro Glu Asp Leu Pro Ser Gly Phe Pro Gln Asn
            900                 905                 910

Leu His Val Thr Gly Leu Thr Thr Ser Thr Thr Glu Leu Ala Trp Asp
            915                 920                 925

Pro Pro Val Leu Ala Glu Arg Asn Gly Arg Ile Ile Ser Tyr Thr Val
            930                 935                 940

Val Phe Arg Asp Ile Asn Ser Gln Gln Glu Leu Gln Asn Ile Thr Thr
945                 950                 955                 960

Asp Thr Arg Phe Thr Leu Thr Gly Leu Lys Pro Asp Thr Thr Tyr Asp
                965                 970                 975

Ile Lys Val Arg Ala Trp Thr Ser Lys Gly Ser Gly Pro Leu Ser Pro
                980                 985                 990

Ser Ile Gln Ser Arg Thr Met Pro Val Glu Gln Val Phe Ala Lys Asn
            995                 1000                1005

Phe Arg Val Ala Ala Ala Met Lys Thr Ser Val Leu Leu Ser Trp Glu
            1010                1015                1020

Val Pro Asp Ser Tyr Lys Ser Ala Val Pro Phe Lys Ile Leu Tyr Asn
1025                1030                1035                1040

Gly Gln Ser Val Glu Val Asp Gly His Ser Met Arg Lys Leu Ile Ala
                1045                1050                1055

Asp Leu Gln Pro Asn Thr Glu Tyr Ser Phe Val Leu Met Asn Arg Gly
            1060                1065                1070

Ser Ser Ala Gly Gly Leu Gln His Leu Val Ser Ile Arg Thr Ala Pro
            1075                1080                1085

Asp Leu Leu Pro His Lys Pro Leu Pro Ala Ser Ala Tyr Ile Glu Asp
            1090                1095                1100

Gly Arg Phe Asp Leu Ser Met Pro His Val Gln Asp Pro Ser Leu Val
1105                1110                1115                1120

Arg Trp Phe Tyr Ile Val Val Pro Ile Asp Arg Val Gly Gly Ser
            1125                1130                1135

Met Leu Thr Pro Arg Trp Ser Thr Pro Glu Glu Leu Glu Leu Asp Glu
                1140                1145                1150

Leu Leu Glu Ala Ile Glu Gln Gly Gly Glu Glu Gln Arg Arg Arg Arg
                1155                1160                1165

Arg Gln Ala Glu Arg Leu Lys Pro Tyr Val Ala Ala Gln Leu Asp Val
            1170                1175                1180

Leu Pro Glu Thr Phe Thr Leu Gly Asp Lys Lys Asn Tyr Arg Gly Phe
1185                1190                1195                1200

Tyr Asn Arg Pro Leu Ser Pro Asp Leu Ser Tyr Gln Cys Phe Val Leu
```

1205                1210                1215
Ala Ser Leu Lys Glu Pro Met Asp Gln Lys Arg Tyr Ala Ser Ser Pro
            1220                1225                1230

Tyr Ser Asp Glu Ile Val Val Gln Val Thr Pro Ala Gln Gln Gln Glu
            1235                1240                1245

Glu Pro Glu Met Leu Trp Val Thr Gly Pro Val Leu Ala Val Ile Leu
            1250                1255                1260

Ile Ile Leu Ile Val Ile Ala Ile Leu Leu Phe Lys Arg Lys Arg Thr
1265                1270                1275                1280

His Ser Pro Ser Ser Lys Asp Glu Gln Ser Ile Gly Leu Lys Asp Ser
            1285                1290                1295

Leu Leu Ala His Ser Ser Asp Pro Val Glu Met Arg Arg Leu Asn Tyr
            1300                1305                1310

Gln Thr Pro Gly Met Arg Asp His Pro Pro Ile Pro Ile Thr Asp Leu
            1315                1320                1325

Ala Asp Asn Ile Glu Arg Leu Lys Ala Asn Asp Gly Leu Lys Phe Ser
            1330                1335                1340

Gln Glu Tyr Glu Ser Ile Asp Pro Gly Gln Gln Phe Thr Trp Glu Asn
1345                1350                1355                1360

Ser Asn Leu Glu Val Asn Lys Pro Lys Asn Arg Tyr Ala Asn Val Ile
            1365                1370                1375

Ala Tyr Asp His Ser Arg Val Ile Leu Thr Ser Ile Asp Gly Val Pro
            1380                1385                1390

Gly Ser Asp Tyr Ile Asn Ala Asn Tyr Ile Asp Gly Tyr Arg Lys Gln
            1395                1400                1405

Asn Ala Tyr Ile Ala Thr Gln Gly Pro Leu Pro Glu Thr Met Gly Asp
            1410                1415                1420

Phe Trp Arg Met Val Trp Glu Gln Arg Thr Ala Thr Val Val Met Met
1425                1430                1435                1440

Thr Arg Leu Glu Glu Lys Ser Arg Val Lys Cys Asp Gln Tyr Trp Pro
            1445                1450                1455

Ala Arg Gly Thr Glu Thr Cys Gly Leu Ile Gln Val Thr Leu Leu Asp
            1460                1465                1470

Thr Val Glu Leu Ala Thr Tyr Thr Val Arg Thr Phe Ala Leu His Lys
            1475                1480                1485

Ser Gly Ser Ser Glu Lys Arg Glu Leu Arg Gln Phe Gln Phe Met Ala
            1490                1495                1500

Trp Pro Asp His Gly Val Pro Glu Tyr Pro Thr Pro Ile Leu Ala Phe
1505                1510                1515                1520

Leu Arg Arg Val Lys Ala Cys Asn Pro Leu Asp Ala Gly Pro Met Val
            1525                1530                1535

Val His Cys Ser Ala Gly Val Gly Arg Thr Gly Cys Phe Ile Val Ile
            1540                1545                1550

Asp Ala Met Leu Glu Arg Met Lys His Glu Lys Thr Val Asp Ile Tyr
            1555                1560                1565

Gly His Val Thr Cys Met Arg Ser Gln Arg Asn Tyr Met Val Gln Thr
            1570                1575                1580

Glu Asp Gln Tyr Val Phe Ile His Glu Ala Leu Leu Glu Ala Ala Thr
1585                1590                1595                1600

Cys Gly His Thr Glu Val Pro Ala Arg Asn Leu Tyr Ala His Ile Gln
            1605                1610                1615

Lys Leu Gly Gln Val Pro Pro Gly Glu Ser Val Thr Ala Met Glu Leu
            1620                1625                1630

```
Glu Phe Lys Leu Leu Ala Ser Ser Lys Ala His Thr Ser Arg Phe Ile
        1635                1640                1645

Ser Ala Asn Leu Pro Cys Asn Lys Phe Lys Asn Arg Leu Val Asn Ile
    1650                1655                1660

Met Pro Tyr Glu Leu Thr Arg Val Cys Leu Gln Pro Ile Arg Gly Val
1665                1670                1675                1680

Glu Gly Ser Asp Tyr Ile Asn Ala Ser Phe Leu Asp Gly Tyr Arg Gln
        1685                1690                1695

Gln Lys Ala Tyr Ile Ala Thr Gln Gly Pro Leu Ala Glu Ser Thr Glu
        1700                1705                1710

Asp Phe Trp Arg Met Leu Trp Glu His Asn Ser Thr Ile Ile Val Met
        1715                1720                1725

Leu Thr Lys Leu Arg Glu Met Gly Arg Glu Lys Cys His Gln Tyr Trp
        1730                1735                1740

Pro Ala Glu Arg Ser Ala Arg Tyr Gln Tyr Phe Val Val Asp Pro Met
1745                1750                1755                1760

Ala Glu Tyr Asn Met Pro Gln Tyr Ile Leu Arg Glu Phe Lys Val Thr
        1765                1770                1775

Asp Ala Arg Asp Gly Gln Ser Arg Thr Ile Arg Gln Phe Gln Phe Thr
        1780                1785                1790

Asp Trp Pro Glu Gln Gly Val Pro Lys Thr Gly Glu Gly Phe Ile Asp
        1795                1800                1805

Phe Ile Gly Gln Val His Lys Thr Lys Glu Gln Phe Gly Gln Asp Gly
        1810                1815                1820

Pro Ile Thr Val His Cys Ser Ala Gly Val Gly Arg Thr Gly Val Phe
1825                1830                1835                1840

Ile Thr Leu Ser Ile Val Leu Glu Arg Met Arg Tyr Glu Gly Val Val
        1845                1850                1855

Asp Met Phe Gln Thr Val Lys Thr Leu Arg Thr Gln Arg Pro Ala Met
        1860                1865                1870

Val Gln Thr Glu Asp Gln Tyr Gln Cys Tyr Arg Ala Ala Leu Glu Tyr
        1875                1880                1885

Leu Gly Ser Phe Asp His Tyr Ala Thr
        1890                1895

<210> SEQ ID NO 44
<211> LENGTH: 440
<212> TYPE: PRT
<213> ORGANISM: unknown
<220> FEATURE:
<223> OTHER INFORMATION: Consensus sequence

<400> SEQUENCE: 44

Leu Leu Ile Gly Ser Thr Ser Glu Pro Ala Tyr Asp Lys Ser Val Cys
 1               5                  10                  15

Asp Ser Asn Asn Lys Glu Tyr Met Gly Ile Glu Val Tyr Val Glu Ala
            20                  25                  30

Thr Leu Asp Glu Pro Leu Lys Gln Thr Thr Cys Glu Ser Glu Ile His
        35                  40                  45

Lys Tyr Gly Ala Ser Val Ser Asn Gly Gly Leu Asn Ile Ser Val Asp
    50                  55                  60

Leu Leu Asn Cys Phe Leu Asn Phe His Thr Val Gly Val Tyr Thr Asn
65                  70                  75                  80

Arg Asp Thr Gly Val Tyr Thr Asn Arg Asp Thr Val Tyr Ala Lys Phe
                85                  90                  95

Ala Ser Leu Asp Pro Ser Thr Glu Pro Ile Asn Ser Met Thr His Asp
```

-continued

```
                100                 105                 110
Asp Leu Val Lys Leu Thr Glu Glu Cys Ile Val Asp Ile Tyr Leu Lys
            115                 120                 125

Cys Glu Val Asp Lys Thr Lys Asp Phe Met Lys Asn Gly Asn Arg Leu
        130                 135                 140

Lys Pro Arg Asp Phe Lys Thr Val Pro Pro Ser Asn Val Gly Ser Met
145                 150                 155                 160

Ile Glu Leu Gln Ser Asp Tyr Cys Val Glu Asp Val Thr Ala Tyr Val
            165                 170                 175

Lys Ile Tyr Asp Glu Cys Gly Asn Ile Lys Gln His Ser Ile Pro Thr
        180                 185                 190

Leu Arg Asp Tyr Phe Thr Thr Lys Asn Gly Gln Pro Arg Lys Ile Leu
            195                 200                 205

Lys Lys Lys Phe Asp Ser Cys Gly Lys Thr His Thr Cys Pro Pro Cys
        210                 215                 220

Pro Ala Pro Glu Gly Ala Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser His Glu Asp Pro Glu Val Lys Phe Asn Trp Tyr Val
        260                 265                 270

Asp Gly Val Glu Val His Asn Ala Lys Thr Lys Pro Arg Glu Glu Gln
            275                 280                 285

Tyr Asn Ser Thr Tyr Arg Val Val Ser Val Leu Thr Val Leu His Gln
        290                 295                 300

Asp Trp Leu Asn Gly Lys Glu Tyr Lys Cys Lys Val Ser Asn Lys Ala
305                 310                 315                 320

Leu Pro Ala Pro Ile Glu Lys Thr Ile Ser Lys Ala Lys Gly Gln Pro
            325                 330                 335

Arg Glu Pro Gln Val Tyr Thr Leu Pro Pro Ser Arg Asp Glu Leu Thr
        340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
        370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
            405                 410                 415

Ser Cys Ser Val Met His Glu Ala Leu His Asn His Tyr Thr Gln Lys
        420                 425                 430

Ser Leu Ser Leu Ser Pro Gly Lys
            435                 440
```